(12) United States Patent
Chang

(10) Patent No.: US 11,357,850 B2
(45) Date of Patent: Jun. 14, 2022

(54) METHODS FOR TREATING BREAST CANCER USING INOS-INHIBITORY COMPOSITIONS

(71) Applicant: The Methodist Hospital, Houston, TX (US)

(72) Inventor: Jenny Chee Ning Chang, Houston, TX (US)

(73) Assignee: The Methodist Hospital, Houston, TX (US)

( * ) Notice: Subject to any disclaimer, the term of this patent is extended or adjusted under 35 U.S.C. 154(b) by 0 days.

(21) Appl. No.: 16/581,630

(22) Filed: Sep. 24, 2019

(65) Prior Publication Data

US 2020/0306371 A1  Oct. 1, 2020

Related U.S. Application Data

(63) Continuation of application No. 15/486,183, filed on Apr. 12, 2017, now Pat. No. 10,420,838, which is a continuation of application No. 15/289,871, filed on Oct. 10, 2016, now abandoned, which is a continuation of application No. PCT/US2015/025009, filed on Apr. 8, 2015.

(60) Provisional application No. 61/976,956, filed on Apr. 8, 2014.

(51) Int. Cl.

| A61K 39/395 | (2006.01) |
|---|---|
| A61P 35/00 | (2006.01) |
| A61K 31/337 | (2006.01) |
| A61K 31/4422 | (2006.01) |
| A61K 33/243 | (2019.01) |
| A61K 31/198 | (2006.01) |
| A61K 31/277 | (2006.01) |
| A61K 31/4427 | (2006.01) |
| A61K 31/4439 | (2006.01) |
| A61K 31/444 | (2006.01) |
| A61K 31/496 | (2006.01) |
| A61K 31/554 | (2006.01) |
| A61K 31/675 | (2006.01) |
| A61K 31/155 | (2006.01) |
| A61K 31/223 | (2006.01) |
| A61K 39/00 | (2006.01) |

(52) U.S. Cl.
CPC .......... *A61K 39/395* (2013.01); *A61K 31/155* (2013.01); *A61K 31/198* (2013.01); *A61K 31/223* (2013.01); *A61K 31/277* (2013.01); *A61K 31/337* (2013.01); *A61K 31/444* (2013.01); *A61K 31/4422* (2013.01); *A61K 31/4427* (2013.01); *A61K 31/4439* (2013.01); *A61K 31/496* (2013.01); *A61K 31/554* (2013.01); *A61K 31/675* (2013.01); *A61K 33/243* (2019.01); *A61P 35/00* (2018.01); *A61K 2039/505* (2013.01)

(58) Field of Classification Search
None
See application file for complete search history.

(56) References Cited

U.S. PATENT DOCUMENTS

| 5,747,532 A | 5/1998 | Lai |
|---|---|---|
| 6,573,284 B1 | 6/2003 | Riley et al. |
| 7,678,391 B2 | 3/2010 | Graham et al. |
| 2002/0037928 A1 | 3/2002 | Jaen et al. |
| 2003/0060510 A1 | 3/2003 | Dreyer |
| 2003/0144298 A1 | 7/2003 | Curwen et al. |
| 2003/0215528 A1 | 11/2003 | Graham et al. |
| 2005/0245544 A1 | 11/2005 | Bell et al. |
| 2005/0271596 A1 | 12/2005 | Friedman et al. |
| 2006/0116515 A1 | 6/2006 | Gahman et al. |
| 2008/0069904 A1 | 3/2008 | Oronsky et al. |
| 2008/0139558 A1 | 6/2008 | Smith et al. |
| 2008/0221068 A1 | 9/2008 | Wallner et al. |
| 2008/0299123 A1 | 12/2008 | Altevogt et al. |
| 2012/0195869 A1 | 8/2012 | Terman |
| 2020/0016265 A1* | 1/2020 | Chang .................. A61K 31/496 |

FOREIGN PATENT DOCUMENTS

| JP | 2005-527510 A | 9/2005 |
|---|---|---|
| JP | 2012-503606 A | 2/2012 |
| WO | WO 2005/082407 A1 | 9/2005 |
| WO | WO 2006/086544 A2 | 8/2006 |
| WO | WO 2007/101213 A2 | 9/2007 |
| WO | WO 2007/123777 A2 | 11/2007 |
| WO | WO 2008/103615 A1 | 8/2008 |
| WO | WO 2009/029592 A1 | 3/2009 |

(Continued)

OTHER PUBLICATIONS

Alexander, JH et al., "Effect of tilarginine acetate in patients with acute myocardial infarction and cardiogenic shock: the triumph randomized controlled trial," *J.Am. Med. Assoc.*, 297(15):1657-1666 (Apr. 2007).

Al-Hajj, M et al., "Prospective identification of tumorigenic breast cancer cells," *Proc. Nat'l. Acad. Sci. USA*, 100(7):3983-3988 (Apr. 2003).

(Continued)

*Primary Examiner* — My-Chau T. Tran
(74) *Attorney, Agent, or Firm* — Haynes and Boone, LLP

(57) ABSTRACT

Disclosed are methods for treating one or more mammalian cancers, particularly, human breast cancers, including triple-negative breast cancer (TNBC), that employ therapeutically-effective amounts of one or more iNOS pathway-inhibitory compounds, such as L-NMMA, in combination with one or more selected calcium channel antagonists, one or more chemotherapeutic agents, one or more anti-PD-1 antibodies, and one or more doses of ionizing radiation. Also disclosed are pharmaceutical formulations that comprise these compositions, as well as methods for their use in treating refractory, metastatic, and/or relapsed cancers, or, for use in the management or reversal of treatment resistance in one or more types of human breast cancer.

24 Claims, 65 Drawing Sheets
(31 of 65 Drawing Sheet(s) Filed in Color)
Specification includes a Sequence Listing.

(56) References Cited

FOREIGN PATENT DOCUMENTS

| | | |
|---|---|---|
| WO | WO 2011/032000 A2 | 3/2011 |
| WO | WO 2013/018829 A1 | 2/2013 |

OTHER PUBLICATIONS

Ambs, S et al., "Frequent nitric oxide synthase-2 expression in human colon adenomas: implication for tumor angiogenesis and colon cancer progression," *Cancer Res.*, 58(2):334-341 (Jan. 1998).

Andreopoulou et al., "Treatment of Hormone Receptor Negative Breast Cancer", *Hot Topics in Oncology*, 7:7-22, (2010).

Arcos et al., "Inducible Nitric Oxide Synthase-Mediated Proliferation of a T Lymphoma Cell Line", *Nitric Oxide*, 8(2):111-118 (Mar. 2003).

Babykutty, S et al., "Insidious role of nitric oxide in migration/invasion of colon cancer cells by upregulating MMP-2/9 via activation of cGMP-PKG-ERK signaling pathways," *Clin. Exp. Metastasis9*, 29(5):471-492 (Jun. 2012).

Botteri et al., "Therapeutic Effect of [beta]-Blockers in Triple-Negative Breast Cancer Postnenopausal Women", *Breast Cancer Research and Treatment*, 140(3):567-575 (2013).

Brown, RW et al., "Prognostic value of Ki-67 compared to S-phase fraction in axillary node-negative breast cancer," *Clin. Cancer Res.*, 2:585-592 (Mar. 1996).

Bulut, AS et al., "Significance of inducible nitric oxide synthase expression in benign and malignant breast epithelium: an immunohistochemical study of 151 cases," *Virchows Arch.*, 447(1):24-30 (Jul. 2005).

Burke, AJ et al., "The yin and yang of nitric oxide in cancer progression," *Carcinogenesis*, 34(3):503-512 (Mar. 2013).

Cameron, D et al., "Adjuvant bevacizumab-containing therapy in triple-negative breast cancer (BEATRICE): primary results of a randomised, phase 3 trial," *Lancet Oncol.*, 14(10):933-942 (Sep. 2013).

Campbell, PJ et al., "Identification of somatically acquired rearrangements in cancer using genome-wide massively parallel paired-end sequencing," *Nat. Genet.*, 40(6):722-729 (Jun. 2008).

Campbell, PJ et al., "The patterns and dynamics of genomic instability in metastatic pancreatic cancer," *Nature*, 467(7319):1109-1113 (Oct. 2010).

Carlisle, RE et al., "TDAG5 1 mediates epithelial-to-mesenchymal transition in human proximal tubular epithelium," *Am. J. Physiol. Renal Physiol.*, 303(3):F467-F481 (Aug. 2012).

Chang, JC et al., "Gene expression patterns in formalin-fixed, paraffin-embedded core biopsies predict docetaxel chemosensitivity in breast cancer patients," *Breast Cancer Res. Treat.*, 108(2):233-240 (Mar. 2008).

Chang, JC et al., "Gene expression profiling for the prediction of therapeutic response to docetaxel in patients with breast cancer," *Lancet*, 362:362-369 (Aug. 2003).

Chang, JC et al., "Patterns of resistance and incomplete response to docetaxel by gene expression profiling in breast cancer patients," *J. Clin. Oncol.*, 23(6): 1169-1177 (Feb. 2005).

Chen, J et al., "A restricted cell population propagates glioblastoma growth after chemotherapy," *Nature*, 488(7412):522-526 (Aug. 2012).

Chen, Q et al., "Untargeted plasma metabolite profiling reveals the broad systemic consequences of xanthine oxidoreductase inactivation in mice," *PLoS One*, 7(6):e37149 doi: 10.1371/journal.pone.0037149 (Jun. 2012).

Chinje, EC et al., "17β-Oestradiol treatment modulates nitric oxide synthase activity in MDA231 tumour with implications on growth and radiation response," *Br. J. Cancer*, 86(1):136-142 (Jan. 2002).

Chowdhury, R et al., "Nitric oxide produced endogenously is responsible for hypoxia-induced HIF-1α stabilization in colon carcinoma cells," *Chem. Res. Toxicol.*, 25(10):2194-2202 (Oct. 2012).

Cotter, G et al., "L-NMMA (a nitric oxide synthase inhibitor) is effective in the treatment of cardiogenic shock," *Circulation*, 101:1358-1361 (Jan. 2000).

Creighton, CJ et al., "Residual breast cancers after conventional therapy display mesenchymal as well as tumor-initiating features," *Proc. Nat'l. Acad. Sci. USA*, 106(33):13820-13825 (Aug. 2009).

Crowell et al., "Is Inducible Nitric Oxide Synthase a Target for Chemoprevention", *Molecular Cancer Therapeutics*, 2:815-823 (Aug. 2003).

Curtis, C et al., "The genomic and transcriptomic architecture of 2,000 breast tumours reveals novel subgroups," *Nature*, 486(7403):346-352 (Apr. 2012).

Daub, H et al., "Kinase-selective enrichment enables quantitative phosphoproteomics of the kinome across the cell cycle," *Mol. Cell*, 31:438-448 (Aug. 2008).

Dave, B et al., "Epithelial-mesenchymal transition, cancer stem cells and treatment resistance," *Breast Cancer Res.*, 14(1):202 (Jan. 2012).

Dave, B et al., "Selective small molecule stat3 inhibitor reduces breast cancer tumor-initiating cells and improves recurrence free survival in a human-xenograft model," *PLoS One* 7(8):e30207 (Aug. 2012).

De Wilt et al., "Nitric Oxide Synthase Inhibition Results in Synergistic Anti-Tumor Activity with Melphalan and Tumour Necrosis Factor Alpha-Based Isolated Limb Perfusions", *British Journal of Cancer*, 83(9):1176-1182, (2000).

Dery, MA et al., "Endoplasmic reticulum stress induces PRNP prion protein gene expression in breast cancer," *Breast Cancer Res.*, 15(2):R22 (Mar. 2013).

Diehn, M et al., "Association of reactive oxygen species levels and radioresistance in cancer stem cells," *Nature*, 458(7239):780-783 (Apr. 2009).

Driessens, G et al., "Defining the mode of tumour growth by clonal analysis," *Nature*, 488(7412):527-30 (Aug. 2012).

Edwards, P et al., "Tumor cell nitric oxide inhibits cell growth in vitro, but stimulates tumorigenesis and experimental lung metastasis in vivo," *J. Surg. Res.*, 63(1):49-52 (Jun. 1996).

Eglimez et al., "Nitric Oxide Short-Circuits Interleukin-12-Medicated Tumor Regression", *Cancer Immunol Immunother*, 60(6):839-845 (2011).

Eyler, CE et al., "Glioma stem cell proliferation and tumor growth are promoted by nitric oxide synthase-2," *Cell*, 146(1):53-66 (Jul. 2011).

Fan, M et al., "Phosphorylated VEGFR2 and hypertension: potential biomarkers to indicate VEGF-dependency of advanced breast cancer in anti-angiogenic therapy," *Breast Cancer Res. Treat.*, 143(1):141-151 (Jan. 2014).

Gampenrieder, SP et al., "Hypertension as a predictive marker for bevacizumab in metastatic breast cancer: results from a retrospective matched-pair analysis," *Anticancer Res.*, 34(1):227-233 (Jan. 2014).

Gerlinger, M et al., "Intratumor heterogeneity and branched evolution revealed by multiregion sequencing," *N. Engl. J. Med*, 366(10):883-892 (Mar. 2012).

Ginestier C et al., "ALDH1 is a marker of normal and malignant human mammary stem cells and a predictor of poor clinical outcome," *Cell Stem Cell*, 1(5):555-567 (Nov. 2007).

Glynn, SA et al., "Increased NOS2 predicts poor survival in estrogen receptor-negative breast cancer patients," *J. Clin. Invest.*, 120(11):3843-3854 (Nov. 2010).

Gralow, JR, "Breast cancer 2004. Progress and promise on the clinical front," *Phys. Med.*, 21(Suppl 1):2 (2006).

Granados-Principal et al., Inhibition of iNOS as a Novel Effective Targeted Therapy Against Triple-Negative Breast Cancer, *Breast Cancer Research*, 17(1):25 (2015).

Grisham, MB et al., "Nitric oxide I. Physiological chemistry of nitric oxide and its metabolites: implications in inflammation," *Am. J. Physiol.*, 276(Pt. 1):G315-G321 (Feb. 1999).

International Preliminary Report on Patentability issued for Application No. PCT/US2015/025009, dated Oct. 12, 2016, 11 pages.

International Search Report and Written Opinion issued for Application No. PCT/US2015/025009, dated Aug. 12, 2015, 22 pages.

Jadeski, LC et al., "Nitric oxide promotes murine mammary tumour growth and metastasis by stimulating tumour cell migration, invasiveness and angiogenesis," *Int. J. Cancer*, 86(1):30-39 (Apr. 2000).

(56) References Cited

OTHER PUBLICATIONS

Janakiram et al., "iNOS-Selective Inhibitors for Cancer Prevention: Promise and Progress", *Future Med Chem.*, 4(17):2193-2204, (Nov. 2012).
Jiang, Y et al., "Deep-sequencing reveals clonal evolution patterns and mutation events associated with relapse in B-cell lymphomas," *Genome Biol.*, 15(8):432 (Aug. 2014).
Kasap, C, et al., "DrugTargetSeqR., a genomics- and CRISPR-Cas9-based method to analyze drug targets," *Nat. Chem. Biol.*, 10(8):626-628 (Aug. 2014).
Kim, RK et al., "Fractionated radiation-induced nitric oxide promotes expansion of glioma stem-like cells," *Cancer Sci.*, 104(9):1172-U77 (Sep. 2013).
Korkaya, H et al., "Breast cancer stem cells, cytokine networks, and the tumor microenvironment," *J. Clin. Invest.*, 121(10):3804-3809 (Oct. 2011).
Kostourou et al., "The Role of Tumour-Derived iNOS in Tumour Progression and Angiogenesis", *British Journal of Cancer*, 104:83-90 (2011).
Kuefer, MU et al., "cDNA cloning, tissue distribution, and chromosomal localization of myelodysplasia/myeloid leukemia factor 2 (MLF2)," *Genomics*, 35(2):392-396 (Jul. 1996).
Landis, MD et al., "Patient-derived breast tumor xenografts facilitating personalized cancer therapy," *Breast Cancer Res.*, 15(1):201 (Jan. 2013).
Lee, HE et al., "An increase in cancer stem cell population after primary systemic therapy is a poor prognostic factor in breast cancer," *Br. J. Cancer*, 104:1730-1738 (May 2011).
Li, X et al., "Intrinsic resistance of tumorigenic breast cancer cells to chemotherapy," *J. Nat 'l. Cancer Inst.*, 100(9):672-679 (Apr. 2008).
Lian, N et al., "Transforming growth factor β suppresses osteoblast differentiation via the vimentin activating transcription factor 4 (ATF4) axis," *J. Biol. Chem.*, 287(43):35975-35984 (Oct. 2012).
Lin et al., "Reciprocal Activation of Macrophages and Breast Carcinoma Cells by Nitric Oxide and Colony-Stimulating Factor-1", *Carcinogenis*, 31(12):2039-2048 (Sep. 2010).
Loibl, S et al., "The role of early expression of inducible nitric oxide synthase in human breast cancer," *Eur. J. Cancer*, 41(12):265-271 (Jan. 2005).
Lopez, A et al., "Multiple-center, randomized, placebo-controlled, double-blind study of the nitric oxide synthase inhibitor 546C88: effect on survival in patients with septic shock," *Crit. Care Med.*, 32(1):21-30 (Jan. 2004).
Massi, D et al., "Inducible nitric oxide synthase expression in benign and malignant cutaneous melanocytic lesions," *J. Pathol.*, 194(2):194-200 (Jun. 2001).
Matrone, C et al., "HIF-1α reveals a binding activity to the promoter of iNOS gene after permanent middle cerebral artery occlusion," *J. Neurochem.*, 90(2):368-378 (Jul. 2004).
Mohsin, SK et al., "Neoadjuvant trastuzumab induces apoptosis in primary breast cancers," *J. Clin. Oncol.*, 23(11):2460-2468 (Apr. 2005).
Molina, H et al., "Global proteomic profiling of phosphopeptides using electron transfer dissociation tandem mass spectrometry," *Proc. Nat'l. Acad. Sci. USA*, 104(7):2199-2204 (Feb. 2007).
Murohara, T et al., "Nitric oxide synthase modulates angiogenesis in response to tissue ischemia," *J. Clin. Invest.*, 101(11):2567-2578 (Nov. 1998).

Nadano, D et al., "A human gene encoding a protein homologous to ribosomal protein L39 is normally expressed in the testis and derepressed in multiple cancer cells," *Biochim. Biophys. Acta*, 1577(3):430-436 (Sep. 2002).
Nagelkerke, A et al., "Hypoxia stimulates migration of breast cancer cells via the PERK/ATF4/LAMP3-arm of the unfolded protein response," *Breast Cancer Res.*, 15(1):R2 (Jan. 2013).
Nousiainen, M et al., "Phosphoproteome analysis of the human mitotic spindle," *Proc. Nat 'l. Acad. Sci. USA*, 103(14):5391-5396 (Apr. 2006).
Office Action issued for European Patent Application No. 15719050.5, dated Nov. 22, 2018, 7 pages.
Office Action issued for Japanese Patent Application No. 2016-561279, dated Sep. 12, 2018, 15 pages (with translation).
Office Action issued for Japanese Patent Application No. 2016-561279, dated Jun. 18, 2019, 4 pages.
Ohtsu, N et al., "Antitumor effects of inhibitors of nitric oxide synthase or cyclooxygenase-2 on human KB carcinoma cells overexpressing COX-2," *Oncol. Rep.*, 24(1):31-36 (Jul. 2010).
Okayama, H et al., "NOS2 enhances KRAS-induced lung carcinogenesis, inflammation, and microRNA-21 expression," *Int. J. Cancer*, 132(1):9-18 (Jan. 2013).
Pan, YX et al., "Activation of the ATF3 gene through a coordinated amino acid-sensing response programme that controls transcriptional regulation of responsive genes following amino acid limitation," *Biochem. J.*, 401(1):299-307 (Jan. 2007).
Pang, Y et al., "TGF-β signaling in myeloid cells is required for tumor metastasis," *Cancer Discov.*, 3(8):936-951 (Aug. 2013).
Rhodes, DR et al., "Oncomine 3.0: genes, pathways, and networks in a collection of 18,000 cancer gene expression profiles," *Neoplasia*, 9(2):166-180 (Feb. 2007).
Sarfati et al., "Identifying Important Comorbidity Among Cancer Populations Using Administrative Data: Prevalence and Impact on Survival", *Asia-Pacific Journal of Clinical Oncology*, 12:47-56 (2016).
Schepers, AG et al., "Lineage tracing reveals Lgr5+ stem cell activity in mouse intestinal adenomas," *Science*, 337(6095):730-735 (Aug. 2012).
Schott, AF et al., "Preclinical and clinical studies of gamma secretase inhibitors with docetaxel on human breast tumors," *Clin. Cancer Res.*, 19(6):1512-1524 (Mar. 2013).
Sen, S et al., "Mitochondrial-associated nitric oxide synthase activity inhibits cytochrome c oxidase: implications for breast cancer," *Free Radic. Biol. Med.*, 57:210-220 (Apr. 2013).
Singapore Written Opinion issued for Application No. 11201607795U dated Nov. 9, 2017, 8 pages.
Thamrongwittawatpong et al., "The Effect of NG-monomethyl-L-arginine and Tamoxifen on Nitric Oxide Production in Breast Cancer Cells Stimulated by Oestrogen and Progesterone," European Journal of Surgery, 2001, vol. 167, p. 484-489.
Tojo et al., "Effects of Antihypertensive Drugs on Nitric Oxide Synthase Activity in Rat Kidney", Database Accesion No. PREV199699059711; & *Kidney International Supplement*, Databas Biosis (Online), 0(55):S1380-S140, (1996).
Zhang, et al. "Targeting Therapy with Mitosomal Daunorubicin Plus Amlodpine Has the Potential to Circumvent Intrinsic Resistant Breast Cancer," Molecular Pharmaceutics, 2011, vol. 8, No. 1, p. 162-175.
Examination Report issued for French Patent Application No. 2015243537, dated Oct. 11, 2019, 4 pages.
Third Office Action issued for Chinese Patent Application No. 201580018474.1, dated Jul. 31, 2020, 12 pages (with translation).

* cited by examiner

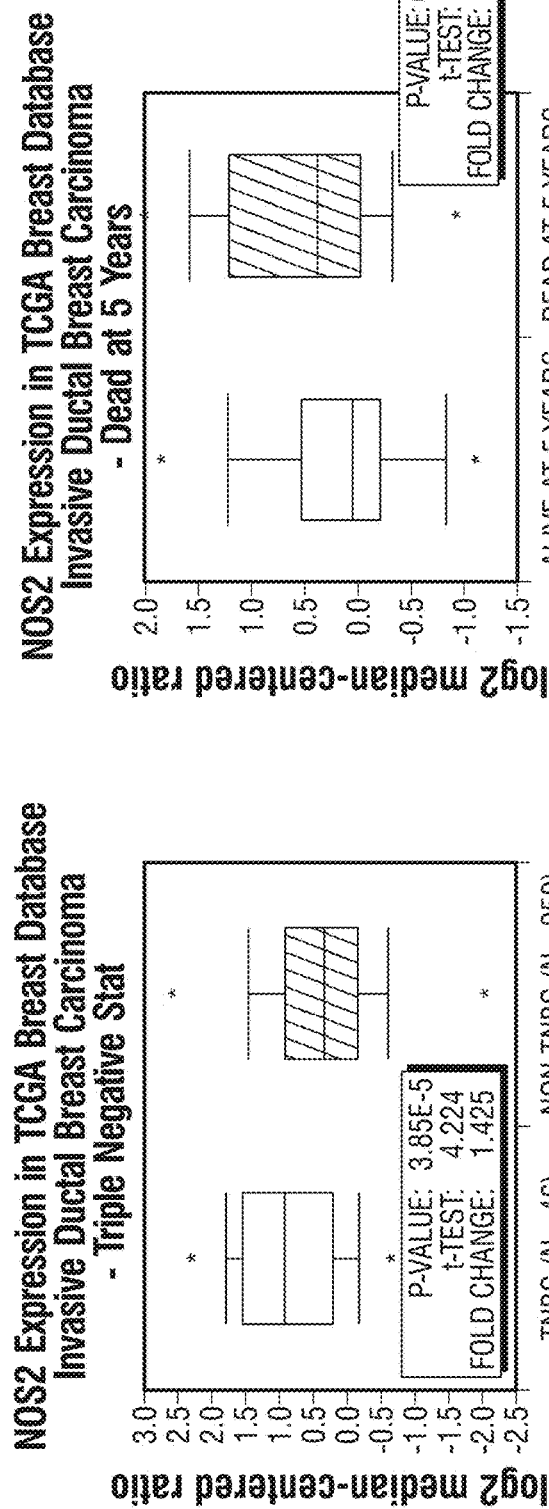
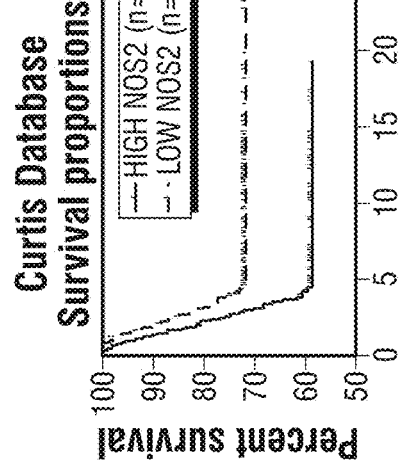
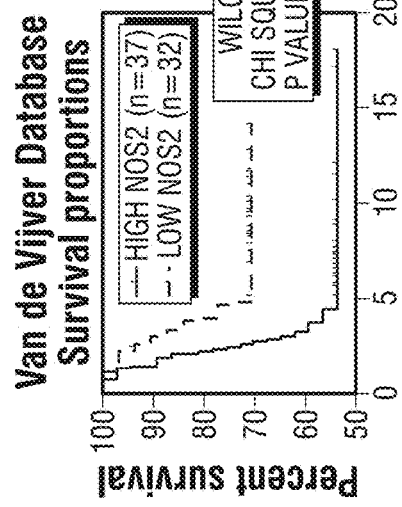
FIG. 1A
FIG. 1B
FIG. 1C
FIG. 1D

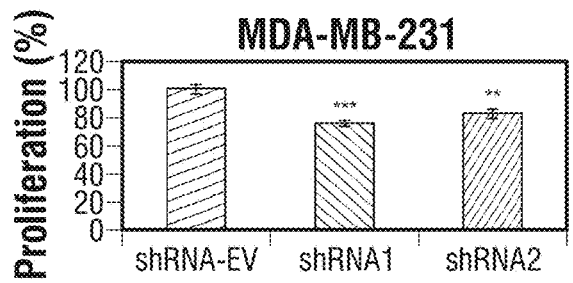
*FIG. 3A*
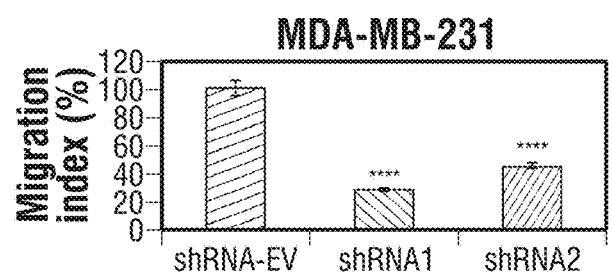
*FIG. 3B*
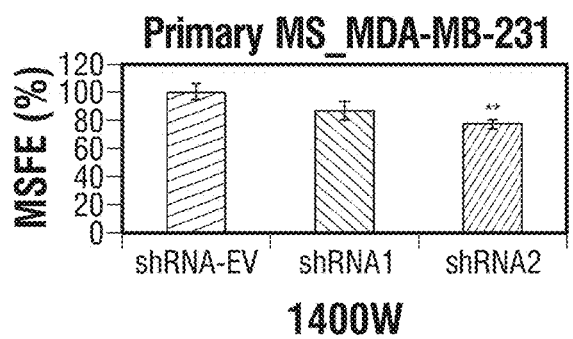 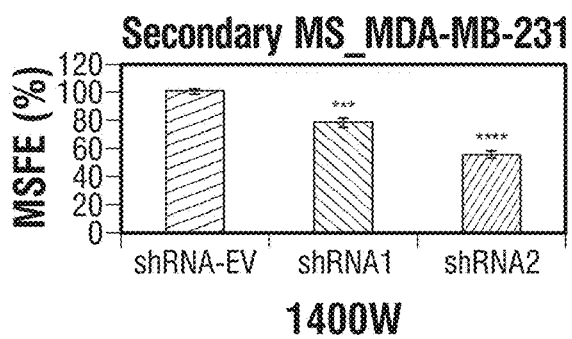
*FIG. 3C*
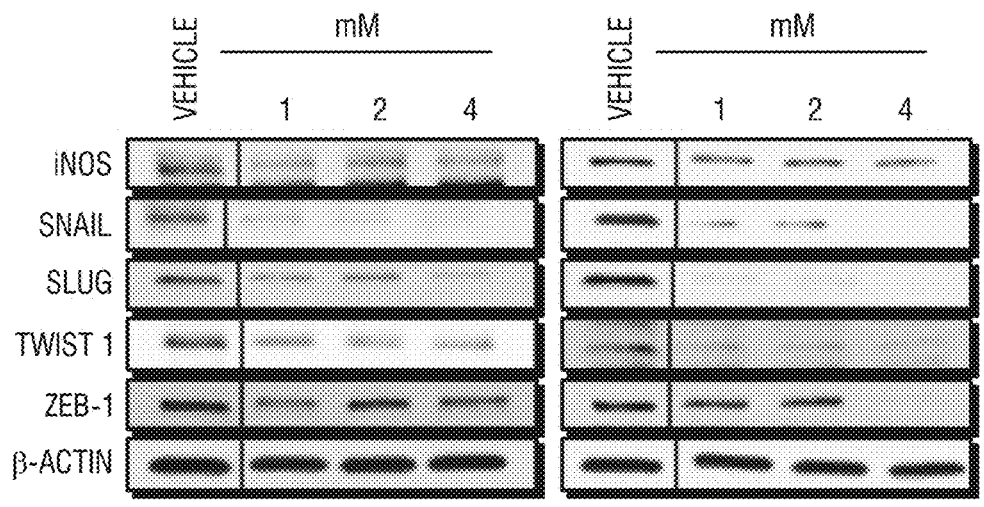
*FIG. 3D*

| LIMITING DILUTION ASSAY (n=5) | 1.5 WEEKS | 2.5 WEEKS |
|---|---|---|
| | 5x10⁵ CELLS | 1x10⁵ CELLS |
| VEHICLE | 5/5 | 5/5 |
| L-NAME | 3/5 | 0/5 * |

| LIMITING DILUTION ASSAY (n=12) | | |
|---|---|---|
| | 5 WEEKS | 6 WEEKS |
| | $5 \times 10^4$ CELLS | $2 \times 10^4$ CELLS |
| VEHICLE | 12/12 | 6/12 |
| L-NMMA | 1/12 * | 3/12 * |
| CHEMO | 8/12 | 10/12 |
| COMBO | 4/12 * | 5/12 * |

*FIG. 5F*

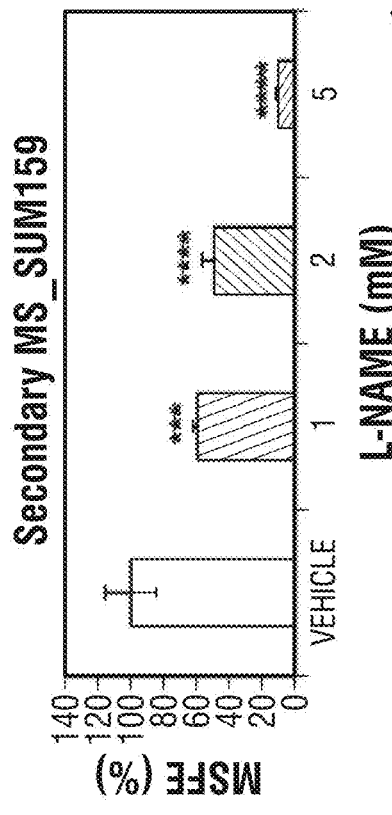
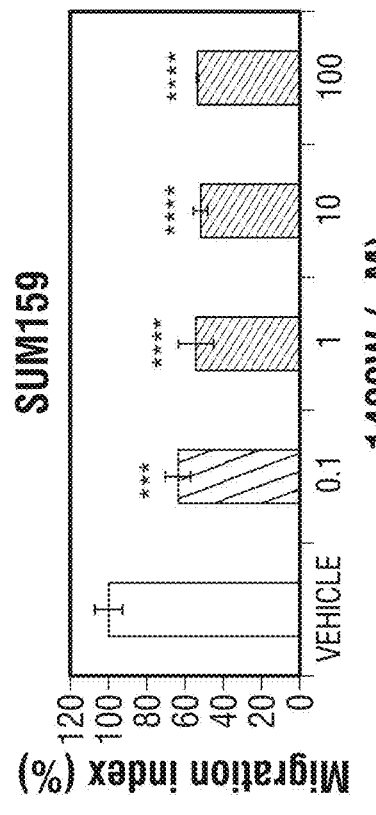
FIG. 9C
FIG. 9D
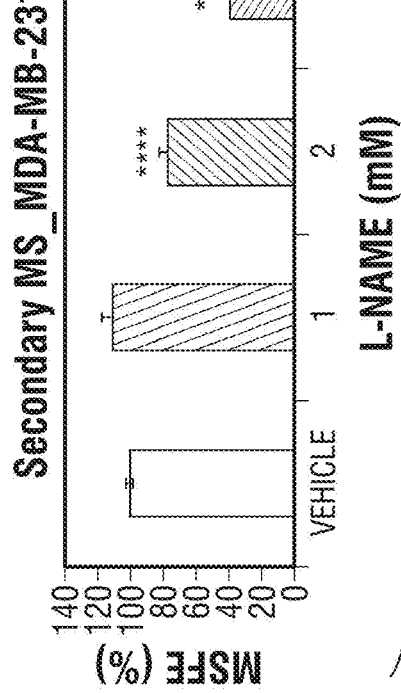
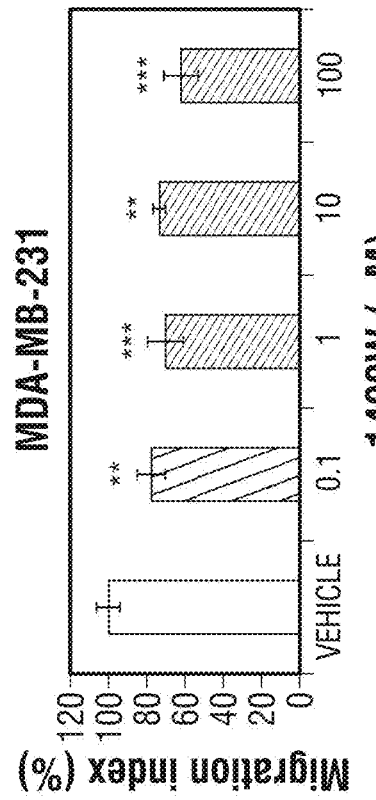

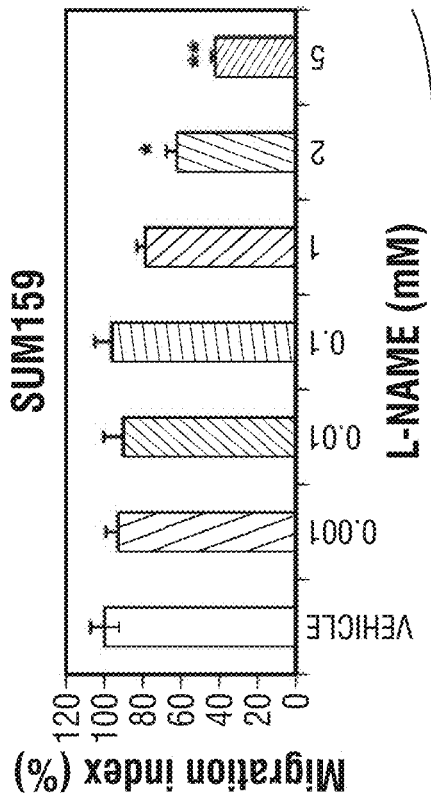
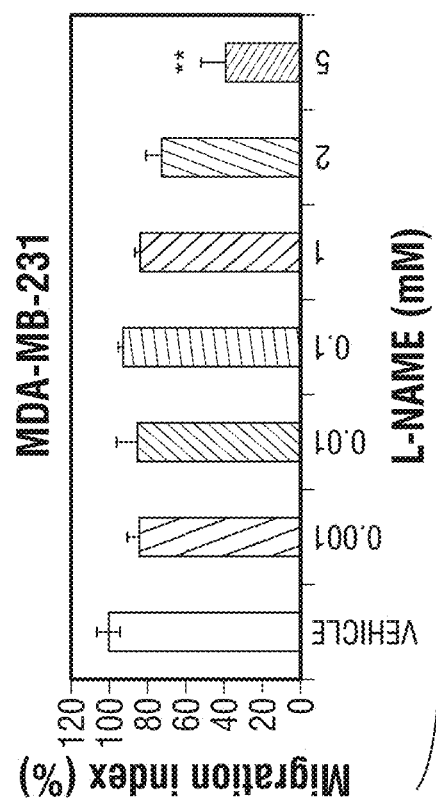
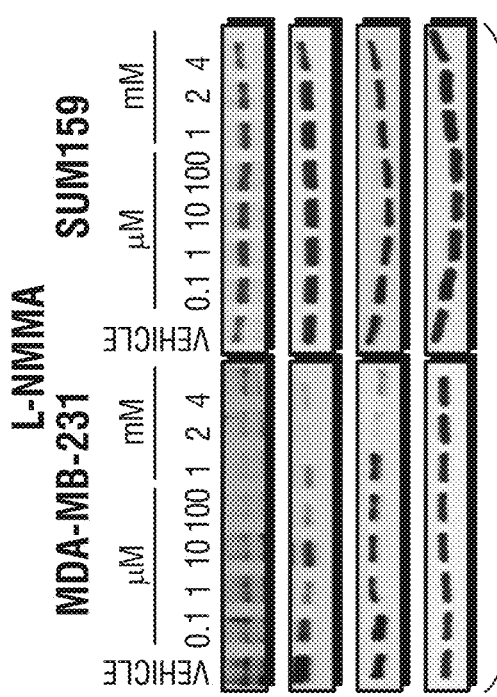
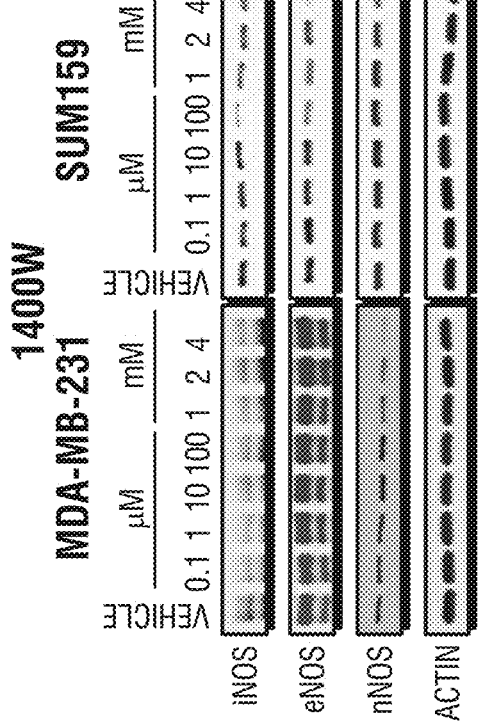
FIG. 10A, FIG. 10B, FIG. 10C

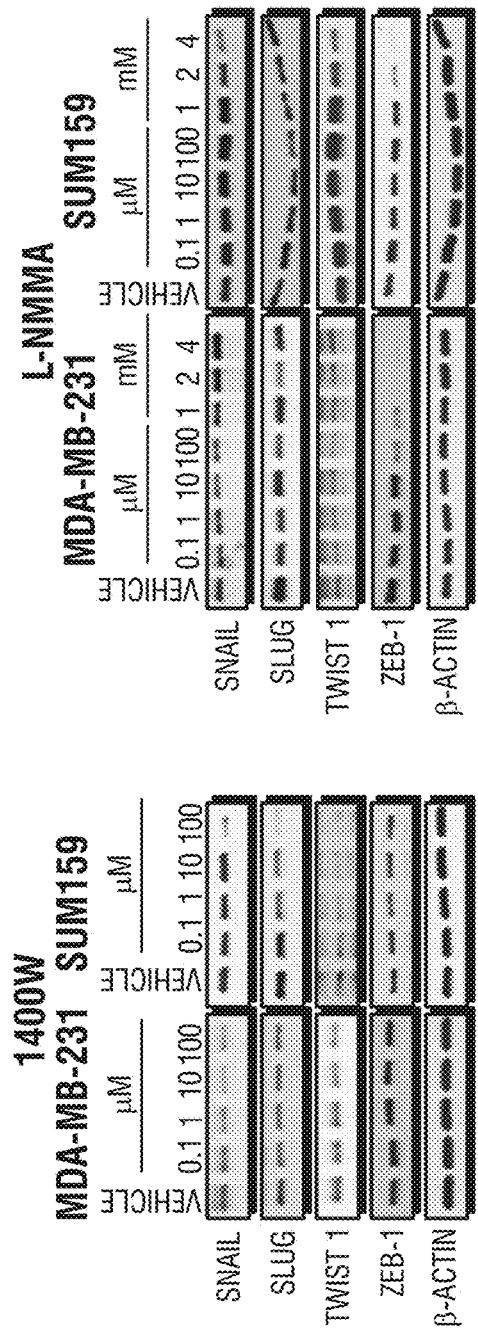
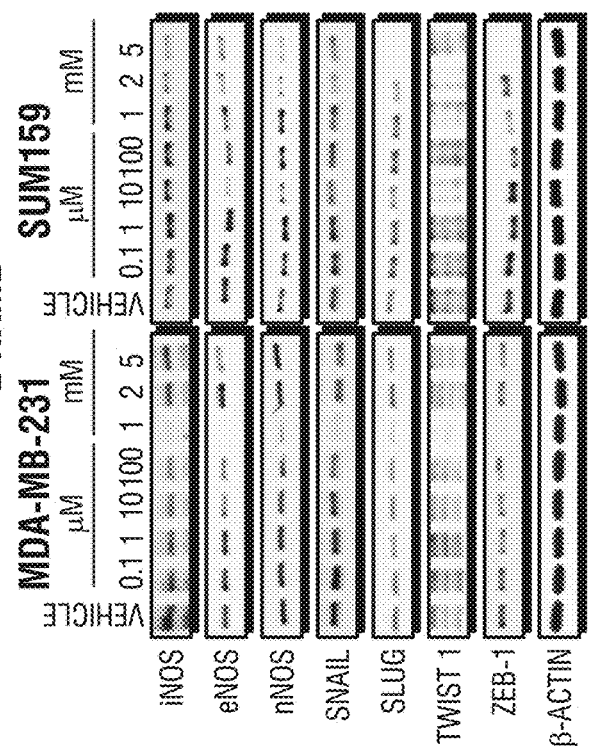
FIG. 10D  FIG. 10E  FIG. 10F

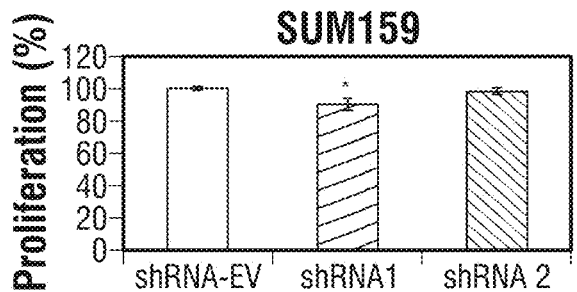
*FIG. 11A*
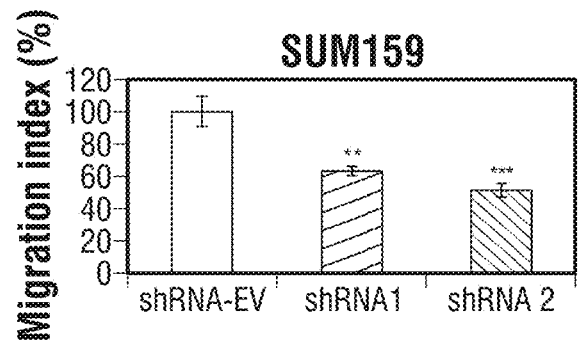
*FIG. 11B*
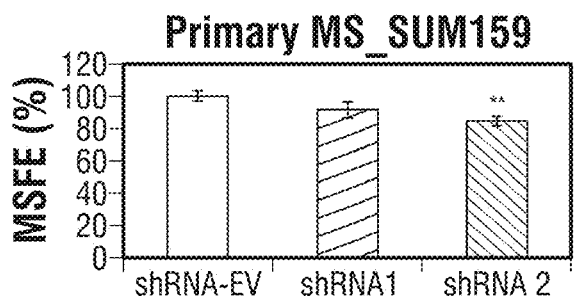
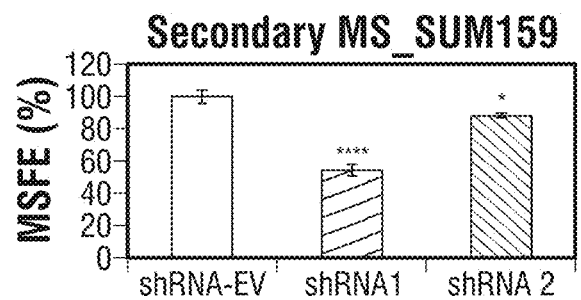
*FIG. 11C*
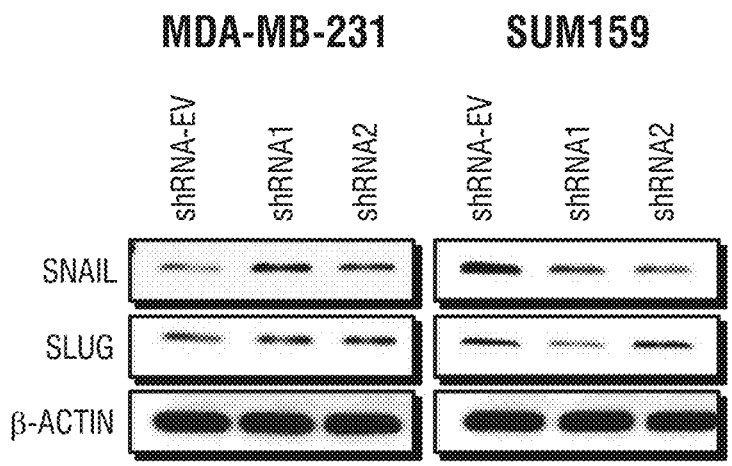
*FIG. 11D*
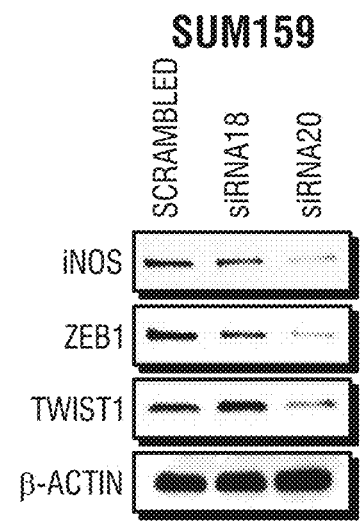
*FIG. 11E*

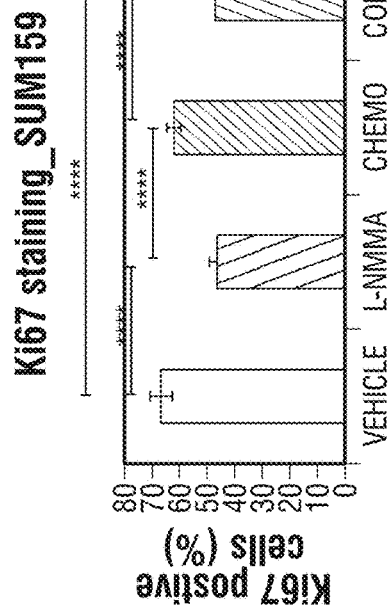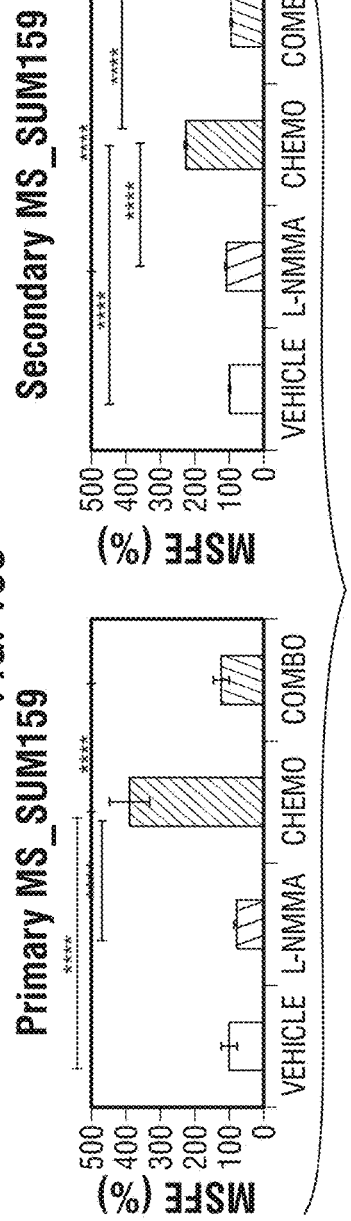
FIG. 13C
FIG. 13D
FIG. 13E

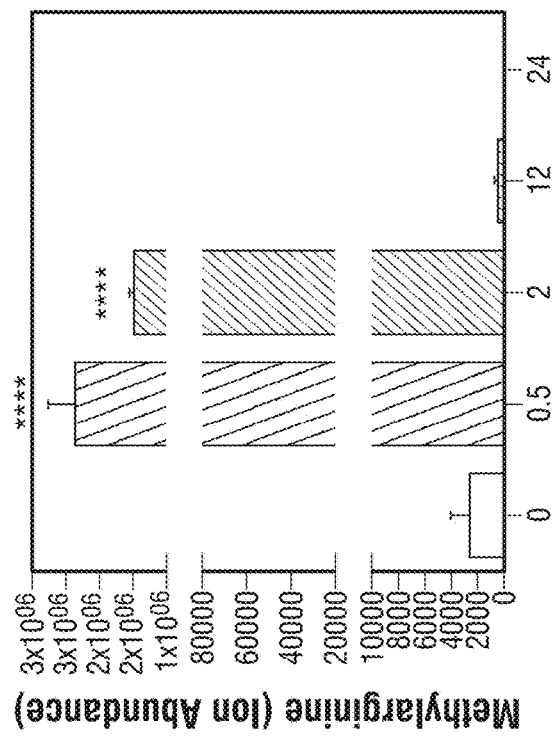
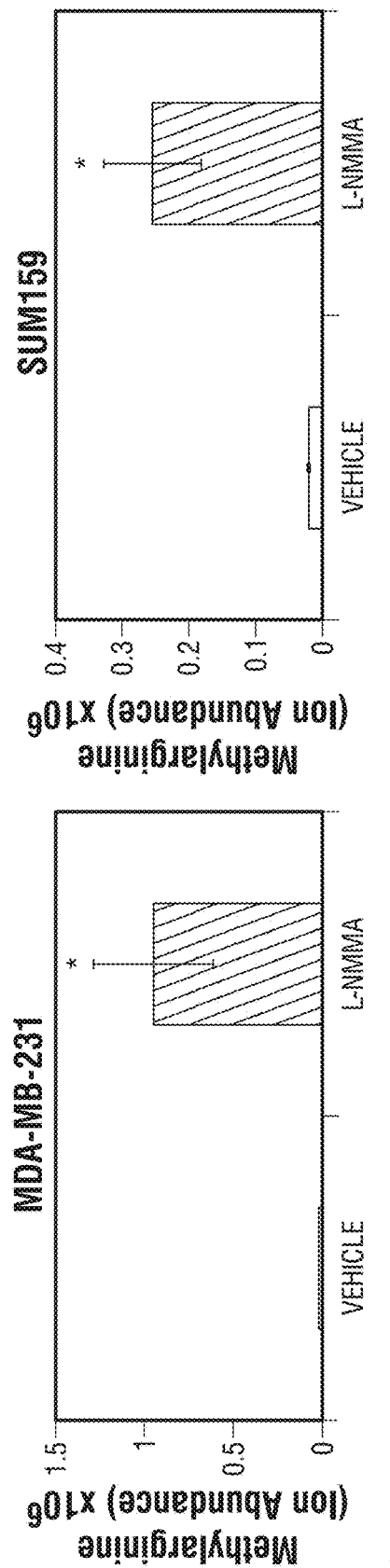
FIG. 14C
FIG. 14D

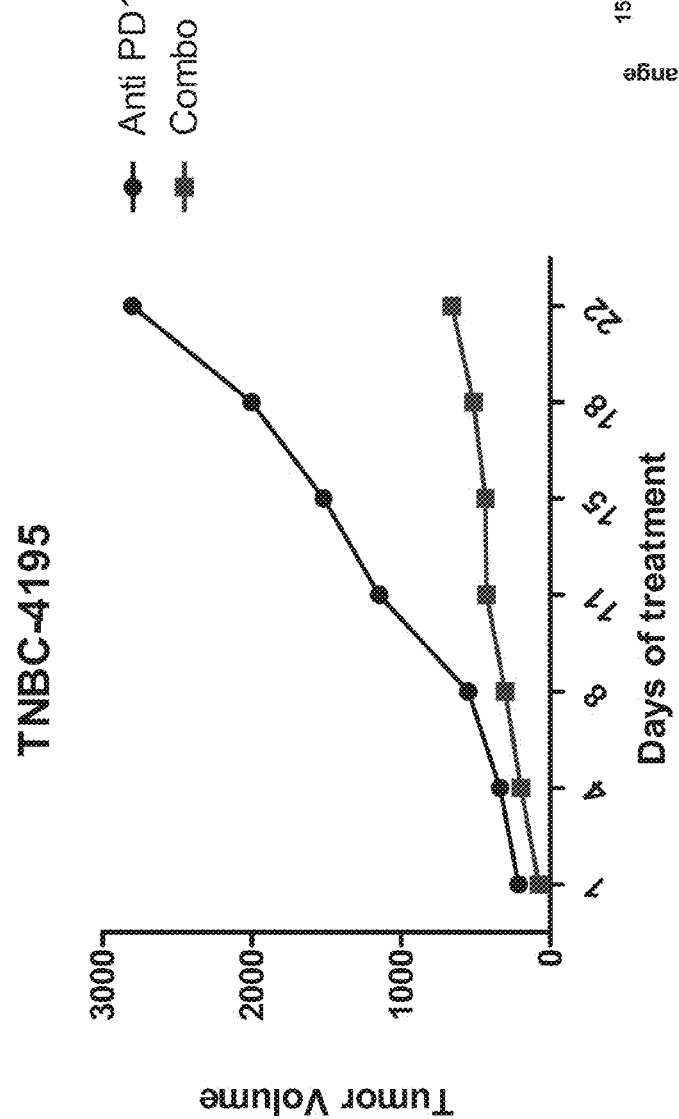
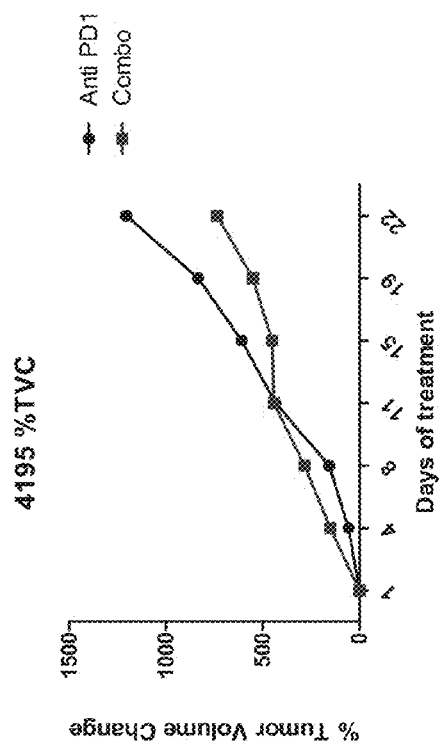
FIG. 23A
FIG. 23B

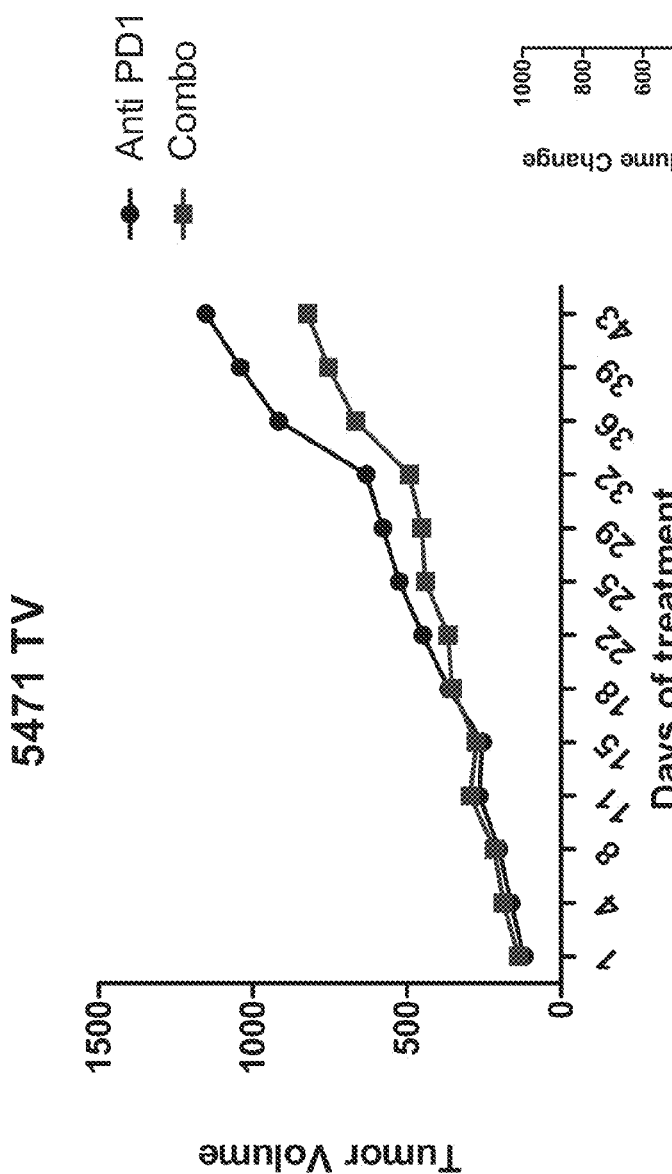
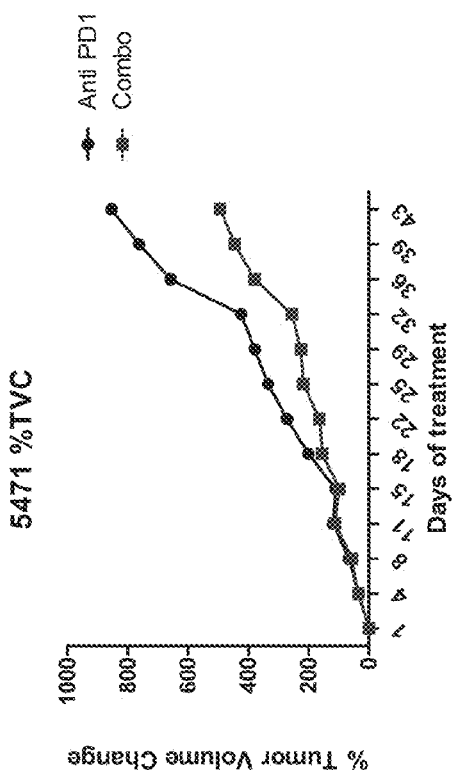
FIG. 24A
FIG. 24B

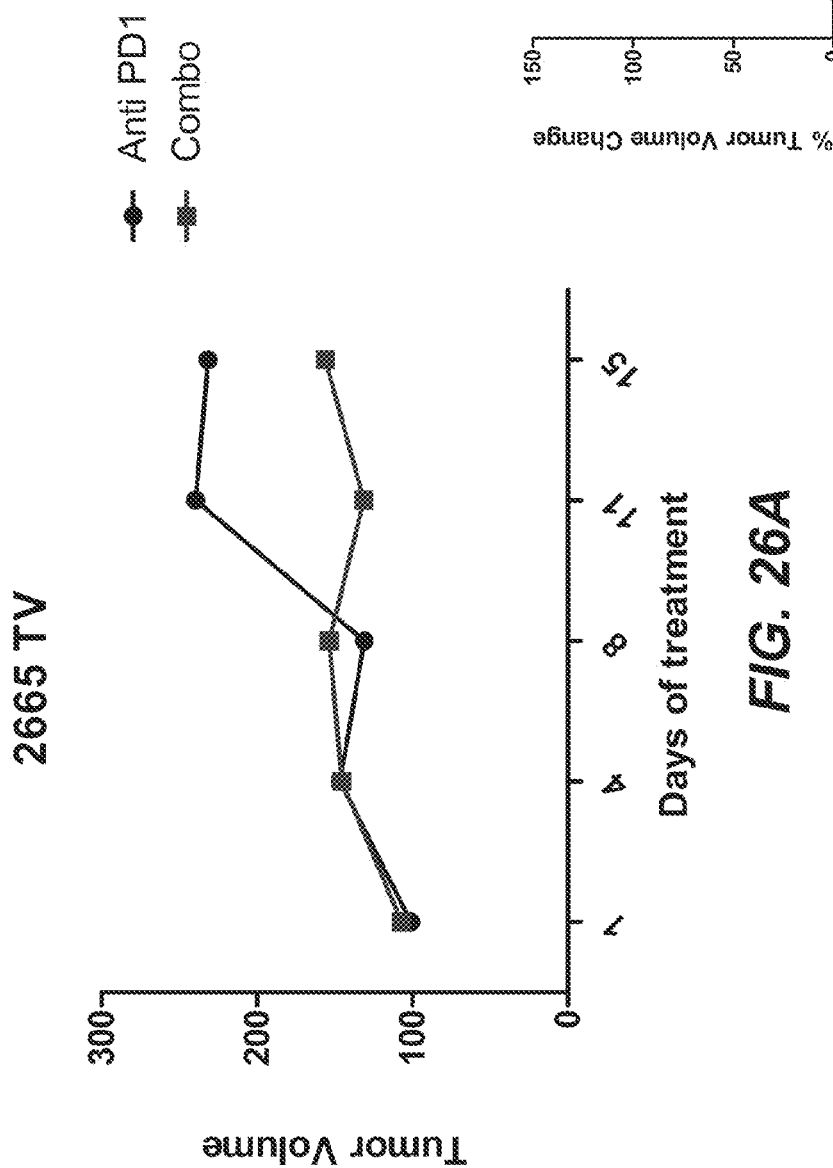
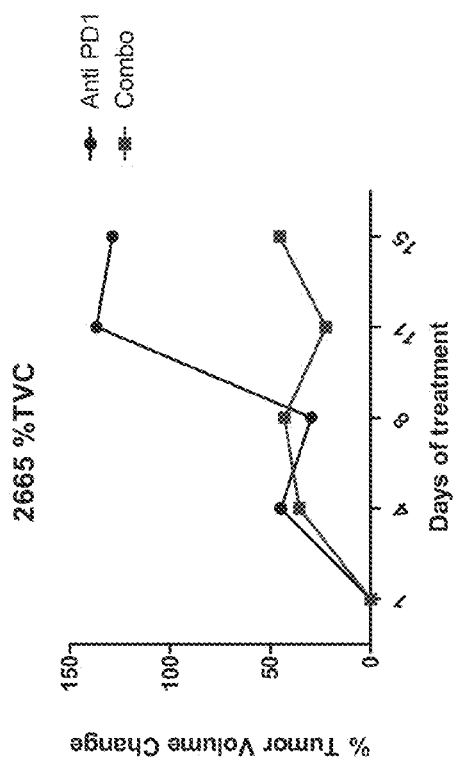
FIG. 26A
FIG. 26B

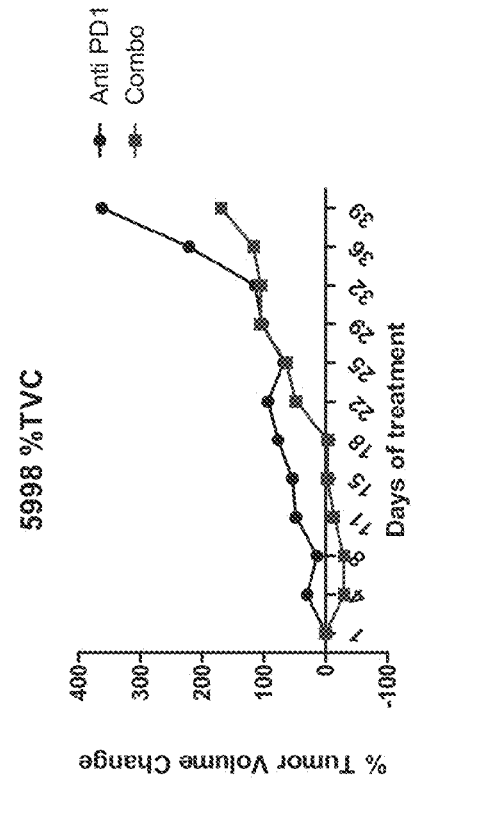
FIG. 30A
FIG. 30B
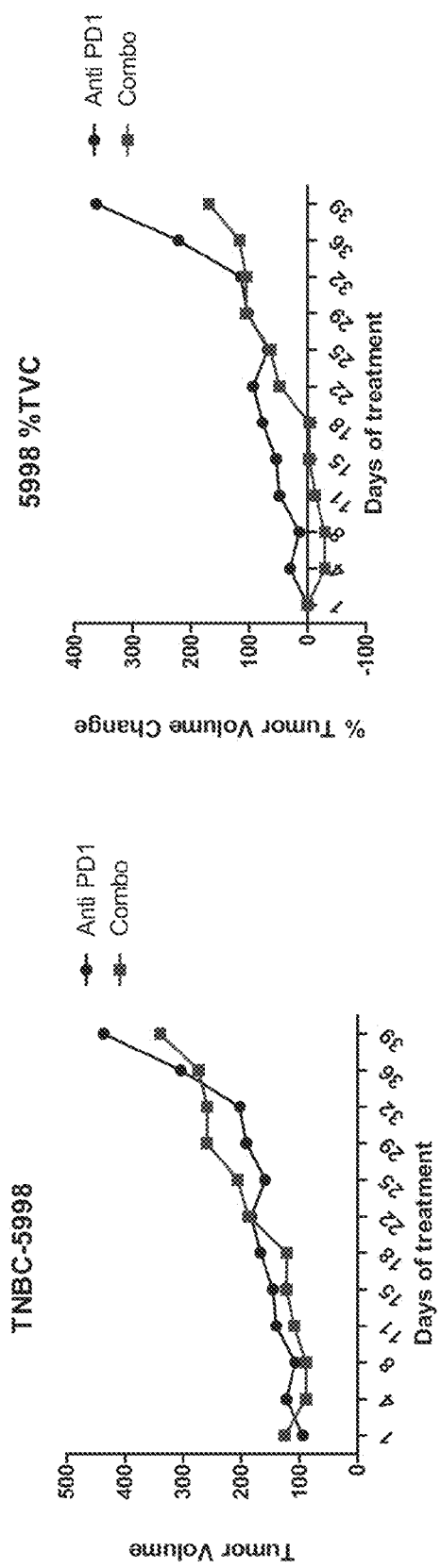
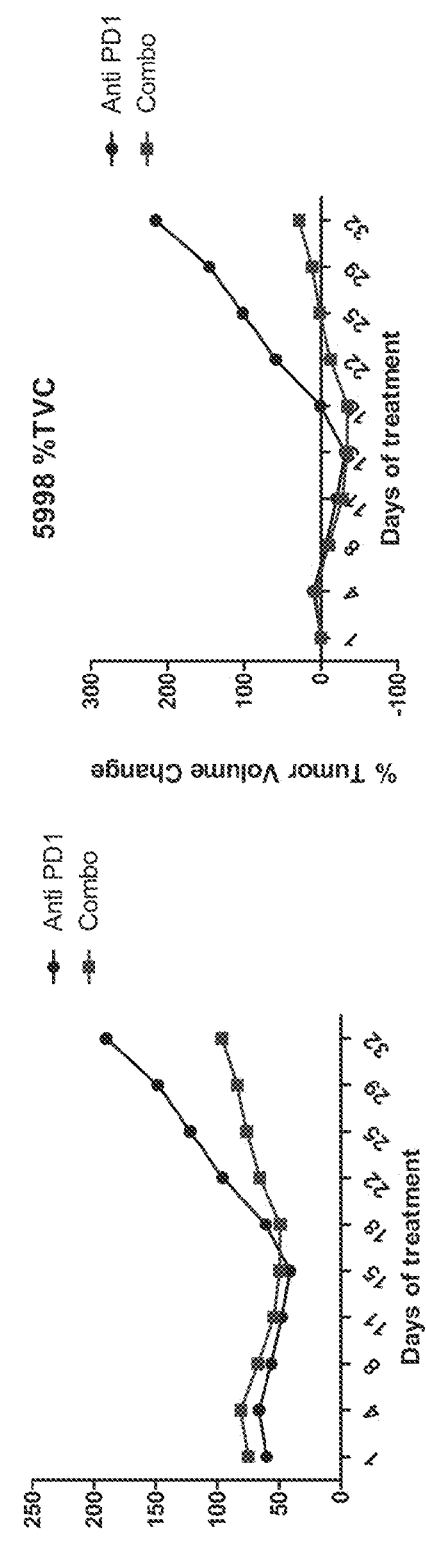
FIG. 30C
FIG. 30D

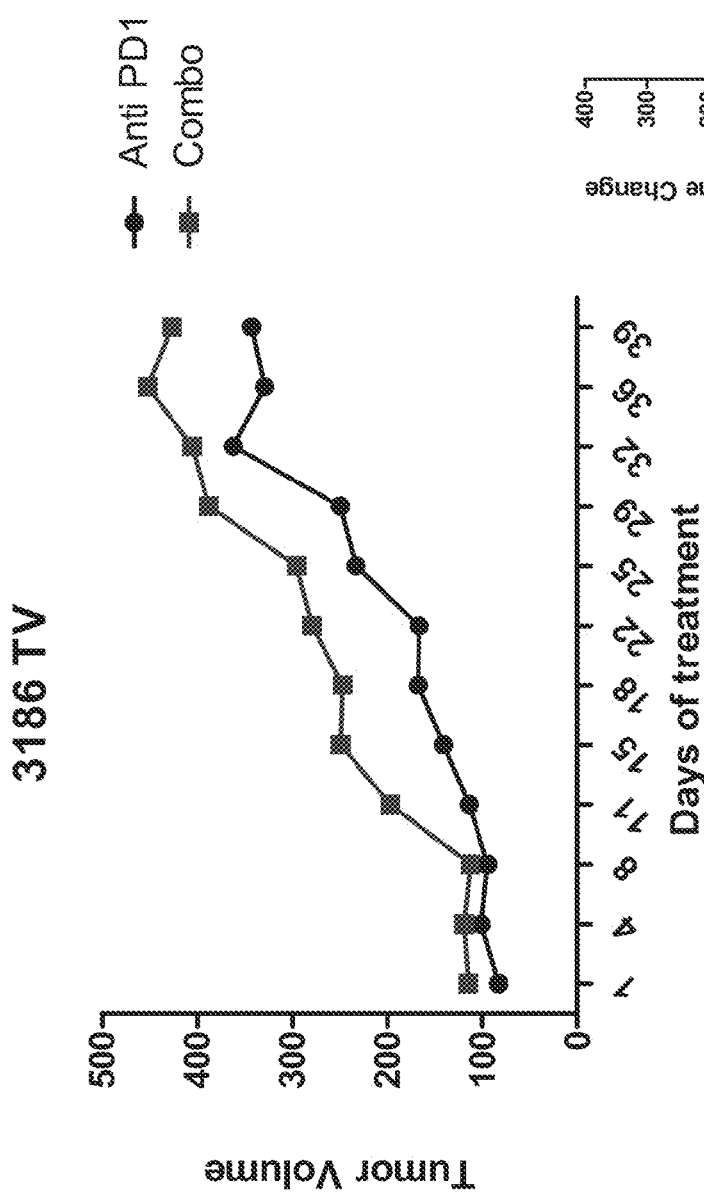
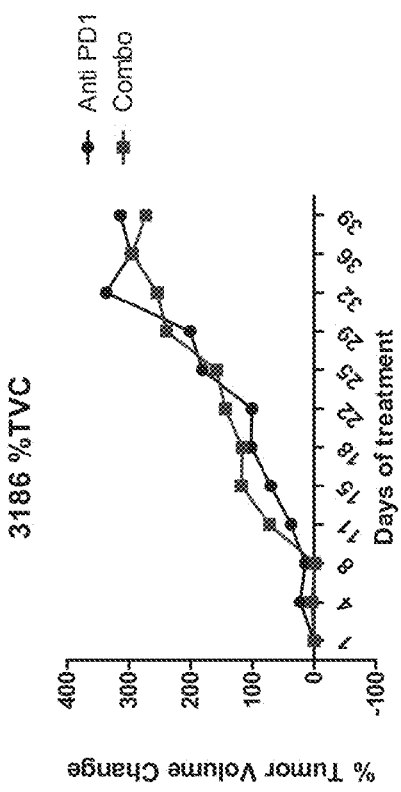
FIG. 31A
FIG. 31B

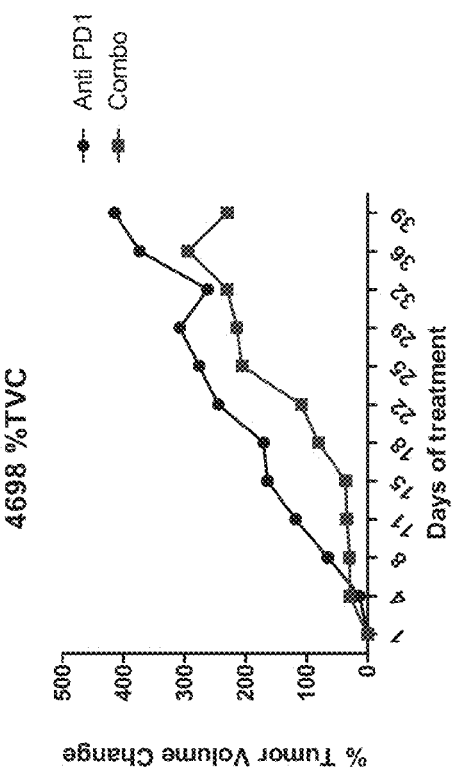
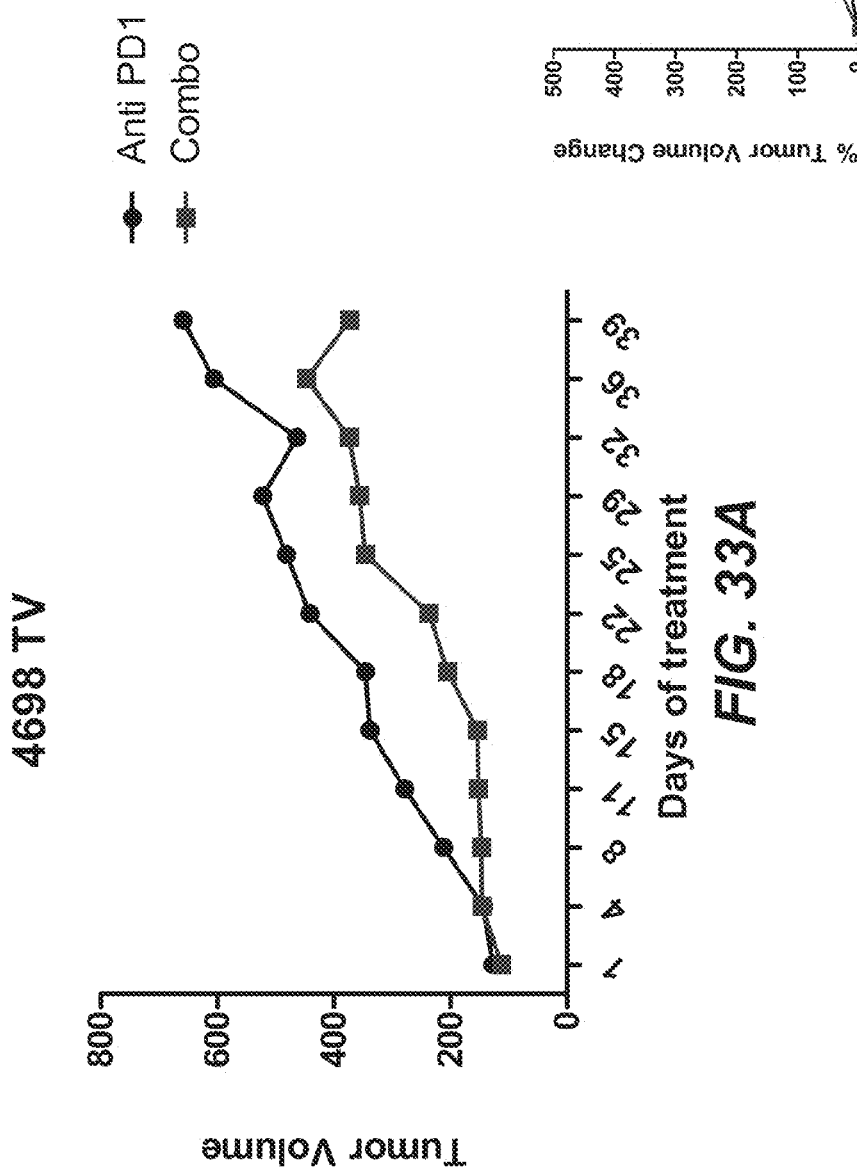
FIG. 33A
FIG. 33B

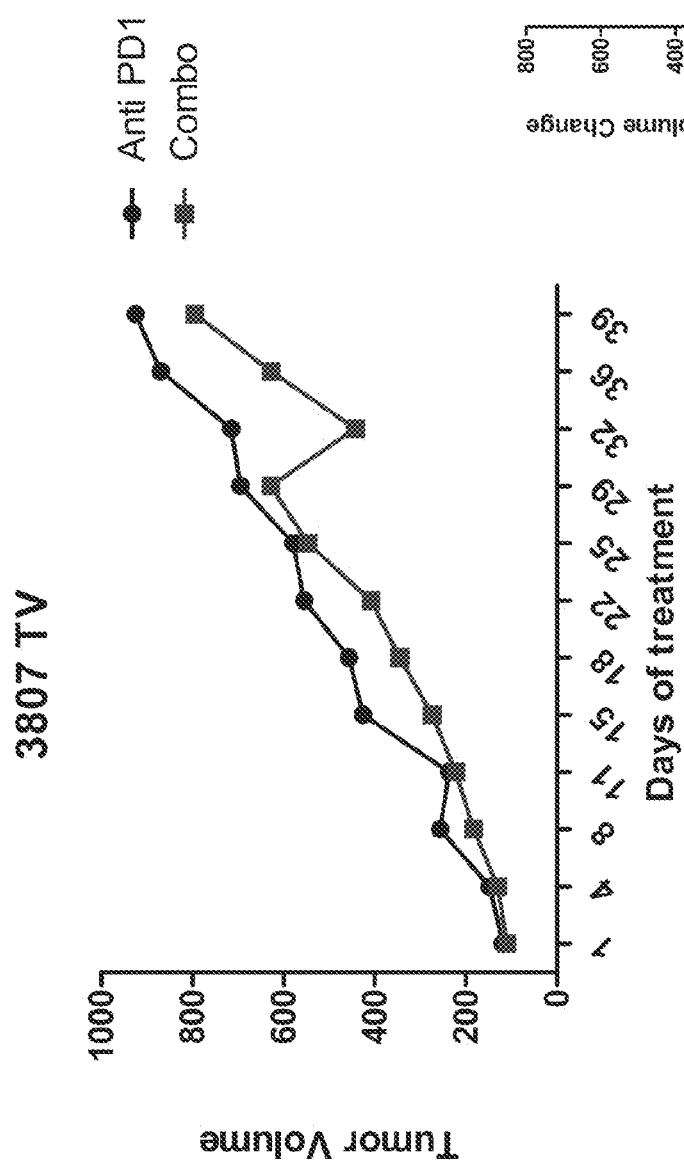
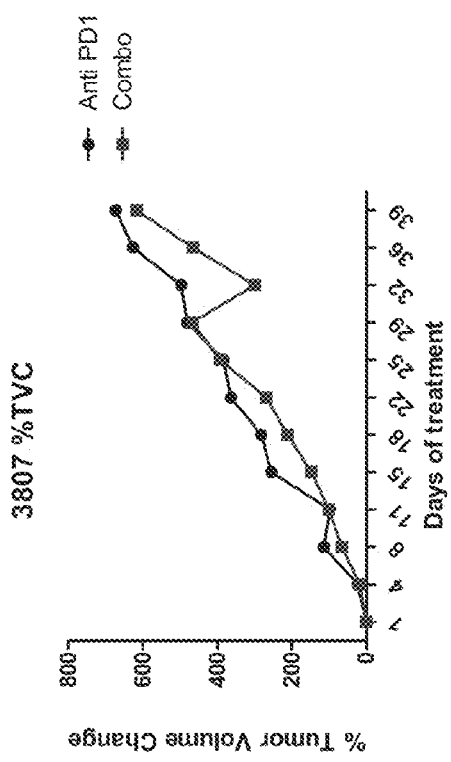
FIG. 34A
FIG. 34B

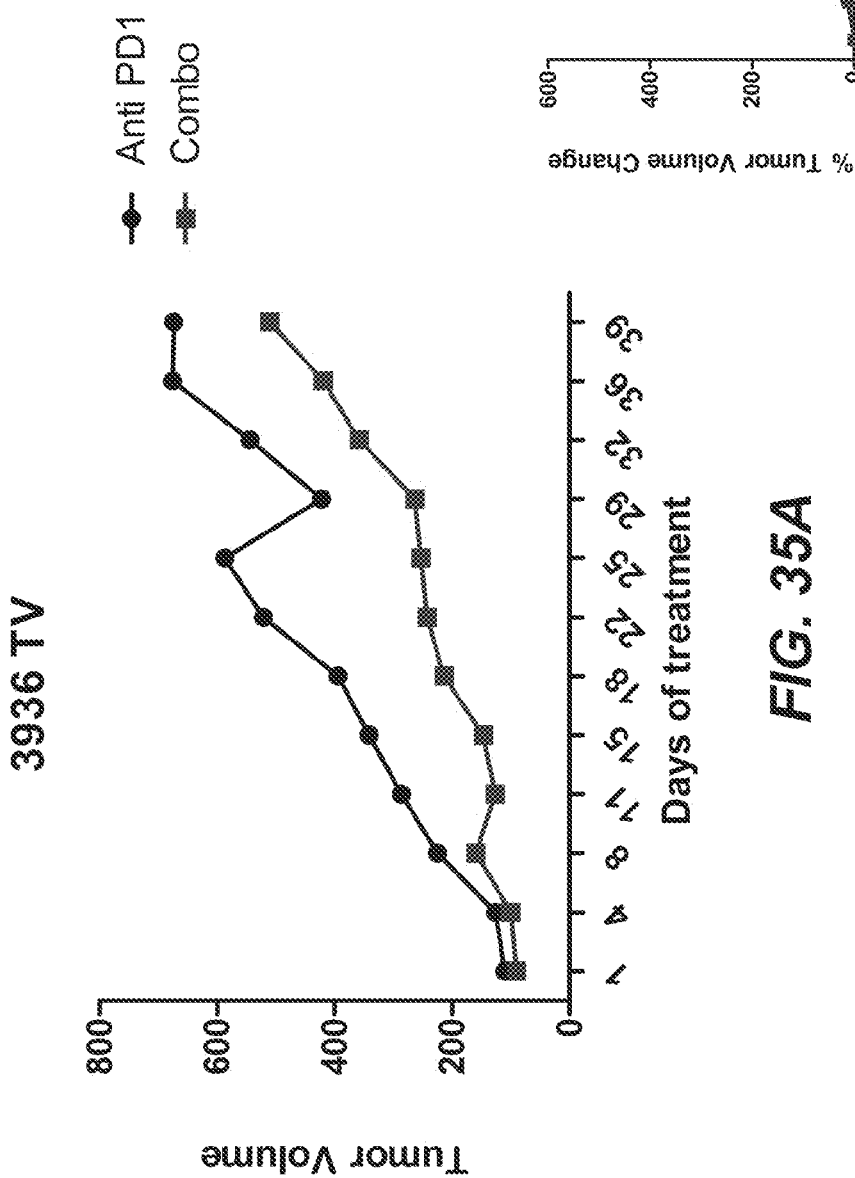
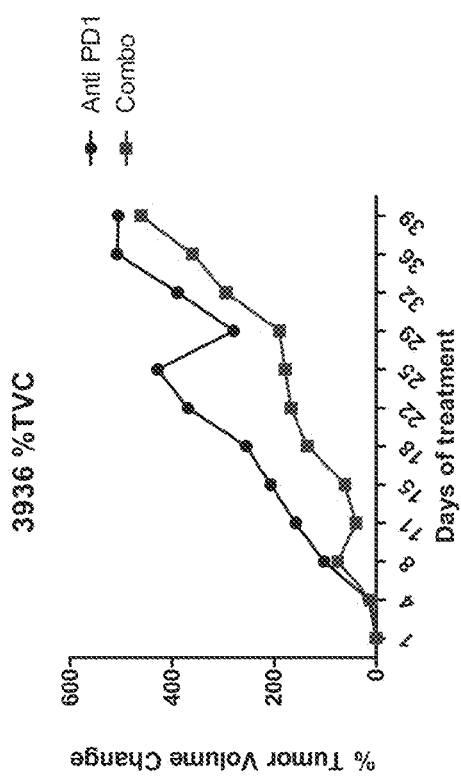
FIG. 35A
FIG. 35B

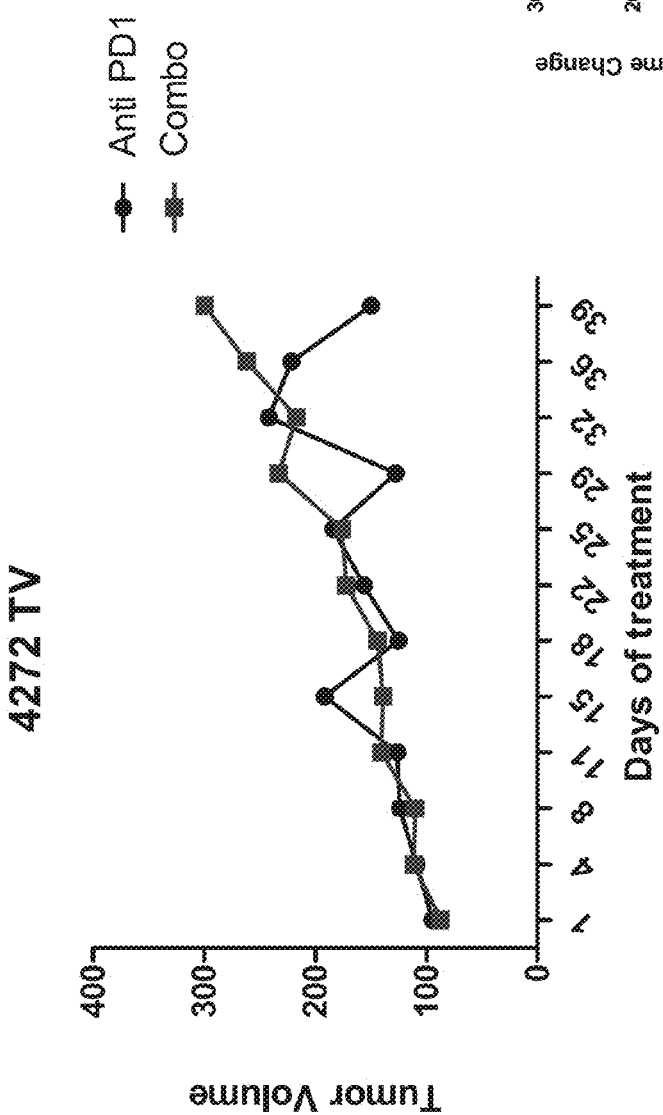
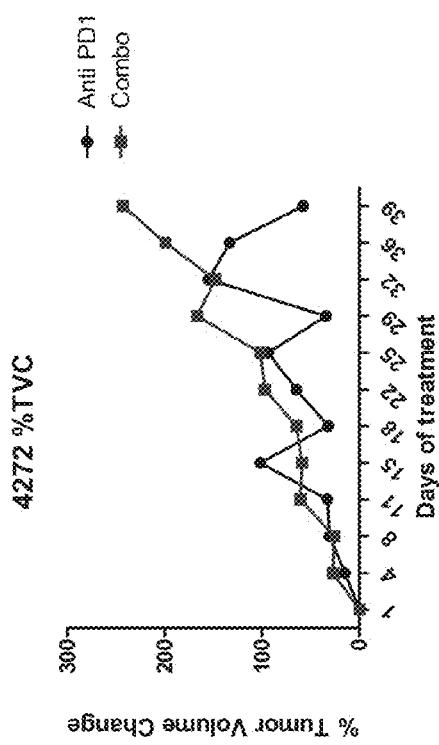
FIG. 36A
FIG. 36B

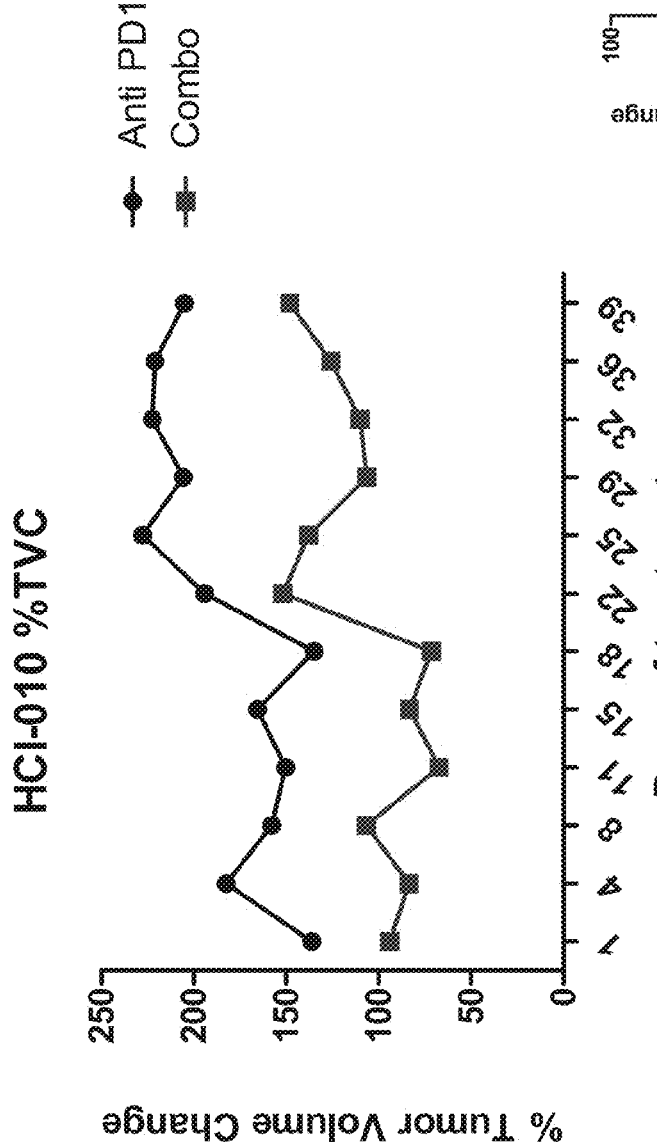
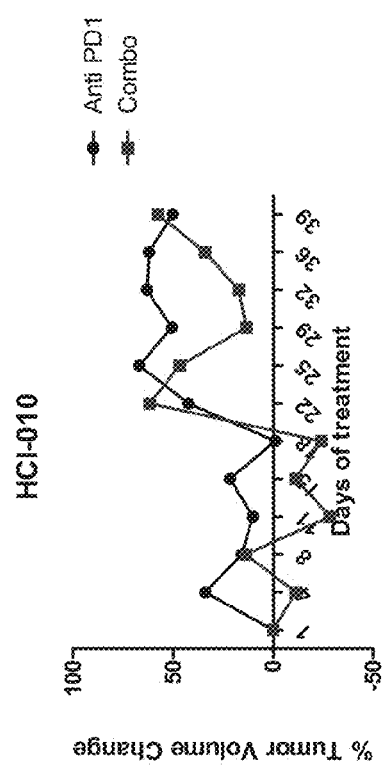
FIG. 38A
FIG. 38B

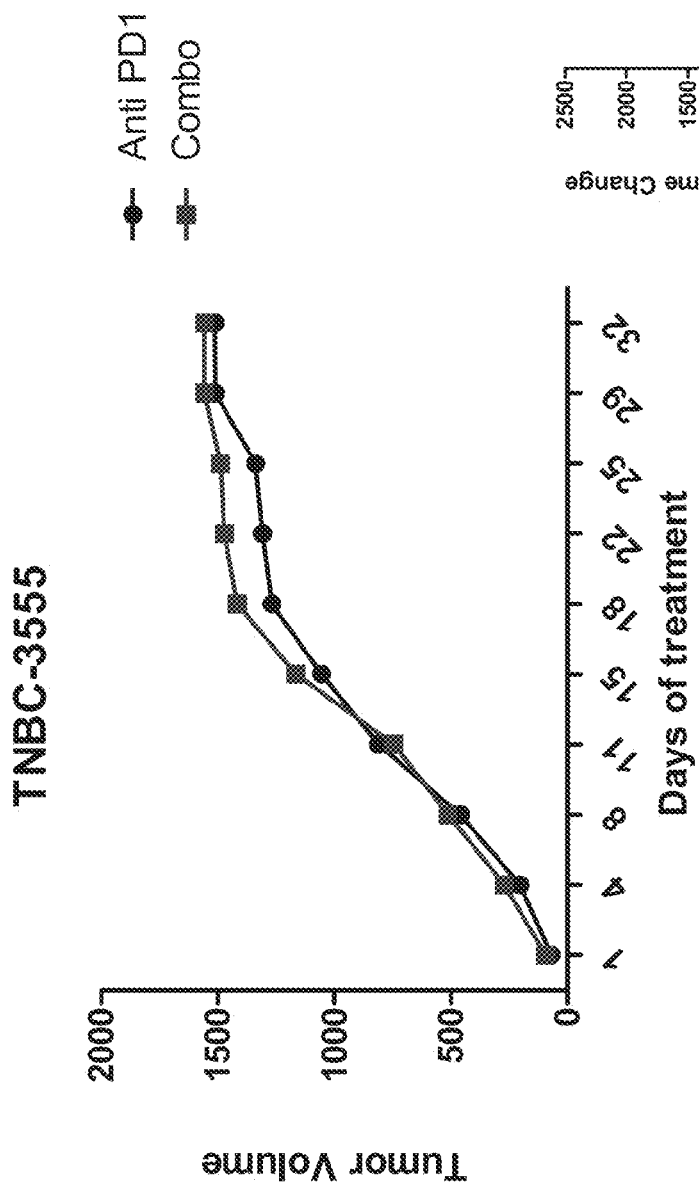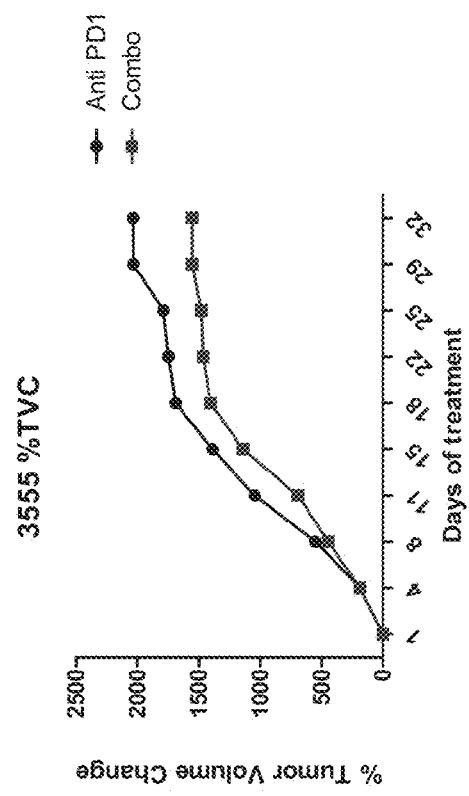
FIG. 40A
FIG. 40B

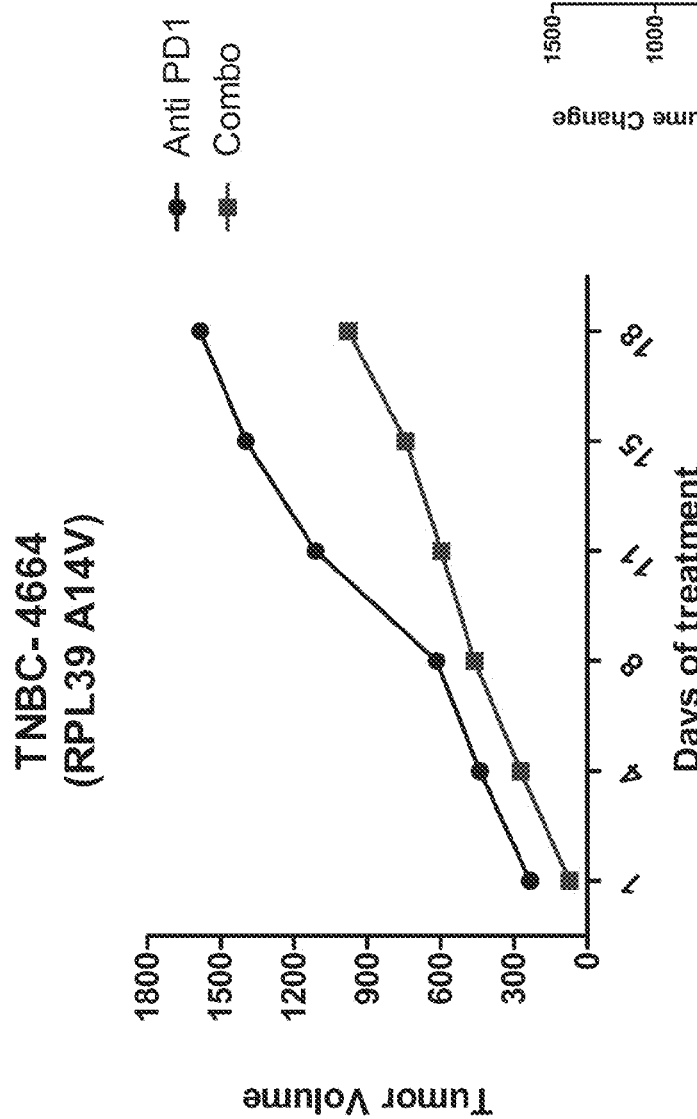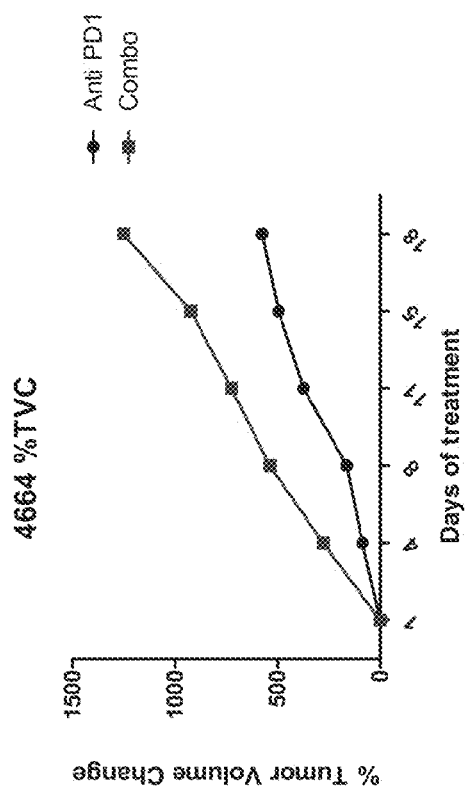
FIG. 41A
FIG. 41B

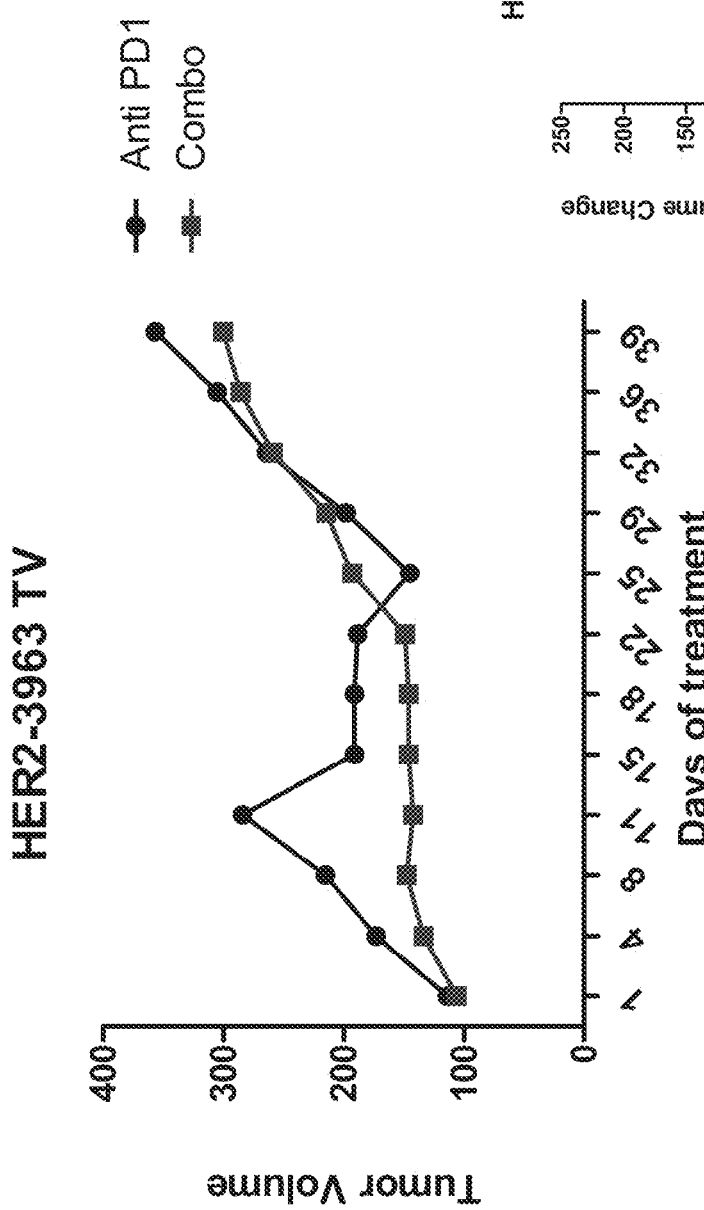
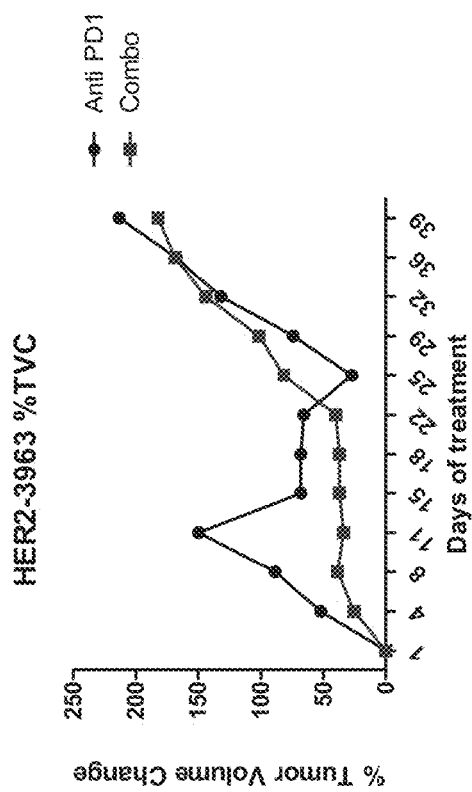
FIG. 42A
FIG. 42B

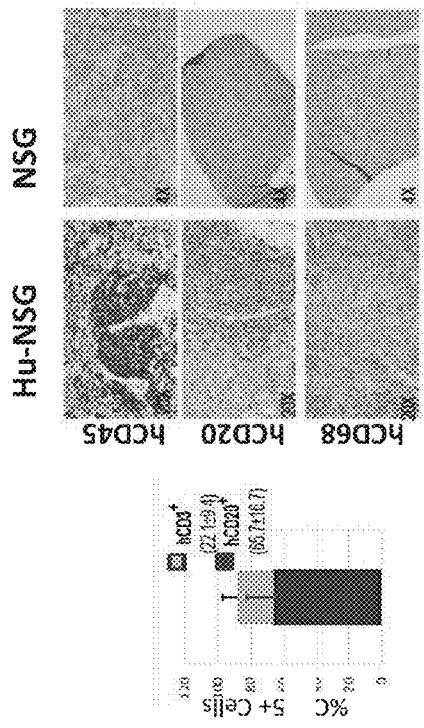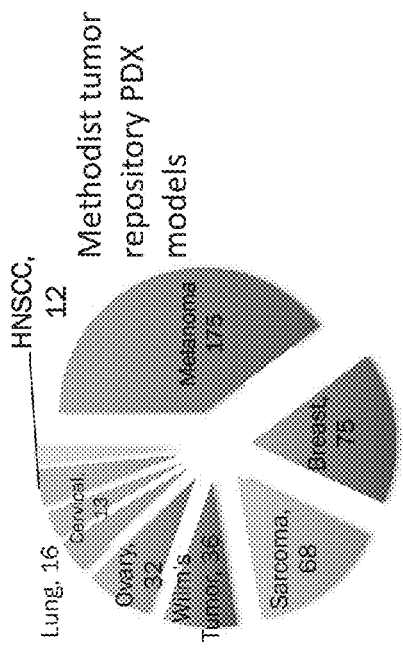

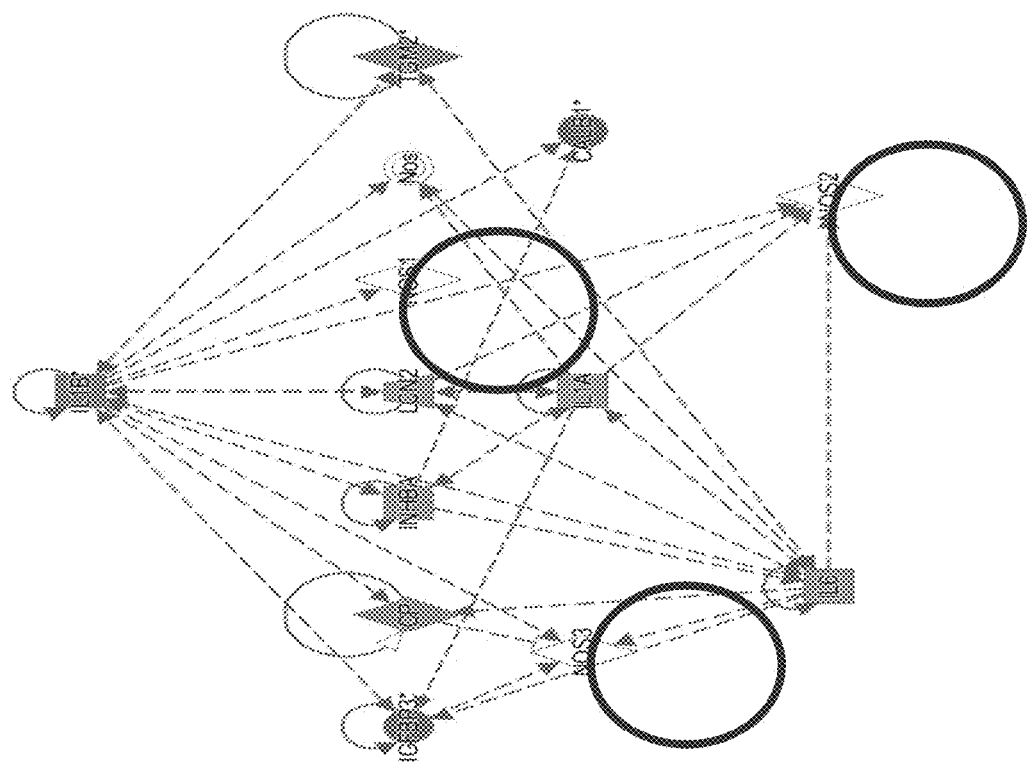
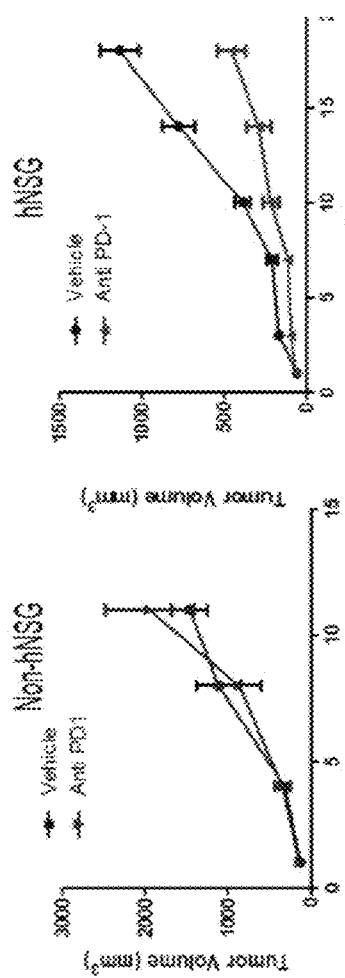
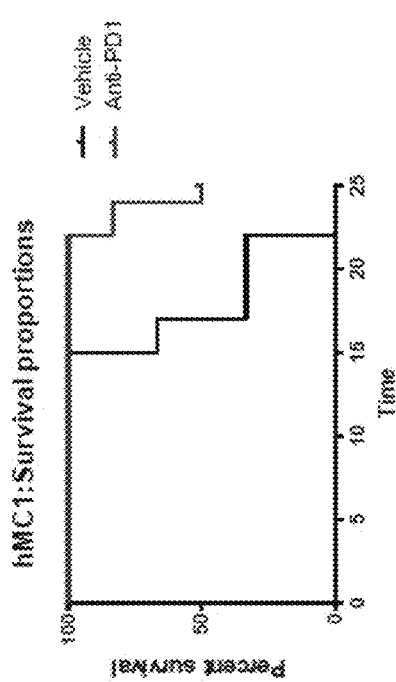
FIG. 46A  FIG. 46B  FIG. 46C  FIG. 46D

METHODS FOR TREATING BREAST CANCER USING INOS-INHIBITORY COMPOSITIONS

CROSS-REFERENCE TO RELATED APPLICATIONS

The present application is a continuation of U.S. patent application Ser. No. 15/486,183, filed Apr. 12, 2017, (pending; to issue as U.S. Pat. No. 10,420,838), which is a continuation of U.S. patent application Ser. No. 15/289,871, filed Oct. 10, 2016 (abandoned); which claims priority to PCT Intl. Pat. Appl. No. PCT/US2015/025009, filed Apr. 8, 2015 (nationalized); and U.S. Provisional Patent Application No. 61/976,956; filed Apr. 8, 2014; the contents of each of which is specifically incorporated herein in its entirety by express reference thereto.

STATEMENT REGARDING FEDERALLY SPONSORED RESEARCH OR DEVELOPMENT

This invention was made with government support under grant R01-CA138197 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present invention generally relates to the fields of medicine and oncology. In particular, this disclosure provides improved chemotherapeutic compositions for the treatment and/or amelioration of one or more symptoms of mammalian cancers, including, for example, human breast cancers. In illustrative embodiments, methods are provided for treating such cancers that employ administration of one or more effectors of the iNOS pathway. In exemplary embodiments, formulations of iNOS inhibitors, including for example, $N^G$-methyl-L-arginine acetate (L-NMMA; $C_7H_{16}N_4O_2 \cdot CH_3CO_2H$; MW 248.28; CAS 53308-83-1), in combination with one or more selected calcium channel antagonists, are provided as part of a multi-focal therapy that includes co-administration of at least one chemotherapeutic agent and or one or more doses of ionizing radiation for the treatment of mammalian breast cancers, and particularly, for the treatment of triple-negative breast cancer in humans, a refractory form of the disease that is resistant to conventional chemotherapeutics, and for which the prognosis is typical poor.

Description of Related Art

Despite the significant advances in breast cancer biology, there has been limited progress in the treatment of advanced breast cancer, with little change in the overall survival for women with treatment resistant metastatic breast cancer over the last several decades. It is notable that approximately 40,000 women with metastatic breast cancer die each year because of treatment resistance and failure of current therapies. Classical models of carcinogenesis can be described as random or "stochastic" in which any cell can be transformed by accumulating the right combination of mutations. An alternative model is that subpopulations or clones of cells retain key stem-like properties including the capacity for self-renewal that drives carcinogenesis, as well as differentiation, which contributes, to cellular heterogeneity. Experimental evidence supporting this intratumoral clonal heterogeneity was first reported in human leukemia by Dick et al. These concepts were then extended to solid tumors by some groups demonstrating that human breast cancers were driven by stem-like cells characterized by cell surface expression of $CD44^+7$ $CD24^{-/low3}$. Large-scale sequencing analyses of solid cancers have provided further evidence of the extensive heterogeneity within individual tumors. This intratumoral heterogeneity may be a major contributor to treatment resistance and treatment failure. Different subpopulations may be associated with heterogeneous protein function that may foster tumor adaptation and lead to therapeutic failure through Darwinian selection. Accordingly, the subpopulations of cells with stem-like properties within a heterogeneous bulk tumor have been shown to be responsible for tumor initiation and recurrence.

Three groups have recently and independently provided direct and functional evidence for the presence of cells with stem-like properties by lineage tracing experiments in glioblastomas (GBM), squamous skin tumors, and intestinal adenomas, further corroborating the hierarchical nature of cancer. These independent groups confirm that only a fraction of cells within the bulk tumor have clonogenic potential and that this fraction is intrinsically resistant to chemotherapy.

Triple-Negative Breast Cancer

TNBC is an aggressive and lethal form of cancer that lacks estrogen (ERα), progesterone (PR) and human epidermal growth factor (HER-2) receptors with no approved targeted therapeutic options. Despite numerous advances, treatment resistance and metastasis are the main causes of death in TNBC patients. Resistance to conventional treatment and onset of metastases may arise from a subpopulation of cells with tumor-initiating capacity. Residual tumors after chemotherapy are enriched in $CD44^+/CD24^{-/low}$ cells that display self-renewal capacity and mesenchymal features. These cancer stem cells (CSCs) can serve to re-initiate tumor growth and seed metastases. Thus, combinatorial treatment with conventional chemotherapy and anti-CSC compounds would be required to reduce tumor burden, recurrence, as well as metastasis to distant organs. Unfortunately, no such combinations are presently available for routine use in clinic.

Presently, there is no targeted treatment for TNBC. Inducible nitric oxide synthase (iNOS) has been found to promote breast tumor aggressiveness. Previous studies have demonstrated that high endogenous iNOS expression correlates with, and is predictive of, poor TNBC patient survival rates. In spite of the advances made to date in the treatment of breast cancer, clinicians still concur, however, that there remains a significant need for the development of new chemotherapeutically-active agents for use in its treatment, and particularly in the treatment of TNBC.

Indeed, there is still a significant unmet medical need for new agents that are effective in the treatment of hyperproliferative disorders, and particularly breast cancers that have become resistant to conventional chemotherapeutics.

Hypertension Comorbidity in Breast Cancer Patients

High blood pressure is one of the most common disorders that enhance morbidity in women with breast cancer (Sarfati et al., 2013; Gampenrieder et al., 2014). Chemotherapy-induced hypertension is a common effect that increases patient mortality in metastatic and TNBC (Cameron et al., 2013; Fan et al., 2014). Thus, the concomitant administration of one or more anti-hypertensive drugs that are able to counter the untoward hypertensive side effects of chemotherapy administration represents an important consideration for improving patient wellness and increasing survival.

The present invention has demonstrated the synergistic effects of co-administration of calcium channel blockers (presently used in clinic as traditional anti-hypertensive drugs) in both in vitro and in vivo models for treating various cancers, including TNBC.

BRIEF SUMMARY OF THE INVENTION

The present invention addresses this and other unmet deficiencies inherent in the relevant oncological and pharmaceutical arts by providing formulations of iNOS inhibitors, either alone, or in combination with one or more calcium ion antagonists (slow-channel blockers), as chemotherapeutic agents for treating mammalian cancers, such as human melanomas, head/neck cancers, and breast cancers, including metastatic and/or TNBC, in particular. The invention also provides methods of using and repurposing iNOS inhibitory compounds in new cancer treatment modalities, which advantageously provide unexpected benefits to patients in need of such treatment.

In an overall and general sense, the present disclosure first provides pharmaceutical compositions for treating and/or ameliorating one or more symptoms of cancer in a mammal in need thereof. In exemplary embodiments, such chemotherapeutic formulations include: a therapeutically-effective amount of at least a first iNOS-inhibitory compound, either 1) alone, 2) in combination with: a) a therapeutically-effective amount of one or more anti-hypertensive agents, such as a calcium channel antagonist; c) one or more conventional chemotherapeutic, therapeutic, diagnostic, or palliative compounds; b) a therapeutically-effective amount of one or more anti-hypertensive agents, such as a calcium channel antagonist; or 3) together with an anti-hypertensive agent from b) and one or more conventional compounds from c).

In the practice of the invention, exemplary iNOS-inhibitory compounds include, without limitation, $N^G$-monomethyl-L-arginine [L-NMMA], (N-[[3-(aminomethyl)phenyl]methyl]-ethanimidamide) [1400 W], ($N^5$-[imino(nitroamino)methyl]-L-ornithine methyl ester) [L-NAME; $C_7H_{15}N_5O_4 \cdot HCl$; MW=269.69; CAS 51298-62-5], as well as salts, derivatives, and combinations thereof.

Likewise, in the practice of various aspects the present disclosure, exemplary calcium channel antagonists [calcium channel blockers (CCBs)] include, without limitation, one or more dihydropyridine CCBs selected from the group consisting of amlodipine (NORVASC®; Pfizer), clevidipine (CLEVIPREX®, Chiesi Farmaceutici SpA.) felodipine (PLENDIL®, AstraZeneca), lacidipine (LACIPIL®, GlaxoSmithKline, London, ENGLAND; MOTENS®, Boehringer-Ingelheim BmbH, Ingelheim, GERMANY), nicardipine (CARDENE®, EKR Therapeutics, Inc.), nifedipine (ADALAT®; Bayer Pharmaceutical, New Haven, Conn., USA; AFEDITAB®, Watson Pharmaceutical/Actavis, Inc.; PROCARDIA®, Pfizer Labs Division, Pfizer, Inc.); ercanidipine; isradipine (DYNACIRC®, GlaxoSmithKline, LLC); nimodipine (N ALIVE®, Arbor Pharmaceuticals, Atlanta, Ga., USA); nilvadipine ARCO29, Archer Pharmaceuticals, Sarasota, Fla., USA); azelnidipine (CAL-BLOCK®, Daiichi-Sankyo, Tokyo, JAPAN); and combinations thereof.

In illustrative embodiments, the inventor has demonstrated a synergistic therapeutic outcome could be achieved when one or more iNOS inhibitors and one or more calcium channel antagonists were co-administered. In one such embodiment, a particularly surprising and unexpected synergy was obtained when the iNOS inhibitor, L-NMMA, and the calcium channel antagonist, amlodipine besylate (NORVASC®, 3-ethyl-5-methyl(±)-2-[(2-aminoethoxy) methyl] 4-(2-chlorophenyl)-1,4-dihydro-6-methyl-3,5-pyridinedicarboxylate, monobenzene sulphonate; $C_{20}H_{25}ClN_2O_5 \cdot C_6H_6O_3S$; MW=567.1), were co-administered to cancer cell lines, such as TNBC.

Optionally, the compositions described in the present disclosure may further also include one or more additional distinct iNOS inhibitors, and/or one or more additional distinct anti-hypertensive agents, and/or one or more additional distinct conventional treatments.

In certain embodiments, the inventor contemplates the formulation of co-therapies that include one or more iNOS-inhibitory compounds formulated with one or more additional active ingredients, including, without limitation, one or more anti-hypertensive, antineoplastic, cytotoxic, cytostatic, or chemotherapeutic agents, or any combinations thereof.

Exemplary chemotherapeutic agents include, without limitation, anti-cancer compounds such as cyclophosphamide, doxorubicin, 5-fluorouracil, docetaxel, paclitaxel, trastuzumab, methotrexate, epirubicin, cisplatin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, a topoisomerase inhibitors (including topoisomerase I and II inhibitors), as well as derivatives, analogs, salts, active metabolites, or one or more combinations thereof.

Exemplary therapeutic agents include, without limitation, one or more of an immunomodulating agent, a neuroactive agent, an anti-inflammatory agent, an anti-lipidemic agent, a hormone, a receptor agonist or antagonist, or an anti-infective agent, or a compound selected from a protein, a peptide an antibody, an enzyme, an RNA, a DNA, an siRNA, an mRNA, a ribozyme, a hormone, a cofactor, a steroid, an antisense molecule, and combinations thereof.

Likewise, administration of the chemotherapeutic formulations disclosed herein may be further augmented with one or more additional cancer therapies, including, without limitation, administering a therapeutically-effective amount of radiation to the mammal undergoing treatment.

In the practice of the present disclosure, the disclosed chemotherapeutic compositions may be administered systemically to the animal in a single administration, or alternatively, in multiple administrations over a period of from one or more weeks to one or more months, as deemed necessary by the medical provider attending the treatment regimen.

Preferably, the iNOS-inhibitory, anti-cancer compositions disclosed herein with further include one or more pharmaceutically-acceptable carriers, buffers, diluents, vehicles, excipients, or any combination thereof suitable for administration to a mammalian host cell, and to a human host cell, in particular.

In another embodiment, the present disclosure provides a method for treating or ameliorating one or more symptoms of cancer in an animal in need thereof. Such method, in an overall and general sense includes at least the step of administering to an animal in need thereof, an effective amount of one or more of the chemotherapeutic compositions disclosed herein, for a time sufficient to treat or ameliorate the one or more symptoms of the cancer in the animal.

In another embodiment, the present disclosure provides a method for treating or ameliorating one or more symptoms of cancer in a mammalian subject. In an overall and general sense, the method includes at least the step of administering to the mammalian subject in need thereof a therapeutically-effective amount of one or more of the chemotherapeutic compositions disclosed herein, for a time effective to treat or ameliorate the one or more symptoms of the cancer in the subject.

In certain embodiments, it is contemplated that the disclosed chemotherapeutic formulations to be particularly useful in conditions where the cancer is diagnosed or identified as a refractory, a metastatic, a relapsed, or a treatment-resistant cancer, including, for example, wherein the cancer is diagnosed or identified as a treatment-resistant melanoma, head/neck, or breast cancer.

The present disclosure also provides a method of treating or ameliorating one or more symptoms of cancer in an animal in need thereof. Such a method generally includes at least the step of administering to the animal (either systemically, or locally at one or more regions or sites within, or about the body of the animal) an effective amount of at least a first chemotherapeutic iNOS-inhibitory formulation disclosed herein, or an analog, an agonist, an antagonist, or a derivative or salt thereof, either alone, or in combination with one or more calcium channel antagonists, for a time sufficient to treat or ameliorate the one or more symptoms of the cancer in the animal.

In a further aspect, the present disclosure also provides a method for inhibiting the growth of a cancer cell or tumor in an animal. This method, in an overall and general sense includes providing to one or more cells or tissues of the body of an animal in need thereof, an amount of one or more of the chemotherapeutic iNOS-inhibitory formulations disclosed herein, in an amount and for a time effective to inhibit the growth of the cancer cell or the tumor.

In another aspect, the present disclosure provides a method for treating cancer in a subject, and preferably in a human. In an overall and general sense, the method generally includes administering to the subject in need thereof, a therapeutically-effective amount of one or more of the iNOS-inhibitory, chemotherapeutic formulations disclosed herein, alone, or in combination with one or more calcium channel antagonists, such as one or more anti-hypertensive calcium channel antagonist compounds disclosed herein, one or more additional chemotherapeutic agents, a therapeutically effective amount of an ionizing radiation, or any combination thereof. Exemplary additional compositions, which may be co-administered to the subject, include, without limitation, one or more conventional anti-cancer drugs. Alternatively, the methods of the present disclosure may also include one or more surgical interventions, such as tumor resection, or may further optionally include one or more courses of therapeutically effective ionizing radiation (i.e., radiation therapy).

The present disclosure also provides a method of treating or ameliorating one or more symptoms of cancer in a mammal. Such methods generally include administering to the mammal an effective amount of an iNOS-inhibitory, chemotherapeutic formulation as disclosed herein, either alone, or in combination with one or more anti-hypertensives, and calcium channel antagonists in particular, alone, or further in combination with one or more conventional chemotherapeutic agents, for a time sufficient to treat or ameliorate the one or more symptoms of the cancer in the mammal.

The present disclosure also provides pharmaceutical composition for use in the therapy of cancer in an animal subject, wherein the composition comprises one or more of the iNOS-inhibitory, chemotherapeutic formulations disclosed herein, either alone, or in combination with one or more calcium channel antagonists, and may include such a use for treating, or ameliorating one or more symptoms of malignant breast cancer in a human subject.

The present disclosure also provides a method of altering, affecting, destroying, or killing one or more mammalian cells within or about the body of an animal that has, is suspected of having, or has been diagnosed with one or more forms of mammalian cancer, including, without limitation, breast cancer, lung cancer, prostate cancer, fibrosarcoma, synovial sarcoma, pancreatic cancer, melanoma, head/neck, and other forms of the disease. Such methods generally involve providing to one or more animal cells a therapeutically-effective amount of one or more of the disclosed iNOS-inhibitory, chemotherapeutic compositions, either alone, or in combination with one or more anti-hypertensives, including calcium channel antagonists in particular, for a time sufficient to treat, and/or ameliorate the one of more symptoms of cancer in the animal.

Also provided herein are methods of altering, modulating, controlling, increasing, and/or attenuating at least one component, pathway, enzyme, or step involved in the process of hyperproliferative cell grown within or about the body of an animal, by providing to one or more cells, tissues, and/or organs of a subject in need thereof an effective amount of one of more of the disclosed iNOS-inhibitory, chemotherapeutic compositions, either alone, or in combination with one or more calcium channel antagonists, for a time effective to alter, modulate, control, increase, and/or attenuate at least one component, pathway, enzyme, or step involved in the process of hyperproliferative cell growth within such cells, tissues, organ, and/or body.

Further provided herein are methods for treating and/or ameliorating at least one symptom of a mammalian cancer (including, without limitation, human melanomas, head/neck cancers, and breast cancers, including metastatic, and/or therapy-resistant cancers, such as TNBC.

INOS-Inhibitory Compounds and Formulations Thereof

As noted herein, the iNOS-inhibitory, chemotherapeutic formulations of the present invention may be employed as a single cancer treatment modality, or alternatively may be combined with one or more additional chemotherapeutics, diagnostic reagents, and/or such like, including, without limitation, one or more proteins, peptides, polypeptides (including, without limitation, enzymes, antibodies, antigens, antigen binding fragments, etc.); RNA molecules (including, without limitation, siRNAs, iRNAs, mRNAs, tRNAs, and catalytic RNAs, such as ribozymes and the like); DNA molecules (including, without limitation, oligonucleotides, polynucleotides, genes, coding sequences (CDS), introns, exons, plasmids, cosmids, phagemids, baculovirus, vectors [including, without limitation, viral vectors, virions, viral particles and such like]); peptide nucleic acids, detection agents, imaging agents, contrast agents, detectable gas, radionuclides, or such like, and one or more additional chemotherapeutic agents, surgical intervention (e.g., tumor resection), radiotherapy, and the like, or any combination thereof as part of a multifactorial, or multifocal treatment plan for the affected patient.

The chemotherapeutic formulations disclosed herein may also further optionally include one or more additional components to aid, facilitate, or improve delivery of the iNOS-inhibitory, chemotherapeutic formulations, including, without limitation, one or more liposomes, particles, lipid complexes, and may further optionally include one or more binding agents, cell surface active agents, surfactants, lipid complexes, niosomes, ethosomes, transferosomes, phospholipids, sphingolipids, sphingosomes, or any combination thereof, and may optionally be provided within a pharmaceutical formulation that includes one or more nanoparticles, microparticles, nanocapsules, microcapsules, nanospheres, microspheres, or any combination thereof.

The pharmaceutical compositions may also be admixed with one or more pharmaceutically-acceptable carriers, diluents, excipients, or any combination thereof, and may further optionally be formulated to include a liposome, a surfactant, a niosome, an ethosome, a transferosome, a phospholipid, a sphingosome, a nanoparticle, a microparticle, or any combination thereof.

Preferably, the chemotherapeutic formulations disclosed herein will be at least substantially stable at a pH from about 4.2 to about 8.2, and more preferably, will be substantially stable at a pH of from about 5 to about 7.5. Preferably, the active ingredients will be substantially active at physiological conditions of the animal into which they are being administered.

Chemotherapeutic Methods and Use

Another important aspect of the present disclosure concerns methods for using the disclosed iNOS-inhibitory, chemotherapeutic formulations for treating and/or ameliorating one or more symptoms of mammalian cancer, including, without limitation, human melanomas, head/neck cancers, and breast cancers, such as metastatic or therapy-resistant TNBC. Such methods generally involve administering to a mammal (and in particular, a human in need thereof) at least one anti-cancer composition disclosed herein, in an amount and for a time sufficient to treat (or, alternatively, to ameliorate one or more symptoms thereof) the cancer in an affected mammal, such as a human.

In certain embodiments, the chemotherapeutic formulations described herein may be provided to the animal in a single treatment modality (either as a single administration, or alternatively, in multiple administrations over a period of from several hrs to several days, or even several weeks or more), as may be necessary to treat the cancer and/or ameliorate its symptom(s). Alternatively, in some embodiments, it may be desirable to continue the treatment, or to include it in combination with one or more additional modes of therapy, for a period of several weeks to several months or longer. In other embodiments, it may be desirable to provide the therapy in combination with one or more existing, or conventional, treatment regimens.

The present disclosure also provides for the use of one or more of the disclosed chemotherapeutic compositions in the manufacture of a medicament for therapy and/or for the amelioration of one or more symptoms of cancer, and particularly for use in the manufacture of a medicament for treating and/or ameliorating one or more symptoms of a mammalian cancer, including, without limitation, human melanomas, head/neck cancers, and breast cancers, such as metastatic, and/or therapy-resistant forms of the disease, such as, TNBC.

The present disclosure also provides for the use of one or more of the disclosed iNOS inhibitor/calcium channel antagonist formulations in the manufacture of a medicament for the treatment of cancer, and in particular, the treatment of human, melanomas, head/neck cancers, and breast cancers, including, for example, metastatic and/or therapy-resistant forms of such cancers.

Therapeutic Kits

Therapeutic kits including one or more of the disclosed iNOS-inhibitory formulations and instructions for using the kit in a particular cancer treatment modality also represent preferred aspects of the present disclosure. These kits may further optionally include one or more additional anti-cancer compounds, one or more diagnostic reagents, or one or more additional therapeutic compounds, pharmaceuticals, or such like.

The kits as described herein may be packaged for commercial distribution, and may further optionally include one or more delivery devices adapted to deliver the chemotherapeutic composition(s) to an animal (e.g., syringes, injectables, and the like). Such kits typically include at least one vial, test tube, flask, bottle, syringe or other container, into which the pharmaceutical composition(s) may be placed, and preferably suitably aliquotted. Where a second pharmaceutical is also provided, the kit may also contain a second distinct container into which this second composition may be placed. Alternatively, the plurality of pharmaceutical compositions disclosed herein may be prepared in a single mixture, such as a suspension or solution, and may be packaged in a single container, such as a vial, flask, syringe, catheter, cannula, bottle, or other suitable single container.

Kits in accordance with one or more aspects of the present disclosure may also typically include a retention mechanism adapted to contain or retain the vial(s) or other container(s) in close confinement for commercial sale, such as, e.g., injection or blow-molded plastic containers into which the desired vial(s) or other container(s) may be retained to minimize or prevent breakage, exposure to sunlight, or other undesirable factors, or to permit ready use of the composition(s) included within the kit.

Pharmaceutical Formulations

In certain embodiments, the present disclosure concerns formulation of one or more chemotherapeutic and/or diagnostic compounds in a pharmaceutically acceptable formulation for delivery to one or more cells or tissues of an animal, either alone, or in combination with one or more other modalities of diagnosis, prophylaxis and/or therapy. The formulation of pharmaceutically acceptable excipients and carrier solutions is well known to those of ordinary skill in the art, as is the development of suitable dosing and treatment regimens for using the particular compositions described herein in a variety of treatment regimens.

In certain circumstances it will be desirable to deliver the disclosed chemotherapeutic compositions in suitably-formulated pharmaceutical vehicles by one or more standard delivery devices, including, without limitation, subcutaneously, parenterally, intravenously, intramuscularly, intrathecally, orally, intraperitoneally, transdermally, topically, by oral or nasal inhalation, or by direct injection to one or more cells, tissues, or organs within or about the body of an animal.

The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, transdermal, subdermal, and/or intraperitoneal administration. In this regard, the compositions of the present disclosure may be formulated in one or more pharmaceutically acceptable vehicles, including for example sterile aqueous media, buffers, diluents, etc. For example, a given dosage of active ingredient(s) may be dissolved in a particular volume of an isotonic solution (e.g., an isotonic NaCl-based solution), and then injected at the proposed site of administration, or further diluted in a vehicle suitable for intravenous infusion (see, e.g., "Remington's Pharmaceutical Sciences" 15th Edition, pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

Sterile injectable compositions may be prepared by incorporating the disclosed compositions in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The compositions disclosed herein may also be formulated in a neutral or salt form.

Pharmaceutically acceptable salts include the acid addition salts (formed with the free amino groups of the protein), and which are formed with inorganic acids such as, without limitation, hydrochloric or phosphoric acids, or organic acids such as, without limitation, acetic, oxalic, tartaric, mandelic, and the like. Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount, dosage regimen, formulation, and administration of chemotherapeutics disclosed herein will be within the purview of the ordinary-skilled artisan having benefit of the present teaching. It is likely, however, that the administration of a therapeutically-effective (i.e., a pharmaceutically-effective) amount of the disclosed compositions may be achieved by a single administration, such as, without limitation, a single injection of a sufficient quantity of the delivered agent to provide the desired benefit to the patient undergoing such a procedure. Alternatively, in some circumstances, it may be desirable to provide multiple, or successive administrations of the compositions, either over a relatively short, or even a relatively prolonged period, as may be determined by the medical practitioner overseeing the administration of such compositions to the selected individual.

Typically, formulations of one or more of the compositions described herein will contain at least a chemotherapeutically-effective amount of a first active agent. Preferably, the formulation may contain at least about 0.001% of each active ingredient, preferably at least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more preferably, from about 0.2 to about 60 weight % or volume %, based upon the total formulation. Naturally, the amount of active compound(s) in each composition may be prepared in such a way that a suitable dosage will be obtained in any given unit dose of the compound. Factors such as solubility, bioavailability, biological $t_{i}/2$, route of administration, product shelf life, as well as other pharmacological considerations will be contemplated by one of ordinary skill in the art of preparing such pharmaceutical formulations, and as such, a variety of dosages and treatment regimens may be desirable.

Administration of the chemotherapeutic compositions disclosed herein may be administered by any effective method, including, without limitation, by parenteral, intravenous, intramuscular, or even intraperitoneal administration as described, for example, in U.S. Pat. Nos. 5,543,158; 5,641,515; and 5,399,363 (each of which is specifically incorporated herein in its entirety by express reference thereto). Solutions of the active compounds as free-base or pharmacologically acceptable salts may be prepared in water suitably mixed with a surfactant, such as hydroxypropylcellulose, or other similar fashion. The pharmaceutical forms adapted for injectable administration include sterile aqueous solutions or dispersions, and sterile powders for the extemporaneous preparation of sterile injectable solutions or dispersions including without limitation those described in U.S. Pat. No. 5,466,468 (which is specifically incorporated herein in its entirety by express reference thereto). In all cases, the form must be sterile and must be fluid to the extent that easy syringeability exists. It must be at least sufficiently stable under the conditions of manufacture and storage, and must be preserved against the contaminating action of microorganisms, such as viruses, bacteria, fungi, and such like.

The carrier(s) can be a solvent or dispersion medium including, without limitation, water, ethanol, polyol (e.g., glycerol, propylene glycol, and liquid polyethylene glycol, and the like, or a combination thereof), one or more vegetable oils, or any combination thereof, although additional pharmaceutically-acceptable components may be included.

Proper fluidity of the pharmaceutical formulations disclosed herein may be maintained, for example, by the use of a coating, such as e.g., a lecithin, by the maintenance of the required particle size in the case of dispersion, by the use of a surfactant, or any combination of these techniques. The inhibition or prevention of the action of microorganisms can be brought about by one or more antibacterial or antifungal agents, for example, without limitation, a paraben, chlorobutanol, phenol, sorbic acid, thimerosal, or the like. In many cases, it will be preferable to include an isotonic agent, for example, without limitation, one or more sugars or sodium chloride, or any combination thereof. Prolonged absorption of the injectable compositions can be brought about by the use in the compositions of agents delaying absorption, for example without limitation, aluminum monostearate, gelatin, or a combination thereof.

While systemic administration is contemplated to be effective in many embodiments of the present disclosure, it is also contemplated that formulations disclosed herein be suitable for direct injection into one or more organs, tissues, or cell types in the body. Administration of the disclosed compositions may be conducted using suitable means, including those known to the one of ordinary skill in the relevant medical arts.

The pharmaceutical formulations disclosed herein are not in any way limited to use only in humans, or even to primates, or mammals. In certain embodiments, the methods and compositions disclosed herein may be employed using avian, amphibian, reptilian, or other animal species. In preferred embodiments, however, the compositions of the present disclosure are preferably formulated for administration to a mammal, and in particular, to humans, in a variety of diagnostic and/or therapeutic regimens. The compositions disclosed herein may also be provided in formulations that are acceptable for veterinary administration, including, without limitation, to selected livestock, exotic or domesticated animals, companion animals (including pets and such like), non-human primates, as well as zoological or otherwise captive specimens, and such like.

BRIEF DESCRIPTION OF THE DRAWINGS

The following drawings form part of the present specification and are included to demonstrate certain aspects of the present invention. The patent or application file contains at least one drawing executed in color. Copies of this patent or patent application publication with color drawing(s) will be provided by the Office upon request and payment of the necessary fee.

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The invention may be better understood by reference to the following description taken in conjunction with the accompanying drawings, in which like reference numerals identify like elements, and in which:

Figure 1E:
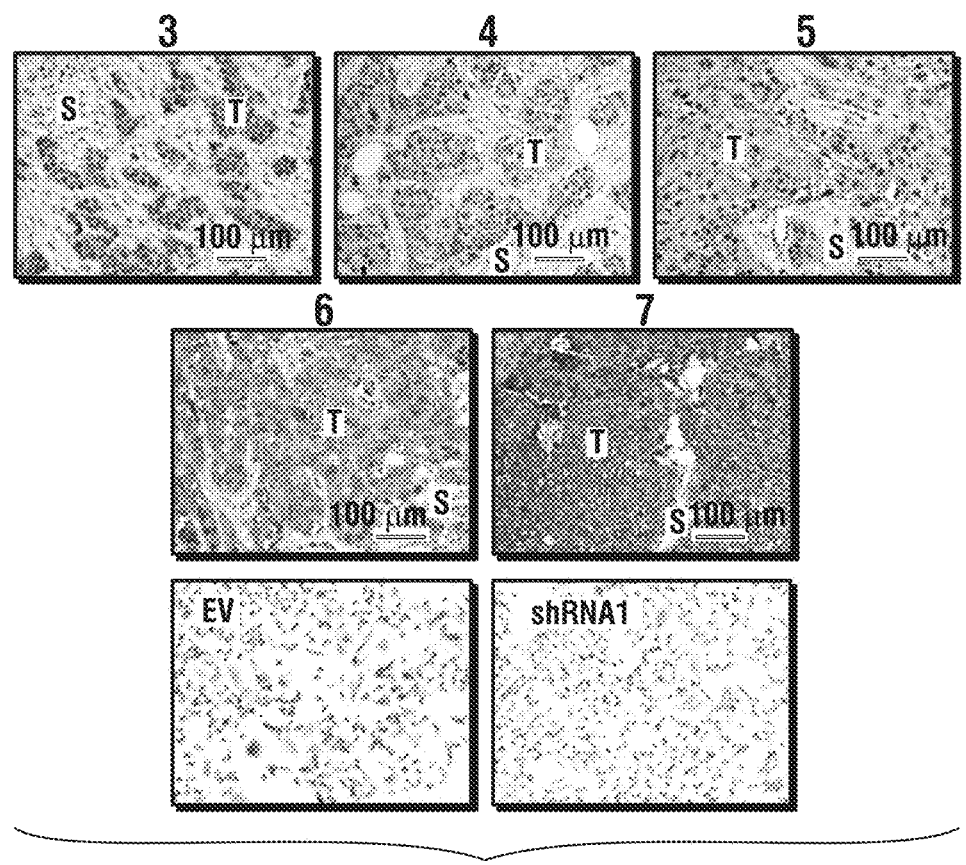
Figure 1F:
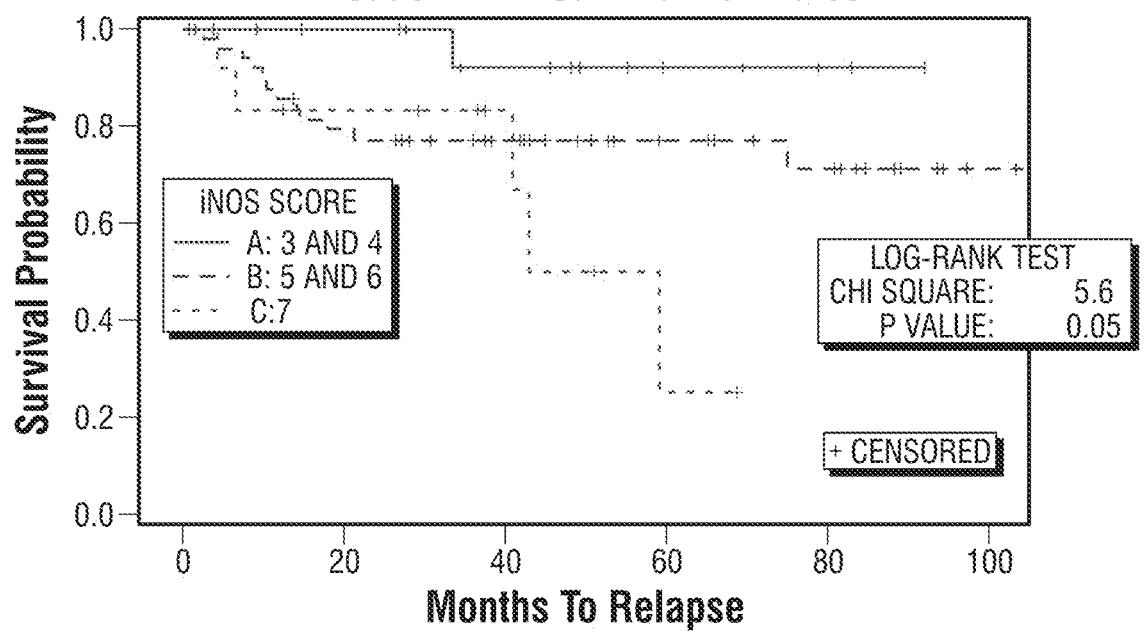
Figure 3E:
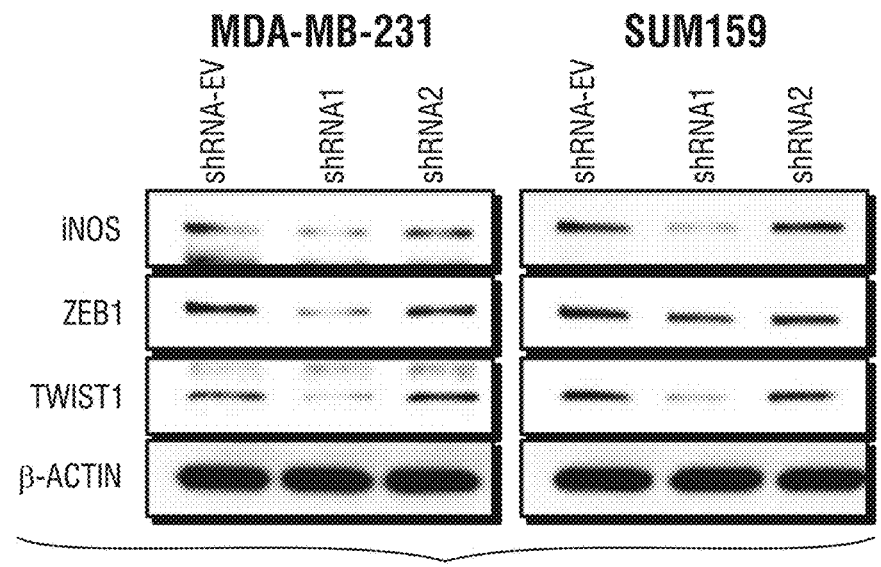
Figure 3F:
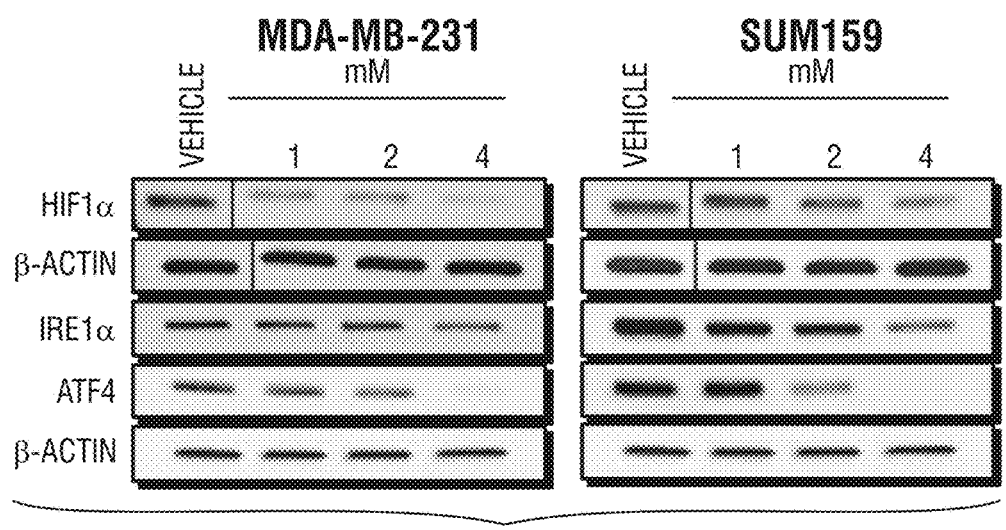
Figure 3G:
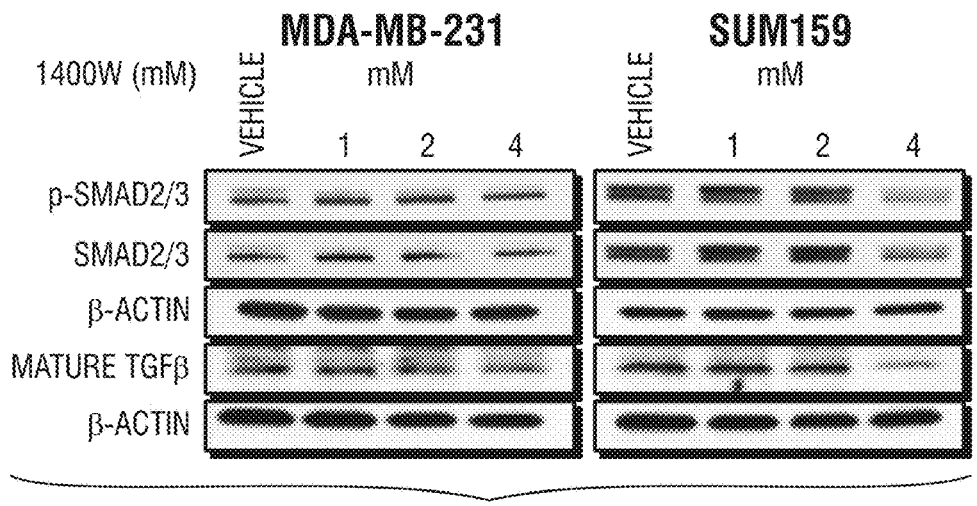
Figures 3H, 3I, 3J:
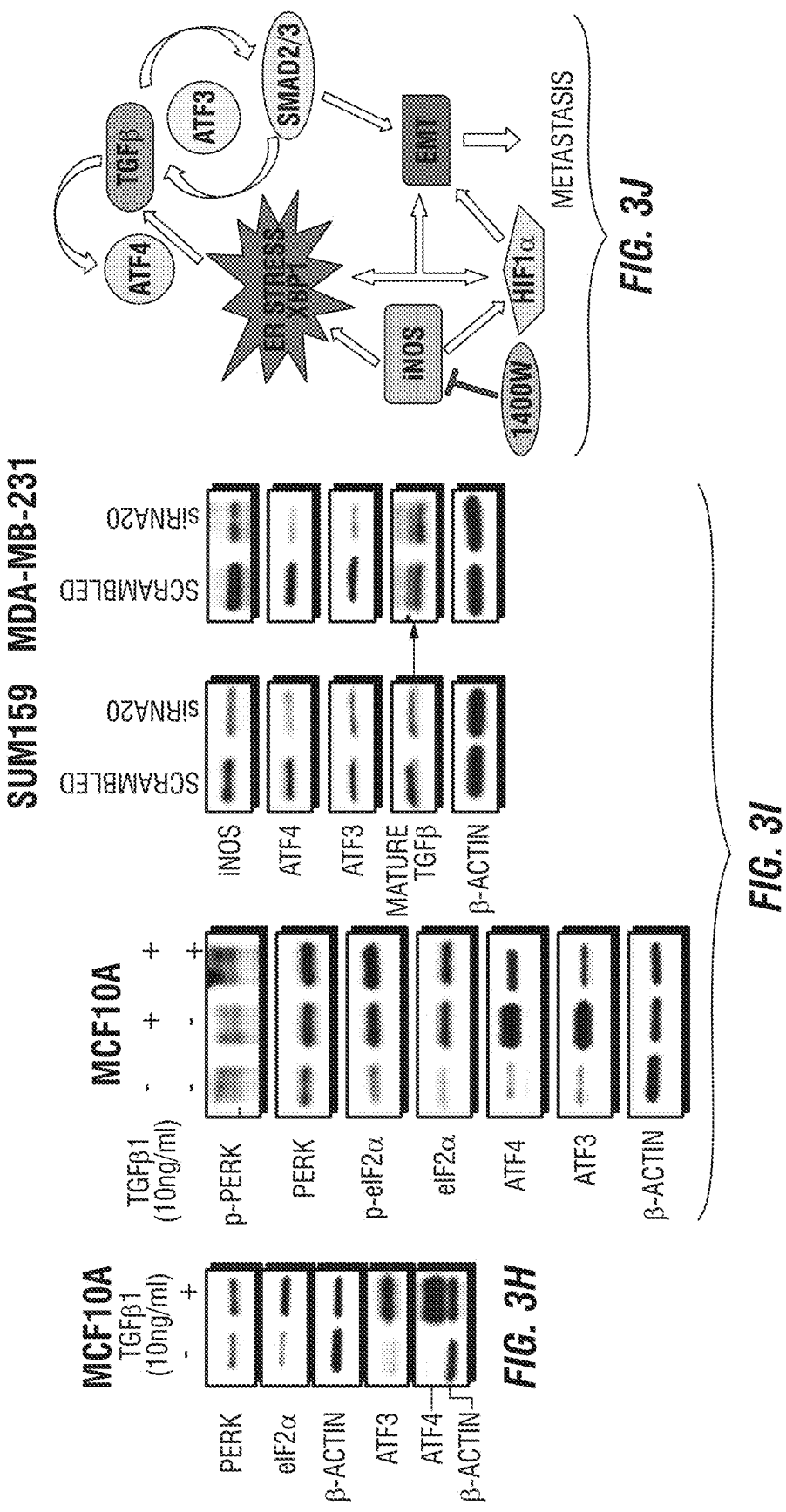
Figure 4A:
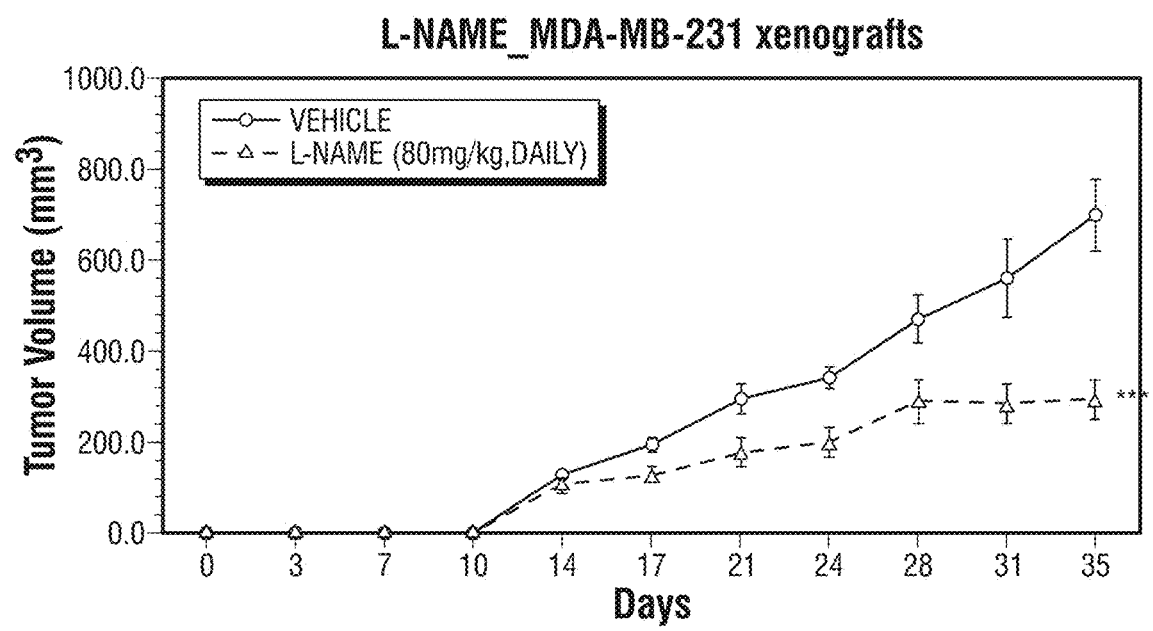
Figure 4B:
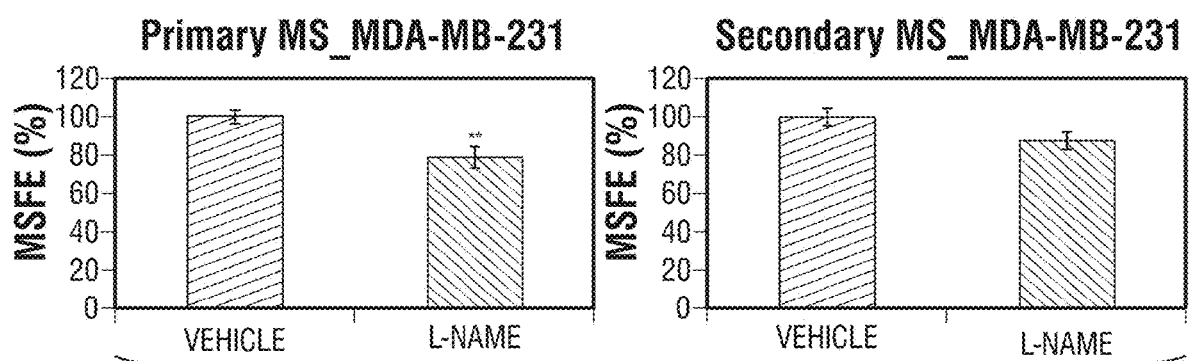
Figures 4C, 4D:
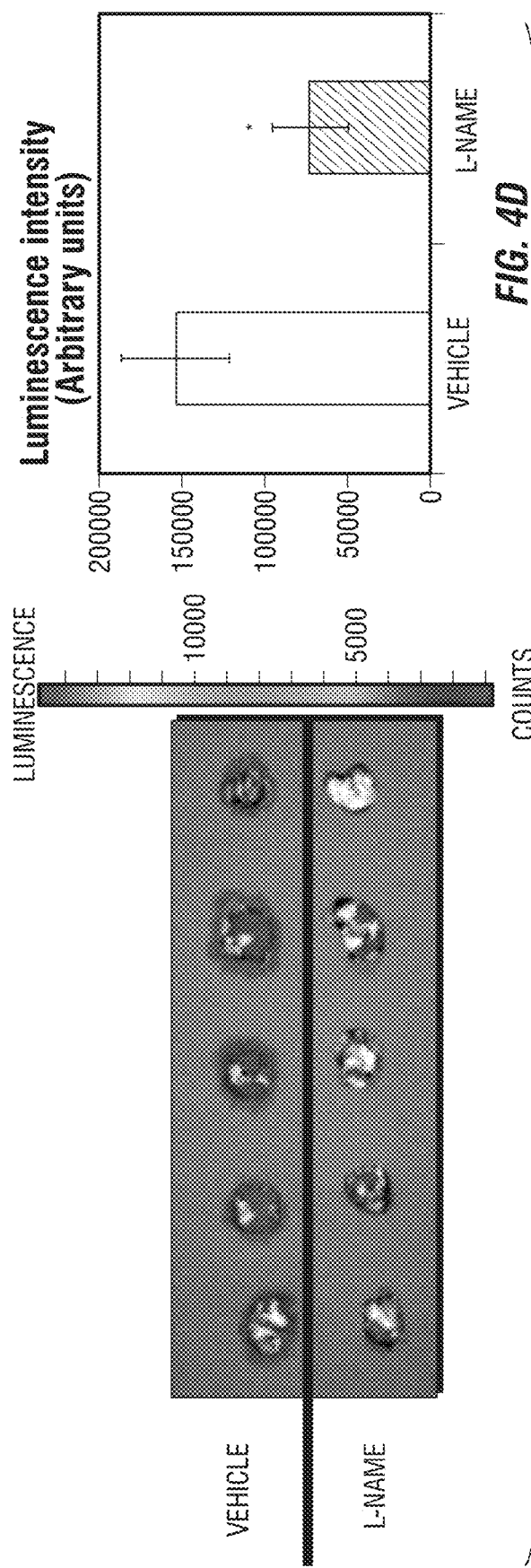
Figure 5A:
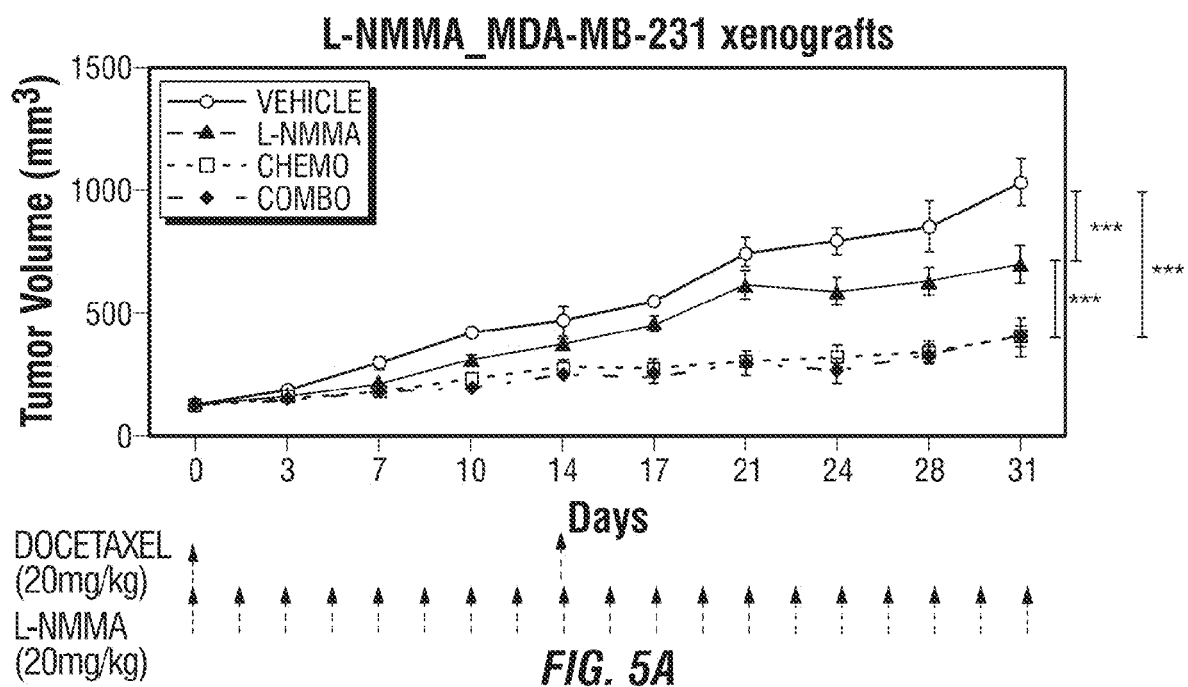
Figure 5B:
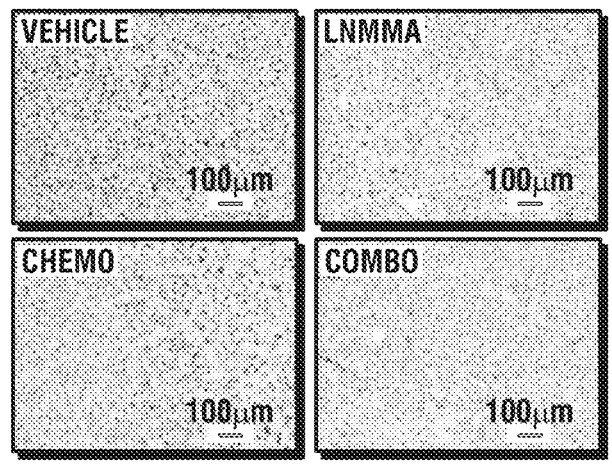
Figure 5C:
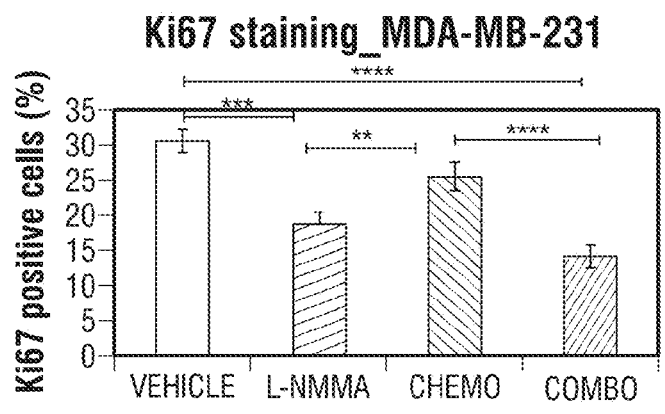
Figure 5D:
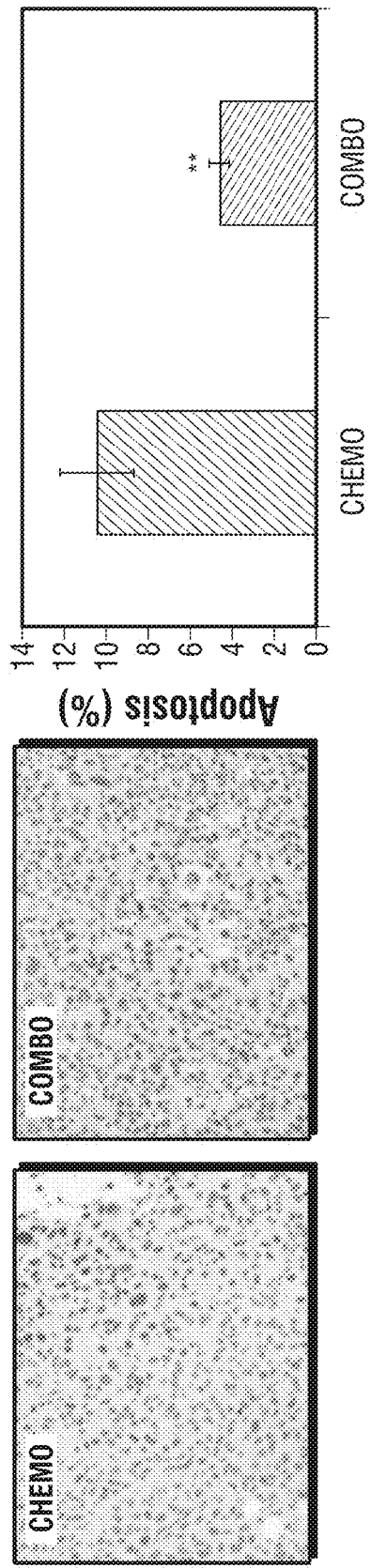
Figure 5E:
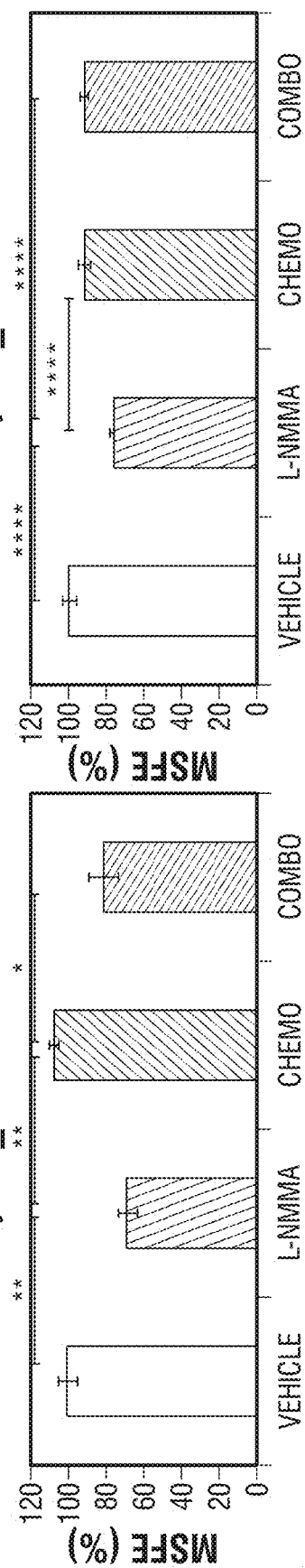
Figure 6A:
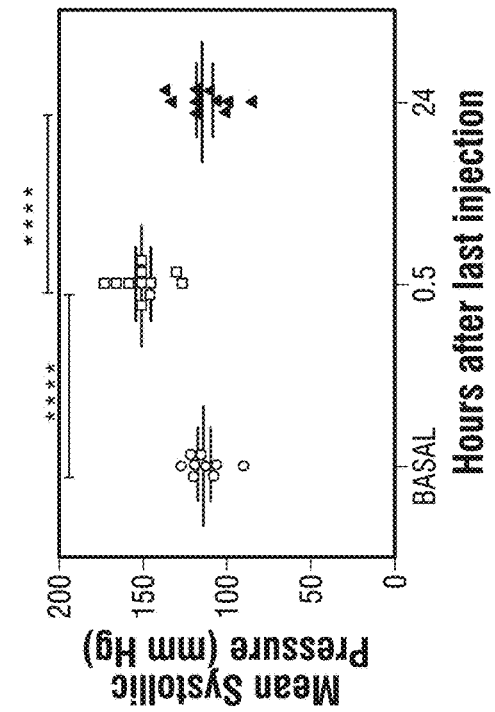
Figure 6B:
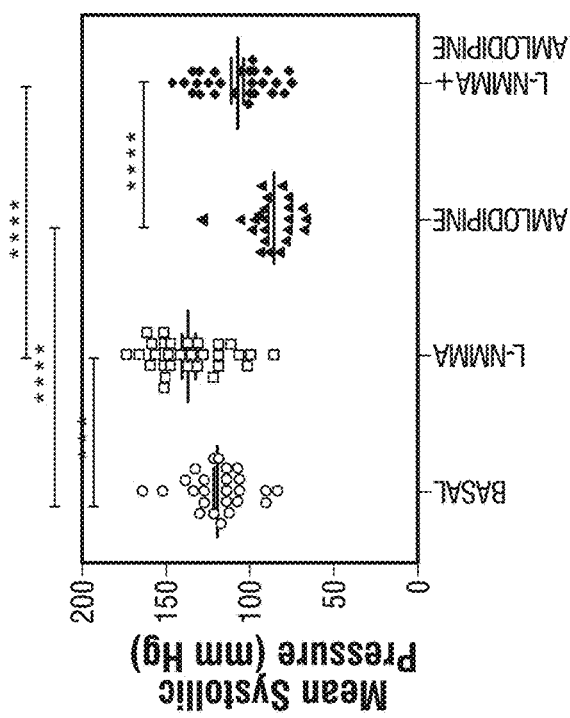
Figure 6C:
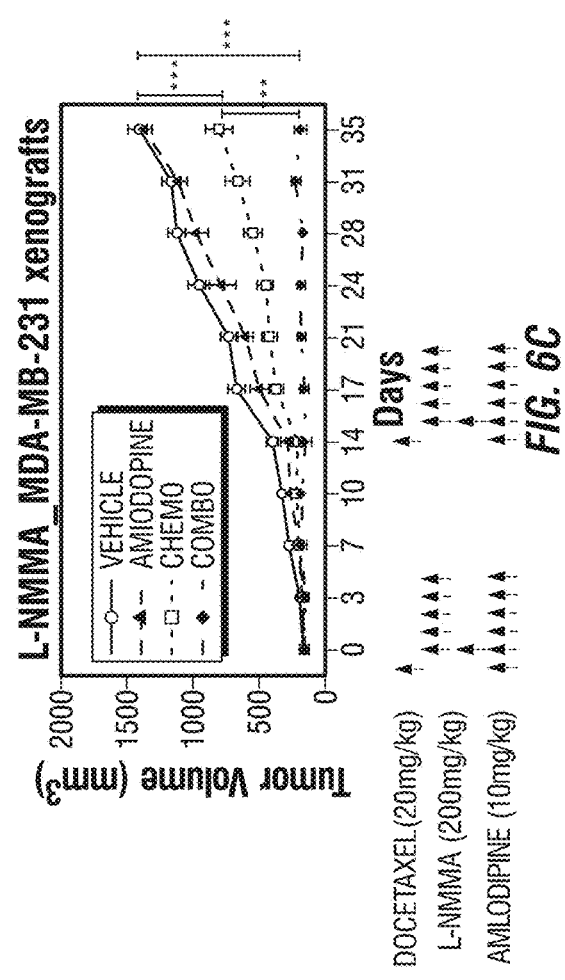
Figure 6D:
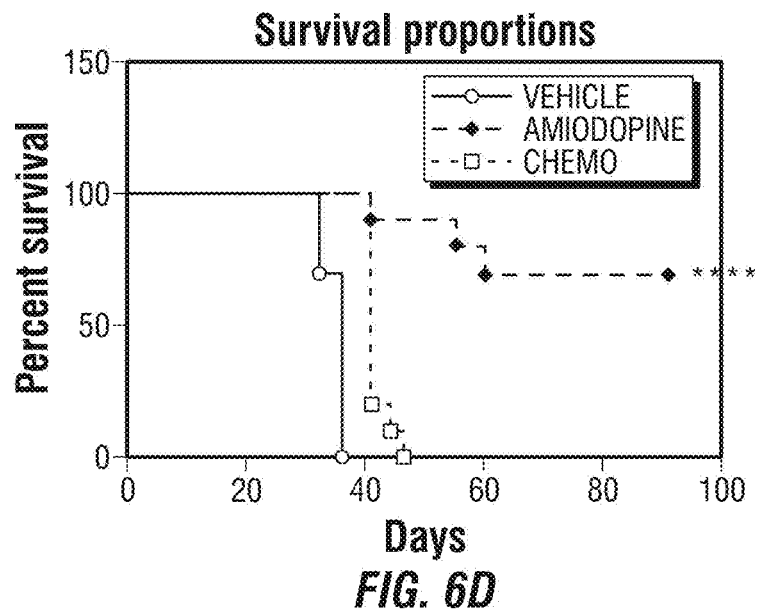
Figure 6E:
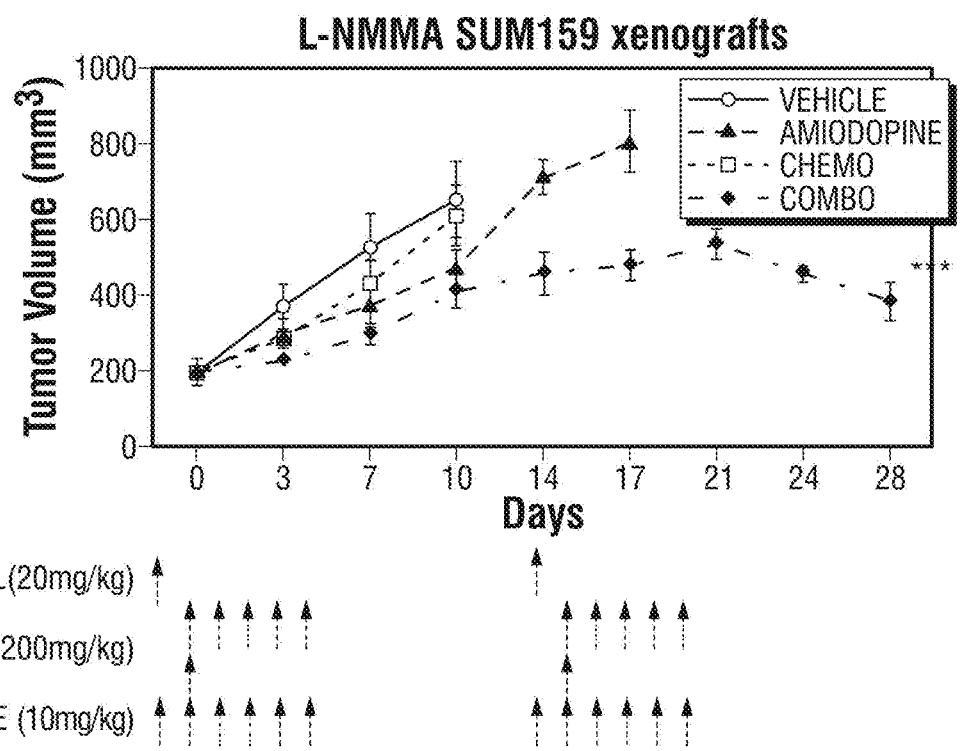
Figure 7A:
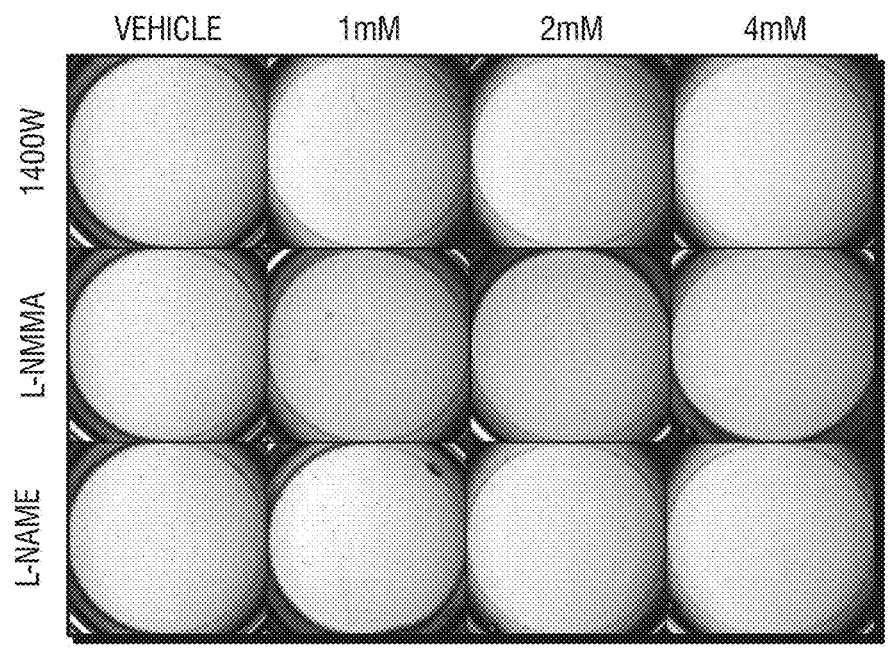
Figure 7B:
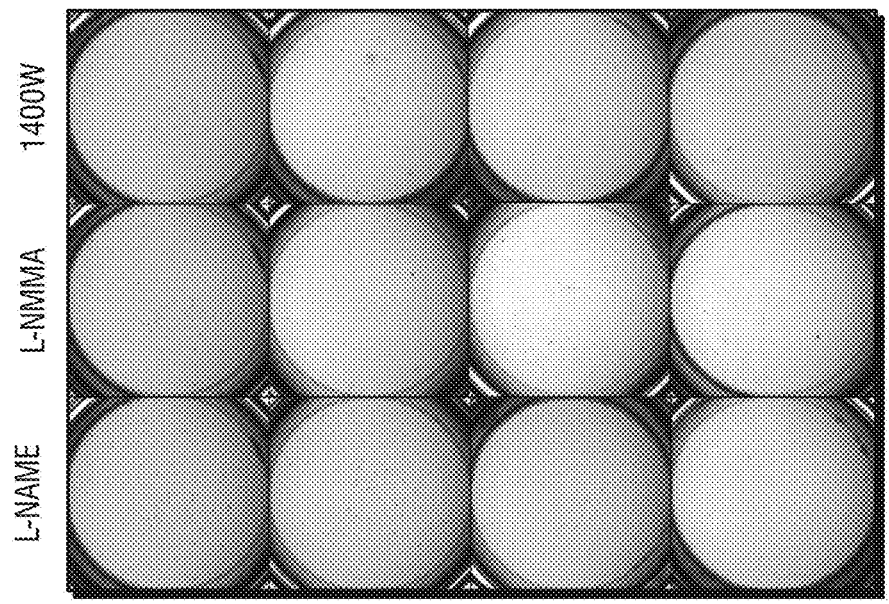
Figure 8A:
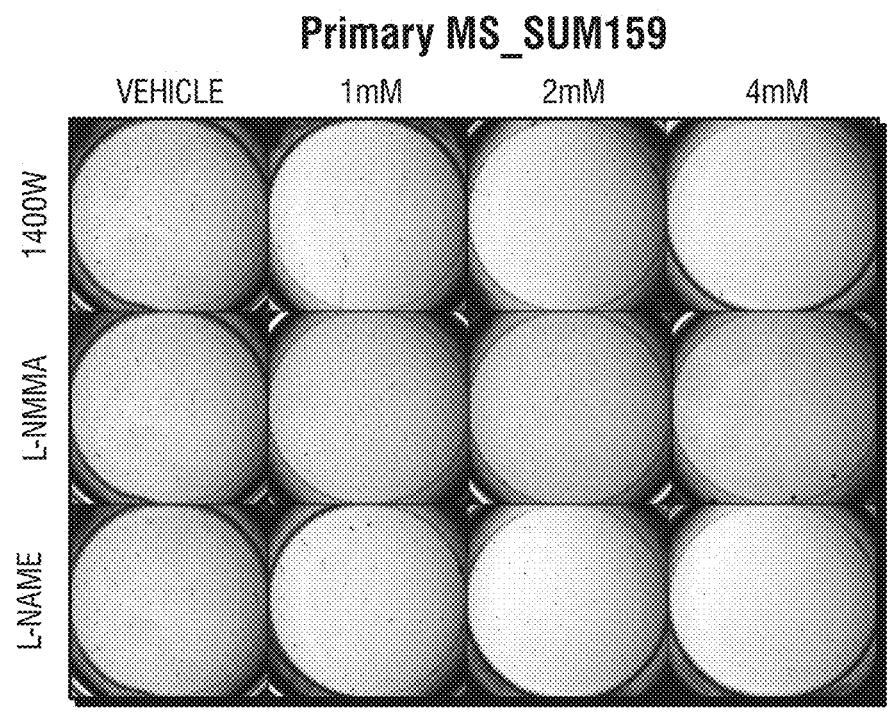
Figure 8B:
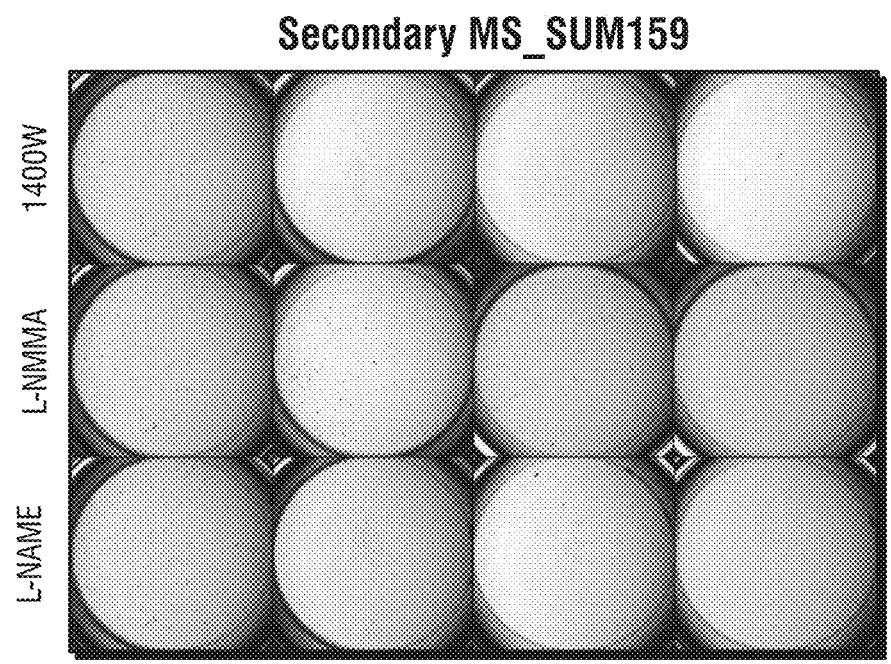
Figure 10G:
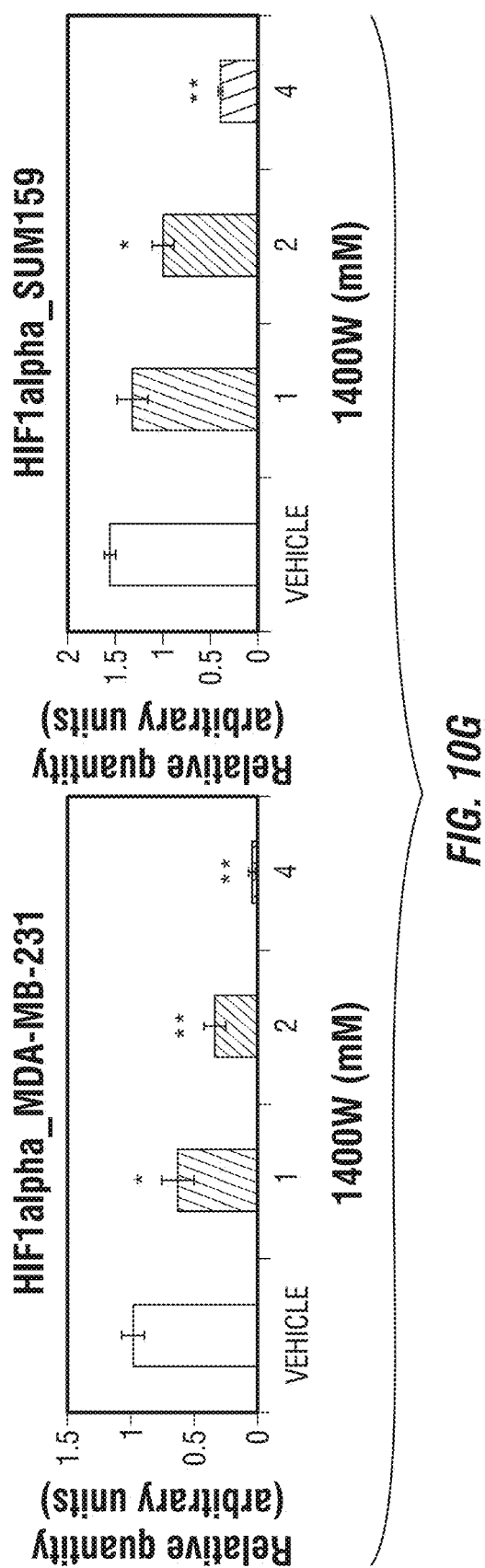
Figure 11F:
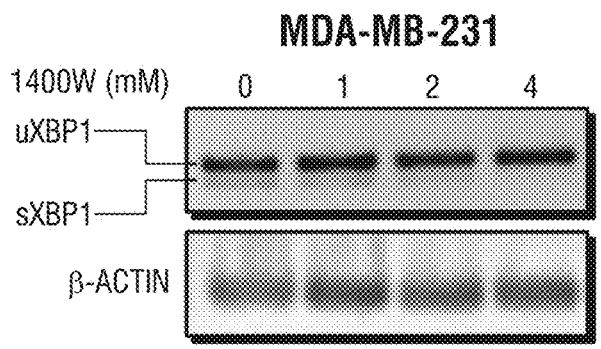
Figure 11G:
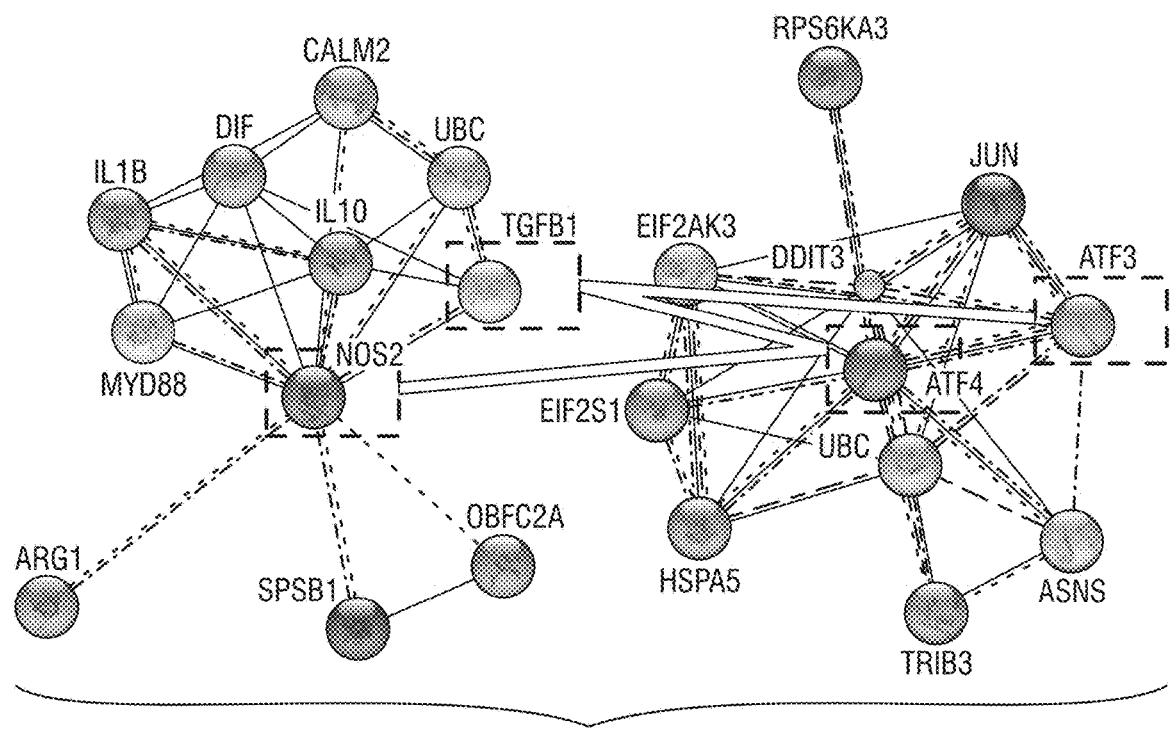
Figure 11H:
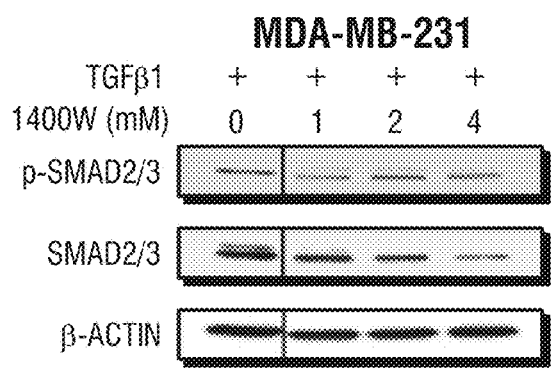
Figure 11I:
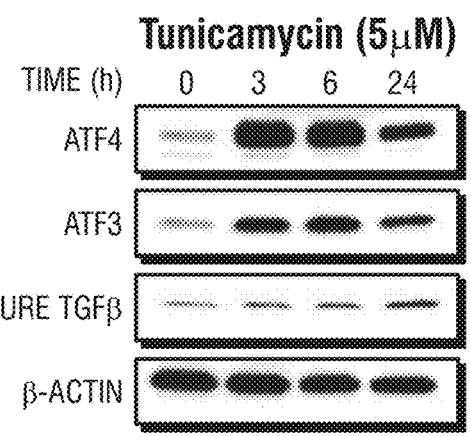
Figure 12A:
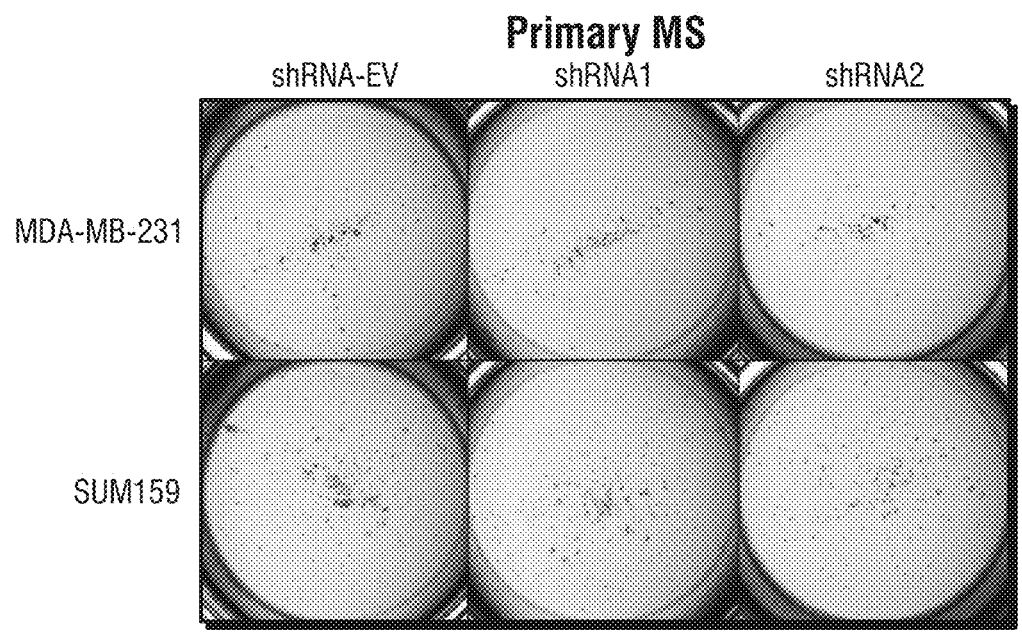
Figure 12B:
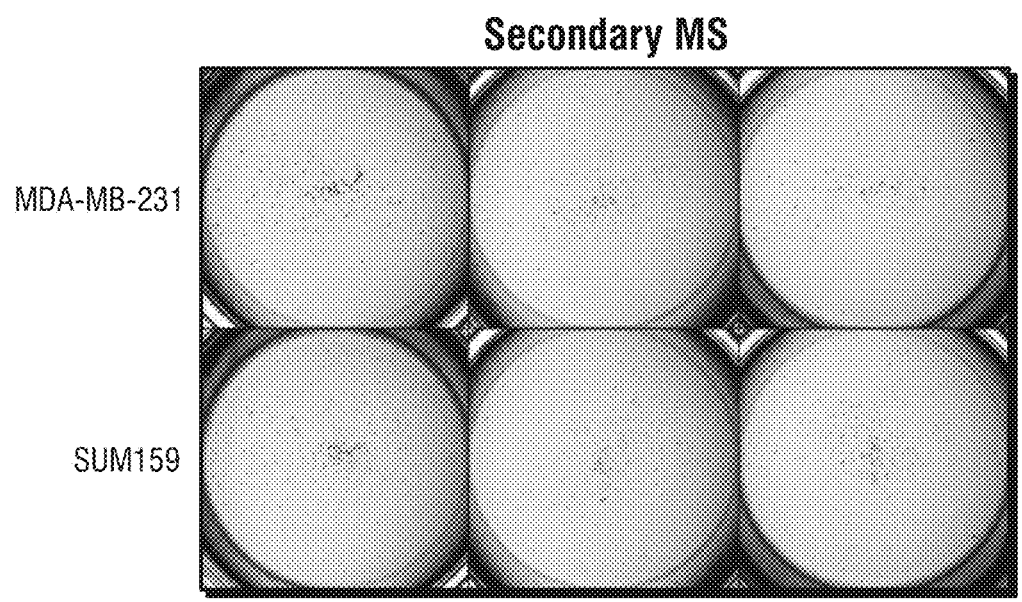
Figure 12C:
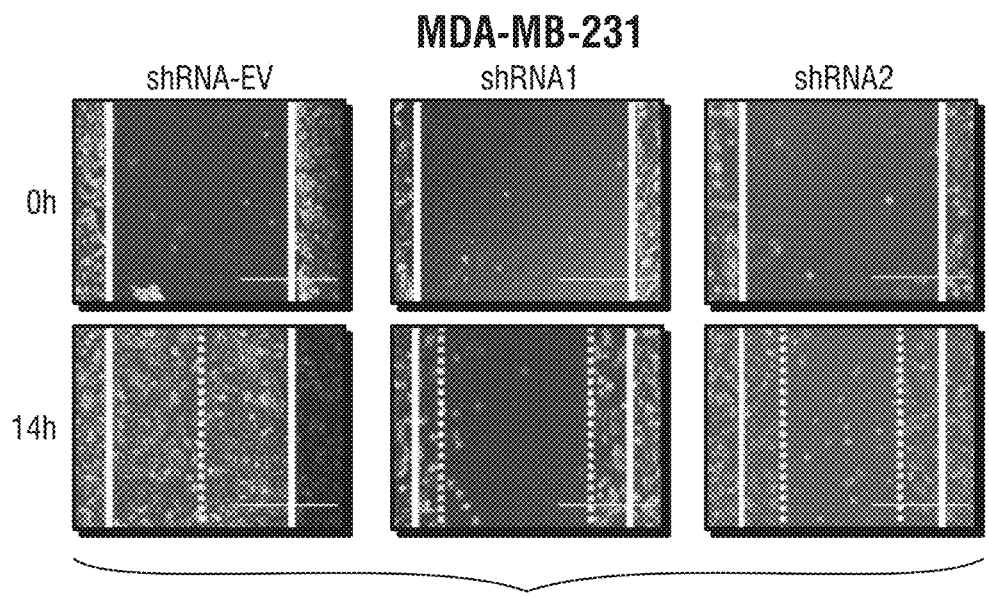
Figure 12D:
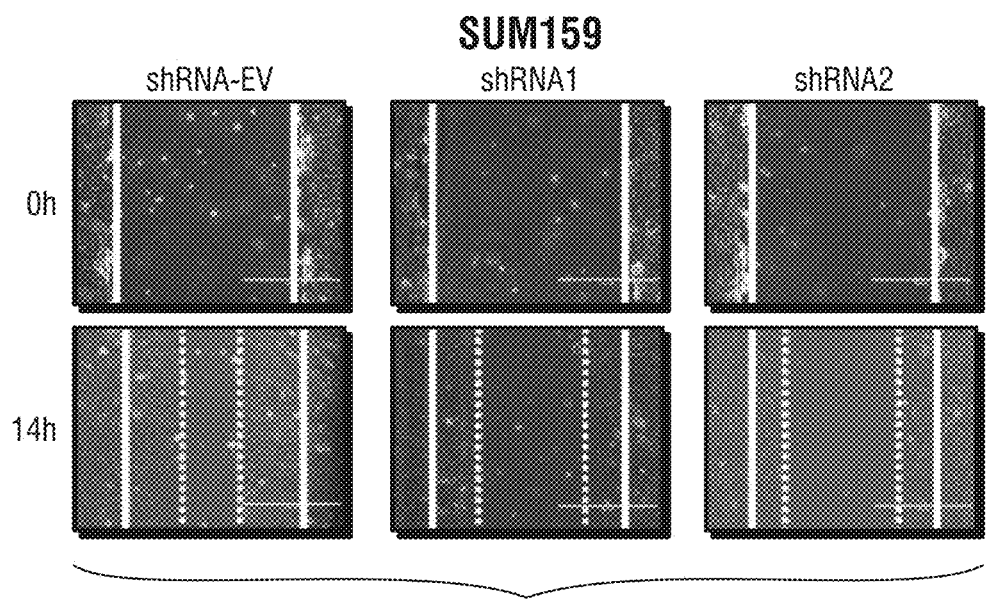
Figure 13A:
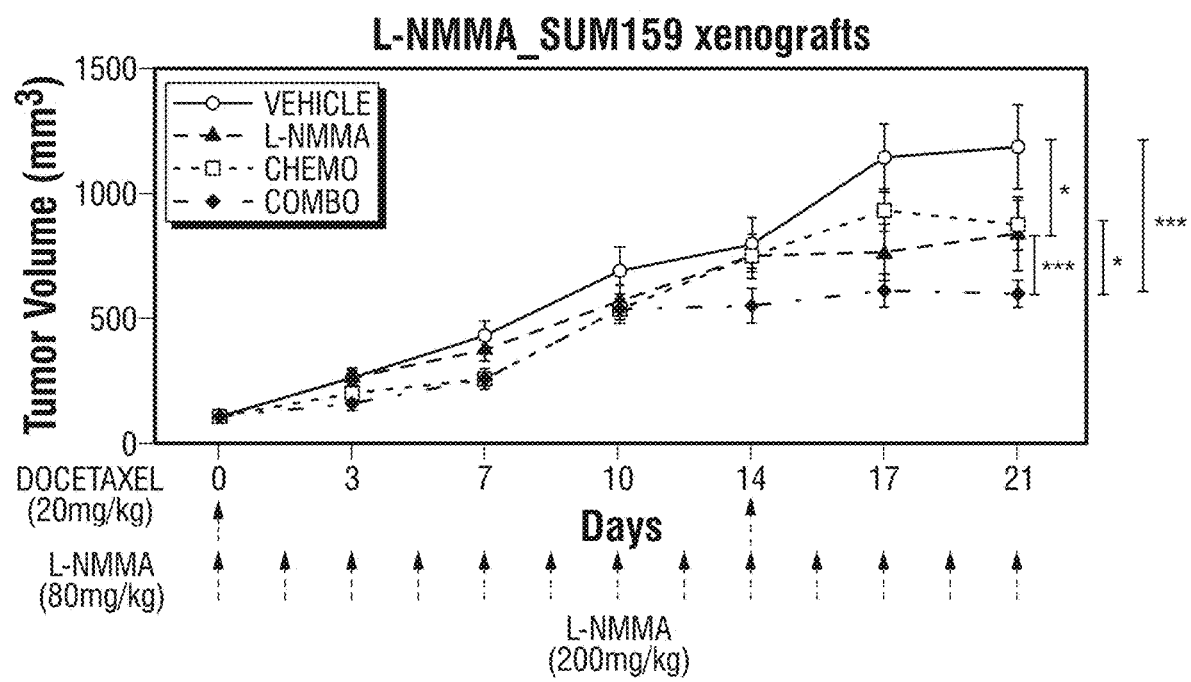
Figure 13B:
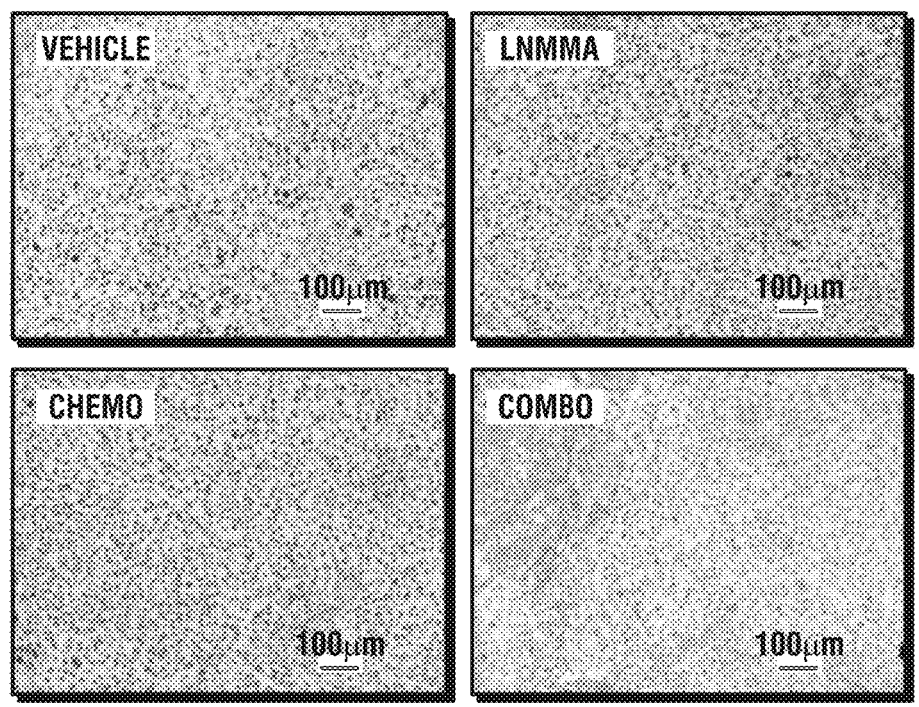

FIG. 1A, FIG. 1B, FIG. 1C, FIG. 1D, FIG. 1E, and FIG. 1F illustrate the enhanced NOS2 expression correlates with poor patient survival in invasive TNBC. Oncomine Cancer Microarray analysis of The Cancer Genome Atlas (TCGA) database (FIG. 1A and FIG. 1B). FIG. 1A: Higher NOS2 mRNA expression in invasive TNBC vs. non-TNBC. P=3.85E-5, t-test. FIG. 1B: High NOS2 expression correlates with death at 5 years in invasive breast carcinoma. P=0.037, t-test. Kaplan-Meier survival analysis in Van de Vijver (n=69; p=0.04) (FIG. 1C) and Curtis (n=260; p=0.01) (FIG. 1D) (Wilcoxon test) breast databases show that high NOS2 expression correlates with worse overall survival of TNBC patients (FIG. 1E) Immunohistochemical analysis of TNBC human samples for iNOS protein expression. Weak-to-moderate (3-4), moderate-to-strong (5-6), and strong (7) were the cut-off established for further analysis of survival. Several samples showed expression in both tumor (T) and stromal (S) cells (original optical objective: 20×). MDA-MB-231 cells transfected either with NOS2-directed shRNA (shRNA1) or empty vector (EV) were used as negative and positive controls for iNOS staining, respectively (original optical objective: 10×). Counterstain: hematoxylin. FIG. 1F: Increased iNOS expression is associated with less patient survival when compared with low iNOS expression. Kaplan-Meier survival analysis of TNBC human patient samples (n=83). P=0.05, Log-Rank test;

FIG. 2A, FIG. 2B, FIG. 2C, FIG. 2D, FIG. 2E, and FIG. 2F illustrate the effects of iNOS inhibitors on the tumorigenicity of TNBC cell lines. Proliferation (FIG. 2A and FIG. 2B), primary (FIG. 2C) and secondary (FIG. 2D) mammospheres and migration index (FIG. 2E and FIG. 2F) of MDA-MB-231 and SUM159 cell lines treated with 1400 W and L-NMMA for 96 hrs. Results were normalized to Vehicle. Data are presented as mean±SEM. **p<0.0001, *p<0.001, **p<0.01, *p<0.05, One-way ANOVA and Bonferroni's post-hoc test;

FIG. 3A, FIG. 3B, FIG. 3C, FIG. 3D, FIG. 3E, FIG. 3F, FIG. 3G, FIG. 311, FIG. 3I, and FIG. 3J show iNOS knockdown impairs tumorigenicity and EMT by a dual impact on HIF1α and endoplasmic reticulum (ER) stress/TGFβ/AFT4/ATF3 crosstalk. Proliferation (FIG. 3A), migration (FIG. 3B), and self-renewal capacity (primary and secondary mammospheres) (FIG. 3C) in MDA-MB-231 cells transfected with two different NOS2-directed shRNAs (shRNA1, shRNA2) compared with empty vector (shRNA-EV). Western blot analysis of NOS isoforms (iNOS, eNOS, nNOS) and EMT transcription factors in MDA-MB-231 and SUM159 cell lines treated with 1400 W (FIG. 3D) and shRNA-mediated NOS2 knockdown (FIG. 3E). Selective iNOS inhibition reduced hypoxia (HIF1α), ER stress markers (IRE1α, ATF4) (FIG. 3F), phospho-Smad2/3, Smad2/3 and mature TGFβ protein levels in MDA-MB-231 and SUM159 cells (FIG. 3G). FIG. 3H: Recombinant TGFβ1 (10 ng/mL for 24 hrs) activates the PERK/eIF2α/ATF4/ATF3 axis in MCF10A. FIG. 3I: Effects on the PERK/eIF2α/ATF4/ATF3 axis by co-treatment of recombinant TGFβ1 (10 ng/mL) and 1400 W (4 mM) for 24 hrs in MCF10A cells. iNOS, ATF4, ATF3 and mature TGFβ protein levels in siRNA-mediated NOS2 knockdown (siRNA20) MCF10A cells for 96 hrs. FIG. 3J: Selective iNOS inhibition is postulated to impair EMT and tumor cell migration by an impact on HIF1α, ER stress (IRE1α/XBP1) and the crosstalk between ATF4, ATF3 and TGFβ. Results were normalized to empty vector. Data are presented as mean±SEM. **p<0.0001, *p<0.001, **p<0.01. One-way ANOVA and Bonferroni's post-hoc test;

FIG. 4A, FIG. 4B, FIG. 4C, and FIG. 4D show a decrease in tumor initiation and lung metastases in MDA-MB-231 xenografts. FIG. 4A: Tumor volume of MDA-MB-231 breast xenografts (n=5/group) after daily injection of L-NAME (80 mg/kg, i.p.). Two-way ANOVA and Bonferroni's post hoc test. FIG. 4B: Primary and secondary MSFE of cancer cells isolated from tumor tissue. Student's t-test. FIG. 4C: Tumor-initiating capacity of tumor cells assayed by the limiting dilution method. Fisher's exact test. FIG. 4D: Luminescence of MDA-MB-231 L/G tumor cells in lungs of vehicle- and L-NAME-treated mice. Student's t-test. Results were normalized to vehicle. Data are presented as mean±SEM. *p<0.001, p<0.01, *p<0.05;

FIG. 5A, FIG. 5B, FIG. 5C, FIG. 5D, FIG. 5E, and FIG. 5F illustrate the in vivo effects of L-NMMA in MDA-MB-231 xenografts. FIG. 5A: Tumor volume of MDA-MB-231 breast xenografts (n=10/group) treated with vehicle, L-NMMA, chemotherapy, and combination. Two-way ANOVA and Bonferroni's post-hoc test. FIG. 5B: Illustrative images of Ki67 staining in vehicle, L-NMMA, docetaxel and combination groups. Original optical objective:

10×. Counterstain: hematoxylin. FIG. 5C: Cell proliferation of tumor xenografts is depicted as Ki67 positive cells. 1,000 cells were counted from 10 different fields and percentage was determined. FIG. 5D: Nuclear cleaved caspase-3 staining in Chemo and Combo groups; 1,000 cells were counted from 10 different fields and percentage was determined. FIG. 5E: Primary and secondary MSFE of breast cancer cells isolated from tumor tissue. One-way ANOVA and Bonferroni's post-hoc test. FIG. 5F: Tumor-initiating capacity of tumor cells assayed by the limiting dilution method. Fisher's exact test. Results were normalized to vehicle. Data are presented as mean±SEM. **$p<0.0001$, *$p<0.001$, **$p<0.01$, *$p<0.05$;

FIG. 6A, FIG. 6B, FIG. 6C, FIG. 6D, and FIG. 6E show the clinically-relevant dose regimen of L-NMMA in orthotopic mouse models of TNBC. FIG. 6A: Mean systolic pressure of mice (n=5) giving one cycle of the dose rate proposed in this study. One-way ANOVA and Bonferroni's post hoc test. FIG. 6B: Mean systolic pressure of mice 30 min and 24 hrs after the last injection of one cycle treatment (n=5). One-way ANOVA and Bonferroni's post-hoc test. FIG. 6C: Tumor volume of MDA-MB-231 breast xenografts (n=10/group) treated with vehicle, amlodipine, docetaxel, and combination (docetaxel+L-NMMA). Two-way ANOVA and Bonferroni's post hoc test. FIG. 6D: Kaplan-Meier survival curve of vehicle-, chemotherapy-, and combo-treated MDA-MB-231 xenograft-bearing mice. Wilcoxon test. FIG. 6E: Tumor volume of SUM159 breast xenografts treated with vehicle, amlodipine, docetaxel, and combination (docetaxel+L-NMMA). Two-way ANOVA and Bonferroni's post-hoc test. Data are presented as mean±SEM. **$p<0.0001$, *$p<0.001$;

FIG. 7A and FIG. 7B show representative images of mammospheres in MDA-MB-231 cells treated with iNOS inhibitors. Illustrative images of primary (FIG. 7A) and secondary (FIG. 7B) mammospheres after treatment with 1400 W, L-NMMA (vehicle, 1, 2, 4 mM) and L-NAME (Vehicle, 1, 2, 5 mM) for 96 hrs;

FIG. 8A and FIG. 8B show representative images of mammospheres in SUM159 cells treated with iNOS inhibitors. Illustrative images of primary (FIG. 8A) and secondary (FIG. 8B) mammospheres after treatment with 1400 W, L-NMMA (vehicle, 1, 2, 4 mM) and L-NAME (vehicle, 1, 2, 5 mM) for 96 hrs;

FIG. 9A, FIG. 9B, FIG. 9C, FIG. 9D, and FIG. 9E show effects of L-NAME and micromolar concentrations of 1400 W and L-NMMA on the tumorigenicity of TNBC cell lines. Proliferation (FIG. 9A), primary (FIG. 9B) and secondary (FIG. 9C) mammospheres of MDA-MB-231 and SUM159 cell lines treated with L-NAME. Impact of 1400 W (FIG. 9D) and L-NMMA (FIG. 9E) at micromolar concentrations on the migration index in MDA-MB-231 and SUM159 cells. Results were normalized to vehicle. Data are presented as mean±SEM. **$p<0.0001$, *$p<0.001$, **$p<0.01$, *$p<0.05$; one-way ANOVA and Bonferroni's post-hoc test;

FIG. 10A, FIG. 10B, FIG. 10C, FIG. 10D, FIG. 10E, FIG. 10F, and FIG. 10G show migration and Western blot analyses of NOS isoforms, EMT transcription factors and hypoxia in TNBC cell lines treated with iNOS inhibitors. FIG. 10A: Tumor cell migration after treatment with L-NAME in MDA-MB-231 and SUM159 cell lines. Western blot analysis of NOS isoforms (iNOS, eNOS and nNOS) in MDA-MB-231 and SUM159 cells treated with 1400 W (FIG. 10B) and L-NMMA (FIG. 10C). EMT markers protein levels in MDA-MB-231 and SUM159 cells after treatment with micromolar concentrations of 1400 W (FIG. 10D) or L-NMMA (FIG. 10E). FIG. 10F: Western blot analysis of NOS isoforms and the EMT transcription factors in MDA-MB-231 and SUM159 cell lines treated with L-NAME. FIG. 10G: Quantification of HIF1α protein levels relative to β-actin in MDA-MB-231 and SUM159 cells treated with 1400 W. Results were normalized to vehicle. Data are presented as mean±SEM. **$p<0.01$, *$p<0.05$, One-way ANOVA and Bonferroni's post-hoc test;

FIG. 11A, FIG. 11B, FIG. 11C, FIG. 11D, FIG. 11E, FIG. 11F, FIG. 11G, FIG. 11H, and FIG. 11I show NOS2 knockdown decreases cell tumorigenicity, EMT transcription factors, spliced XBP1 and Smad2/3 signaling. Crosstalk between ER stress and TGFβ. Proliferation (FIG. 11A), migration (FIG. 11B) and primary and secondary mammospheres (FIG. 11C) of SUM159 cells transfected with two different NOS2-directed shRNAs (shRNA1, shRNA2) compared with empty vector (shRNA-EV). FIG. 11D: EMT transcription factors Snail and Slug in shRNA-mediated NOS2 knockdown MDA-MB-231 and SUM159 cells. FIG. 11E: Changes in Zeb1 and Twist1 protein levels were confirmed in SUM159 cells transfected with two different NOS2-directed siRNA (siRNA18, siRNA20; 100 nM siRNA) for 96 hrs. FIG. 11F: Unspliced XBP1 (uXBP1), spliced XBP1 (sXBP1) and β-Actin RT-PCR cDNA amplicons from MDA-MB-231 cells treated with 1400 W for 96 hrs. FIG. 11G: Protein-protein interaction analysis (STRING 9.1) deciphered a link between NOS2, TGFβ1 and ATF4/ATF3 axis. FIG. 11H: The iNOS inhibitor, 1400 W, is able to reduce the Smad2/3 signaling in MDA-MB-231 cells under treatment with recombinant TGFβ1 (10 ng/mL) for 72 hrs. FIG. 11I: Tunicamycin (5 μM) confirmed the crosstalk between ER stress and TGFβ through ATF4/ATF3 transcription factors. Results were normalized to empty vector. Data are presented as mean±SEM. **$p<0.0001$, *$p<0.001$, **$p<0.01$, *$p<0.05$; one-way ANOVA and Bonferroni's post-hoc test;

FIG. 12A, FIG. 12B, FIG. 12C, and FIG. 12D show representative images of mammospheres and wound healing assay in shRNA-mediated NOS2 knockdown cells. Illustrative images of primary and secondary mammospheres (FIG. 12A and FIG. 12B) and migration (wound healing assay) (FIG. 12C and FIG. 12D) in SUM159 and MDA-MB-231 cells transfected with two different NOS2-directed shRNAs (shRNA1, shRNA2) or empty vector (sRNA-EV);

FIG. 13A, FIG. 13B, FIG. 13C, FIG. 13D, and FIG. 13E show the in vivo effects of L-NMMA in SUM159 xenografts. FIG. 13A: Tumor volume of SUM159 breast xenografts (n=10/group) treated with vehicle, L-NMMA, chemotherapy and combination. Two-way ANOVA and Bonferroni's post-hoc test. FIG. 13B: Illustrative images of Ki67 staining in vehicle, L-NMMA, chemotherapy (docetaxel), and combination groups. Original optical objective: 10×. Counterstain: hematoxylin. FIG. 13C: Cell proliferation of tumor xenografts is depicted as Ki67 positive cells. 1,000 cells were counted from 10 different fields and percentage was determined. One-way ANOVA and Bonferroni's post-hoc test. Primary and secondary MSFE of breast cancer cells isolated from tumor tissue. FIG. 13D: One-way ANOVA and Bonferroni's post-hoc test. FIG. 13E: Tumor-initiating capacity of tumor cells assayed by the limiting dilution method. Fisher's exact test. Results were normalized to vehicle. Data are presented as mean±SEM. **$p<0.0001$, *$p<0.001$, **$p<0.01$, *$p<0.05$.

Figure 14A:
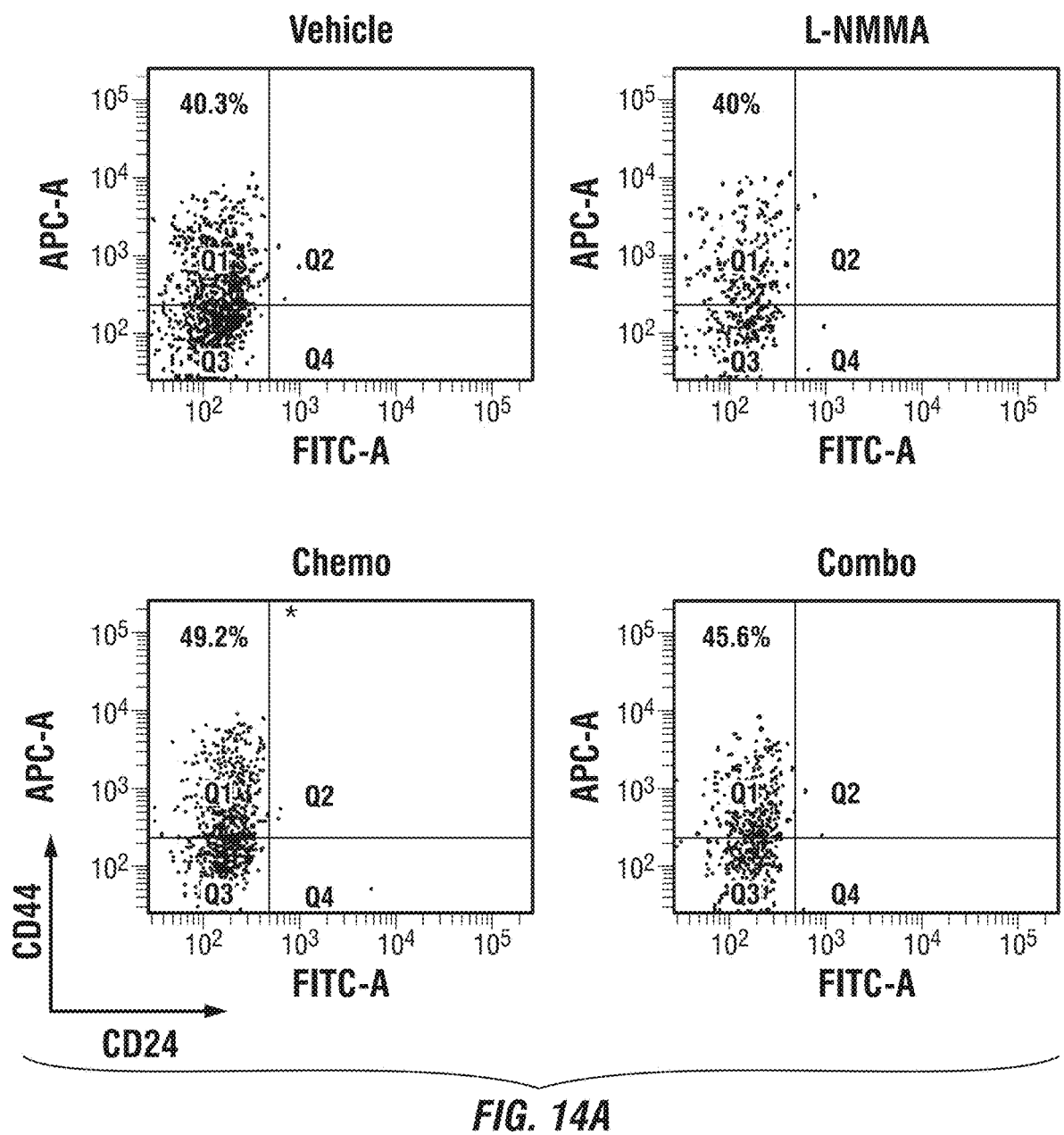
Figure 14B:
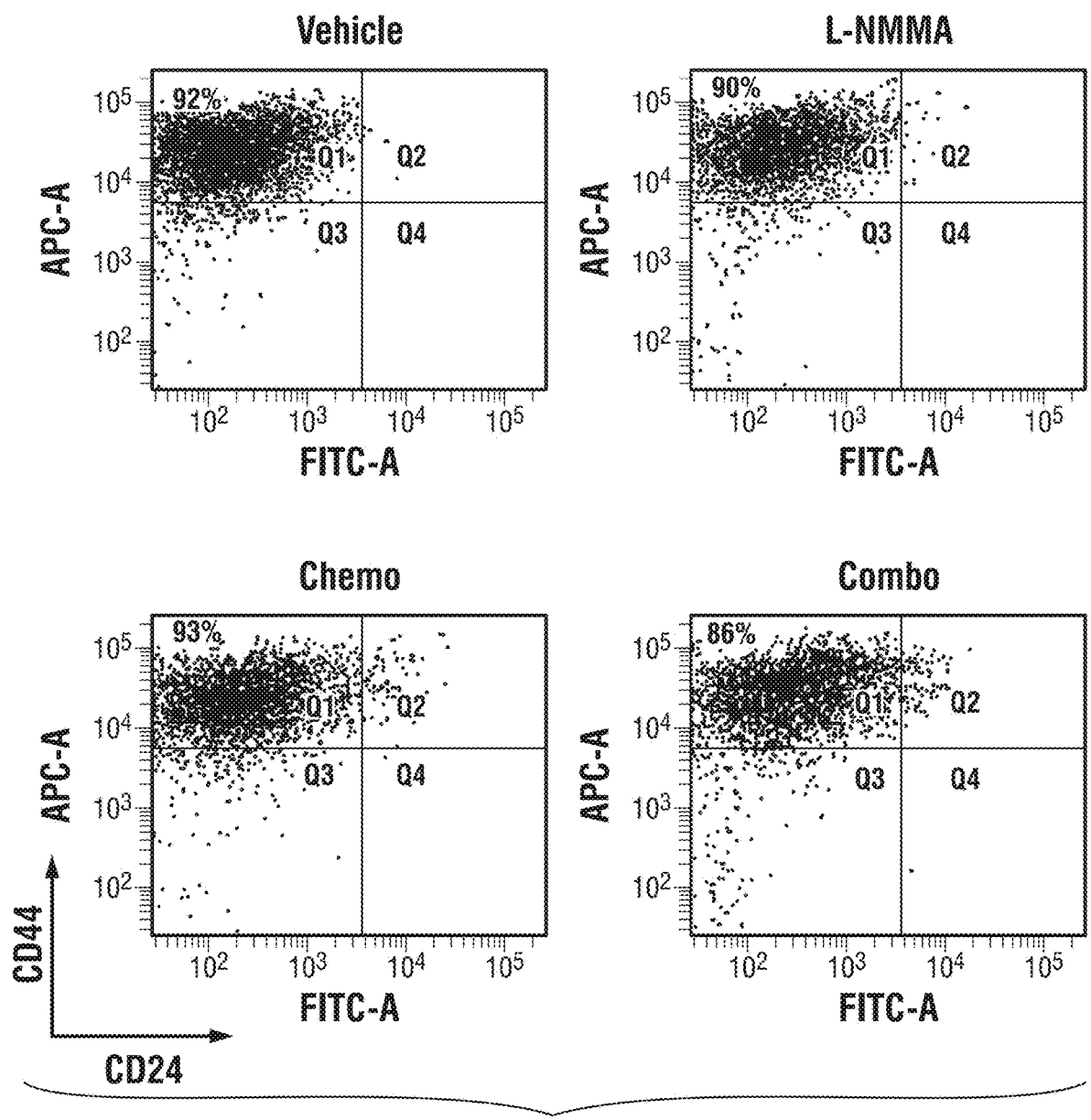
Figure 14E:
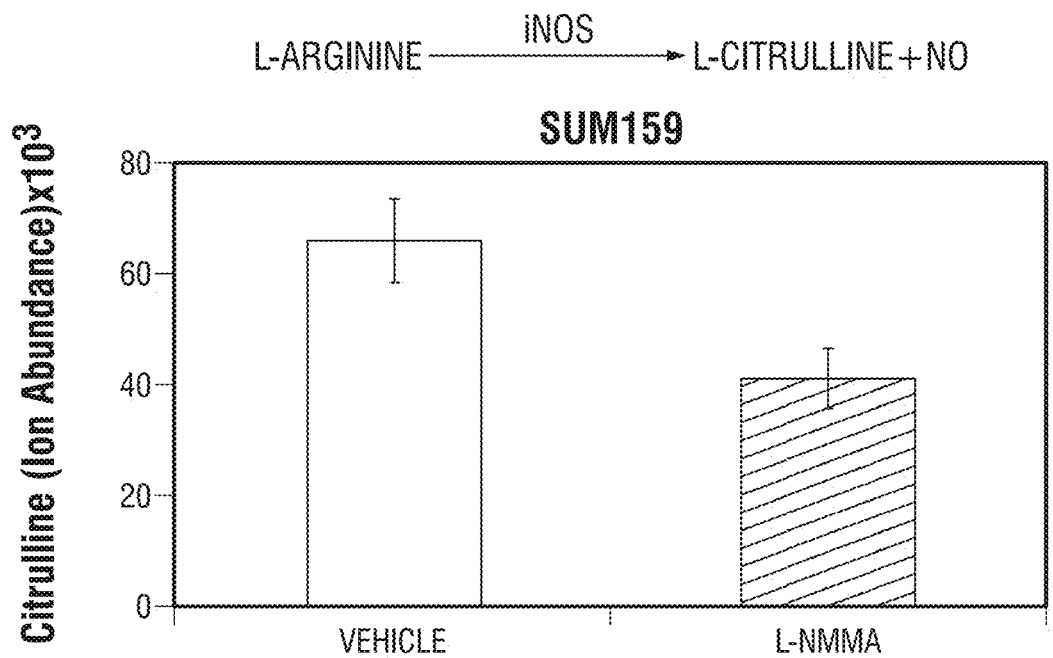
Figure 14F:
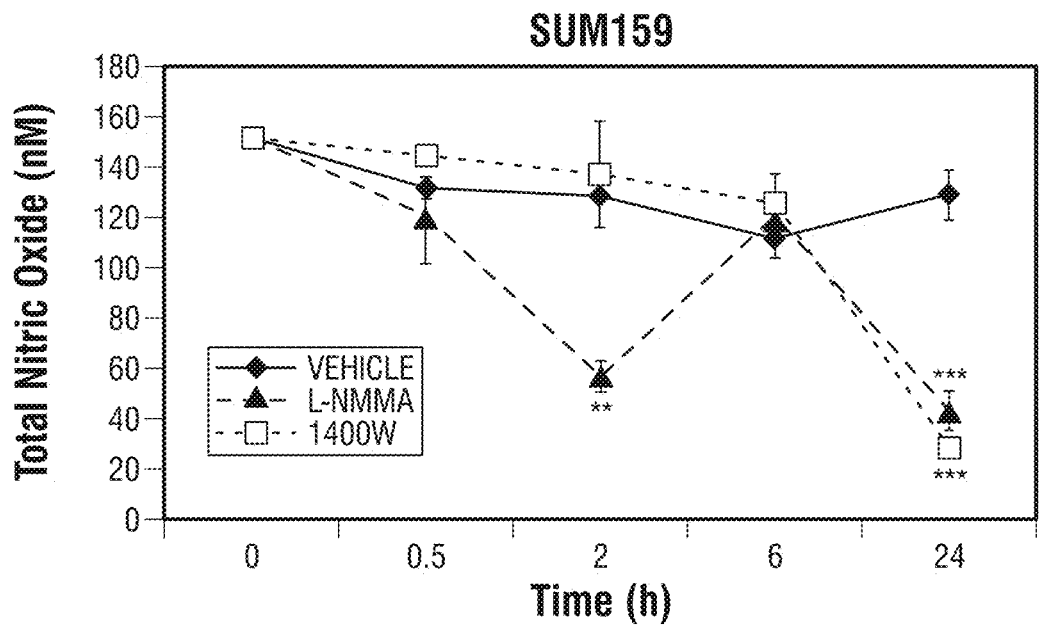
Figure 15A:
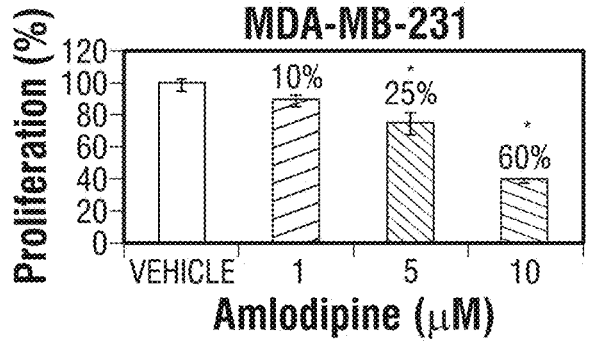
Figure 15B:
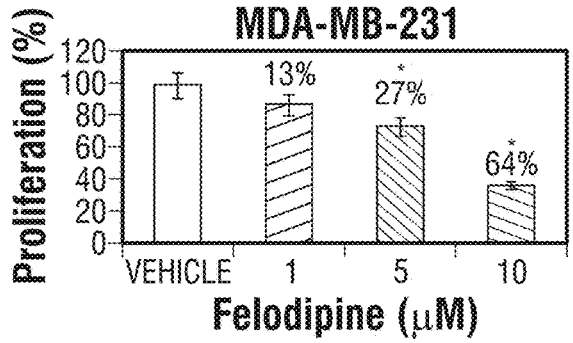
Figure 15C:
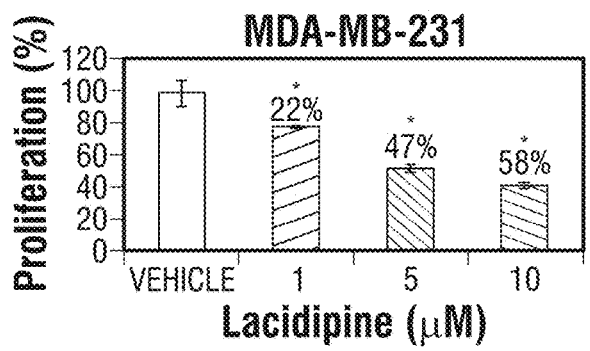
Figure 15D:
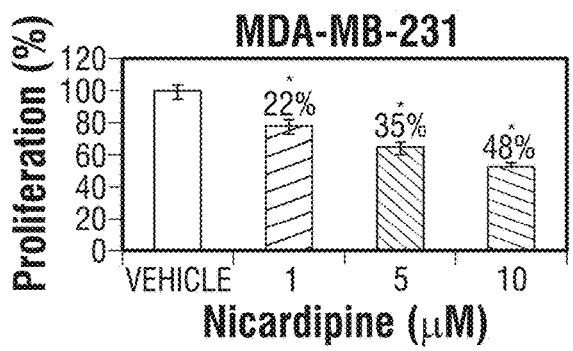
Figure 15E:
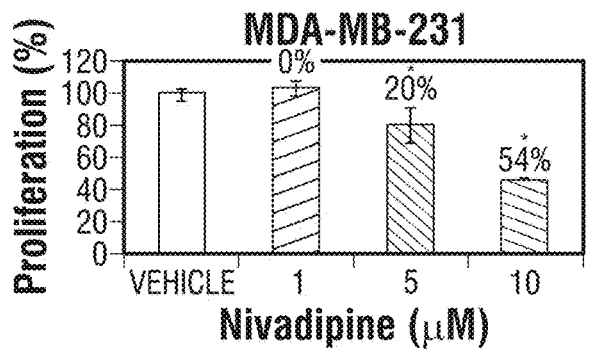
Figure 15F:
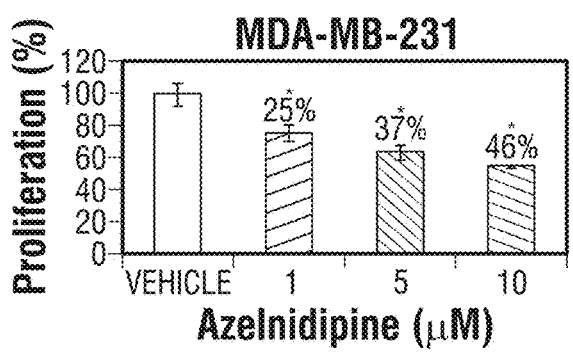
Figure 16A:
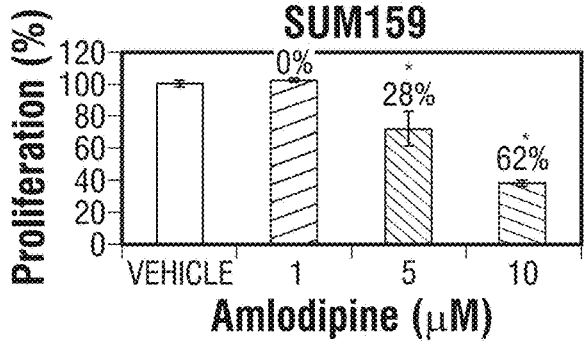
Figure 16B:
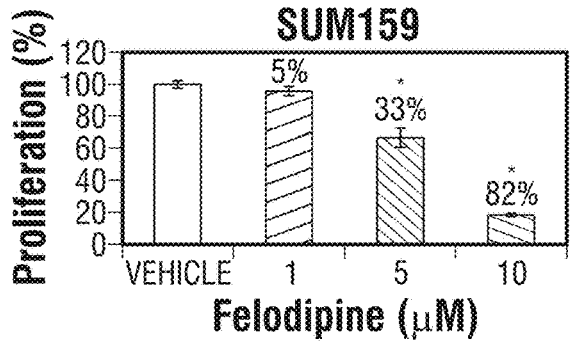
Figure 16C:
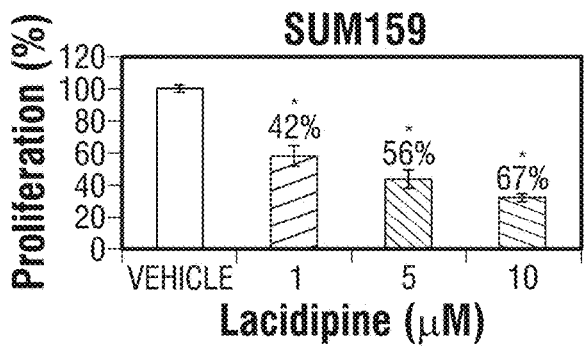
Figure 16D:
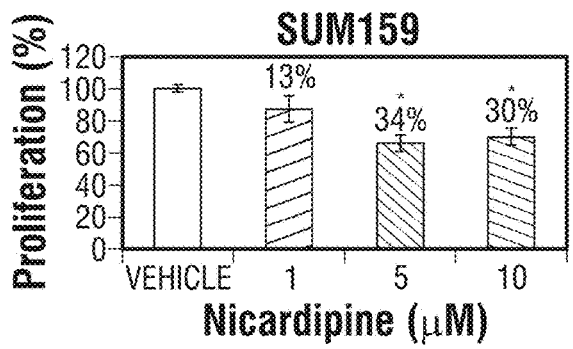
Figure 16E:
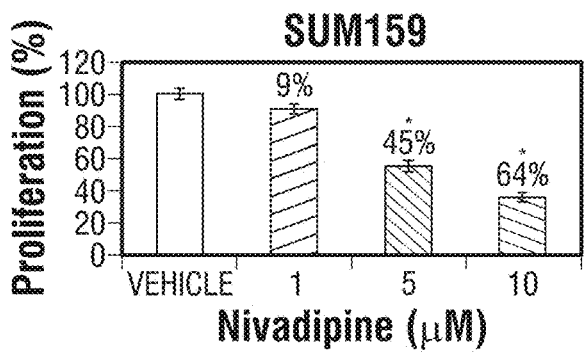
Figure 16F:
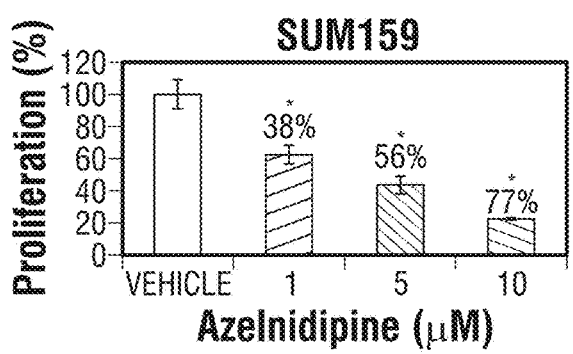
Figure 17A:
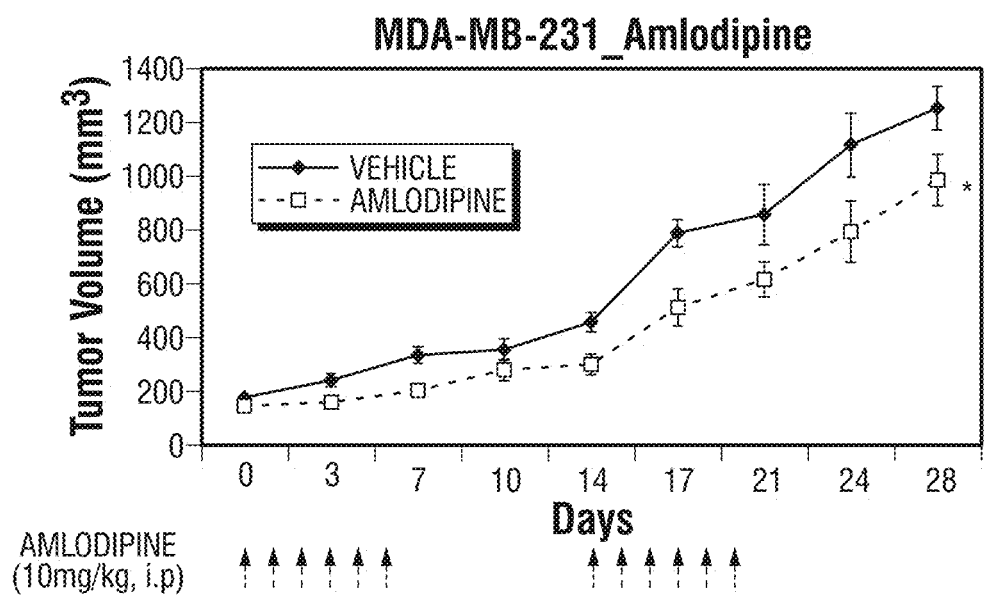
Figure 17B:
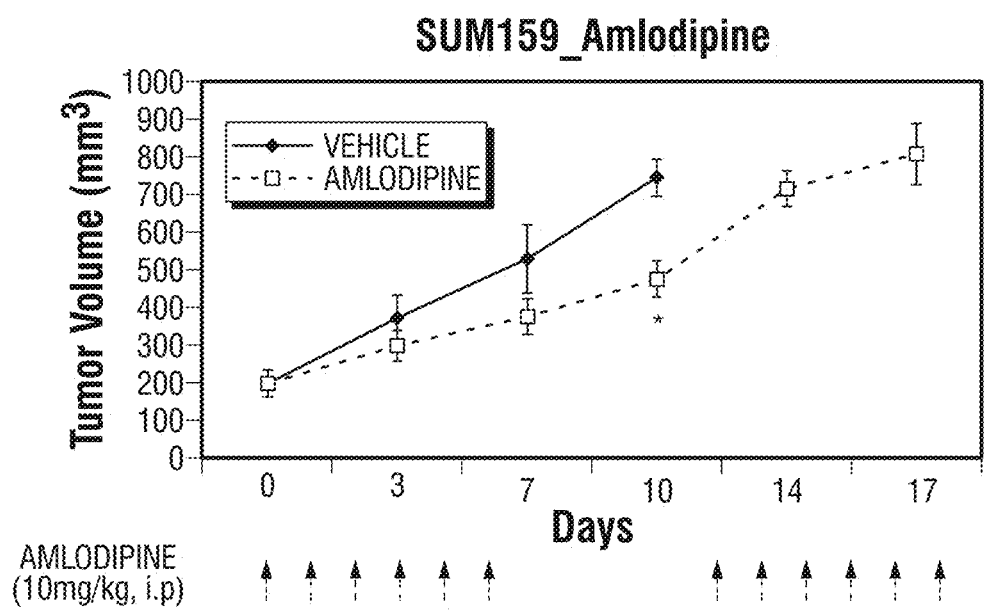
Figure 18A:
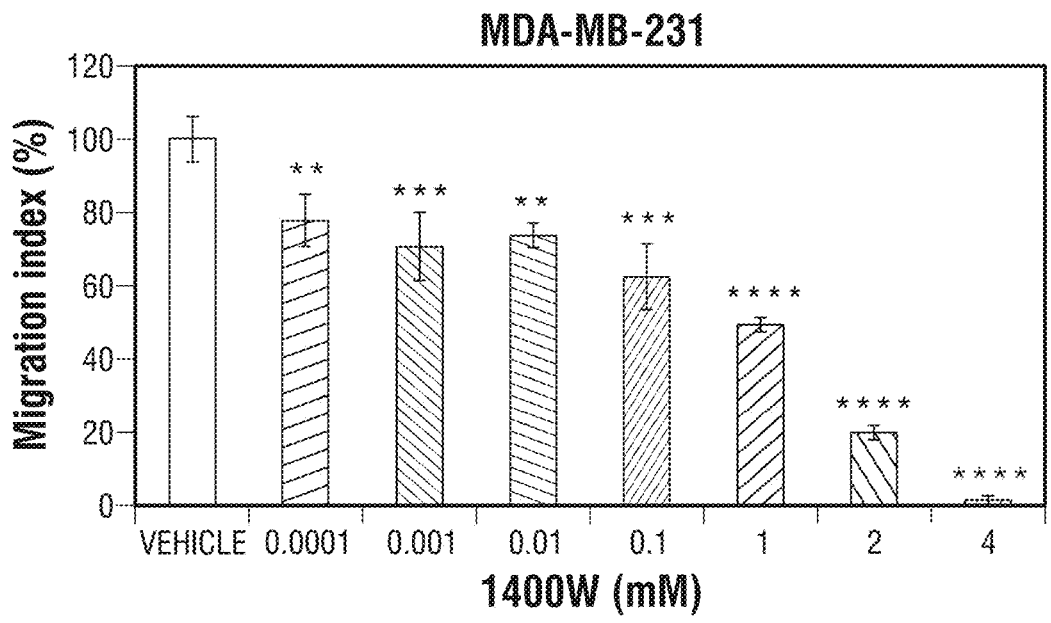
Figure 18B:
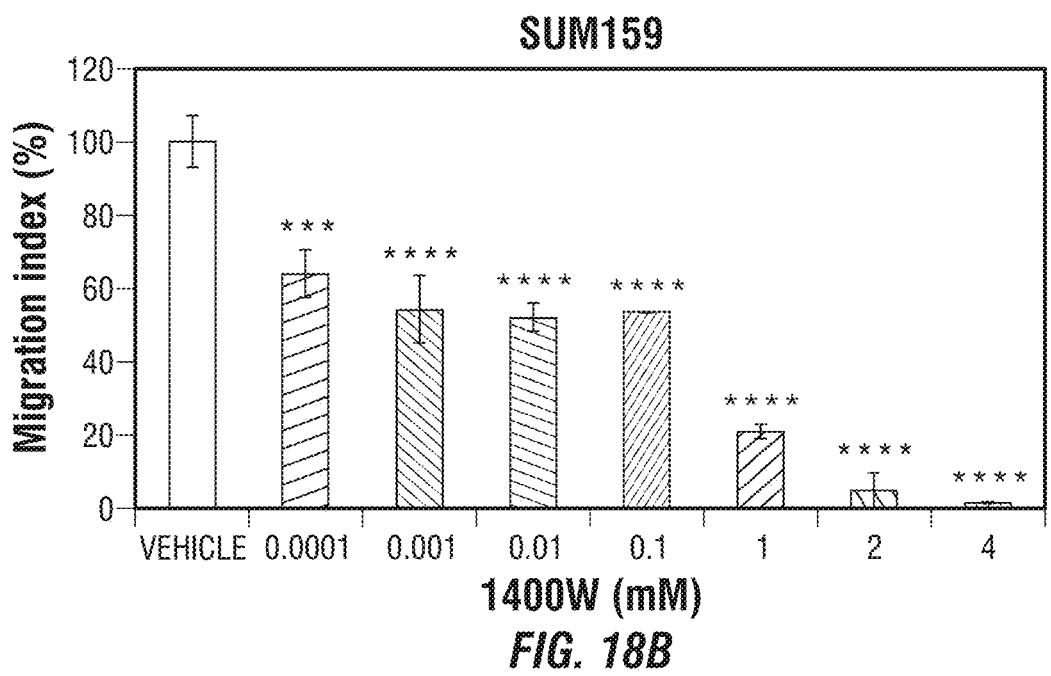
Figure 19A:
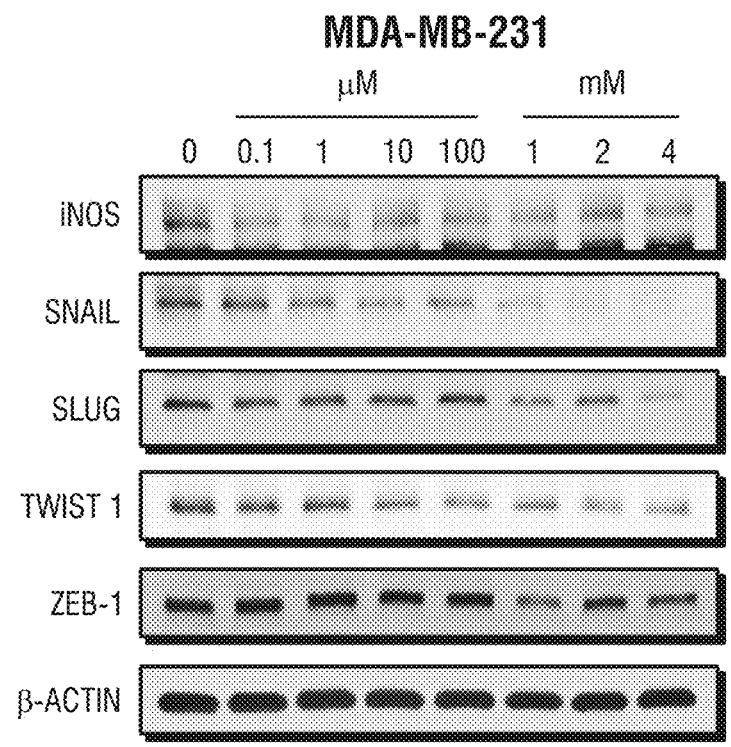
Figure 19B:
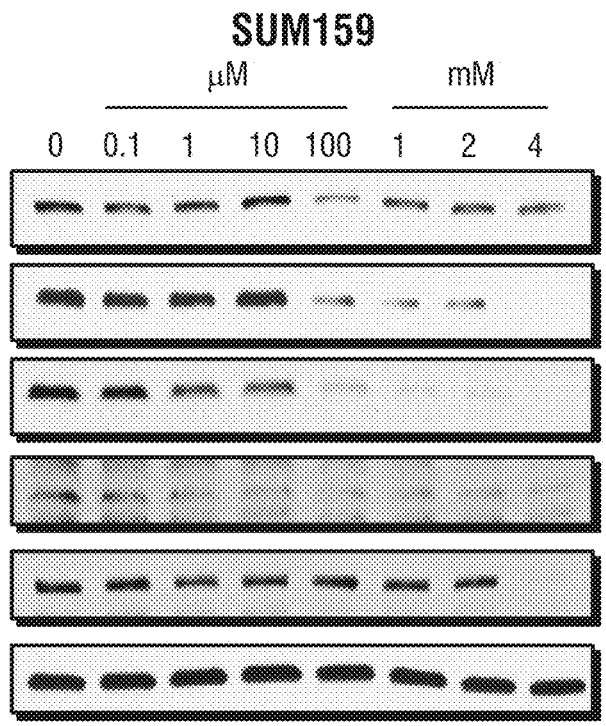
Figure 20A:
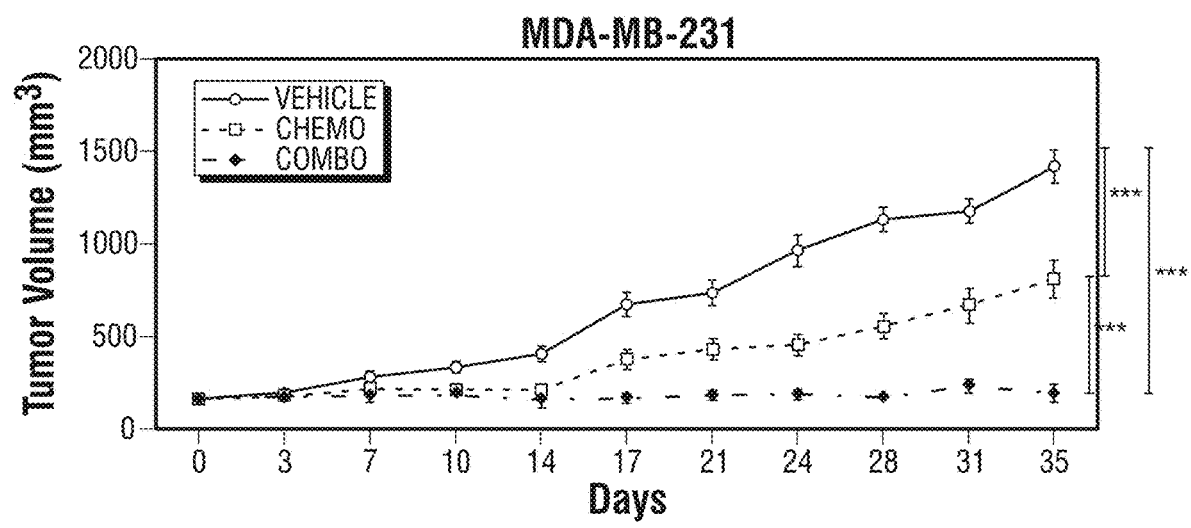
Figure 20B:
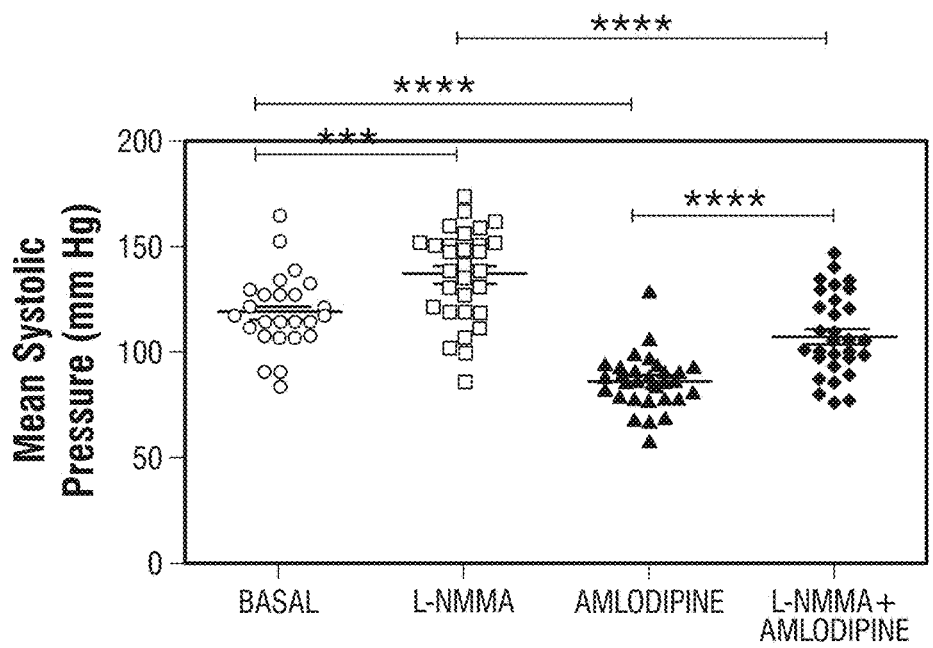
Figure 20C:
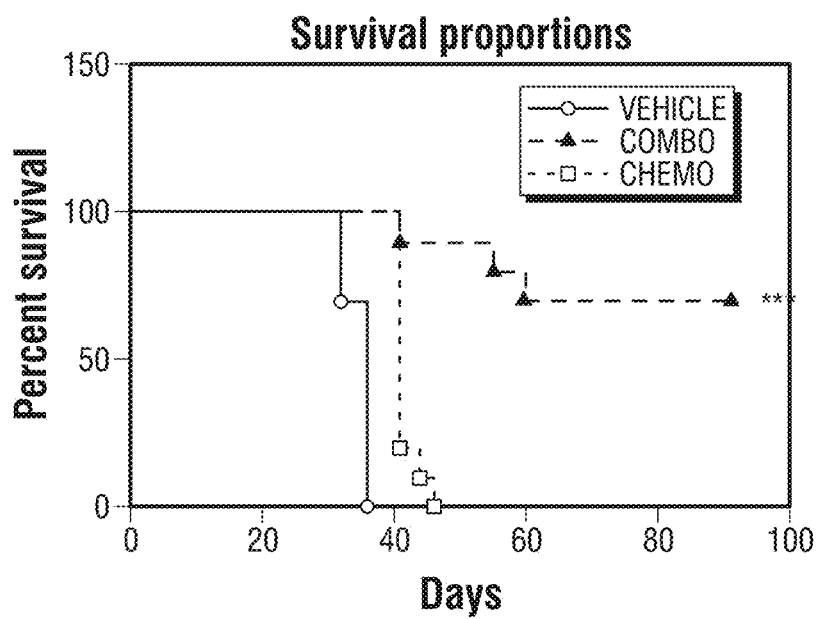
Figure 20D:
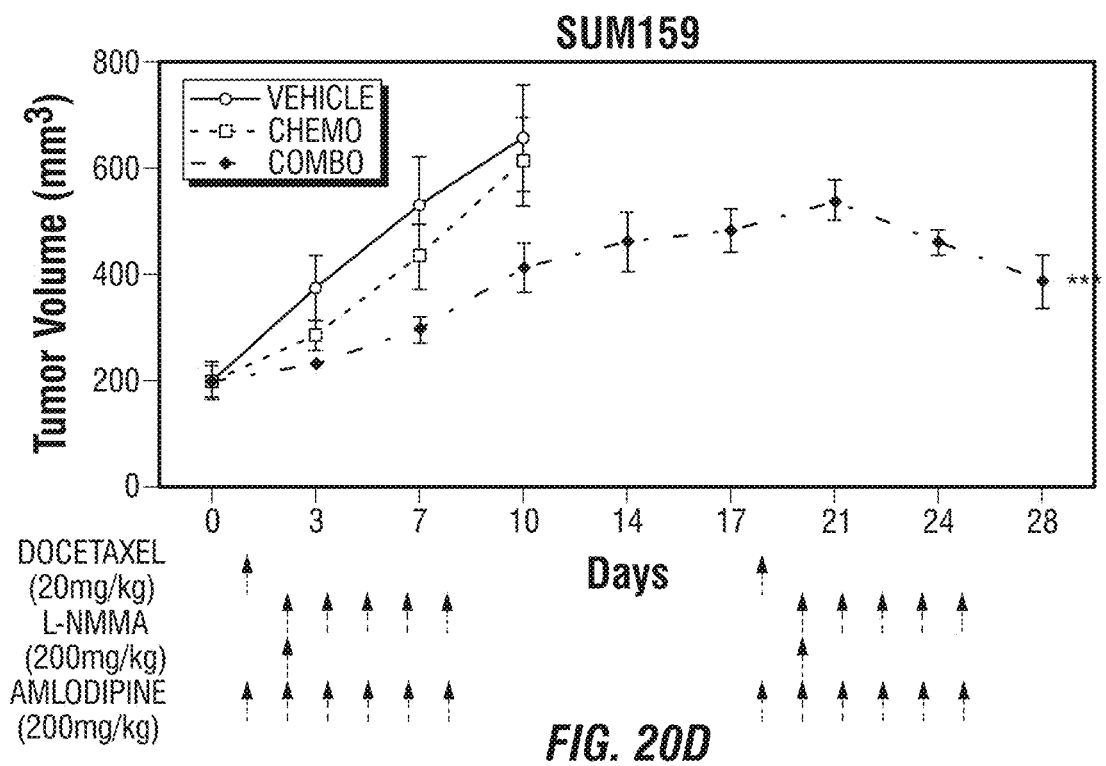
Figure 21:
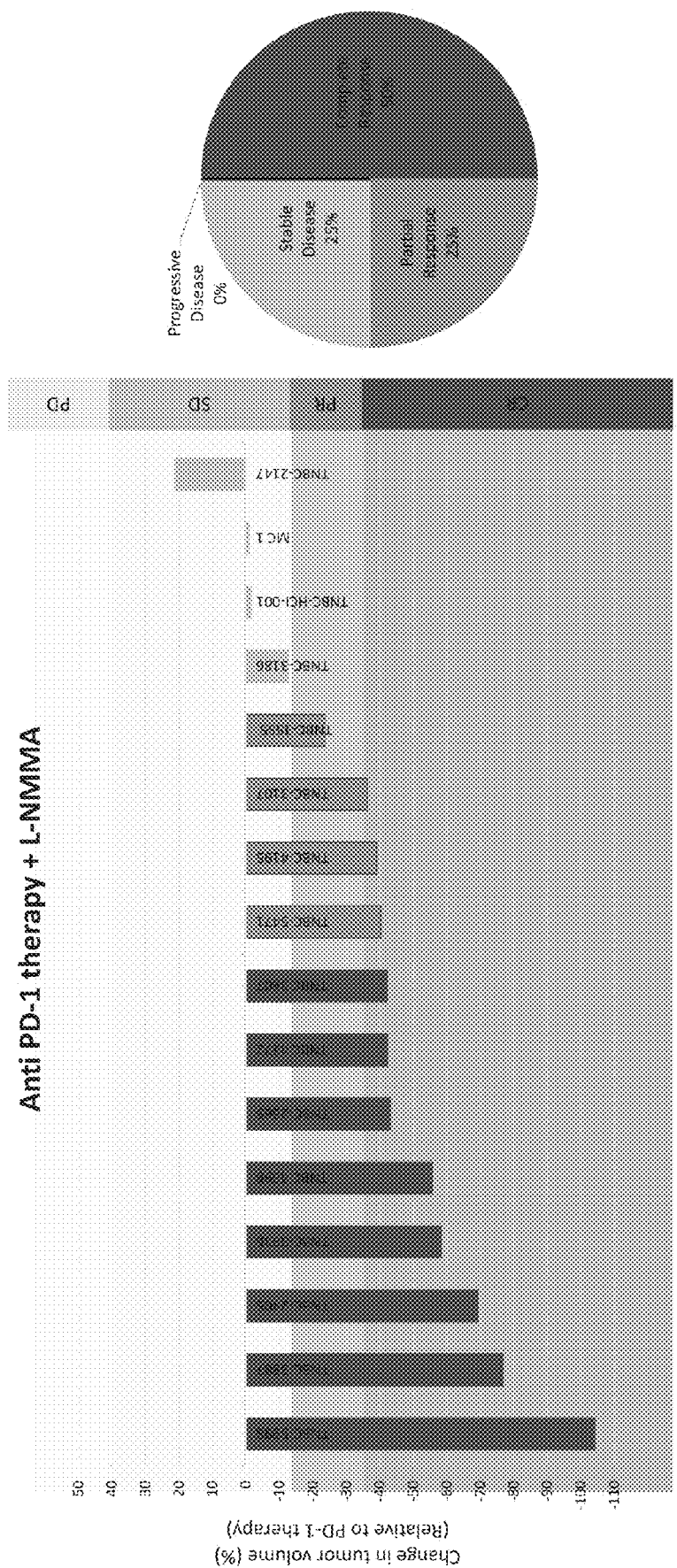
Figure 22:
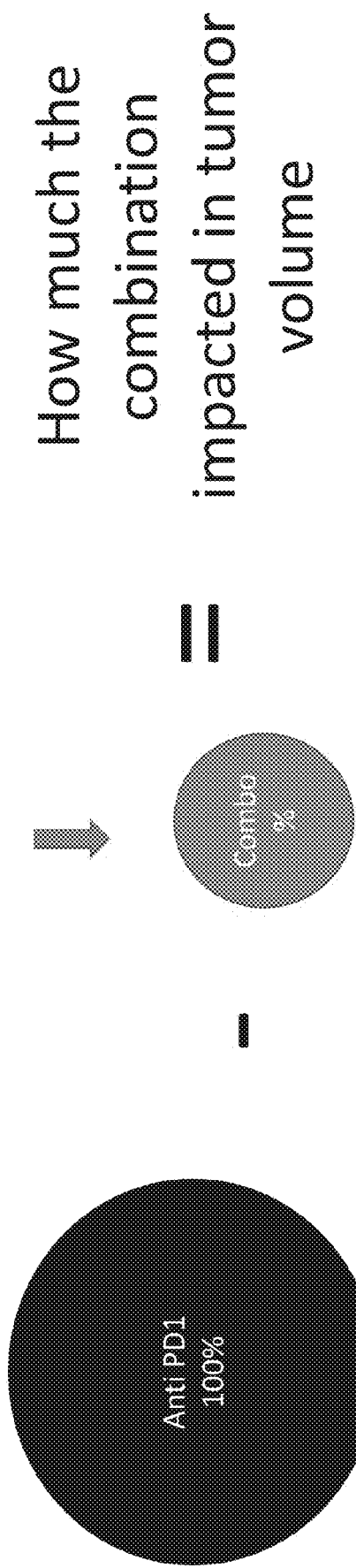
Figures 25A, 25B:
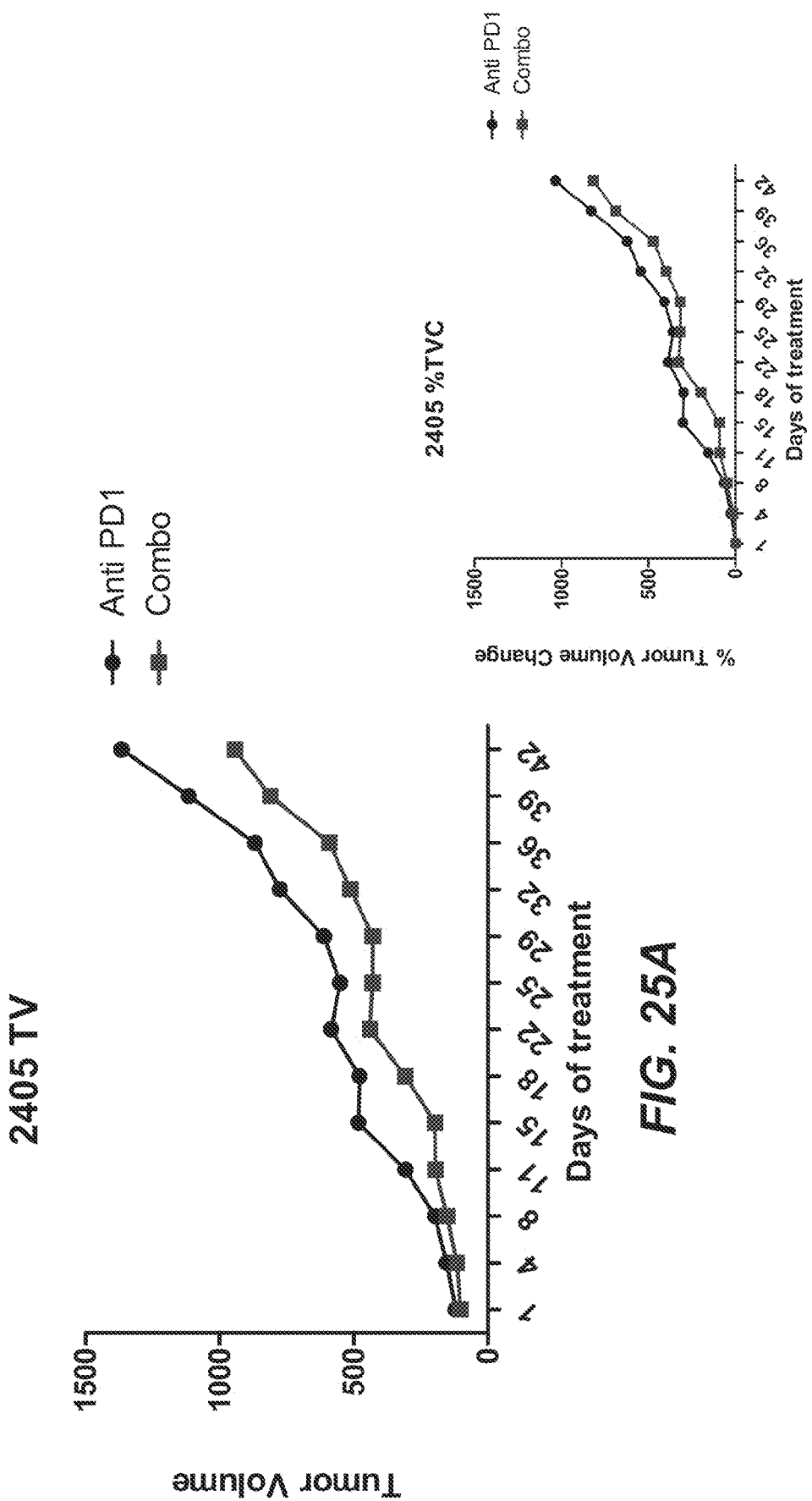
Figure 27:
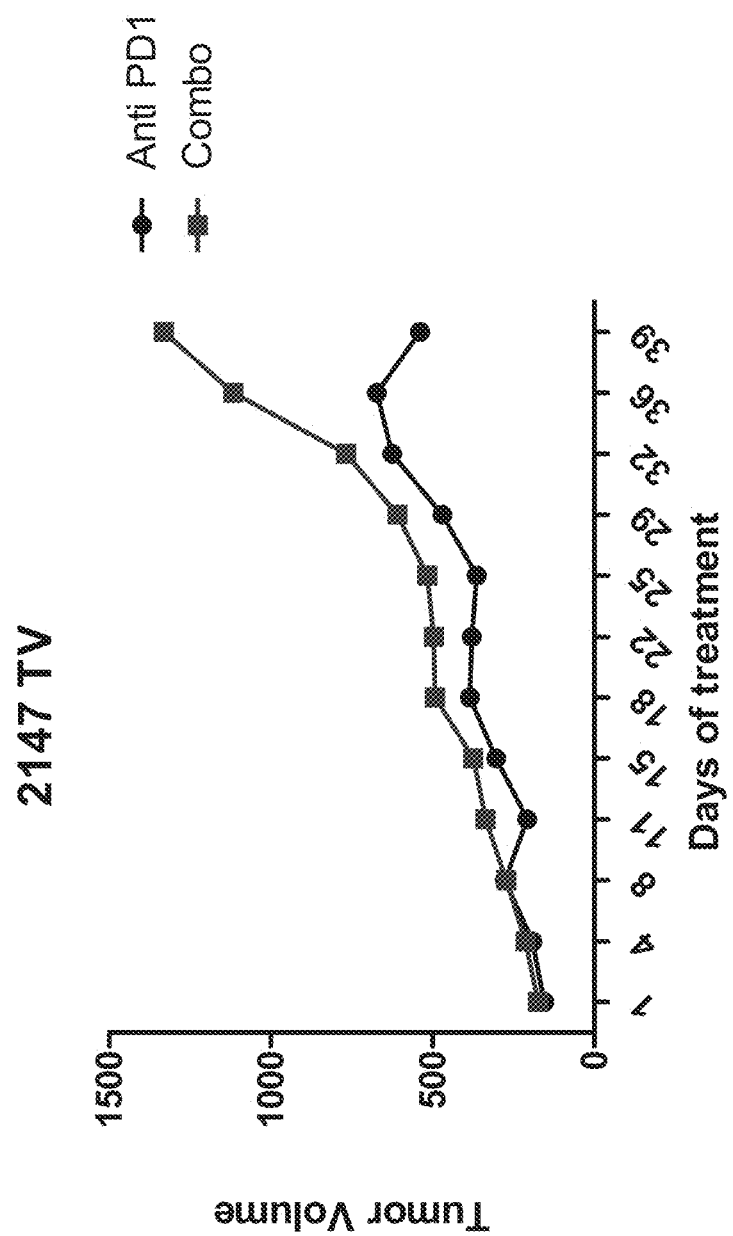
Figures 28A, 28B:
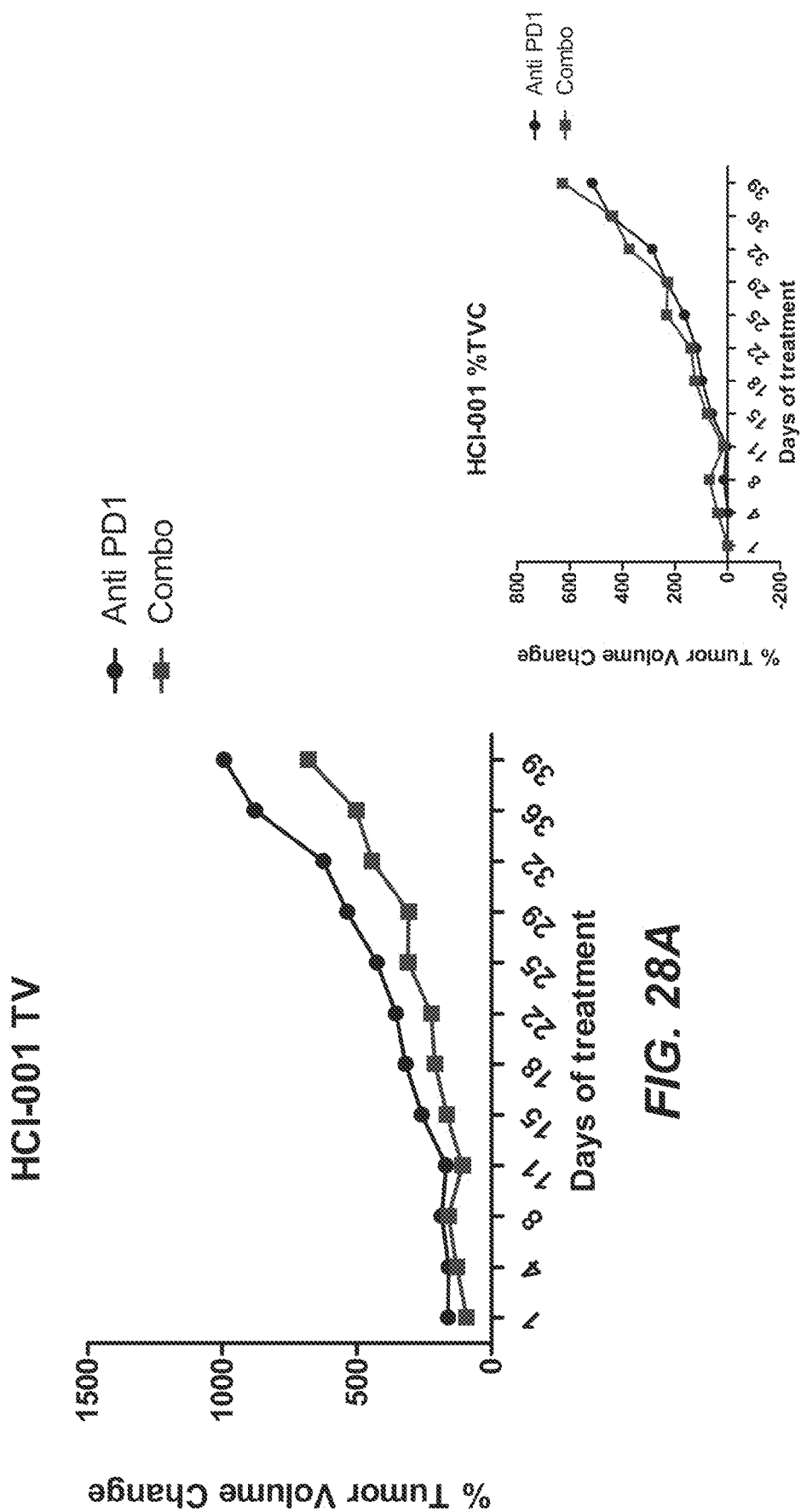
Figures 29A, 29B:
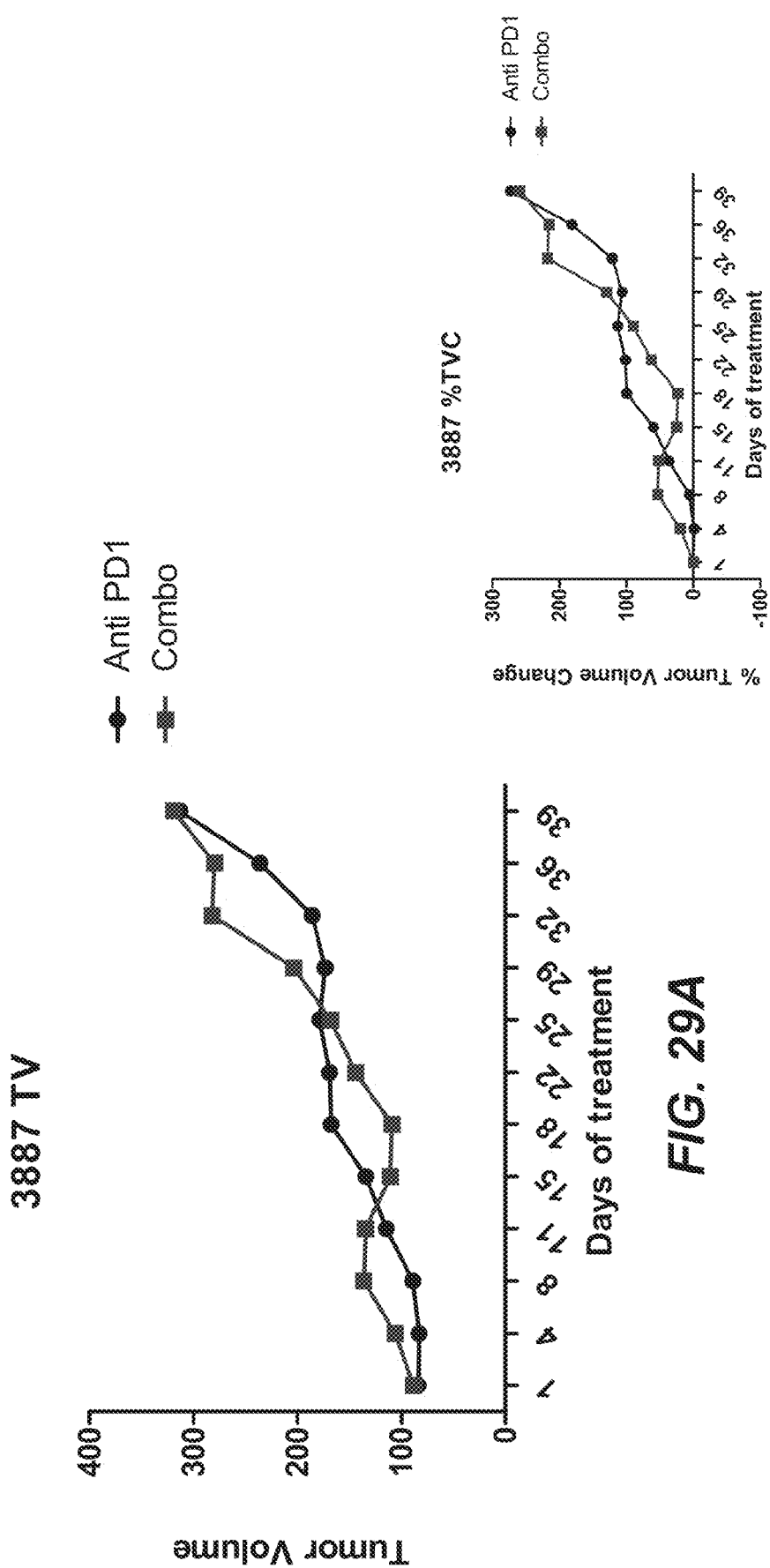
Figures 32A, 32B:
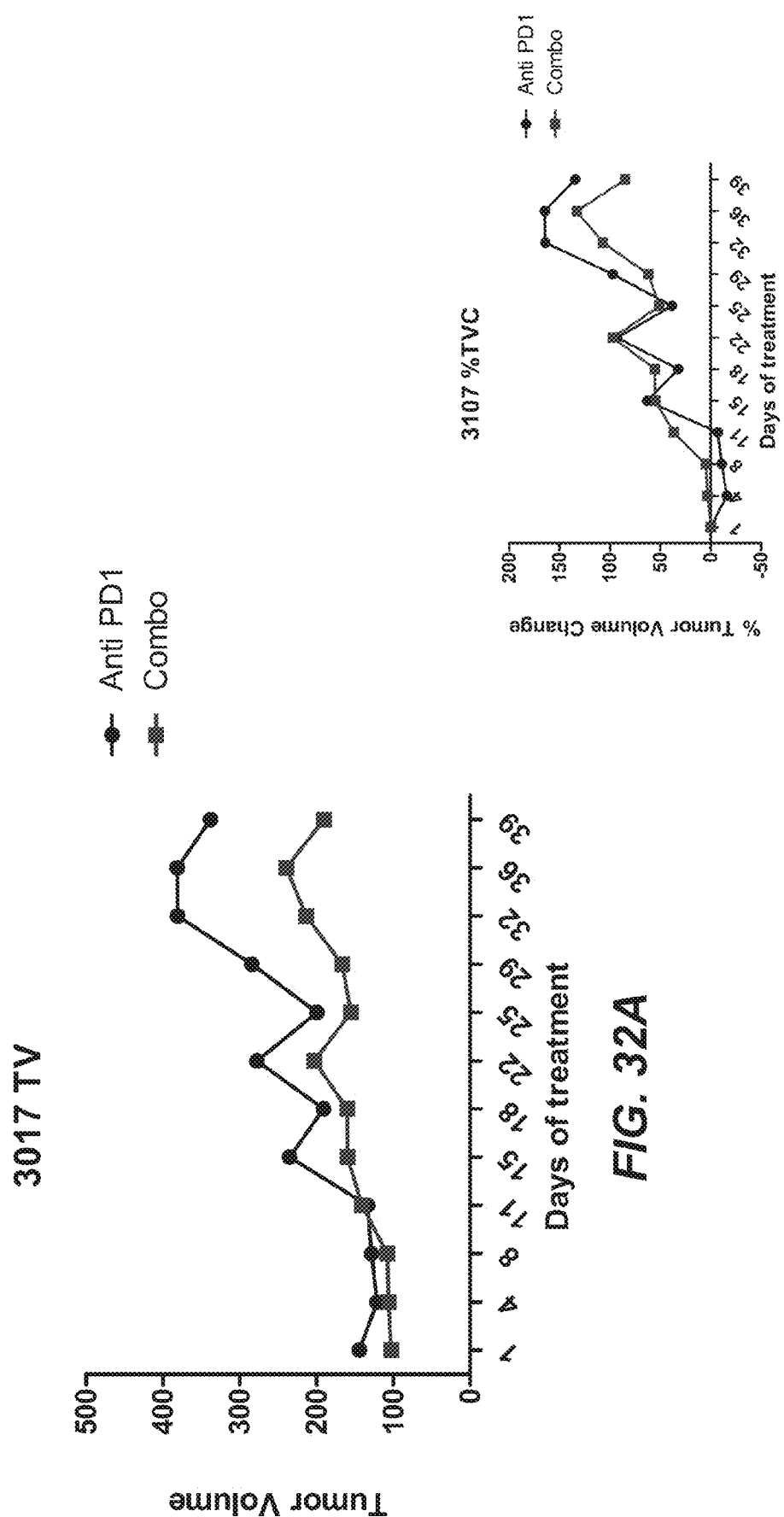
Figure 37A:
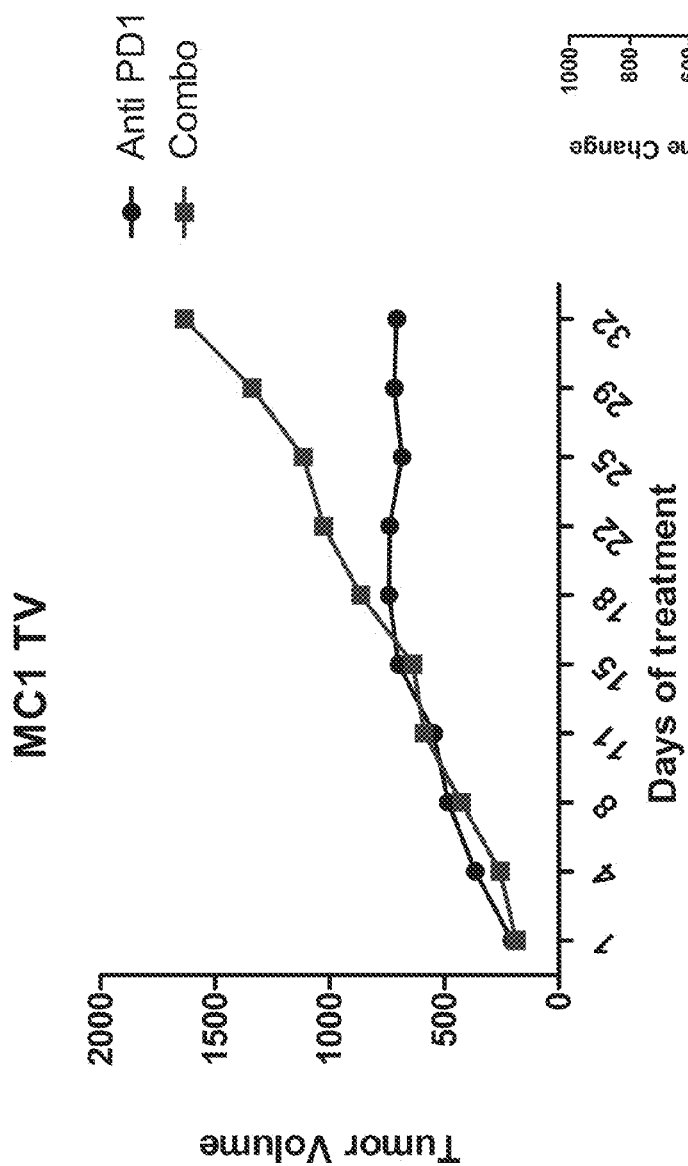
Figure 37B:
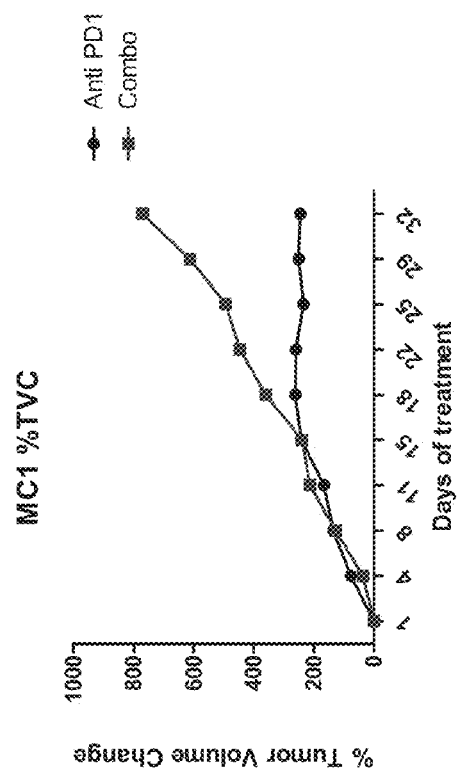
Figures 39A, 39B:
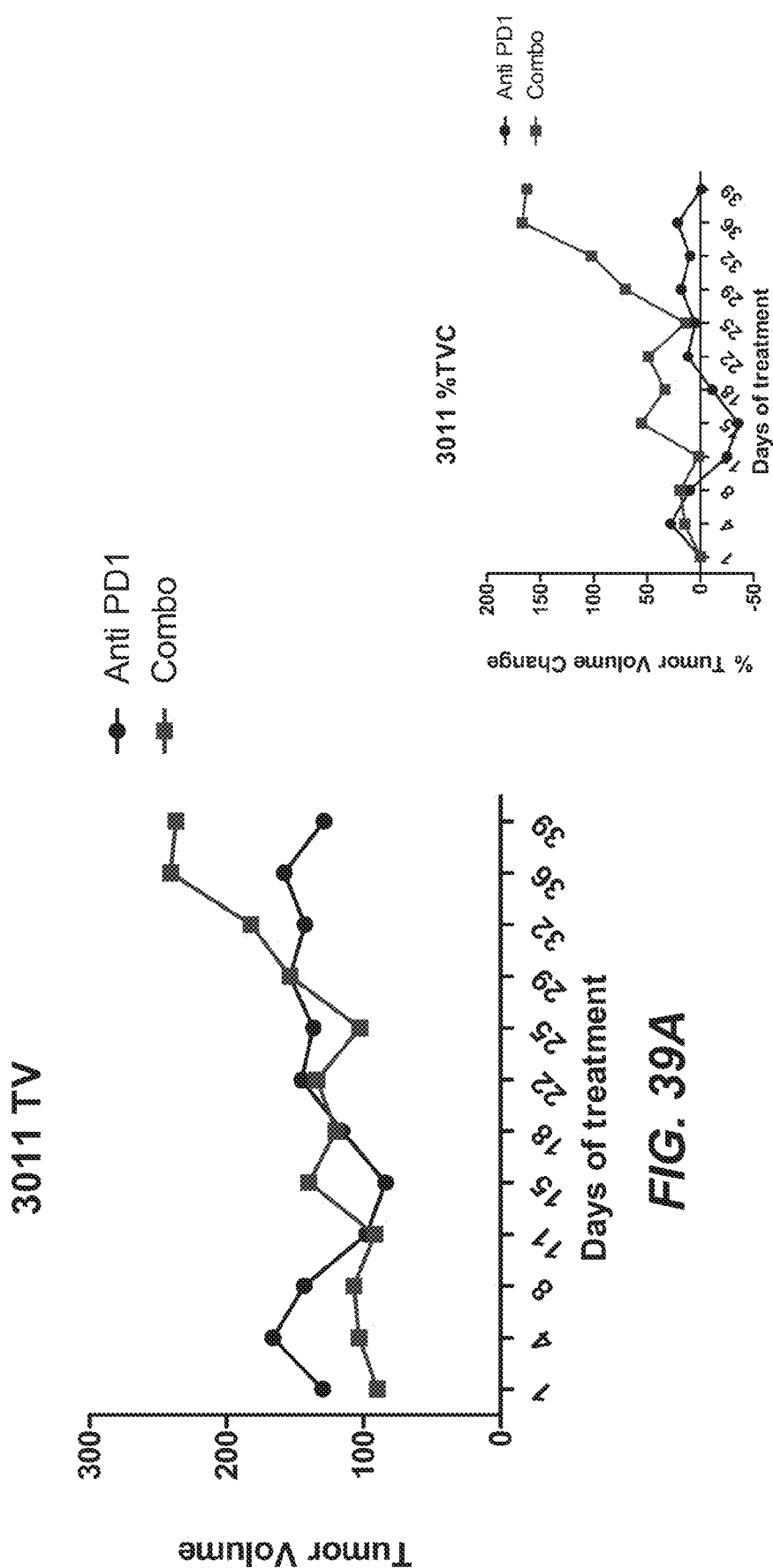
Figures 43A, 43B:
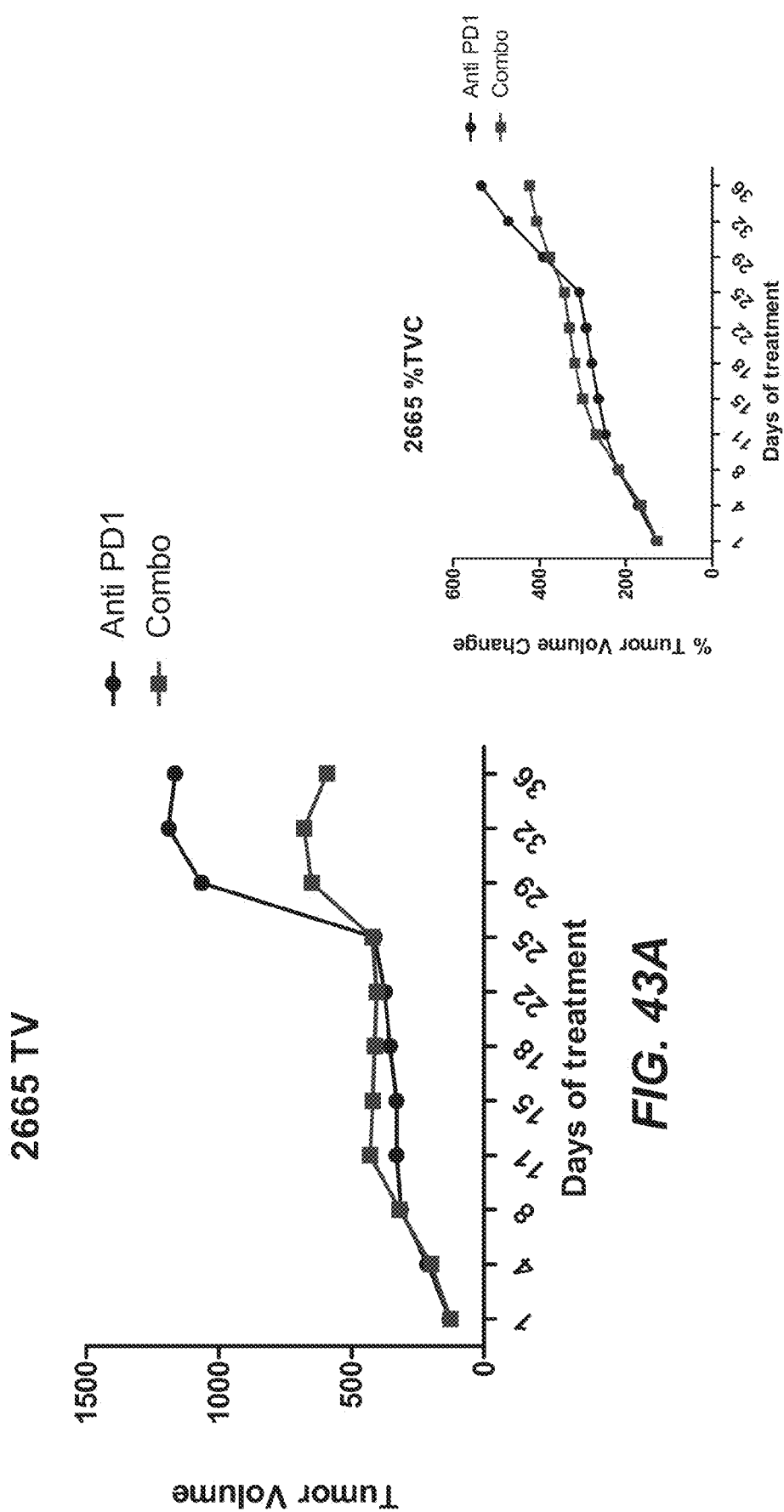
Figures 44A, 44B:
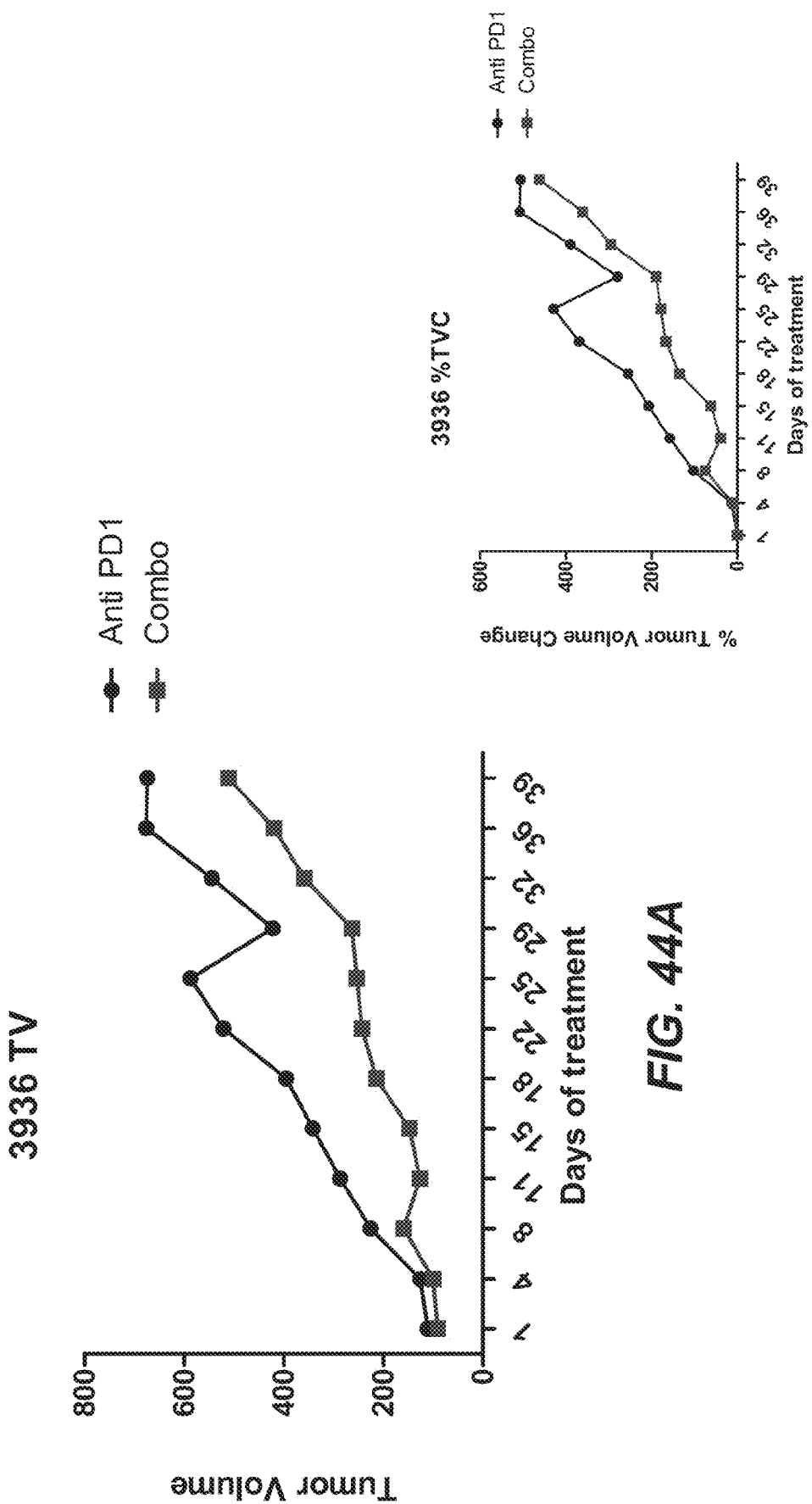

FIG. 14A, FIG. 14B, FIG. 14C, FIG. 14D, FIG. 14E, and FIG. 14F show L-NMMA levels in plasma and tumor tissue. $CD44^+/CD24^{-/low}$ population in L-NMMA-treated xenografts. Flow cytometric analysis (% Parent) of $CD44^+/CD24^{-/low}$ cells isolated from SUM159 (FIG. 14A) and MDA-MB-231 (FIG. 14B) xenograft tumor tissue of mice treated with vehicle, L-NMMA, docetaxel and combination (docetaxel+L-NMMA). FIG. 14C and FIG. 14D: Ratiometric quantification of methylarginine in plasma and tumor tissue (MDA-MB-231 and SUM159 xenografts) by LC-MS/MS (Student's t-test). FIG. 14E: iNOS catalyzes the reaction of L-arginine to L-citrulline+nitric oxide (NO). Ratiometric quantification of citrulline SUM159 xenograft tissue LC-MS/MS (Student's t-test). FIG. 14F: Total nitric oxide production in SUM159 cells treated with L-NMMA and 1400 W (4 mM) for 0.5, 2, 6 and 24 hrs. Results were normalized to vehicle. Data are presented as mean±SEM. **$p<0.0001$, *$p<0.001$, **$p<0.01$, *$p<0.05$; one-way ANOVA and Bonferroni's post-hoc test;

FIG. 15A, FIG. 15B, FIG. 15C, FIG. 15D, FIG. 15E, and FIG. 15F show the effects of calcium channel antagonists on proliferation in MDA-MB-231 cells (percentage of decrease in proliferation is shown above bars);

FIG. 16A, FIG. 16B, FIG. 16C, FIG. 16D, FIG. 16E, and FIG. 16F show the effects of calcium channel antagonists on cellular proliferation in SUM159 cells (percentage of decrease in proliferation is shown above bars);

FIG. 17A and FIG. 17B illustrate the anti-tumor activity of amlodipine mouse models of triple negative breast cancer;

FIG. 18A and FIG. 18B show the migration of MDA-MB-231 and SUM159 cells was assessed by "wound healing" assay. Briefly, $3\times10^5$ cells were plated in a 6-well plate until confluence in growth medium. Cells in monolayer were treated with 1400 W (0, 0.0001, 0.001, 0.01, 0.1, 1, 2, 4 mM) in low serum conditions (1%) for 72 hrs and 24 hrs regular growth medium in presence of inhibitor for 24 hrs (96 hrs total). A "wound" was then created in the cell monolayer. Images were taken at 0 and 12 hrs. Wound-healing capacity was determined with the software Image J. Data were replicated in three independent experiments. Results were normalized to vehicle;

FIG. 19A and FIG. 19B show the effects of selective iNOS inhibition on epithelial-mesenchymal (EMT)-inducing factors were tested by Western blot in MDA-MB-231 and SUM159 cell lines. Cells were treated with 1400 W (0.1, 1, 10, 100 µM; 1, 2, 4 mM) for 96 hrs. Protein levels of iNOS and EMT-inducing factors were determined by Western blot with antibodies against: iNOS (N-20) and Twist1 (L-21) (Santa Cruz Biotechnology), Snail (C15D3), Slug (C19G7) and TCF8/Zeb1 (D80D3) (Cell Signaling) (1:1000 dilution). β-actin (Cell Signaling; 1:2000) was used as loading control;

FIG. 20A, FIG. 20B, FIG. 20C, and FIG. 20D show MDA-MB-231 and SUM159 cells ($3\times10^6$) were injected in the right mammary fat pad of female SCID Beige mice (n=10/group). The clinically-relevant dose regimen consisted on two cycles of docetaxel (20 mg/kg, i.p., on day 0) 12 hrs before being combined with L-NMMA (400 mg/kg on day 1, and 200 mg/kg for 4 additional days by oral gavage) and amlodipine on day 0 (10 mg/kg, i.p., daily, for 6 days). Docetaxel alone, as well as saline (i.p.)+sterile water (oral gavage) were used as controls. The combination of L-NMMA and docetaxel was able to decrease tumor growth in MDA-MB-231 and SUM159 xenografts (FIG. 20A and FIG. 20D). Amlodipine prevented the L-NMMA-induced increase of blood pressure (FIG. 20B). This dose regimen also improved survival compared to docetaxel alone in MDA-MB-231 xenografts (FIG. 20C). **$p<0.0001$, *$p<0.001$;

FIG. 21 shows h-NSG mice growing TNBC orthotropic tumors were randomized and treated with anti PD-1 antibody, or LNMMA 200 mg/kg+anti PD-1 antibody. Tumor volumes were measured twice weekly. % Tumor volume change difference between TNBC h-PDX treated with pembrolizumab (KEYTRUDA®; Merck) against a combination of pembrolizumab and L-NMMA. Eight TNBC models show complete response, 4 partial response, and 4 stable disease when compared to monotherapy with pembrolizumab alone;

FIG. 22 shows an illustrative calculation for determining how much the combination effects tumor volume;

FIG. 23A and FIG. 23B show the extent that the combination of L-NMMA and amlodipine improves the effects of anti-PD1 antibody against the TNBC-4195 tumor cell line;

FIG. 24A and FIG. 24B show the extent that the combination of L-NMMA and amlodipine improves the effects of anti-PD1 antibody against the 5471 TV tumor cell line;

FIG. 25A and FIG. 25B show the extent that the combination of L-NMMA and amlodipine improves the effects of anti-PD1 antibody against the 2405 TV tumor cell line;

FIG. 26A and FIG. 26B show the extent that the combination of L-NMMA and amlodipine improves the effects of anti-PD1 antibody against the 2665 TV tumor cell line;

FIG. 27 shows the extent that the combination of L-NMMA and amlodipine improves the effects of anti-PD1 antibody against the 4147 TV tumor cell line;

FIG. 28A and FIG. 28B show the extent that the combination of L-NMMA and amlodipine improves the effects of anti-PD1 antibody against the HCl-001 TV tumor cell line;

FIG. 29A and FIG. 29B show the extent that the combination of L-NMMA and amlodipine improves the effects of anti-PD1 antibody against the 3887 TV tumor cell line;

FIG. 30A, FIG. 30B, FIG. 30C, and FIG. 30D show the extent that the combination of L-NMMA and amlodipine improves the effects of anti-PD1 antibody against the TNBC 5998 tumor cell line;

FIG. 31A and FIG. 31B show the extent that the combination of L-NMMA and amlodipine improves the effects of anti-PD1 antibody against the 3186 TV tumor cell line;

FIG. 32A and FIG. 32B show the extent that the combination of L-NMMA and amlodipine improves the effects of anti-PD1 antibody against the 3017 TV tumor cell line;

FIG. 33A and FIG. 33B show the extent that the combination of L-NMMA and amlodipine improves the effects of anti-PD1 antibody against the 4698 TV tumor cell line;

FIG. 34A and FIG. 34B show the extent that the combination of L-NMMA and amlodipine improves the effects of anti-PD1 antibody against the 3807 TV tumor cell line;

FIG. 35A and FIG. 35B show the extent that the combination of L-NMMA and amlodipine improves the effects of anti-PD1 antibody against the 3936 TV tumor cell line;

FIG. 36A and FIG. 36B show the extent that the combination of L-NMMA and amlodipine improves the effects of anti-PD1 antibody against the 4272 TV tumor cell line;

FIG. 37A and FIG. 37B show the extent that the combination of L-NMMA and amlodipine improves the effects of anti-PD1 antibody against the MC1 TV tumor cell line;

FIG. 38A and FIG. 38B show the extent that the combination of L-NMMA and amlodipine improves the effects of anti-PD1 antibody against the HCl-010 TV tumor cell line;

FIG. 39A and FIG. 39B show the extent that the combination of L-NMMA and amlodipine improves the effects of anti-PD1 antibody against the 3011 TV tumor cell line;

FIG. 40A and FIG. 40B show the extent that the combination of L-NMMA and amlodipine improves the effects of anti-PD1 antibody against the TNBC-3555 tumor cell line;

FIG. 41A and FIG. 41B show the extent that the combination of L-NMMA and amlodipine improves the effects of anti-PD1 antibody against the TNBC-4664 tumor cell line;

FIG. 42A and FIG. 42B show the extent that the combination of L-NMMA and amlodipine improves the effects of anti-PD1 antibody against the HER2-3963 TV tumor cell line;

FIG. 43A and FIG. 43B show the extent that the combination of L-NMMA and amlodipine improves the effects of anti-PD1 antibody against the 2665 TV tumor cell line;

FIG. 44A and FIG. 44B show the extent that the combination of L-NMMA and amlodipine improves the effects of anti-PD1 antibody against the 3936 TV tumor cell line;

FIG. 45A, FIG. 45B, and FIG. 45C show humanized PDX models and mouse avatars; and FIG. 46A, FIG. 46B, FIG. 46C, and FIG. 46D show anti-PD1 activity and upregulation of NO signaling in Hu-PDX models.

BRIEF DESCRIPTION OF THE SEQUENCES

SEQ ID NO:1 is an exemplary DNA oligonucleotide forward primer, useful in accordance with one or more aspects of the present disclosure;

SEQ ID NO:2 is an exemplary DNA oligonucleotide reverse primer, useful in accordance with one or more aspects of the present disclosure;

SEQ ID NO:3 is an exemplary DNA oligonucleotide forward primer, useful in accordance with one or more aspects of the present disclosure; and SEQ ID NO:4 is an exemplary DNA oligonucleotide reverse primer, useful in accordance with one or more aspects of the present disclosure.

DESCRIPTION OF ILLUSTRATIVE EMBODIMENTS

Illustrative embodiments of the present disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

It has been demonstrated that breast cancer cells with stem-like properties are intrinsically resistant to conventional therapy. Since this initial discovery, others have confirmed the result by establishing the resistance of these cells to conventional chemotherapy and radiation therapy. Studies have also supported the finding that an increase in the stem-like cell population is associated with a worse prognosis. These findings have fundamental clinical implications.

Current development of cancer therapeutics is largely based on identifying agents with the ability to cause bulk tumor regression in animal models or in clinical trials; however, an exclusive focus on drugs that elicit tumor regression by killing actively cycling or fully differentiated cells may spare the critical population of therapy-resistant cells. These observations have recently been extended to breast cancer, and I have shown that subpopulations of chemoresistant cells within the bulk primary tumor had the propensity to metastasize through an array of different adaptive mechanisms.

A tumorigenic signature has also been identified from patient breast cancer biopsies and, subsequently, a functional approach was used to identify novel targets for treatment resistance from this gene set. Using shRNA knockdown of the 477 genes in the tumorigenic signature, a high throughput mammosphere formation efficiency (MSFE) screen was performed. This approach identified two target proteins, RPL39 and MLF2. RPL39 was previously recognized as a component of the 60S ribosomal complex located on chromosome X (XQ24) with a proposed role in spermatogenesis and protein translation. MLF2 is located on chromosome 12 and may participate in chromosomal aberrations and cellular defense responses. While little is known about the role of RPL39 in cancer, there is even more limited knowledge available on MLF2. A series of amino acid modifications of MLF2 on Ser 144, 152 and 238 and a somatic mutation (Phe80Cys) has been linked to colorectal cancer. Notably, RPL39 and MLF2 overexpression increased cell migration, proliferation and mammosphere formation, suggesting a potentially important function for these two genes in cancer.

Comprehensive understanding of the mechanisms of RPL39 and MLF2 is a salient prerequisite for the confirmation of these two genes as novel cancer targets. By mutual exclusivity analysis of RPL39 and MLF2 using. The Cancer Genome Atlas (TCGA) database, RPL39 and MLF2 were found to exclusively co-occur (p<0.00001), suggesting a shared mechanistic pathway for both genes. Using microarray analysis, "cellular effects of sildenafil (VIAGRA®)" i.e., nitric oxide (NO) signaling was identified as the primary pathway that linked both RPL39 and MLF2. The role of NO signaling was then confirmed by inducing iNOS (inducible nitric oxide synthase) protein with overexpression of RPL39 and MLF2, and reducing iNOS protein levels with siRNA (small interfering ribonucleic acid) silencing of RPL39 and MLF2. In the literature, the role of NOS signaling in breast cancer biology has not been extensively studied. Reports to date suggest that high NO concentrations are cytotoxic to cancer cells whereas lower NO concentrations can enhance tumor growth.

Two novel cancer genes (RPL39 and MLF2) have been previously identified that play a role in treatment resistance and lung metastases. It was shown that upregulation of NO signaling was a common mechanistic pathway for both genes. Inhibition of NO signaling with L-NMMA was shown to diminish the number of treatment resistant cells, as well as lung metastases in human TNBC cell lines.

Checkpoint inhibitors (CPI), including anti-PD1, have been shown to have single-agent activity across diverse solid tumor types. Durable responses are still seen in only a minority of patients. Emerging data suggest that an immunologically-inflamed/activated tumor immune microenvironment (TIME) is associated with CPI activity. NO and nitric oxide synthases (NOS) are major drivers of immunosuppression in solid tumors, and a significant barrier to immunotherapy. NOS inhibition reconditions/activates the immunosuppressive TIME of solid tumors, and NOS inhibition enhances the efficacy of other immune-modulating treatments in preclinical models (e.g., chemoradiotherapy and anti-PD-1).

Present data suggests that pretreatment with one or more pan-NOS inhibitors (such as L-NMMA) can reverse the immunosuppressive TIME of solid tumors, thereby unmasking their responsiveness to pembrolizumab and other CPIs.

Programmed Death-1

Cancer immunotherapy harnesses and boosts the innate powers of the immune system to fight cancer and represents the most promising new cancer treatment approach since the development of chemotherapeutic agents in the late 1940s. Because of the extraordinary memory and specificity of the immune system, immunotherapy has the potential to achieve complete, long-lasting remissions with few or no side effects in cancer patients, regardless of their cancer type. Immunotherapies targeting programmed death-1 (PD-1) have shown unprecedented rates of durable clinical responses in patients with various cancer types. Upregulation of programmed death-ligand 1 (PD-L1) and its ligation to PD-1 on antigen-specific CD8+ T-cells (termed adaptive immune resistance) represents a major mechanism by which cancer tissues limit the host immune response. Under healthy conditions, PD-1, expressed on the cell surface of activated T-cells, functions to down-modulate unwanted or excessive immune responses, including autoimmune reactions. PD-1 (encoded by the gene Pdcd1) is an immunoglobulin (Ig) superfamily member related to CD28 and cytotoxic T-lymphocyte-associated antigen-4 (CTLA-4) that has been shown to negatively regulate antigen receptor signaling upon engagement of its ligands (PD-L1 and/or PD-L2).

The mechanism by which PD-1 down-modulates T-cell responses is similar to but distinct from that of CTLA-4, as both molecules regulate an overlapping set of signaling proteins. PD-1 was shown to be expressed on activated lymphocytes including peripheral $CD4^+$ and $CD8^+$ T-cells, B-cells, regulatory T-cells (Tregs), and natural killer cells. PD-1 expression has also been shown during thymic development on $CD4^-CD8^-$ (double negative) T-cells as well as subsets of macrophages and dendritic cells. The ligands for PD-1 (PD-L1 and PD-L2) are constitutively expressed or can be induced in a variety of cell types, including non-hematopoietic tissues and various tumors. Binding of either PD-1 ligand to PD-1 inhibits T-cell activation triggered through the T-cell receptor. PD-L1 is expressed at low levels on various non-hematopoietic tissues, most notably on vascular endothelium, whereas PD-L2 protein is only detectably expressed on antigen-presenting cells found in lymphoid tissue and chronic inflammatory environments. PD-L2 is thought to control immune T-cell activation in lymphoid organs, whereas PD-L1 serves to dampen unwarranted T-cell function in peripheral tissues. Although healthy organs express little (if any) PD-L1, a variety of cancers have been demonstrated to express abundant levels of this T-cell inhibitor. PD-1 has been suggested to regulate tumor-specific T-cell expansion in subjects with melanoma. This suggests that the PD-1/PD-L1 pathway plays a critical role in tumor immune evasion and should be considered an attractive target for therapeutic intervention.

Pembrolizumab

Pembrolizumab (MK-3475; KEYTRUDA®, Merck) is a potent and highly-selective humanized monoclonal antibody of the IgG4/κ isotype designed to directly block the interaction between PD-1 and its ligands, PD-L1 and PD-L2. Antibody-mediated PD-1 blockade with pembrolizumab and other similar agents reinvigorates the immune system, allowing for cancer cell targeting and destruction. Pembrolizumab is one of a number of closely-related therapies dubbed 'immune checkpoint blockade." On Sep. 4, 2014, KEYTRUDA® (pembrolizumab) was approved by the United States Food and Drug Administration (FDA) for the treatment of patients with unresectable or metastatic melanoma and disease progression following ipilimumab (and, if BRAF V600-mutation-positive, a BRAF inhibitor). FDA approval was based on the results from KEYNOTE-001 (NCT01295827) and KEYNOTE-002 (NCT01704287). KEYNOTE-001 was an open-label, first-in-human Phase Ib study of pembrolizumab in patients with progressive, locally-advanced, or metastatic carcinomas. The melanoma cohort included patients with advanced disease, previously treated with ipilimumab, or (for BRAF mutation carriers) ipilimumab in combination with a BRAF inhibitor.

After mandatory biopsy, patients were treated with one of three doses of pembrolizumab for 12 weeks; responders continued on treatment until disease progression. Among 173 patients treated with the recommended 2 mg/kg pembrolizumab dose, the overall response rate was 24%, with a duration of response (DoR) of 1.4 to 8.5 months.

The ongoing KEYNOTE-002 is a partially-blinded, randomized, Phase II study designed to evaluate 2 doses of pembrolizumab versus a chemotherapy control arm in subjects with ipilimumab-refractory metastatic melanoma. Subjects (n=540) were randomized to receive pembrolizumab 2 mg/kg every 3 weeks (Q3W; n=180), pembrolizumab 10 mg/kg Q3W (n=181), or chemotherapy (according to current clinical practice; n=179). Subjects assigned to the control chemotherapy arm could cross over to the experimental pembrolizumab arm once progression was confirmed (approximately ≥Week 12). Based on 410 progression-free survival (PFS) events, PFS was improved in the pembrolizumab 2 mg/kg (hazard ratio [HR]: 0.57; 95% confidence interval [CI]: 0.45-0.73; P<0.0001) and pembrolizumab 10 mg/kg groups (HR: 0.50; CI: 0.39-0.64; P<0.0001) compared with the chemotherapy group. The 6-month PFS rate was 34% (95% CI: 27-41) in the pembrolizumab 2 mg/kg group, 38% (95% CI: 31-45) in the pembrolizumab 10 mg/kg group, and 16% (95% CI: 10-22) in the chemotherapy group. Grade 3-4 treatment-related adverse events (AEs) occurred in 20 (11%) patients in the pembrolizumab 2 mg/kg group, 25 (14%) patients in the pembrolizumab 10 mg/kg group, and 45 (26%) patients in the chemotherapy group. The most common Grade 3-4 treatment-related AE in the pembrolizumab groups was fatigue (2 [1%] of 178 patients in the 2 mg/kg group and 1 [<1%] of 179 patients in the pembrolizumab 10 mg/kg group compared with 8 [5%] of 171 patients in the chemotherapy group). Other Grade 3-4 treatment-related AEs included generalized edema and myalgia (each in 2 [1%] patients) in the pembrolizumab 2 mg/kg group; hypopituitarism, colitis, diarrhea, decreased appetite, hyponatremia, and pneumonitis (each in 2 [1%] patients) in the pembrolizumab 10 mg/kg group; and anemia (9 [5%] patients), fatigue (8 [5%] patients), neutropenia (6 [4%] patients), and leucopenia (6 [4%] patients) in the chemotherapy group.

Results of the KEYNOTE-006 study (NCT01866319) led to the expanded indication of pembrolizumab for the front-line treatment of patients with unresectable or metastatic melanoma. KEYNOTE-006 was a randomized, controlled Phase III study of pembrolizumab versus ipilimumab in subjects with unresectable stage III or IV advanced melanoma with no more than one prior systemic therapy. Subjects (n=834) were randomized to receive pembrolizumab 10 mg/kg Q3W, pembrolizumab 10 mg/kg every two weeks (Q2W), or four cycles of ipilimumab 3 mg/kg Q3W. The estimated 6-month PFS rates were 47.3% and 46.4% for pembrolizumab Q2W and Q3W, respectively, compared with 26.5% for ipilimumab (HR:0.58; P<0.001 for both pembrolizumab regimens vs. ipilimumab; 95% CI: 0.46-0.72 and 0.47-0.72, respectively). Estimated 12-month survival rates were 74.1% for pembrolizumab Q2W, 68.4% for pembrolizumab Q3W, and 58.2% for ipilimumab (HR for pembrolizumab Q2W: 0.63; 95% CI: 0.47-0.83; P=0.0005; HR for pembrolizumab Q3W: 0.69; 95% CI: 0.52-0.90; P=0.0036). Response rates were higher for pembrolizumab Q2W and Q3W compared with ipilimumab (33.7% and 32.9% vs. 11.9%; both P<0.001). Response rate was similar between the two pembrolizumab regimens. Rates of Grade 3-5 treatment-related AEs were lower in the pembrolizumab Q2W and Q3W groups than in the ipilimumab group (13.3% and 10.1% vs. 19.9%).

Pembrolizumab has also been approved for the treatment of metastatic non-small cell lung cancer (NSCLC) and recurrent or metastatic head and neck squamous cell carcinoma. On Oct. 2, 2015 KEYTRUDA® (pembrolizumab) received accelerated FDA approval for the treatment of patients with metastatic PD-L1-positive NSCLC whose disease has progressed on or after platinum-containing chemotherapy or targeted therapy against anaplastic lymphoma kinase or epidermal growth factor receptor, if appropriate. Pembrolizumab is approved for use with a companion diagnostic, the PD-L1 IHC 22C3 pharmDx test, the first test designed to detect PD-L1 expression in NSCLC tumors. FDA approval was based on the results from the Phase Ib KEYNOTE-001 study (NCT01295827) of pembrolizumab in patients with progressive locally advanced or metastatic carcinomas. The NSCLC cohort included 550 patients with metastatic disease. The objective response rate (ORR) in the efficacy population, which comprised 61 patients with PD-L1 strongly positive tumors, was 41% (95% CI: 28.6-54.3); all were partial responses (PRs). At the time of the analysis, responses were ongoing in 21 of 25 (85%) patients, with 11 (44%) patients having a DoR of ≥6 months. The most commonly occurring (≥20%) AEs included fatigue, decreased appetite, dyspnea, and cough. The most frequent (≥2%) serious AEs (SAEs) were pleural effusion, pneumonia, dyspnea, pulmonary embolism, and pneumonitis. Immune-mediated AEs occurred in 13% of patients and included pneumonitis, colitis, hypophysitis, and thyroid disorders.

On Aug. 5, 2016, KEYTRUDA® (pembrolizumab) received accelerated FDA approval for the treatment of patients with recurrent or metastatic head and neck squamous cell carcinoma with disease progression on or after platinum-containing chemotherapy. The approval was based on data from the multicenter, nonrandomized Phase Ib KEYNOTE-012 study (NCT01848834) of pembrolizumab in patients with advanced PD-L1-positive (expression in stroma or ≥1% of tumor cells by immunohistochemistry [IHC]) solid tumors. Patients with recurrent or metastatic head and neck squamous cell carcinoma who had disease progression on or after platinum-containing chemotherapy or following platinum-containing chemotherapy administered as part of induction, concurrent, or adjuvant therapy (n=174) were given pembrolizumab at 10 mg/kg Q2W or 200 mg Q3W. The ORR was 16% (95% CI: 11-22). The median response duration had not been reached at the time of analysis. The range for DoR was 2.4 months to 27.7 months (response ongoing). Among the 28 responding patients, 23 (82%) had responses of 6 months or longer. SAEs occurred in 45% of patients. The most frequent SAEs reported in at least two percent of patients were pneumonia, dyspnea, confusional state, vomiting, pleural effusion, and respiratory failure. The incidence of AEs, including SAEs, was similar between dosage regimens (10 mg/kg Q2W or 200 mg Q3W). The most common AEs (reported in at least 20% of patients) were fatigue (46%), decreased appetite (22%), and dyspnea (20%).

Multiple ongoing clinical trials continue to evaluate pembrolizumab for the treatment of head and neck cancer: KEYNOTE-040 (NCT02252042: A Phase III Randomized Trial of MK-3475 [Pembrolizumab] Versus Standard Treatment in Subjects with Recurrent or Metastatic Head and Neck Cancer); KEYNOTE-048 (NCT02358031: A Phase 3 Clinical Trial of Pembrolizumab [MK-3475] in First Line Treatment of Recurrent/Metastatic Head and Neck Squamous Cell Carcinoma); and KEYNOTE-055 (NCT02255097: A Phase II Clinical Trial of Single Agent Pembrolizumab in Subjects with Recurrent or Metastatic Head and Neck Squamous Cell Carcinoma Who Have Failed Platinum and Cetuximab).

Pembrolizumab has also demonstrated promising clinical activity in triple negative breast cancer (TNBC). In the Phase Ib KEYNOTE-012 study, pembrolizumab was given at 10 mg/kg Q2W to patients with heavily-pretreated, advanced, PD-L1-positive TNBC. Among the 27 patients who were evaluable for antitumor activity, the overall response rate was 18.5% (95% CI: 6.3-38.1). Best overall responses were complete response (CR) in one (3.7%) patient, PR in four (14.8%) patients, stable disease (SD) in seven (25.9%) patients, and progressive disease (PD) in 13 (48.1%) patients. The disease control rate (i.e., percentage of patients with best response of CR, PR, or SD for ≥24 weeks) was 25.9% (95% CI: 11.1-46.3). The patient who experienced a CR had previously received eight lines of therapy for metastatic disease, including anthracycline-, taxane-, and platinum-based regimens, capecitabine (XELODA®), and eribulin (HALAVEN®). Of the four patients who experienced a PR, one patient received one line of prior therapy, one patient received three lines of prior therapy, and two patients received six lines of prior therapy in the metastatic setting. The median time to response was 17.9 weeks (range: 7.3-32.4 weeks), and the median DoR was not yet reached (range: 15.0 to ≥47.3 weeks). Common toxicities were mild, and included arthralgia, fatigue, myalgia, and nausea. Grade ≥3 AEs and treatment-related death occurred in five (15.6%) patients and one patient, respectively. Several ongoing studies are investigating pembrolizumab monotherapy for the treatment of TNBC.

The KEYNOTE-086 study (NCT02447003) is a Phase II trial of pembrolizumab monotherapy in metastatic TNBC patients. The KEYNOTE-119 study (NCT02555657) is an open label, randomized Phase III study of single-agent pembrolizumab versus single-agent chemotherapy per physician's choice for metastatic TNBC. The KEYNOTE-173 study (NCT02622074) is a Phase Ib study to evaluate the safety and clinical activity of pembrolizumab in combination with chemotherapy as neoadjuvant treatment for TNBC. Together, these studies pave the way for expanding the indications for pembrolizumab.

Time and Immune Checkpoint Blockade Response

Immune checkpoint inhibitors such as the anti-PD-1 antibody pembrolizumab have shown great promise for cancer treatment. However, a majority of patients do not respond to this type of treatment, and durable response rates in the trials above have been generally on the order of 15-25%. The tumor immune microenvironment (TIME) has emerged as a critical determinant of immune checkpoint inhibitor response, with responses correlated with an immunologically active T-cell-inflamed microenvironment. Accumulation of immunosuppressive cells such as myeloid-derived suppressor cells (MDSCs) and Tregs and insufficient accumulation of T-cells or tumor-infiltrating lymphocytes (TILs) in the TIME have been implicated in the resistance to immune checkpoint blockade. Under healthy conditions, MDSCs and Tregs play critical roles in immune homeostasis. However, tumor-induced recruitment and activation of Tregs and MDSCs is an important mechanism of tumor-mediated immunosuppression, leading to impaired efficacy of cancer immunotherapy. In vivo studies have shown that elevated MDSCs cause resistance to anti-PD-1 immune checkpoint blockade in vivo, whereas MDSC suppression eradicates metastatic mouse cancers resistant to anti-PD-1 immune checkpoint blockade. Comparison of in vivo anti-PD1-sensitive and anti-PD1-resistant tumors has suggested that intratumoral Tregs might be responsible for limiting anti-PD-1 therapeutic efficacy. Tregs and MDSCs in the TIME represent a significant obstacle to immune checkpoint blockade therapies via suppression of immune checkpoint blockade-mediated antitumor T-cell responses. Immune checkpoint blockade has been shown to be most effective in inflamed tumors populated with tumor-specific CD8+ TILs. Agents capable of increasing the number and activity of T-cells or TILs in the tumor microenvironment may enhance the response to anti-PD-1 therapy.

The Nitric Oxide Synthase Inhibitor, NG-Monomethyl-L-Arginine

It has been shown that NOS expression in the TIME is a powerful driver of tumor-mediated immunosuppression. Therefore, TIME-targeting with NOS inhibitors may offer a novel combinatorial approach to enhance anti-PD-1 therapeutic efficacy. NO is a bioactive molecule that exhibits pleotropic effects within cancer cells and tumors, with concentration-dependent pro- and anti-tumor effects. NO is produced by three different NOS isoforms: neuronal (nNOS), inducible (iNOS), and endothelial (eNOS). The role of iNOS in carcinogenesis, tumor progression, tumor survival, and aggressiveness is well recognized. Increased iNOS expression has been found in various cancers including breast cancer, lung cancer, head and neck cancers, and melanoma. Increased iNOS expression is associated with poor survival in breast cancer, particularly estrogen receptor (ER)α-negative breast cancer and TNBC, head and neck cancers, and melanoma. iNOS inhibitors have preclinical antitumor activity against various tumor types. iNOS inhibition has been shown to inhibit melanoma growth in vivo, and extend the survival of tumor-bearing mice. Furthermore, iNOS inhibition enhanced cis-platin-mediated growth inhibition in cis-platin-sensitive and cis-platin-resistant melanoma cell lines in vitro, and a mouse xenograft model in vivo. NOS inhibition with the pan-NOS inhibitor NG-monomethyl-L-arginine (L-NMMA) decreased cell proliferation, migration, and mammosphere formation in TNBC cell lines and significantly reduced tumor growth, lung metastases, tumor initiation, and self-renewal in TNBC patient-derived xenografts (PDXs). Importantly, iNOS inhibition has been shown to favorably alter the TIME. In syngeneic mouse melanoma models, iNOS inhibition markedly reconditioned the TIME to promote antitumor immunity by depleting immunosuppressive MDSCs, enhancing intratumoral CD8+ cytotoxic T-cell infiltration, and shifting macrophage phenotype from M2 (immunosuppressive) to M1.

Preclinical and Clinical Experience with L-NMMA

The potent antitumor activity of the pan-NOS inhibitor, L-NMMA, against TNBC has been demonstrated both in vitro and in vivo. L-NMMA was found to decrease cell proliferation, migration, and mammosphere formation in TNBC cell lines, and significantly reduce tumor growth, lung metastases, tumor initiation, and self-renewal in TNBC PDXs. Furthermore, L-NMMA in combination with docetaxel significantly inhibited in vivo tumor growth compared with docetaxel alone in TNBC xenograft models. Based on these findings, a Phase Ib/II clinical trial is being led by the inventor using the proprietary combination of L-NMMA and docetaxel in patients with relapsed/refractory TNBC (NCT02834403).

The safety of L-NMMA has been well established, and the anticipated serious AEs are few, known, and documented. TRIUMPH was a randomized, controlled Phase III trial of L-NMMA in patients with acute myocardial infarction and cardiogenic shock. The study was conducted at 130 centers in eight countries in North America and Europe. Inclusion required all of the following: (1) myocardial infarction, confirmed by ischemic symptoms for at least 30 minutes with elevated cardiac markers and/or ST-segment elevation or left bundle-branch block; (2) patency (<70% stenosis) of the infarct artery, either occurring spontaneously and confirmed at angiography or after percutaneous revascularization; (3) refractory cardiogenic shock of less than 24 hrs' duration, confirmed by peripheral signs of tissue hypoperfusion and systolic blood pressure less than 100 mm Hg, despite vasopressor therapy (dopamine ≥7 µg/kg/min or norepinephrine or epinephrine ≥0.15 µg/kg/min) continuing longer than 1 hr after infarct artery patency; (4) clinical or hemodynamic evidence of elevated left ventricular filling pressures; and (5) left ventricular ejection fraction of less than 40%. Hemodynamics and requirement for vasopressor treatment were reconfirmed after randomization just prior to study drug administration; patients with resolving shock were excluded. Between January 2005 and August 2006, 398 patients met the study inclusion criteria and were enrolled. All baseline characteristics were well balanced between the treatment groups. More than one quarter of the population was older than 75 years; the majority was male and of Caucasian race. More than half of the patients had hypertension, while one-third had diabetes; 84 (21%) had a history of heart failure, and almost a third of those had advanced heart failure symptoms in the 6 weeks prior to enrollment. A quarter of the patients had baseline creatinine levels of 1.7 mg/dL (150 mol/L) or higher. The median supported blood pressure just prior to study drug administration was 88/52 mm Hg. Most patients were supported with a single vasopressor at the time of study drug administration. The majority of patients presented with anterior, ST-segment elevation myocardial infarction with left anterior descending infarct artery location. Percutaneous coronary intervention was performed in nearly all patients to achieve the requirement for less than 70% infarct artery stenosis before study entry. L-NMMA had no effect on mortality in patients with myocardial infarction complicated by refractory cardiogenic shock. Importantly, L-NMMA was well tolerated with few AEs other than transient (minutes) reversible hypertension.

The antihypotensive effects of L-NMMA were evaluated in patients with metastatic renal cell carcinoma receiving interleukin-2 (IL-2). Bolus injections of L-NMMA at 3, 6, and 12 mg/kg were shown to be safe when administered to patients with metastatic renal cell carcinoma prior to infusion of IL-2 (n=3 per cohort). L-NMMA was not associated with any hematologic, liver, or renal abnormalities. Doses of 3 and 6 mg/kg did not induce clinically apparent side effects, and blood pressure remained unchanged. A transient increase in systolic blood pressure up to 25 mm Hg in the absence of any other clinical symptoms was observed with the 12 mg/kg dose; however, this increase in blood pressure normalized rapidly (less than 5 min) upon ceasing the infusion.

Preclinical Evidence of the Efficacy of L-NMMA+Pembrolizumab

Both the expression of the PD-1 ligand, PD-L1, and a high mutational load have been associated with response to immune checkpoint inhibitors in clinical trials of anti-PD-1-based therapies in melanoma and lung cancer. Furthermore, expression of PD-L1 is a major patient selection criterion for clinical trials of anti-PD-1 therapies. Therefore, to investigate the potential efficacy of the L-NMMA and pembrolizumab combination, the effect of L-NMMA on PD-L1 expression was determined in the TNBC cell lines MDA-MB-468 and HCC-70. L-NMMA was found to increase the PD-L1 expression in both cell lines. Next, the in vivo activity of the L-NMMA and pembrolizumab combination was evaluated using humanized TNBC PDX mouse models, TNBC-4195, TNBC-4664, and TNBC-3936. Humanized PDXs models are based on the engraftment of hematopoietic stem cells in NOD-scid IL2Rγ$^{null}$ (NSG) immunodeficient mice. Three-week-old NSG mice were irradiated at 240n cGY and after 4 hrs, injected with 4×10$^4$ CD34$^+$ human hematopoietic stem cells (HSCs). After 6-7 weeks, HSC engraftment was assessed by flow cytometric analysis of human CD3$^+$, CD45$^+$, and CD20$^+$ cells in blood. TNBC PDX tumor lines were implanted into the mammary fat pad. When tumors reached 100-250 mm$^3$, mice were sorted into the pembrolizumab and pembrolizumab and L-NMMA treatment groups. Mice were treated for 6 1-week cycles using a 1×1×1 design (i.e., one animal per model per treatment). Pembrolizumab at a dose of 10 mg/kg was administered via tail vein injection on Days 1-5 of every 1-week cycle. L-NMMA was administered via oral gavage at a dose of 400 mg/kg on Day and 200 mg/kg on Days 2-5 of every 1-week cycle. On Day 1, mice were treated first with pembrolizumab, followed by L-NMMA. The calcium channel blocker, amlodipine, was also given to control any L-NMMA-mediated transient increase in blood pressure (10 mg/kg intraperitoneally on Days 1-5 of every 1-week cycle). The pembrolizumab+L-NMMA combination significantly inhibited tumor growth when compared to pembrolizumab treatment alone in all three of the humanized TNBC PDX mouse models. Taken together, these results provided evidence that L-NMMA could enhance the therapeutic efficacy of pembrolizumab.

Pharmaceutical Formulations

The pharmaceutical formulations disclosed herein may further comprise one or more excipients, buffers, or diluents that are particularly formulated for administration to a human patient. Compositions may further optionally comprise one or more microspheres, microparticles, nanospheres, or nanoparticles, and may be formulated for administration to one or more cells, tissues, organs, or body of a human undergoing treatment for a cancer, and breast cancer, in particular.

Formulation of pharmaceutically-acceptable excipients and carrier solutions is well-known to those of skill in the art, as is the development of suitable dosing and treatment regimens for using the particular compositions described herein in a variety of treatment regimens, including e.g., without limitation, oral, parenteral, intravenous, intranasal, intratumoral, and intramuscular routes of administration.

Typically, the iNOS-inhibitory chemotherapeutic formulations of the present disclosure may be formulated to contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound(s) in each diagnostically- or therapeutically-useful composition may be prepared is such a way that a suitable dosage of the diagnostic or therapeutic agent will be obtained in any given unit dose of the chemotherapeutic formulations disclosed herein. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The particular amount of compositions employed, and the particular time of administration, or dosage regimen for compositions employing the disclosed iNOS-inhibitory chemotherapeutic formulations will be within the purview of a person of ordinary skill in the art having benefit of the present teaching. It is likely, however, that the administration of diagnostically- or therapeutically-effective amounts of the disclosed formulations may be achieved by administration of one or more doses of the formulation, during a time effective to provide the desired chemotherapeutic benefit to the patient undergoing such treatment. Such dosing regimens may be determined by the medical practitioner overseeing the administration of the chemotherapeutics, depending upon the particular condition or the patient, the extent of the cancer, etc.

Typically, formulations of the active ingredients in the disclosed compositions will contain an effective amount for the particular therapy regimen of a given patient. Preferably, the formulation may contain at least about 0.1% of each active ingredient, although the percentage of the active ingredient(s) may, of course, be varied, and may conveniently be present in amounts from about 0.5 to about 80 weight % or volume %, or from about 1 to about 70 weight % or volume %, or more preferably, from about 2 to about 50 weight % or volume %, based upon the total formulation. Naturally, the amount of active compound(s) may be prepared in such a way that a suitable dosage will be obtained in any given unit dose of the compound. Factors such as solubility, bioavailability, biological ti/2, route of administration, product shelf life, as well as other pharmacological considerations will be contemplated by one of ordinary skill in the art of preparing such pharmaceutical formulations, and as such, a variety of dosages and treatment regimens may be desirable.

Compositions for the Preparation of Medicaments

Another important aspect of the present disclosure concerns methods for using the disclosed compositions (as well as formulations including them) in the preparation of medicaments for treating or ameliorating the symptoms of various diseases, dysfunctions, or deficiencies in an animal, such as a vertebrate mammal. Use of the disclosed compositions is particular contemplated in the chemotherapeutic treatment of one or more types of cancer in a human, and particular in the treatment of TNBC in a human female.

Such use generally involves administration to the mammal in need thereof one or more of the disclosed iNOS-inhibitory chemotherapeutic compositions, in an amount and for a time sufficient to treat, lessen, or ameliorate one or more symptoms of the cancer in the affected mammal.

Pharmaceutical formulations including one or more of the disclosed chemotherapeutic agents also form part of the present disclosure, and particularly those compositions that further include at least a first pharmaceutically-acceptable excipient for use in the therapy or amelioration of one or more symptoms of mammalian breast cancer, and particularly, for use in the therapy or amelioration of one or more symptoms of TNBC in a human female.

Chemotherapeutics and Formulations Thereof

Increased iNOS expression has been found in breast cancer as well as other different cancers such as lung, colon, melanoma and glioblastoma. Previous reports have demonstrated a correlation between high iNOS expression, aggressiveness, and poor prognosis in breast cancer patients.

Increased iNOS expression has recently been postulated as a prognostic factor for reduced survival in patients with basal-like estrogen receptor-negative breast cancer, through the induction of interleukin-8 (IL-8), CD44, c-Myc (7) and partially due to the activation of the transcription factor Ets-1. Herein, it was hypothesized that enhanced endogenous iNOS expression drives poor patient survival by promoting tumor relapse and metastases through modulation of CSC self-renewal properties and tumor cell migration. It was further hypothesized that, in combination with conventional chemotherapy, the inhibition of endogenous iNOS would reduce the aggressiveness of residual TNBC cells as well as mesenchymal features, and the number of metastases to distant organs, thereby improving survival of patients with TNBC.

In the examples which follow, the inhibition of iNOS with different small molecule inhibitors was demonstrated, including the selective iNOS inhibitor, 1400 W, (N-[[3-(aminomethyl)phenyl]methyl]-ethanimidamide), and two pan-NOS inhibitors, L-NMMA ($N^G$-monomethyl-L-arginine) and L-NAME ($N^5$-[imino(nitroamino)methyl]-L-ornithine methyl ester). L-NMMA has been extensively studied in hundreds of patients for cardiogenic shock, which facilitates its immediate translation into human clinical trials without the need of extensive preclinical testing.

Amlodipine

Amlodipine is a dihydropyridine calcium antagonist that inhibits the transmembrane influx of calcium ions into vascular smooth muscle and cardiac muscle. Experimental data suggest that amlodipine binds to both dihydropyridine and non-dihydropyridine binding sites. The contractile processes of cardiac muscle and vascular smooth muscle are dependent upon the movement of extracellular calcium ions into these cells through specific ion channels. Amlodipine inhibits calcium ion influx across cell membranes selectively, with a greater effect on vascular been seen in intact animals at therapeutic doses. Serum calcium concentration is not affected by amlodipine. Within the physiologic pH range, amlodipine is an ionized compound (pKa=8.6), and its kinetic interaction with the calcium channel receptor is characterized by a gradual rate of association and dissociation with the receptor binding site, resulting in a gradual onset of effect.

Amlodipine is a peripheral arterial vasodilator that acts directly on vascular smooth muscle to cause a reduction in peripheral vascular resistance and reduction in blood pressure. The precise mechanisms by which amlodipine relieves angina have not been fully delineated, but are thought to include the following:

Exertional Angina: In patients with exertional angina, amlodipine reduces the total peripheral resistance (afterload) against which the heart works and reduces the rate pressure product, and thus myocardial oxygen demand, at any given level of exercise.

Vasospastic Angina: Amlodipine has been demonstrated to block constriction and restore blood flow in coronary arteries and arterioles in response to calcium, potassium epinephrine, serotonin, and thromboxane A2 analog in experimental animal models and in human coronary vessels in vitro. This inhibition of coronary spasm is responsible for the effectiveness of amlodipine in vasospastic (Prinzmetal's or variant) angina.

Exemplary Definitions

In accordance with the present disclosure, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs.

The following references provide one of skill with a general definition of many of the terms used in this invention: *Dictionary of Biochemistry and Molecular Biology*, ($2^{nd}$ Ed.) J. Stenesh (Ed.), Wiley-Interscience (1989); *Dictionary of Microbiology and Molecular Biology* ($3^{rd}$ Ed.), P. Singleton and D. Sainsbury (Eds.), Wiley-Interscience (2007); *Chambers Dictionary of Science and Technology* ($2^{nd}$ Ed.), P. Walker (Ed.), Chambers (2007); *Glossary of Genetics* ($5^{th}$ Ed.), R. Rieger et al. (Eds.), Springer-Verlag (1991); and *The HarperCollins Dictionary of Biology*, W. G. Hale and J. P. Margham, (Eds.), HarperCollins (1991).

Although any methods and compositions similar or equivalent to those described herein can be used in the practice or testing of the present disclosure, the preferred methods, and compositions are described herein. For purposes of the present disclosure, the following terms are defined below for sake of clarity and ease of reference:

In accordance with long standing patent law convention, the words "a" and "an," when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

"Biocompatible" refers to a material that, when exposed to living cells, will support an appropriate cellular activity of the cells without causing an undesirable effect in the cells, such as a change in a living cycle of the cells, a change in a proliferation rate of the cells, or a cytotoxic effect.

The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The terms "an effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

As used herein, the term "epitope" refers to that portion of a given immunogenic substance that is the target of (i.e., is bound by), an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, e.g., Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

The term "for example" or "e.g.," as used herein, is used merely by way of example, without limitation intended, and should not be construed as referring only those items explicitly enumerated in the specification.

As used herein, "heterologous" is defined in relation to a predetermined referenced DNA or amino acid sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, "homologous" means, when referring to polypeptides or polynucleotides, sequences that have the same essential structure, despite arising from different origins. Typically, homologous proteins are derived from closely related genetic sequences, or genes. By contrast, an "analogous" polypeptide is one that shares the same function with a polypeptide from a different species or organism but has a significantly different form to accomplish that function. Analogous proteins typically derive from genes that are not closely related.

As used herein, the term "homology" refers to a degree of complementarity between two polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of reagents, components, or pharmaceutically-formulated compositions of the present invention. Optionally, such kit may include one or more sets of instructions for use of the enclosed compositions, such as, for example, in a laboratory or clinical application.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The terms "local administration" or "local delivery," in reference to delivery of a composition, formulation, or device of the invention, refer to delivery that does not rely upon transport of the agent to its intended target tissue via the vascular or lymphatic system from a site of administration that is remote from the intended target tissue. The agent is delivered directly to its intended target tissue or in the vicinity thereof, e.g. by injection or implantation. It will be appreciated that a small amount of the delivered agent may enter the vascular system and may ultimately reach the target tissue via the vascular system.

As used herein, "mammal" refers to the class of warm-blooded vertebrate animals that have, in the female, milk-secreting organs for feeding the young. Mammals include without limitation humans, apes, many four-legged animals, whales, dolphins, and bats. A human is a preferred mammal for purposes of the invention.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally-occurring animals.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

The terms "operably linked" and "operatively linked" as used herein, refer to two or more nucleic acid sequences being linked or joined (and typically are contiguous, or substantially contiguous), and, wherever necessary, joined in such fashion that the protein coding regions therein are both contiguous, and in proper reading frame. In the case of enhancers, however, since many generally function when distanced from the promoter by several kilobases and/or one or more intronic sequences, which may be of variable lengths, some polynucleotide elements may still be "operably linked," yet not physically contiguous with each other.

As used herein, the term "patient" (also interchangeably referred to as "recipient" "host" or "subject") refers to any host that can serve as a recipient for one or more of the vascular access devices as discussed herein. In certain aspects, the recipient will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

The phrase "pharmaceutically-acceptable" refers to molecular entities and compositions that do not produce an allergic or similar untoward reaction when administered to a human, and in particular, when administered to the human eye. The preparation of an aqueous composition that contains a protein as an active ingredient is well understood in the art. Typically, such compositions are prepared as injectables, either as liquid solutions or as suspensions. Alternatively, they may be prepared in solid form suitable for solution or suspension in liquid prior to injection.

As used herein, "pharmaceutically-acceptable salt" refers to a salt that retains the desired biological activity of the parent compound and does not impart any undesired toxicological effects. Such salts may include, but are not limited to, the acid-addition salts formed with inorganic acids, e.g., hydrochloric acid, hydrobromic acid, sulfuric acid, phosphoric acid, nitric acid, and the like; and salts formed with organic acids such as, e.g., acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as, e.g., zinc, calcium, bismuth, barium, magnesium, aluminum, copper, cobalt, nickel, cadmium, and the like; salts formed with an organic cation formed from, e.g., N,N'-dibenzylethylenediamine or ethylenediamine, or any one or more combinations thereof.

As used herein, the term "plasmid" or "vector" refers to a genetic construct that is composed of genetic material (i.e., nucleic acids). Typically, a plasmid or a vector contains an origin of replication that is functional in bacterial host cells, e.g., Escherichia coli, and selectable markers for detecting bacterial host cells including the plasmid. Plasmids and vectors of the present disclosure may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids.

Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about two to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, at least 80%, or at least 90% or more of the material with which it is naturally found (e.g., cellular material such as cellular proteins, peptides, nucleic acids, etc.).

The term "recombinant" indicates that the material (e.g., a polynucleotide or a polypeptide) has been artificially or synthetically (non-naturally) altered by human intervention. The alteration can be performed on the material within or removed from, its natural environment, or native state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

The term "sequence," when referring to amino acids, relates to all or a portion of the linear N-terminal-to-C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5'-to-3' order of nucleotides.

The phrase a "sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X.

The term "biologically functional equivalent" is well understood in the art and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

The term "subject," as used herein, describes an organism, including mammals such as primates, to which treatment with the compositions according to the present invention can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

As used herein, the term "substantially free" or "essentially free" in connection with the amount of a component preferably refers to a composition that contains less than about 10 weight percent, preferably less than about 5 weight percent, and more preferably less than about 1 weight percent of a compound. In preferred embodiments, these terms refer to less than about 0.5 weight percent, less than about 0.1 weight percent, or less than about 0.01 weight percent.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

The terms "substantially corresponds to," "substantially homologous to," or "substantially identical with," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

"Sequential administration" of two or more agents refers to administration of two or more agents to a subject such that the agents are not present together in the subject's body at greater than de minimis concentrations. Administration of the agents may, but need not, alternate. Each agent may be administered multiple times.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence.

% identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L, *Biochemistry*, 3$^{rd}$ Ed. (1988), according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; and (7) Cyclic aliphatic side chains: P.

The term "subject," as used herein, describes an organism, including mammals such as primates, to which treatment with the compositions according to the present disclosure can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

A "sustained release formulation" is a composition of matter that comprises a therapeutic agent as one of its components and further comprises one or more additional components, elements, or structures effective to provide sustained release of the therapeutic agent, optionally in part because of the physical structure of the formulation. Sustained release is release or delivery that occurs either continuously or intermittently over an extended period, e.g., at least several days, at least several weeks, at least several months, at least several years, or even longer, depending upon the particular formulation employed.

"Suitable standard hybridization conditions" for the present invention include, for example, hybridization in 50% formamide, 5×Denhardt's solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

As used herein, the term "structural gene" is intended to generally describe a polynucleotide, such as a gene, that is expressed to produce an encoded peptide, polypeptide, protein, ribozyme, catalytic RNA molecule, or antisense molecule.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

The term "therapeutically practical time period" means a time period necessary for the active agent to be therapeutically effective. The term "therapeutically-effective" refers to reduction in severity and/or frequency of symptoms, elimination of symptoms and/or underlying cause, prevention of the occurrence of symptoms and/or their underlying cause, and improvement or remediation of damage.

A "therapeutic agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally-occurring, or produced by synthetic or recombinant methods, or any combination thereof. Drugs that are affected by classical multidrug resistance, such as the vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the *Physician's Desk Reference* and to Goodman and Gilman's "*Pharmacological Basis of Therapeutics*" tenth edition, Hardman et al. (Eds.) (2001).

As used herein, a "transcription factor recognition site" and a "transcription factor binding site" refer to a polynucleotide sequence(s) or sequence motif(s), which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to those of ordinary skill in the art.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc. As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the term "transformed cell" is intended to mean a host cell whose nucleic acid complement has been altered by the introduction of one or more exogenous polynucleotides into that cell.

"Treat," "treating," or "treatment of" as used herein, each refer to providing any type of medical or surgical management to a subject. Treating can include, but is not limited to, administering a composition comprising a therapeutic agent to a subject. "Treating" includes any administration or application of a compound or composition of the invention to a subject for purposes such as curing, reversing, alleviating, reducing the severity of, inhibiting the progression of, or reducing the likelihood of a disease, disorder, or condition or one or more symptoms or manifestations of a disease, disorder, or condition. In certain aspects, the compositions of the present invention may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorogenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernible from the first label. The use of multiplexing assays, particularly in the context of genetic amplification/detection protocols are well-known to those of ordinary skill in the molecular genetic arts.

The section headings used throughout are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—INOS Inhibition as an Effective Targeted Therapy Against TNBC

As noted above, TNBC is an aggressive form of breast cancer with no effective targeted therapy. iNOS is associated with poor survival in breast cancer patients by increasing tumor aggressiveness. It was hypothesized that inhibition of endogenous iNOS would decrease TNBC aggressiveness by reducing tumor initiation and metastasis through modulation of epithelial-mesenchymal transition (EMT)-inducing factors.

This example describes the use of iNOS inhibitors as a targeted therapy for TNBC. iNOS protein levels were determined in 83 human TNBC tissue and correlated with clinical outcome. Proliferation, mammosphere-forming efficiency, migration, EMT transcription factors were assessed in vitro after iNOS inhibition. Endogenous iNOS targeting was evaluated as potential therapy in TNBC mouse models.

High endogenous iNOS expression was associated with worse prognosis in TNBC patients by gene expression as well as immunohistochemical analysis. Selective iNOS (1400 W) and pan-NOS (L-NMMA and L-NAME) inhibitors diminished cell proliferation, CSC self-renewal, and cell migration in vitro, together with inhibition of EMT transcription factors (Snail, Slug, Twist1, and Zeb1). Impairment of HIF1α, endoplasmic reticulum stress (IRE1α/XBP1) and the crosstalk between ATF4/ATF3 and TGFβ was observed. iNOS inhibition significantly reduced tumor growth, decreased cell proliferation, and reduced the number of lung metastases as well as tumor-initiating and self-renewing capacities. Based on the success of L-NMMA in decreasing tumor growth and enhancing survival rate in TNBC, the inventor proposes an effective targeted therapeutic regimen by re-purposing iNOS inhibitors in general, and the pan-NOS inhibitor L-NMMA in particular (which has already been extensively investigated for cardiogenic shock) as an anti-cancer therapeutic.

Materials and Methods

Oncomine Gene Expression Data Analysis. Relative levels of NOS2 mRNA expression in human triple negative breast cancer were investigated by Oncomine Cancer Microarray database analysis of The Cancer Genome Atlas (TCGA) database (n=593). Patient survival analysis was obtained of two different gene expression data sets.

Cell Culture. Mesenchymal-like triple negative breast cancer cell lines, MDA-MB-231 and SUM159, were purchased from American Type Culture Collection and Asterand, respectively. Unless otherwise specified, cells were treated daily with either 1400 W (0.1, 1, 10, 100 μM; 1, 2, 4 mM), L-NMMA (0.1, 1, 10, 100 μM; 1, 2, 4 mM) or L-NAME (0.1, 1, 10, 100 μM; 1, 2, 5 mM) for 96 hrs. Mammosphere forming efficiency (MSFE), cell proliferation and migration assays are detailed below.

Immunohistochemistry. The paraffin embedded sections of human patients, MDA-MB-231 and SUM159 orthotopic tumor tissue were incubated with either anti-iNOS (1:50 dilution) or anti-Ki67 (1:100 dilution) antibodies. The slides were counterstained with hematoxylin. Additional information is included below.

Animal Studies. Female SCID Beige mice (4-5 weeks old) were housed under standard laboratory conditions (22° C.; 12 hr/12 hr light/dark cycle and free access to food and water). All animal procedures and experimental protocols were performed using institutional and federally-approved Animal Care and Use guidelines. Detailed information is described below.

Statistical Analysis. Data are presented as mean±SEM. A p-value of less than 0.05 was considered as significant.

Reagents. N-[[3-(aminomethyl)phenyl]methyl]-ethanimidamide (1400 W) and $N^5$-[imino(nitroamino)methyl]-L-ornithine methyl ester (L-NAME) were purchased from Cayman Chemical (Ann Arbor, Mich., USA). Tilarginine ($N^G$-monomethyl-L-arginine) (L-NMMA) was from Enzo Life Sciences and kindly supplied by Arginox Pharmaceuticals (Farmingdale, N.Y., USA). Tunicamycin and recombinant human TGF-β1 (CHO cell derived) were obtained from Abcam and Peprotech (Rockyhill, N.J., USA), respectively. Anti-iNOS (N-20), anti-eNOS (C-20), anti-nNOS (R-20), anti-Twist1 (L-21), anti-Twist1 (2C1a), anti-ATF3 (C-19) and anti-CREB-2 (C-20) (ATF4) antibodies were from Santa Cruz Biotechnology, Inc. (Dallas, Tex., USA). Antibodies anti-Snail (C15D3), anti-Slug (C19G7), anti-TCF8/Zeb1 (D80D3), anti-PERK (C33E10), anti-TGFβ, anti-phospho-Smad2 (Ser465/467)/Smad3 (Ser423/425) (D6G10), anti-Smad2/3, anti-IRE1α (14C10), anti-phospho-PERK (Thr980) (16F8), anti-PERK (C33E10), anti-phospho-eIF2α (Ser51) (119A11), anti-eIF2α, anti-β-Actin (13E5), anti-rabbit and anti-mouse IgG (HRP-linked) were obtained from Cell Signaling Technology, Inc. (Danvers, Mass., USA). Anti-HIF1α (EP1215Y) was from Abcam. For immunohistochemistry, anti-Ki67 (SP6) was from Abcam, anti-iNOS (K13-A) was purchased from Novus Biologicals (Littleton, Colo., USA) and anti-cleaved caspase-3 (Asp175) from Cell Signaling (Carlsbad, Calif., USA). PCR primers of XBP1 and β-Actin were from Invitrogen. Mouse anti-human CD24-FITC (clone ML5) and mouse anti-Human CD44-APC (clone G44-26) were from BD Biosciences (Franklin Lakes, N.J., USA). Anti-Mouse MHC Class I (H-2Kd)-PE (clone SF1-1.1.1) was from eBioscience (San Diego, Calif., USA).

Cell culture and mammosphere forming efficiency assay. Mesenchymal-like triple negative breast cancer cell lines, MDA-MB-231 and SUM159 [purchased from American Type Culture Collection (Manassas, Va., USA) and Asterand, respectively] were chosen based on their high expression of EMT markers, metastatic properties, percentage of CD44+/CD24-cells (MDA-MB-231: ~80-90%; SUM159: ~40-50%) and iNOS protein levels. Cells were grown in Dulbecco's Modified Eagle Medium (DMEM) (Gibco) supplemented with 10% fetal bovine serum (Thermo Scientific) and 1% antibiotic-antimycotic (Gibco, Carlsbad, Calif., USA). Stock solutions of iNOS inhibitors (1400 W, L-NMMA, and L-NAME) were made in 1×PBS. Inhibitors were further diluted in cell culture medium prior adding to cells. Unless otherwise specified, cells were treated daily with either 1400 W (0.1, 1, 10, 100 μM; 1, 2, 4 mM), L-NMMA (0.1, 1, 10, 100 μM; 1, 2, 4 mM) or L-NAME (0.1, 1, 10, 100 μM; 1, 2, 5 mM) for 96 hrs. For mammosphere-forming efficiency (MSFE) assay, 2,000 (SUM159) and 5,000 (MDA-MB-231) cells/well were cultured in 0.5% methylcellulose (MethoCult H4100, StemCell Technologies) and MammoCult basal medium supplemented with 10% MammoCult proliferation supplement, 4 μg/mL heparin and 0.48 μg/mL hydrocortisone (StemCell Technologies, Vancouver, BC, CANADA). After treatment with either 1, 2, and 4 mM (1400 W and L-NMMA) or 1, 2, and 5 mM L-NAME for 96 hrs, primary mammospheres (MS) were scanned and counted using a colony counter (GelCount, Oxford Optronicx Abington, UNITED KINGDOM). Primary MSFE was evaluated dividing mammosphere number by cell number. After trypsinization of primary MS, single cells were grown in 0.5% methylcellulose and mammosphere medium (as described above) in absence of treatment. Secondary MS were scanned, counted and secondary MSFE were assessed. For the mouse model of lung metastasis, MDA-MB-231 cells were transfected with a luciferase/GFP-based dual-reporter plasmid and stable clones (MDA-MB-231 L/G) selected with 1 mg/mL blasticidin (InvivoGen, San Diego, Calif., USA).

Cell proliferation assay. Effects of iNOS inhibition on cell proliferation were assayed with the WST-1 method. Briefly, 500 (SUM159) and 1,000 (MDA-MB-231) cells/well were plated in a 96-well plate and treated with either 1, 2, and 4 mM (1400 W and L-NMMA) or 1, 2, and 5 mM L-NAME for 96 hrs. Proliferation rate was determined by adding premixed WST-1 reagent (Clontech). After incubation at 37° C. for 3 hrs, absorbance was read at 450 nm (reference wavelength 690 nm).

Cell migration capacity. Cell migration was determined with a "wound healing assay." Briefly, $3 \times 10^5$ cells/well were grown in 6-well plates until confluence. Cells in monolayer were treated with different concentrations of 1400 W, L-NMMA, and L-NAME in starvation conditions (1% serum) for 72 hrs. To avoid an impact on cell proliferation, low serum medium was changed by regular growth medium in presence of inhibitors for 24 hrs (96 hrs total). A "wound" was then created in the cell monolayer with a 100-4, pipette tip. Images were taken at 0 hrs, and cells were allowed to heal the wound for 12 hrs. Wound-healing capacity was determined with the software Image J. Data were replicated in three independent experiments.

Lentiviral-mediated shRNA knockdown. GIPZ NOS2 lentiviral shRNA clones (shRNA1-V3LHS_360691; shRNA2-V2LHS_111769) and GIPZ Lentiviral Empty Vector shRNA Control were purchased from Thermo Scientific. MDA-MB-231 and SUM159 cells were treated with the lentiviral particles and polybrene (6 µg/mL) (Sigma-Aldrich; St. Louis, Mo., USA) for 48 hrs. shRNA-bearing cell clones were selected with puromycin (2 µg/mL) (Sigma-Aldrich) for 1 week. Cells were then harvested and plated for proliferation, mammosphere, wound healing, and Western blot assays.

siRNA-mediated NOS2 knockdown. SUM159 and MDA-MB-231 cells were transfected with scrambled siRNA, siRNA18 (s9618) or siRNA20 (s9620) (Silencer Select, Ambion, Austin, Tex., USA) for 96 hrs. Briefly, cells grown in 6-well plates (100,000 cells/well) were transfected in serum-, antibiotic/antimycotic-free DMEM medium with NOS2 siRNA or scrambled siRNA (100 nM) packaged in Lipofectamine RNAiMAX® (Invitrogen) for 6 hrs. Complete DMEM medium was added and cells were grown for 96 hrs.

Nitric oxide production in SUM159 cells. Cells were treated with L-NMMA or 1400 W for 24 hrs in phenol red- and serum-free DMEM medium. Aliquots of cell culture supernatant were taken at 0, 0.5, 2, 6 and 24 hrs for nitrate+nitrite (total nitric oxide) production with the nitrate/nitrite fluorometric assay kit (Cayman Chemical) following manufacturer's instructions.

Western Blot. Cells were cultured at a density of $2.5 \times 10^5$ cells/well in 6-well plates with or without iNOS inhibitors for 96 hrs. Cells were resuspended in 1× lysis buffer (Cell Signaling Technology, Inc.) and 1× protease/phosphatase inhibitor cocktail (Thermo Scientific). Samples (30 µg protein) were boiled in 4×LDS sample buffer (Thermo Scientific) containing 3-mercaptoethanol (Sigma-Aldrich) and subjected to SDS-PAGE electrophoresis in 4-20% polyacrylamide gels (Bio-Rad, Hercules, Calif., USA). Proteins were transferred onto nitrocellulose membranes (Bio-Rad) and non-specific binding was avoided incubating with 5% non-fat dry milk in 1×Tris-buffered saline (TBS) for 1 hr. Membranes were incubated overnight at 4° C. with primary antibodies (1:1,000 dilution; anti-β-Actin, 1:2,000 dilution). After washing and incubation with the appropriate secondary antibodies for 1 hr (1:2,000 dilution), membranes were washed and incubated with enhanced chemiluminescence substrate. Protein bands were developed in autoradiography films (Denville Scientific, Inc., Holliston, Mass., USA).

RT-PCR Analysis of Spliced XBP1. Total RNA was extracted from MDA-MB-231 and SUM159 cells with the RNeasy micro kit (Qiagen, Valencia, Calif., USA) and cDNA was synthetized with the iScript cDNA Synthesis kit (Bio-Rad) following the manufacturer's instructions. The PCR amplification (50 ng cDNA) was done with 2.5 U/µL Taq DNA polymerase (native, 5 U/µL), 0.2 mM dNTP, 1.5 mM $MgCl_2$ (50 mM) and 0.5 µM of each primer.

The primers used were:

```
XBP1-Forward
5'-GGGTCCAAGTTGTCCAGAATGC-3';      (SEQ ID NO: 1)

XBP1-Reverse
5'-TTACGAGAGAAAACTCATGGC-3';       (SEQ ID NO: 2)

β-Actin-Forward
5'-CTGGAACGGTGAAGGTGACA-3';        (SEQ ID NO: 3)
and

β-Actin-Reverse
5'-AAGGGACTTCCTGTAACAATGCA-3'.     (SEQ ID NO: 4)
```

The PCR conditions were 1 cycle at 95° C. for 5 min, 25 cycles of 30 sec at 95° C., 1 min at 50° C., and 1 min at 68° C., followed by 1 cycle at 68° C. for 5 min. cDNA amplicons were resolved in 2% agarose.

Immunohistochemistry. The paraffin embedded sections of human patients, MDA-MB-231 and SUM159 orthotopic tumor tissue were subjected to antigen retrieval using Tris-HCl buffer (pH=9.0) and blocked for 5 min using hydrogen peroxide. The human patient samples and xenograft tumors were then incubated for 1 hr at room temperature with anti-iNOS (1:50 dilution), anti-Ki67 (1:100 dilution) and anti-cleaved caspase-3 (1:50) antibodies. The samples were developed with the peroxidase-based EnVision™ kit (Dako, Carpentaria, Calif., USA) and compared to negative controls to eliminate false positives. The slides were counterstained with hematoxylin. iNOS score method: intensity (0-3): negative, weak, moderate, strong; distribution (0-4): <10%, 10-30%, >30-50%, >50-80%, >80%. Total score can be divided into 4 groups: negative (0-1), weak (2-3), moderate (4-5) and strong (6-7). MDA-MB-231 cells transfected either with NOS2-directed shRNA (shRNA1) or empty vector (EV), were used as negative and positive controls for iNOS staining, respectively.

Animal Studies. Female SCID Beige mice (4-5 weeks old) (Harlan Laboratories, Houston, Tex., USA) were housed under standard laboratory conditions (22° C.; 12 hrs/12 hrs light/dark cycle and free access to food and water). Either MDA-MB-231 or SUM159 cells ($3 \times 10^6$) were injected in the right mammary fat pad. Once the tumors reached 150-200 $mm^3$, the mice were randomized into different groups as follows (n=10/group): 1) Vehicle (saline, i.p.), 2) L-NMMA (either 80 mg/kg or 200 mg/kg, i.p., daily), 3) Docetaxel (20 mg/kg), 4) Combo (L-NMMA and docetaxel).

For the lung metastases-preventing study, MDA-MB-231 L/G cells were implanted as described above. The mice were randomized and treatments started 48 hrs after cell injection (n=5/group): 1) Vehicle (saline, i.p.), 2) L-NAME (80 mg/kg, i.p., daily for 35 days). Previous injection of luciferin, lungs were removed and washed in cold DMEM+ 10% FBS+1% antibiotics/antimycotic. Then, lungs were incubated in cold DMEM media containing 50 µM luciferin for 10 min. This protocol avoids the time lapse between lung extraction and exposure to luciferin. Fluorescent cancer cells were detected with an IVIS-200 in vivo imaging system (Perkin Elmer, Inc., Santa Clara, Calif., USA).

The clinically relevant dose regimen consisted on two cycles of Docetaxel (Bridgewater, N.J., USA) (20 mg/kg, i.p., on day 0) twelve hrs before being combined with L-NMMA (400 mg/kg on day 1, and 200 mg/kg for 4 additional days by oral gavage) and amlodipine on day 0 (10 mg/kg, i.p., daily, for 6 days). Docetaxel alone, as well as saline (i.p.)+sterile water (oral gavage) were used as controls.

Self-renewal and tumor-initiating capacity was determined by MSFE and limiting-dilution assays, respectively, in single cells isolated from tumor tissue. Briefly, breast tumor tissue was minced, digested in DMEM:F12 medium with 100 U/mL of collagenase type 3 (Worthington, Lakewood, N.J., USA) and 0.8 U/mL of dispase (Gibco, Carlsbad, Calif., USA) at 37° C. for 45 min. MSFE was assayed in isolated single cells as stated above. The limiting dilution assay (LDA) was performed injecting either $5 \times 10^4$ or $2 \times 10^4$ isolated cells from tumor tissue in the mammary fat pad of SCID Beige mice (n=12/group). Flow cytometric analysis of $CD44^+/CD24^{-/low}$ cell population was assayed using published methods.

Metabolite profiling by liquid chromatography-tandem mass spectrometry (LC-MS/MS). MDA-MB-231 and SUM159 xenograft tissue from animal studies (L-NMMA given daily) as well as plasma samples were prepared as previously described. L-NMMA (200 mg/kg) was orally administered by gavage to female SCID Beige mice (n=5). Blood was drawn before (baseline, 0 hrs) and after L-NMMA administration (0.5, 2, 12, 24 hrs). LC-MS/MS platform used for metabolite profiling was previously described. Ratiometric quantification of methylarginine (L-NMMA) and citrulline was determined as ion abundance levels in plasma and tumor tissue.

Blood Pressure Measurements. Blood pressure (BP) was measured in 15 female SCID Beige mice for 3 days (basal BP) and subsequently treated with one cycle of the clinically relevant dose regimen (n=5/group) as follows: amlodipine (10 mg/kg, i.p.) for 6 days (start at day 0), L-NMMA (200 mg/kg, gavage) for 5 days (start at day 1) and combination (L-NMMA+amlodipine). The average daily blood pressure was determined by averaging the average of the last 10 of 20 blood pressure measurements for the last three consecutive days of the cycle treatment using a computerized tail cuff monitor (BP-2000 Series II, Visitech, Sunderland, UNITED KINGDOM).

Statistical Analyses. All data were analyzed using the GraphPad™ Prism software (GraphPad Software, Inc., La Jolla, Calif., USA). Data are presented as mean±SEM. Statistical significance between two groups was analyzed by two-tailed Student's t-test. Experiments with more than three groups were analyzed with one-way ANOVA (analysis of variance) followed by Bonferroni's post-hoc test. Statistical analysis of tumor volume was assessed by two-way ANOVA and Bonferroni's post-hoc test. Fisher's exact test was used to determine significant differences in the limiting dilution assays. Survival proportions were assessed using a Kaplan-Meier method and further analyzed with either Wilcoxon or Log-Rank test. Proliferation, MSFE, migration index, and Ki67 staining are normalized to Vehicle group (100%). A p-value of less than 0.05 was considered as significant.

Results

Enhanced iNOS expression correlates with poor patient survival in invasive TNBC. iNOS has been described to be mediator of metastasis in different cancer types. Elevated iNOS expression has been linked to poor survival in ERα-negative breast cancer patients. The inventor hypothesized that enhanced iNOS expression in TNBC correlates with poor patient survival and metastases.

Oncomine Cancer Microarray database analysis of NOS2 (iNOS mRNA expression) expression in breast cancers was performed. Analysis of The Cancer Genome Atlas (TCGA) database showed that NOS2 mRNA expression was significantly higher in invasive TNBC patient samples (n=46) vs. non-TNBC (n=250) (fold change 1.425, p=$3.85 \times 10^{-5}$, Student's t-test) (FIG. 1A). Patient-survival analysis demonstrated a correlation between increased NOS2 expression and worse survival at 5 years in patients with invasive ductal breast carcinoma (n=79) (fold change 1.275, p=0.037, Student's t-test). Among them, 46 samples were TNBC (n=37 with high NOS2 expression; n=9 with low iNOS expression) (FIG. 1B). The inventor and colleagues further examined whether NOS2 expression correlates with worse survival in two additional databases of TNBC patients. Analysis of Van de Vijver (n=69 samples) and Curtis (n=260 samples) databases confirmed that high NOS2 expression was associated with survival in TNBC patients (FIG. 1C and FIG. 1D).

Next, the inventor and colleagues examined iNOS protein expression by immunohistochemistry in 83 surgically-resected, TNBC-primary breast cancer samples, and correlated expression with known patient outcome. iNOS was primarily cytoplasmic, but some cells exhibited both cytoplasmic and nuclear localization (FIG. 1E). Overall score showed that iNOS levels were weak to moderate (score 3-4) in 14 samples (16.9%) (FIG. 1E, FIG. 3 and FIG. 4), moderate to strong (score 5-6) in 50 samples (60.2%) (FIG. 1E), and strong (score 7) in 19 specimens (22.9%) (FIG. 1E). This stratification was used to analyze the correlation of iNOS expression and patient survival using the Kaplan-Meier analysis. Consistent with mRNA mining analysis (FIG. 1C and FIG. 1D), the inventor confirmed that enhanced iNOS protein levels were associated with worse patient survival when compared to low iNOS expression (p=0.05, Chi-square test) (FIG. 1F). These results demonstrate that increased iNOS by mRNA and protein expression in invasive TNBC is associated with poor patient survival.

Figure 2A:
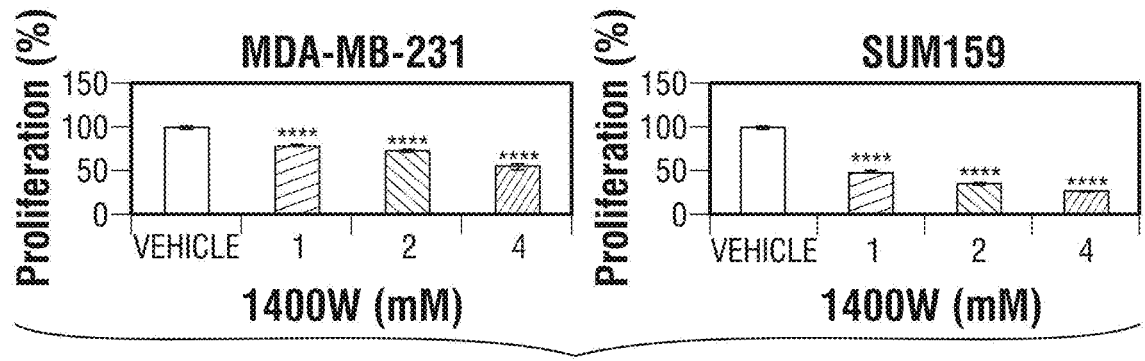
Figure 2B:
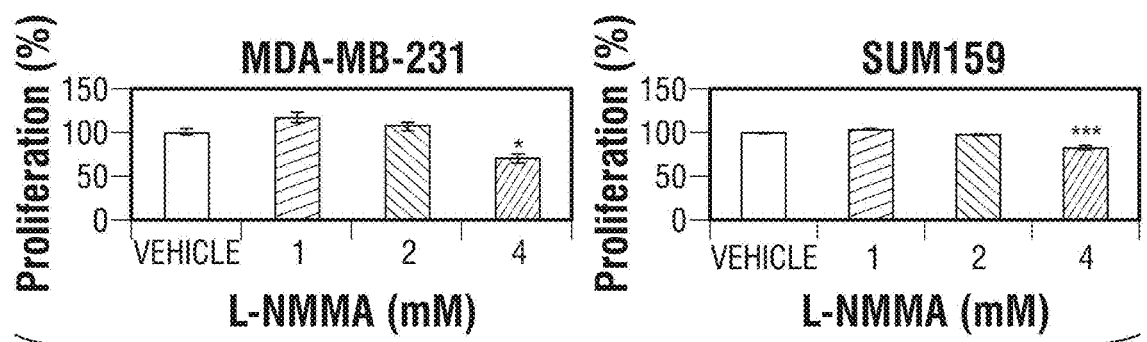
Figure 9A:
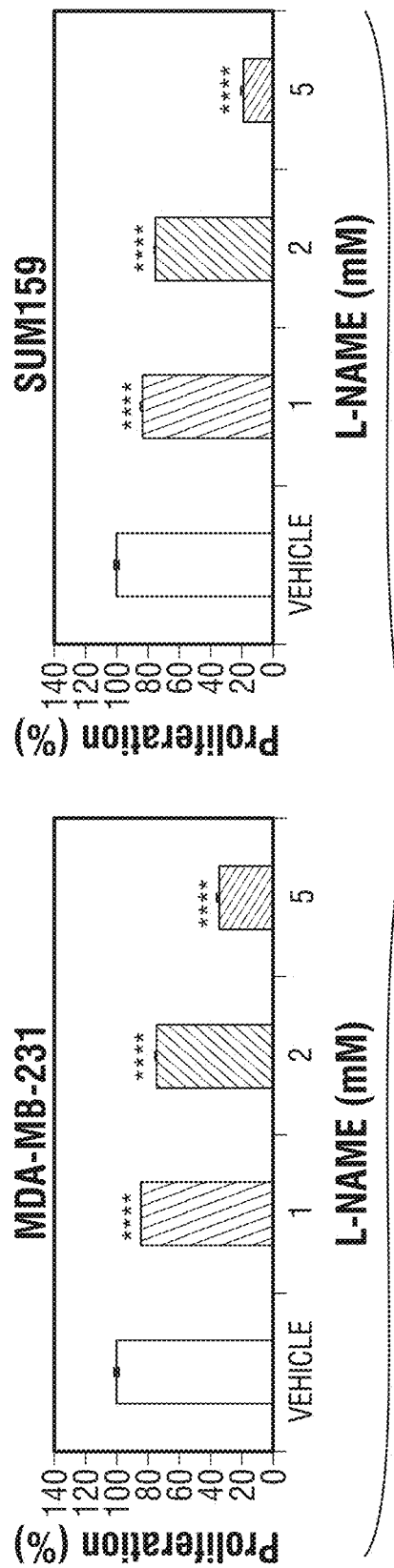

Inhibition of iNOS decreases tumorigenicity of TNBC cells. The inventor and colleagues assessed the effects of iNOS inhibition on proliferation in SUM159 and MDA-MB-231 cell lines after treatment with the selective iNOS inhibitor, 1400 W, and the pan-NOS inhibitors, L-NMMA and L-NAME, for 96 hrs (FIG. 2A). High concentrations of 1400 W (1, 2 and 4 mM) were able to significantly decrease proliferation in both cell lines (FIG. 2A). Similar results were observed after treatment with L-NAME (FIG. 9A). L-NMMA at the highest concentration (4 mM) showed anti-proliferative activity in both cell lines (FIG. 2B).

Figure 2C:
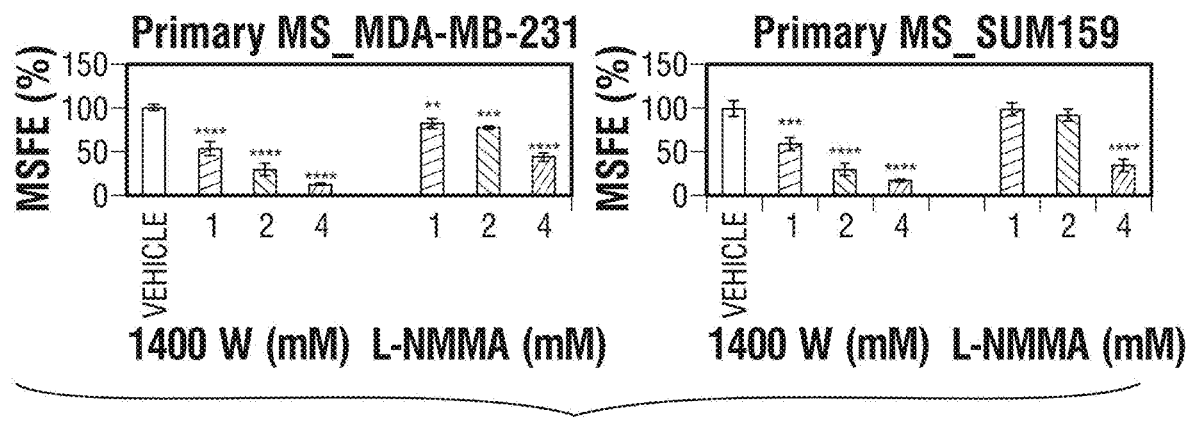
Figure 2D:
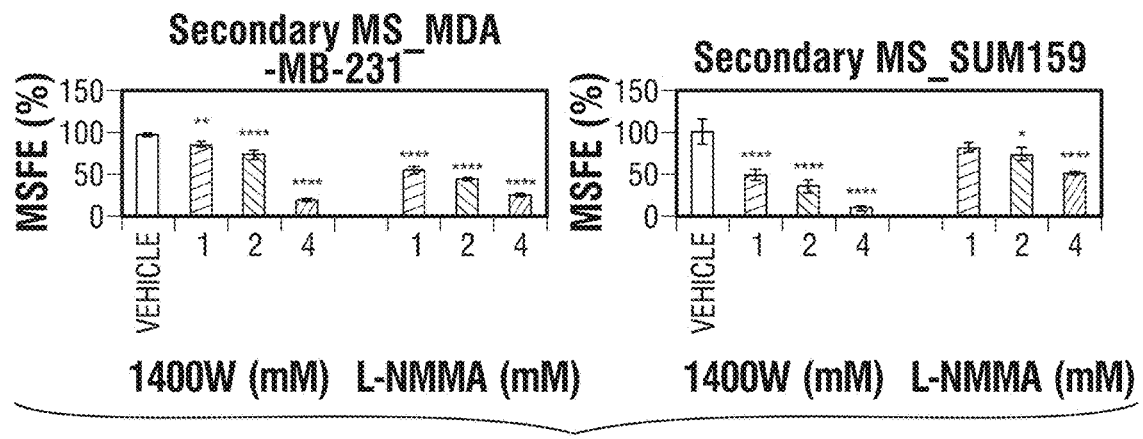
Figure 2E:
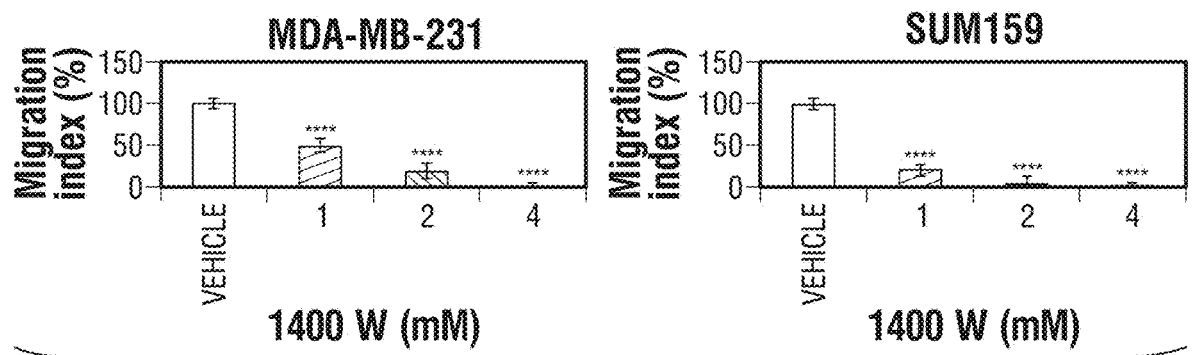
Figure 2F:
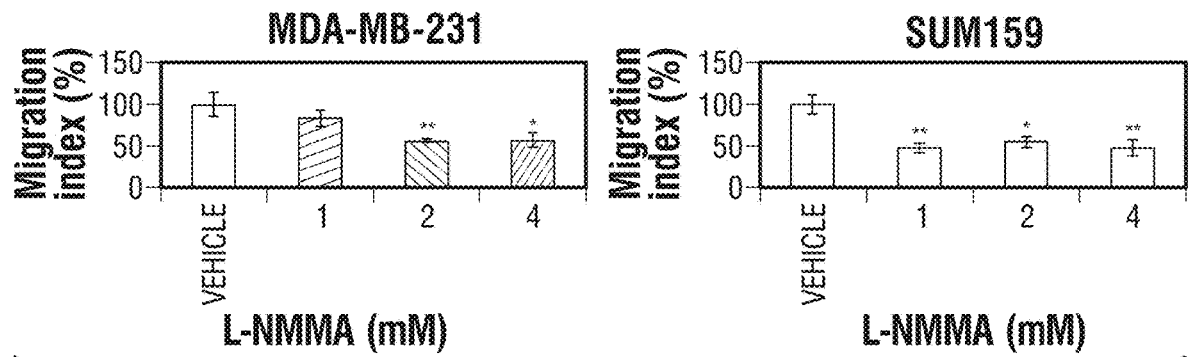
Figure 9B:
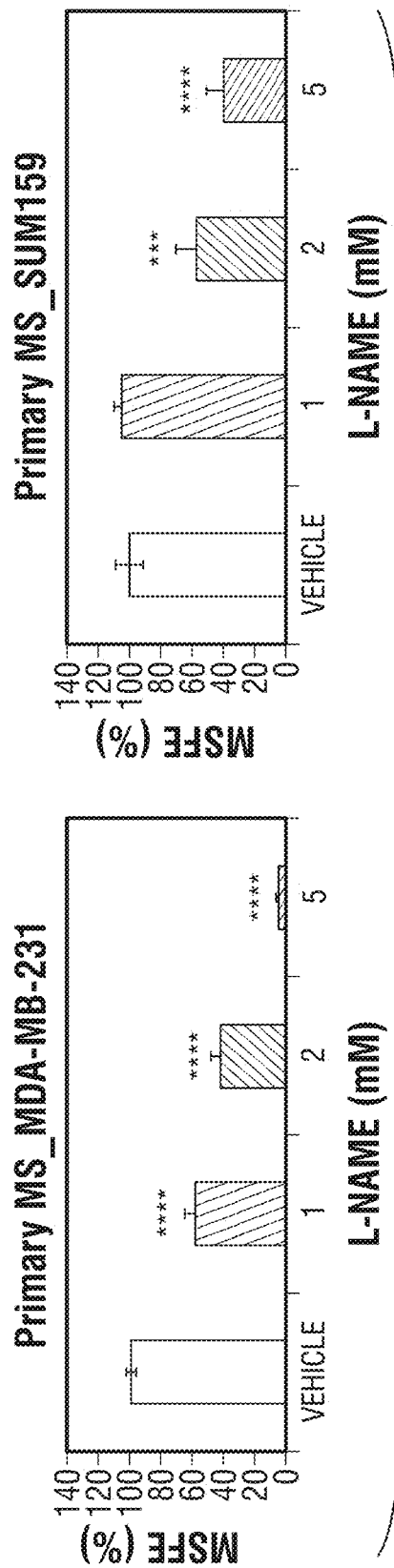
Figure 9E:
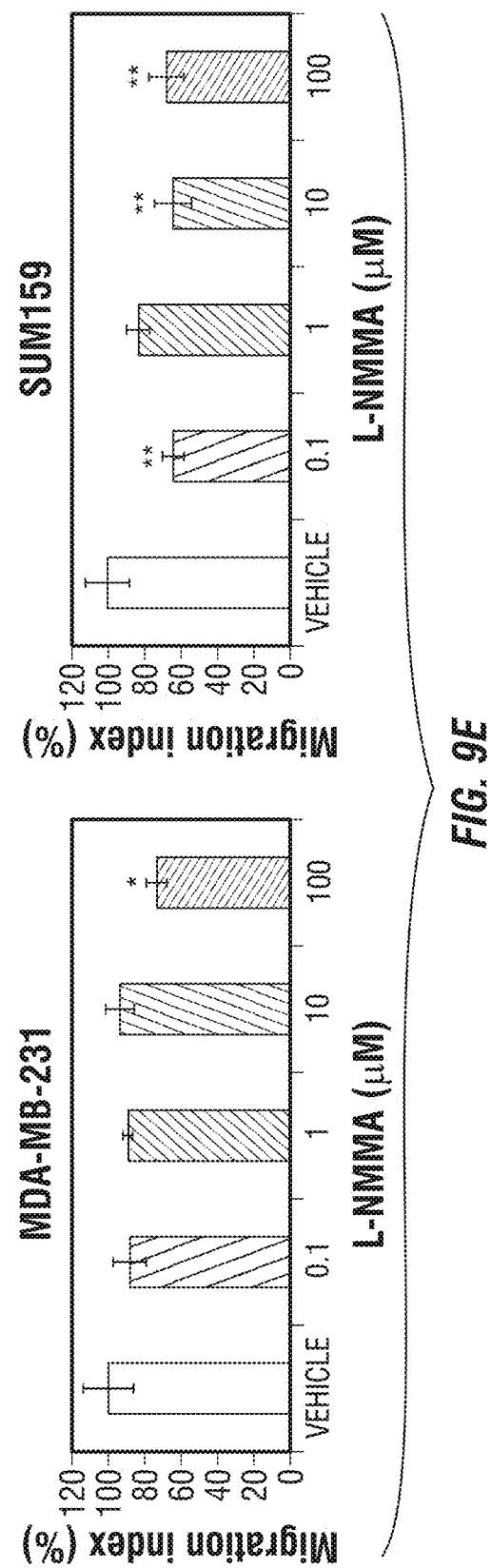

Resistance to treatment and metastasis may arise from a subpopulation of cancer stem cells (CSC) within a heterogeneous primary cancer that can serve to re-initiate tumor growth and seed metastases. Here, the inventor and colleagues investigated the effect of iNOS inhibition on cancer stem cell self-renewal by using the mammosphere forming efficiency (MSFE) assay. iNOS inhibition decreased the MSFE of primary mammospheres (MS) in both cell lines (FIG. 2C). Similar effects were found for L-NAME (FIG. 9B). The inventor identified reduced secondary MSFE in both cell lines for all the inhibitors tested (FIG. 2D and FIG. 9C). As the findings show an enhanced iNOS expression in invasive TNBC (FIG. 1A), the inventor further investigated the role of iNOS in cell migration using a wound healing assay. The selective iNOS inhibition with 1400 W caused a marked dose-dependent decrease in migration in both cell lines in millimolar (FIG. 2E) and micromolar range (FIG. 9D). L-NMMA-treated cells showed reduction in migration capacity (FIG. 2F). Lower concentrations at micromolar range were not consistent and less effective (FIG. 9E). Similar results were found for L-NAME (FIG. 10A). These results were further confirmed in shRNA-mediated iNOS (NO52) knockdown MDA-MB-231 (FIG. 3A, FIG. 3B and FIG. 3C) and SUM159 cells (FIG. 11A, FIG. 11B and FIG. 11C). Collectively, the results indicate that basal levels of iNOS have a major role on CSC self-renewal and migrating properties of TNBC cell lines, with a less pronounced effect in proliferation.

Suppression of endogenous iNOS could impair EMT and cell migration by impairing HIF1α and the endoplasmic reticulum (ER) stress/TGFβ/AFT4/ATF3 crosstalk. Transdifferentiation of polarized epithelial cells to mesenchymal cells (EMT) is evoked during tumor invasion and metastasis. The inventor then considered the impact of iNOS inhibition on EMT-inducing transcription factors in the mesenchymal-like TNBC MDA-MB-231 and SUM159 cells by Western blot. The inventor first examined the impact on NOS isoforms (iNOS, eNOS, and nNOS) after either selective or pan-inhibition (FIG. 3D; FIG. 10B, FIG. 10C and FIG. 10F). The findings revealed that selective iNOS blockade with 1400 W caused a reduction in protein levels of the EMT transcription factors Snail, Slug, and Twist1 in both cell lines at millimolar (FIG. 3D) and micromolar concentrations (FIG. 10D). Zeb1 protein levels were decreased at millimolar concentrations (FIG. 3D). Although less consistent, similar results were found for the pan-NOS inhibitors (FIG. 10E and FIG. 10F). iNOS knockdown with shRNA correlated with a decrease of Zeb1 and Twist1 protein levels (FIG. 3E). Snail and Slug were blocked only in SUM159 (FIG. 11D); the inventor found the similar results in MDA-MB-231 after two weeks of clone selection. Decrease of Zeb1 and Twist1 were confirmed by transient iNOS knockdown in SUM159 cells (FIG. 11E). Overall, these data suggest that selective iNOS inhibition efficiently decreases migration of TNBC cell lines, and this is consistently correlated with a decrease of EMT transcription factors.

Different pathways are responsible of inducing EMT and metastasis of tumor cells; among them, nitric oxide is a common denominator of HIF1α and endoplasmic reticulum (ER) stress. The findings indicate that selective iNOS inhibition resulted in a dose-dependent decrease in hypoxia (HIF1α) (FIG. 3F and FIG. 10G) and the ER stress markers IRE1α/splicedXBP1 (FIG. 3F and FIG. 11F) and ATF4 in both cell lines (splicedXBP1 was not detected in SUM159 cells, data not shown) (FIG. 3F). Functional protein-protein interaction (STRING 9.1) analysis unveiled a link between iNOS and TGFβ1 (FIG. 11G). Studies confirmed that 1400 W was able to inhibit TGFβ signaling (phospho-Smad2/3, Smad2/3 and mature TGFβ) in absence (FIG. 3G) and presence of recombinant TGFβ1 (10 ng/mL for 72 hrs) (FIG. 11H) through an undetermined mechanism. Additional protein-protein interaction analyses showed an interaction between ATF4 and ATF3 (FIG. 11G), both activating transcription factors that interact with TGFβ. Experiments confirmed the crosstalk between ER stress through ATF4/ATF3 and TGFβ (FIG. 11I); similarly, recombinant TGFβ1 (10 ng/mL for 24 hrs) induced the PERK/eIF2α/ATF4/ATF3 axis (FIG. 3I1). The results showed that co-treatment of the iNOS inhibitor 1400 W (4 mM) and recombinant TGFβ1 for 24 hrs was able to inhibit the stimulation of ATF4 and ATF3 protein levels by TGFβ1 independently of the PERK/eIF2α pathway. This result was further confirmed in siRNA-mediated iNOS (NO52) knockdown cells (FIG. 3I). Overall, these data demonstrated that iNOS inhibition could impair EMT and tumor cell migration by impairing ER stress (IRE1α/XBP1) and the crosstalk between ATF4, ATF3, and TGFβ.

iNOS inhibition reduces tumor growth, tumor initiating capacity and prevents lung metastases in mouse models of triple negative breast cancer. Based on the in vitro data, the inventor next investigated whether iNOS inhibition was able to prevent tumor initiation and metastasis of breast tumor cells in a mouse model of lung metastases. Daily i.p. injections of 80 mg/kg L-NAME were given to MDA-MB-231 xenograft-bearing mice for 35 days. L-NAME significantly reduced tumor growth (p=0.001) (FIG. 4A) as well as MSFE of primary MS (FIG. 4B). Secondary MSFE was also diminished but not significantly when compared to vehicle group (FIG. 4B). Additionally, tumor-initiating capacity of CSC was assessed with a limiting dilution assay (LDA) by injecting single cells isolated from tumor tissue ($5×10^5$ or $1×10^5$ cells) in the right mammary fat pad. All the animals of vehicle group (n=5) developed tumors whereas treatment with L-NAME yielded 3/5 tumors at 1.5 weeks with $5×10^5$ cells. The same results were observed in vehicle group at 2.5 weeks with $1×10^5$ cells compared to L-NAME-treated group (0/5 tumors) (p<0.05, Fisher's exact test) (FIG. 4D).

The inventor then examined whether iNOS inhibition was able to suppress metastasis to lungs in TNBC xenografts model. The luciferase/GFP-based MDA-MB-231 (MDA-MB-231 L/G) xenograft mouse model mimics the metastatic process to the lungs in patients. In this model of lung metastasis, cells metastasize from the primary tumor to lungs in ~35 days after implantation. MDA-MB-231 L/G cells were injected in the right mammary fat pad of SCID mice and 80 mg/kg L-NAME was given daily for 35 days. Ex vivo imaging of lungs in presence of luciferin showed higher fluorescence in vehicle group compared to L-NAME group (FIG. 4C). These results suggested that iNOS inhibition with daily L-NAME may also prevent metastasis to lungs in the TNBC mouse model.

In order to translate these results into future clinical trials, the pan-NOS inhibitor, L-NMMA, was selected for additional intensive study. Although L-NMMA has been previously investigated for cardiogenic shock, and has been administered to several thousand patients for that indication, the present invention provides the first reported re-purposing of this compound for an anti-cancer indication, and little data pre-dated these results to suggest a preclinical dose that might be effective as an anti-cancer therapeutic.

To answer this question, daily injections of 80 mg/kg L-NMMA were first given to SUM159 xenograft-bearing mice alone or in combination with docetaxel (20 mg/kg). After 10 days, no differential effect was observed between groups, and the daily dose was increased to 200 mg/kg. The tumor growth was efficiently blocked by L-NMMA administered alone or in combination with docetaxel (FIG. 13A). The inventor correlated these results with tumor cell proliferation by immunohistochemistry (Ki67). Higher proliferating rate in vehicle and chemotherapy groups compared to L-NMMA and combination groups (FIG. 13B and FIG. 13C) was observed. The inventor next analyzed the impact on CSC self-renewal by the MSFE assay. Docetaxel showed a dramatic increase in the primary and secondary MSFE of single tumor cells isolated from breast tumor tissue. This increment was efficiently blocked by addition of L-NMMA (combination group) (FIG. 13D). Flow cytometric analysis showed slight increase in $CD44^+/CD24^{-/low}$ population after chemotherapy (FIG. 14A). LDA showed that vehicle, L-NMMA, docetaxel and combination groups exhibited 12/12, 4/12, 12/12, 6/12 tumors, respectively, at 7 weeks with $5×10^4$ cells. At week nine a significant reduction in tumor-initiating capacity was observed as different groups with $2×10^4$ cells yielded 7/12, 0/12, 3/12, 0/12 tumors in vehicle, L-NMMA, docetaxel and combination, respectively (p<0.05, Fisher's exact test) (FIG. 13E).

The role of L-NMMA was then investigated, either alone or in combination with docetaxel in a different TNBC mouse model. Docetaxel (20 mg/kg at days 0 and 21) and 200 mg/kg L-NMMA (daily) were given to MDA-MB-231 xenograft-bearing mice for 31 days. Firstly, reduced tumor growth was found in L-NMMA group compared to vehicle, but there was no change between docetaxel and combination groups (FIG. 5A). These results were further correlated with lower proliferation rate in L-NMMA and combination groups as seen by immunohistochemistry (FIG. 5B and FIG. 5C). Additionally, higher apoptosis levels in docetaxel-treated xenografts were found; these results might offset the high proliferation rate relative to the combination group (FIG. 5D). Primary MS was less for both L-NMMA and combination, compared to vehicle and chemotherapy alone groups. L-NMMA treatment was able to reduce secondary MS, but no change was observed for the combination group (FIG. 5E). Flow cytometric analysis showed no changes in CD44$^+$/CD24$^{-/low}$ population (FIG. 14B). LDA showed that vehicle-treated and docetaxel-treated groups presented 12/12 and 8/12 tumors, respectively, with a significant decrease in L-NMMA-treated (1/12) and combination-treated (4/12) xenografts at 5 weeks with 5×10$^4$ cells. After six weeks, a decrease in both L-NMMA and combination groups (3/12 and 5/12, respectively) compared to vehicle and docetaxel groups (6/12 and 8/12, respectively) was observed (p<0.05, Fisher's exact test) (FIG. 5F). The investigations demonstrate that L-NMMA plasma levels are cleared rapidly (FIG. 14C), whereas it accumulates in the tumor tissue (FIG. 14D) and inhibits the conversion of L-arginine to L-citrulline and NO by iNOS (FIG. 14E) 24 hrs after completion of treatment. This inhibition led to a decrease in total NO production as seen in SUM159 cells (FIG. 14F). Overall, these results demonstrate that in vivo iNOS inhibition with L-NMMA decreased tumor growth, cell proliferation, and tumor-initiating capacity of CSC, together with a significant reduction in lung metastases.

Efficient dose regimen of L-NMMA and Docetaxel with potential clinical application. Clinically, L-NMMA cause acute blood pressure (BP) elevation through inhibition of constitutive eNOS. Here, a regimen is described having an attenuated duration of iNOS inhibitor (in this case, L-NMMA) together with an anti-hypertensive (in this example, amlodipine), for two cycles in two different mouse models of TNBC (MDA-MB-231 and SUM159 xenografts). Standard docetaxel at 20 mg/kg was administered every 2 weeks. L-NMMA was given 24 hrs after chemotherapy, for 5 days at 200 mg/kg, a dosage comparable to previously clinical reports. Blood pressure increment was counteracted using the calcium channel blocker amlodipine (10 mg/kg, daily for 6 days, i.p.). Oral L-NMMA significantly increased the mean systolic pressure (147 mm Hg) compared to basal levels (120 mmHg) in mice, and this elevation was efficiently reversed by amlodipine (10 mg/kg) (FIG. 6A). This elevation in BP was transient and disappeared 24 hrs after the last injection of L-NMMA (FIG. 6B).

The combination of L-NMMA and docetaxel was able to decrease tumor growth in a MDA-MB-231 orthotopic model (FIG. 6C). This dose regimen also improved survival in comparison with docetaxel-treated group (p=0.0001, Wilcoxon test) (FIG. 6D). Similar results were found in SUM159 xenografts (FIG. 6E). Overall, the data shows that the dose regimen proposed herein is effective in reducing tumor growth, and results in greater survival. By combining the administration of the iNOS inhibitor with an anti-hypertensive for at least a portion of the protocol, the untoward adverse side effects of the iNOS inhibitor in transiently increasing BP can be minimized and/or circumvented.

Further combination of the iNOS inhibitor therapy with one or more conventional chemotherapeutics, such as docetaxel) provides additional synergistic treatment benefits and represents a new strategy for overcoming treatment resistance in refractory, metastatic, and TNBC patients.

As discussed herein, TNBC is an extremely aggressive and lethal form of cancer lacking effective targeted therapies. TNBC patients show higher risk of metastasis and tumor relapse. iNOS levels predict a worse survival in patients with basal-like estrogen receptor-negative breast cancer, and it has been suggested to increase tumor aggressiveness by modulating cancer stem cells (CSC) as well as the metastatic propensity of cells. The present invention is the first report to demonstrate that inhibition of the iNOS pathway can decrease tumorigenicity of TNBC cells by affecting cell proliferation, CSC self-renewal, and/or cell migration. The in vivo studies presented in this application demonstrated the efficacy of several exemplary small molecule iNOS inhibitors, such as L-NMMA, as a novel targeted therapy for cancer patients, including those with refractory cancers such as TNBC, and offers the need for an immediate translation of these results into human clinical trials.

These examples demonstrated that NOS2 was commonly increased in invasive TNBC and was associated with poor survival of patients with invasive breast carcinoma. Additional data was shown that demonstrated high iNOS protein levels by immunohistochemistry in eighty-three human TNBC patient samples also correlated with a worsened patient outcome, which is consistent with earlier reports in ERα-negative and invasive breast carcinoma. Kaplan-Meier analysis of the Van de Vijver and Curtis databases, as well as of the human TNBC patient samples, strongly indicates that high iNOS expression was associated with poor overall survival in TNBC patients. These observations also establish that increased iNOS expression may be predictive of poor prognosis in certain subsets of cancer patients.

iNOS expression has been correlated with increased tumor grade and aggressiveness of breast cancer cells. The present invention describes the effect of iNOS on CSC self-renewal, tumor initiation and the migrating capacity of TNBC cells. The anti-tumor activity of iNOS inhibitors has been previously reported in epidermoid carcinoma, oral, glioblastoma, and breast cancer, and is consistent with the in vitro and in vivo findings. Increased iNOS expression has been described to contribute to resistance to conventional treatment by promoting tumor initiation in glioblastoma cells. Additionally, iNOS may influence CSC self-renewal by modulating CD44 and c-Myc in ERα-negative breast cancer. The inventor demonstrated for the first time that iNOS inhibition decreased CSC self-renewal and tumor initiation in both in vitro and in vivo models of TNBC.

Nitric oxide may either promote or inhibit metastatic events depending on endogenous levels. The role of NOS inhibitors on metastasis has been previously studied, but the underlying mechanisms remain unclear. An early study demonstrated that the pan-NOS inhibitor L-NAME may decrease tumor growth and lung metastasis in murine breast cancer model (EMT-6 cells). Similarly, L-NAME inhibited the invasive and migrating potential of two metastatic mammary cell lines (C3L5 and C10). In another study with the metastatic human adenocarcinoma HRT-18 cells, the invasiveness was substantially decreased by daily treatment with 500 μM of the selective iNOS inhibitor 1400 W. More recently, 1400 W was shown to markedly inhibit spontaneous lung metastasis in a mouse model of adenoid cystic carcinoma of the oral cavity.

The present example demonstrated that iNOS inhibition decreased cell migration and lung metastases in in vivo models of TNBC. It has been suggested that NO and iNOS may lead to early metastasis by inducing IL-8 and the CXC chemokine receptor 4. CSCs display mesenchymal features resulting in increased cell migration and metastasis. iNOS inhibition decreased CSC self-renewal and tumor initiation, thus indicating that inhibitors against this pathway could reverse the transition of tumor cells to a more mesenchymal-like phenotype. Consistent with the effect on cell migration, selective iNOS inhibition and NOS2 knockdown decreased transcription factors driving EMT in all the TNBC cell lines tested.

To better understand the mechanism of the effects of endogenous iNOS inhibition in decreasing EMT transcription factors, the impact of the iNOS-selective inhibitor, 1400 W, was analyzed. EMT may be promoted by different signal transduction pathways like TGFβ, Wnt/β-catenin, Notch, Hedgehog, and multiple growth factors. EMT transcription factors (Snail, Slug, Twist1, or Zeb1) are activated by diverse intermediate effectors like c-Myc, Ets, HIF1α, or NFκB. Additionally, ER stress has been linked to EMT in thyroid, alveolar epithelial, and human renal proximal tubule cells through activation of PERK, XBP1 or Grp78. Interestingly, among these disparate signaling networks, iNOS is the common denominator between HIF1α and ER stress. Inhibition of endogenous iNOS-derived NO production was able to reduce HIF1α stabilization and protein levels in colon carcinoma cells. Transcription factors Twist1, Snail, Slug, Zeb1, among others, are directly or indirectly influenced by HIF1α.

Additionally, hypoxia induces ER stress and unfolded protein response (UPR), and it has been recently linked to migration and sphere formation in breast cancer cells by activation of the PERK/ATF4/LAMP3-arm under hypoxic conditions. The results suggest that iNOS inhibition correlates with an impairment of TGFβ signaling via the ER stress ATF4/ATF3-axis. It is known that TGFβ stimulates ATF4 protein levels to suppress differentiation in calvarial osteoblasts. Certain conditions such as ER stress through the PERK/eIF2α axis may activate ATF4 which in turn induces ATF3 transcription, whereas ATF3 itself is an activating transcription factor that enhances TGFβ, mammosphere formation and EMT in cooperation with Twist-1.

Translation of these results into clinical practice represents a next step in this new finding. L-NMMA is a pan-NOS inhibitor that has been extensively studied in several clinical trials of circulatory shock. In the cardiogenic shock trial, L-NMMA proved to be safe and without few adverse events other than transient reversible hypertension. In normotensive patients, L-NMMA was administered to metastatic renal cell carcinoma patients prior to infusion of interleukin-2. Doses of 3 and 6 mg/kg did not induce clinically apparent side effects, and BP remained unchanged. At a dose level of 12 mg/kg, patients experienced increase in systolic BP up to 25 mmHg, without any clinical symptoms, which normalized rapidly on stopping the L-NMMA infusion. To determine a safe and effective regimen with clinical applicability was the main challenge of these preclinical studies. The dose rate in the present study was chosen, with modifications, based on a previous clinical trial in patients with septic shock. These results demonstrated that tumor growth could be restrained by an attenuated regimen of five days of L-NMMA after chemotherapy, given together with amlodipine. Randomized, placebo-controlled, double-blind study of L-NMMA was previously reported in patients with septic shock, up to a maximum of 14 days. The regimen followed consisted of an initial dose of 2.5 mg/kg/hr and then adjusted at different rates (0.5, 1, 2.5, 5, 7.5, 10, 15, and 20 mg/kg/hr). The current dosing regimen for use of L-NMMA as an anti-cancer therapeutic is much lower than that previously reported in the literature for septic shock.

In conclusion, this example provides new evidence about the correlation between enhanced endogenous iNOS expression and poor survival in patients with TNBC. Targeted therapy with iNOS inhibitors has been demonstrated to inhibit not only tumor cell proliferation, but also CSC self-renewal and migration, reducing tumor growth, tumor initiation and the number of lung metastases. Inhibition of metastatic events may be due to a reduction of EMT transcription factors by inhibition of HIF1α, ER stress (IRE1α/splicedXBP1) and the TGFβ/ATF4/ATF3 axis. From these results, a targeted therapeutic regimen, which decreases tumor growth and enhances survival rate in vivo, using the compounds described herein, is defined, and establishes the importance of clinical trials targeting this pathway in TNBC patients.

Example 2—Effects of Calcium Channel Antagonists

Materials and Methods

Cell Proliferation Assay In Vitro. Mesenchymal-like, TNBC cell lines, MDA-MB-231 and SUM159, were grown in DMEM supplemented with 10% fetal bovine serum and 1% antibiotic-antimycotic. Stock solutions of various calcium-channel antagonists (amlodipine, nicardipine, nifedipine, felodipine, isradipine, diltiazem, verapamil, lacidipine, nisoldipine, nitrendipine, nivaldipine, azelnidipine, barnidipine, benidipine, efonidipine, lercanidipine, pranidipine, and manidipine) were prepared in DMSO. Effects on cell proliferation were assayed with the WST-1 method. Briefly, 1,000 (SUM159) and 2,000 (MDA-MB-231) cells/well were plated in a 96-well plate and treated with different concentrations (0, 1, 5, and 10 μM) of calcium channel antagonists for 72 hrs. Proliferation rate was determined by adding premixed WST-1 reagent. After incubation at 37° C. for three hrs, absorbance was read at 450 nm (reference wavelength 690 nm). Results were normalized against vehicle (100%). The antagonists were considered active when proliferation was decreased in ≥30%.

Animal Studies. Female SCID Beige mice (4-5 weeks old) were housed under standard laboratory conditions (22° C.; 12 hr/12 hr light/dark cycle and free access to food and water). Either MDA-MB-231 or SUM159 cells (3×10$^6$) were injected in the right mammary fat pad. Once the tumors reached 150-200 mm$^3$, mice were randomized into different groups as follows (n=5/group): 1) vehicle (saline, i.p.), 2) Amlodipine (10 mg/kg, i.p.), two cycles on day 0 and 14 (daily for 6 days each cycle). All animal procedures and experimental protocols were approved with full adherence to institutional and federal animal use and care guidelines.

Results

Cell Proliferation In Vitro. The anti-proliferative efficacy of several calcium channel antagonists was demonstrated in two different TNBC cell lines (MDA-MB-231 and SUM159). The results showed a dose-dependent decrease in proliferation after treatment with amlodipine, azelnidipine, felodipine, lacidipine, nicardipine, and nivaldipine and in both MDA-MB-231 (FIG. 15A, FIG. 15B, FIG. 15C, FIG. 15D, FIG. 15E, and FIG. 15F) and SUM159 (FIG. 16A, FIG. 16B, FIG. 16C, FIG. 16D, FIG. 16E, and FIG. 16F). In these figures, the percentage of decrease in proliferation is shown above bars.

Animal Studies. The data obtained from in vivo models of TNBC showed that administration of Amlodipine (10 mg/kg) was able to restrain growth of MDA-MB-231 and SUM159 orthotopic tumors (FIG. 17A and FIG. 17B, respectively). The most effective antagonists identified from in vitro results (amlodipine, felodipine, lacidipine, nivaldipine, and azelnidipine) may also be tested for in vivo anti-tumor activity in suitable animal models of TNBC (including, for example, MDA-MB-231 and SUM159). A dose of ~20 mg/kg i.p. was considered to be in the effective range.

REFERENCES

The following references, to the extent that they provide exemplary procedural or other details supplementary to those set forth herein, are specifically incorporated herein by reference in their entirety:

ALEXANDER, J H et al., "Effect of tilarginine acetate in patients with acute myocardial infarction and cardiogenic shock: the TRIUMPH randomized controlled trial," *JAMA*, 297(15):1657-1666 (April 2007).

AL-HAJJ, M et al., "Prospective identification of tumorigenic breast cancer cells," *Proc. Nat'l. Acad. Sci. USA*, 100(7):3983-3988 (April 2003).

ALLRED, D C et al., "Prognostic and predictive factors in breast cancer by immunohistochemical analysis," *Mod. Pathol.*, 11(2):155-168 (February 1998).

AMBS, S et al., "Frequent nitric oxide synthase-2 expression in human colon adenomas: implication for tumor angiogenesis and colon cancer progression," *Cancer Res.*, 58(2):334-341 (January 1998).

BABYKUTTY, S et al., "Insidious role of nitric oxide in migration/invasion of colon cancer cells by upregulating MMP-2/9 via activation of cGMP-PKG-ERK signaling pathways," *Clin. Exp. Metastasis*, 29(5):471-492 (June 2012).

BROWN, R W et al., "Prognostic value of Ki-67 compared to S-phase fraction in axillary node-negative breast cancer," *Clin. Cancer Res.*, 2(3):585-592 (March 1996).

BULUT, A S et al., "Significance of inducible nitric oxide synthase expression in benign and malignant breast epithelium: an immunohistochemical study of 151 cases," *Virchows Arch.*, 447(1):24-30 (July 2005).

BURKE, A J et al., "The yin and yang of nitric oxide in cancer progression," *Carcinogenesis*, 34(3): 503-512 (March 2013).

CAMERON, D et al., "Adjuvant bevacizumab-containing therapy in triple-negative breast cancer (BEATRICE): primary results of a randomised, phase 3 trial," *Lancet Oncol.*, 14(10):933-942 (September 2013).

CAMPBELL, P J et al., "Identification of somatically acquired rearrangements in cancer using genome-wide massively parallel paired-end sequencing," *Nat. Genet.*, 40:722-729 (April 2008).

CAMPBELL, P J et al., "The patterns and dynamics of genomic instability in metastatic pancreatic cancer," *Nature*, 467:1109-1113 (October 2010).

CARLISLE, R E et al., "TDAG51 mediates epithelial-to-mesenchymal transition in human proximal tubular epithelium," *Am. J. Physiol. Renal Physiol.*, 303(3):F467-F481 (August 2012).

CHANG, J C et al., "Gene expression patterns in formalin-fixed, paraffin-embedded core biopsies predict docetaxel chemosensitivity in breast cancer patients," *Breast Cancer Res. Treat.*, 108(2):233-240 (March 2008).

CHANG, J C et al., "Gene expression profiling for the prediction of therapeutic response to docetaxel in patients with breast cancer," *Lancet*, 362(9381):362-369 (August 2003).

CHANG, J C et al., "Patterns of resistance and incomplete response to docetaxel by gene expression profiling in breast cancer patients," *J. Clin. Oncol.*, 23(6):1169-1177 (February 2005).

CHEN, J et al., "A restricted cell population propagates glioblastoma growth after chemotherapy," *Nature*, 488 (7412):522-526 (August 2012).

CHEN, Q et al., "Untargeted plasma metabolite profiling reveals the broad systemic consequences of xanthine oxidoreductase inactivation in mice," *PLoS One*, 7(6): e37149 doi: 10.1371/journal.pone.0037149 (June 2012).

CHINJE, E C et al., "17β-Oestradiol treatment modulates nitric oxide synthase activity in MDA231 tumour with implications on growth and radiation response," *Br. J. Cancer*, 86(1):136-142 (January 2002).

CHOWDHURY, R et al., "Nitric oxide produced endogenously is responsible for hypoxia-induced HIF-1α stabilization in colon carcinoma cells," *Chem. Res. Toxicol.*, 25(10):2194-2202 (October 2012).

COTTER, G et al., "LINCS, "LNAME (a NO synthase inhibitor) in the treatment of refractory cardiogenic shock," *Eur. Heart 1*, 24:1287-1295 (July 2003).

COTTER, G et al., "L-NMMA (a nitric oxide synthase inhibitor) is effective in the treatment of cardiogenic shock," *Circulation*, 101(12):1358-1361 (March 2000).

CREIGHTON, C J et al., "Residual breast cancers after conventional therapy display mesenchymal as well as tumor-initiating features," *Proc. Nat'l. Acad. Sci. USA*, 106(33):13820-13825 (August 2009).

CROWLEY, J, and ANKERST, D P, "*Handbook of Statistics in Clinical Oncology*" ($2^{nd}$ Edition). Boca Raton, Chapman & Hall/CRC Press (2006).

CURTIS, C et al., "The genomic and transcriptomic architecture of 2,000 breast tumours reveals novel subgroups," *Nature*, 486(7403):346-352 (April 2012).

DAUB, H et al., "Kinase-selective enrichment enables quantitative phosphoproteomics of the kinome across the cell cycle," *Mol. Cell*, 31(3):438-448 (August 2008).

DAVE, B et al., "Epithelial-mesenchymal transition, cancer stem cells and treatment resistance," *Breast Cancer Res.*, 14(1):202 (January 2012).

DAVE, B et al., "Selective small molecule stat3 inhibitor reduces breast cancer tumor-initiating cells and improves recurrence free survival in a human-xenograft model," *PLoS One* 7(8):e30207 (August 2012).

DERY, M A et al., "Endoplasmic reticulum stress induces PRNP prion protein gene expression in breast cancer," *Breast Cancer Res.*, 15(2):R22 (March 2013).

DIEHN, M et al., "Association of reactive oxygen species levels and radioresistance in cancer stem cells," *Nature*, 458(7239):780-783 (April 2009).

DRIESSENS, G et al., "Defining the mode of tumour growth by clonal analysis," *Nature*, 488(7412):527-30 (August 2012).

EDWARDS, P et al., "Tumor cell nitric oxide inhibits cell growth in vitro, but stimulates tumorigenesis and experimental lung metastasis in vivo," *J. Surg. Res.*, 63(1):49-52 (June 1996).

EYLER, C E et al., "Glioma stem cell proliferation and tumor growth are promoted by nitric oxide synthase-2," *Cell*, 146(1):53-66 (July 2011).

FAN, M et al., "Phosphorylated VEGFR2 and hypertension: potential biomarkers to indicate VEGF-dependency of advanced breast cancer in anti-angiogenic therapy," *Breast Cancer Res. Treat.*, 143(1):141-151 (January 2014).

GAMPENRIEDER, S P et al., "Hypertension as a predictive marker for bevacizumab in metastatic breast cancer: results from a retrospective matched-pair analysis," *Anticancer Res.*, 34(1):227-233 (January 2014).

GERLINGER, M et al., "Intratumor heterogeneity and branched evolution revealed by multiregion sequencing," *N. Engl. J. Med.*, 366:883-892 (March 2012).

GINESTIER C et al., "ALDH1 is a marker of normal and malignant human mammary stem cells and a predictor of poor clinical outcome," *Cell Stem Cell*, 1(5):555-567 (November 2007).

GLYNN, S A et al., "Increased NOS2 predicts poor survival in estrogen receptor-negative breast cancer patients," *J. Clin. Invest.*, 120(11):3843-3854 (November 2010).

GRALOW, J R, "Breast cancer 2004. Progress and promise on the clinical front," *Phys. Med.*, 21(Suppl 1):2 (2006).

GRISHAM, M B et al., "Nitric oxide I. Physiological chemistry of nitric oxide and its metabolites: implications in inflammation," *Am. J. Physiol.*, 276(Pt. 1):G315-G321 (February 1999).

HOPE, K J et al., "Acute myeloid leukemia originates from a hierarchy of leukemic stem cell classes that differ in self-renewal capacity," *Nat. Immunol.*, 5(7):738-743 (July 2004).

IGNARRO, L J, "Physiology and pathophysiology of nitric oxide," *Kidney Int. Suppl.*, 55:S2-S5 (June 1996).

JADESKI, L C et al., "Nitric oxide promotes murine mammary tumour growth and metastasis by stimulating tumour cell migration, invasiveness and angiogenesis," *Int. J. Cancer*, 86(1):30-39 (April 2000).

JIANG, Y et al., "Deep-sequencing reveals clonal evolution patterns and mutation events associated with relapse in B-cell lymphomas," *Genome Biol.*, 15(8):432 (August 2014).

KASAP, C, et al., "DrugTargetSeqR., "a genomics- and CRISPR-Cas9-based method to analyze drug targets," *Nat. Chem. Biol.*, 10(8):626-628 (August 2014).

KILBOURN, R G et al., "Beneficial versus detrimental effects of nitric oxide synthase inhibitors in circulatory shock: lessons learned from experimental and clinical studies," *Shock*, 7(4):235-246 (April 1997).

KILBOURN, R G et al., "Strategies to reduce side effects of interleukin-2: evaluation of the antihypotensive agent N G-monomethyl-L-arginine," *Cancer J. Sci. Am.*, 6(Suppl. 1):521-530 (February 2000).

KIM, R K et al., "Fractionated radiation-induced nitric oxide promotes expansion of glioma stem-like cells," *Cancer Sci.*, 104(9):1172-1177 (September 2013).

KORKAYA, H et al., "Breast cancer stem cells, cytokine networks, and the tumor microenvironment," *J. Clin. Invest.*, 121(10):3804-3809 (October 2011).

KUEFER, M U et al., "cDNA cloning, tissue distribution, and chromosomal localization of myelodysplasia/myeloid leukemia factor 2 (MLF2)," *Genomics*, 35(2):392-396 (July 1996).

LANDIS, M D et al., "Patient-derived breast tumor xenografts facilitating personalized cancer therapy," *Breast Cancer Res.*, 15(1):201 (January 2013).

LAPIDOT, T et al., "A cell initiating human acute myeloid leukaemia after transplantation into SCID mice," *Nature*, 367(6464):645-648 (February 1994).

LEE, H E et al., "An increase in cancer stem cell population after primary systemic therapy is a poor prognostic factor in breast cancer," *Br. J. Cancer*, 104:1730-1738 (May 2011).

L I, X et al., "Intrinsic resistance of tumorigenic breast cancer cells to chemotherapy," *J. Nat'l. Cancer Inst.*, 100(9):672-679 (April 2008).

LIAN, N et al., "Transforming growth factor β suppresses osteoblast differentiation via the vimentin activating transcription factor 4 (ATF4) axis," *J. Biol. Chem.*, 287(43):35975-35984 (October 2012).

LOIBL, S et al., "The role of early expression of inducible nitric oxide synthase in human breast cancer," *Eur. J. Cancer*, 41(12):265-271 (January 2005).

LOPEZ, A et al., "Multiple-center, randomized, placebo-controlled, double-blind study of the nitric oxide synthase inhibitor 546C88: effect on survival in patients with septic shock," *Crit. Care Med.*, 32(1):21-30 (January 2004).

MASSI, D et al., "Inducible nitric oxide synthase expression in benign and malignant cutaneous melanocytic lesions," *J. Pathol.*, 194(2):194-200 (June 2001).

MATRONE, C et al., "HIF-1α reveals a binding activity to the promoter of iNOS gene after permanent middle cerebral artery occlusion," *J. Neurochem.*, 90(2):368-378 (July 2004).

MOHSIN, S K et al., "Neoadjuvant trastuzumab induces apoptosis in primary breast cancers," *J. Clin. Oncol.*, 23(11):2460-2468 (April 2005).

MOLINA, H et al., "Global proteomic profiling of phosphopeptides using electron transfer dissociation tandem mass spectrometry," *Proc. Nat'l. Acad. Sci. USA*, 104(7):2199-2204 (February 2007).

MUROHARA, T et al., "Nitric oxide synthase modulates angiogenesis in response to tissue ischemia," *J. Clin. Invest.*, 101(11):2567-2578 (November 1998).

NADANO, D et al., "A human gene encoding a protein homologous to ribosomal protein L39 is normally expressed in the testis and derepressed in multiple cancer cells," *Biochim. Biophys. Acta*, 1577(3):430-436 (September 2002).

NAGELKERKE, A et al., "Hypoxia stimulates migration of breast cancer cells via the PERK/ATF4/LAMP3-arm of the unfolded protein response," *Breast Cancer Res.*, 15(1):R2 (January 2013).

NOUSIAINEN, M et al., "Phosphoproteome analysis of the human mitotic spindle," *Proc. Nat'l. Acad. Sci. USA*, 103(14):5391-5396 (April 2006).

OHTSU, N et al., "Antitumor effects of inhibitors of nitric oxide synthase or cyclooxygenase-2 on human K B carcinoma cells overexpressing COX-2," *Oncol. Rep.*, 24(1):31-36 (July 2010).

OKAYAMA, H et al., "NOS2 enhances KRAS-induced lung carcinogenesis, inflammation, and microRNA-21 expression," *Int. J. Cancer*, 132(1):9-18 (January 2013).

PAN, Y X et al., "Activation of the ATF3 gene through a co-ordinated amino acid-sensing response programme that controls transcriptional regulation of responsive genes following amino acid limitation," *Biochem. J.*, 401(1):299-307 (January 2007).

PANG, Y et al., "TGF-β signaling in myeloid cells is required for tumor metastasis," *Cancer Discov.*, 3(8):936-951 (August 2013).

RADISAVLJEVIC, Z, "Inactivated tumor suppressor Rb by nitric oxide promotes mitosis in human breast cancer cells," *J. Cell Biochem.*, 92(1):1-5 (May 2004).

RHODES, D R et al., "Oncomine 3.0: genes, pathways, and networks in a collection of 18,000 cancer gene expression profiles," *Neoplasia*, 9(2):166-180 (February 2007).

SARFATI, D et al., "Identifying important comorbidity among cancer populations using administrative data: Prevalence and impact on survival," Asia Pac. *J. Clin. Oncol.*, doi: 10.1111/ajco.12130 (December 2013).

SCHEPERS, A G et al., "Lineage tracing reveals Lgr5+ stem cell activity in mouse intestinal adenomas," *Science*, 337(6095):730-735 (August 2012).

SCHOTT, A F et al., "Preclinical and clinical studies of gamma secretase inhibitors with docetaxel on human breast tumors," Clin. Cancer Res., 19(6):1512-1524 (March 2013).

SEN, S et al., "Mitochondrial-associated nitric oxide synthase activity inhibits cytochrome c oxidase: implications for breast cancer," Free Radic. Biol. Med., 57:210-220 (April 2013).

SHAH, N P et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (August 2002).

SIEGERT, A et al., "Nitric oxide of human colorectal adenocarcinoma cell lines promotes tumour cell invasion," Br. J. Cancer, 86(8):1310-1315 (April 2002).

SINGH, S K et al., "Identification of a cancer stem cell in human brain tumors," Cancer Res., 63(18):5821-5828 (September 2003).

SJOBLOM, T et al., "The consensus coding sequences of human breast and colorectal cancers," Science, 314 (5797):268-274 (October 2006).

SMALLEY, M, and ASHWORTH, A, "Stem cells and breast cancer. a field in transit," Nat. Rev. Cancer, 3:832-844 (November 2003).

STINGL, J, and CALDAS, C, "Molecular heterogeneity of breast carcinomas and the cancer stem cell hypothesis," Nat. Rev. Cancer, 7(10):791-799 (October 2007).

STORER, B E, "Small-sample confidence sets for the MTD in a phase I clinical trial," Biometrics, 49(4):1117-1125 (December 1993).

SUDA, O et al., "Long-term treatment with N(omega)-nitro-L-arginine methyl ester causes arteriosclerotic coronary lesions in endothelial nitric oxide synthase-deficient mice," Circulation, 106(13): 1729-1735 (September 2002).

SWITZER, C H et al., "Ets-1 is a transcriptional mediator of oncogenic nitric oxide signaling in estrogen receptor-negative breast cancer," Breast Cancer Res., 14(5):R125 (September 2012).

TAKAOKA, K et al., "Effect of a nitric oxide synthase inhibitor and a CXC chemokine receptor-4 antagonist on tumor growth and metastasis in a xenotransplanted mouse model of adenoid cystic carcinoma of the oral floor," Int. J. Oncol., 43(3):737-745 (September 2013).

TANEI, T et al., "Association of breast cancer stem cells identified by aldehyde dehydrogenase 1 expression with resistance to sequential Paclitaxel and epirubicin-based chemotherapy for breast cancers," Clin. Cancer Res., 15(12):4234-4241 (June 2009).

TANG, C H et al., "Hepatocarcinogenesis driven by GSNOR deficiency is prevented by iNOS inhibition," Cancer Res., 73(9):2897-2904 (May 2013).

TANJORE, H et al., "Alveolar epithelial cells undergo epithelial-to-mesenchymal transition in response to endoplasmic reticulum stress," J. Biol. Chem., 286(35):30972-30980 (September 2011).

THAM, Y L et al., "Clinical response to neoadjuvant docetaxel predicts improved outcome in patients with large locally advanced breast cancers," Breast Cancer Res. Treat., 94(3):279-284 (December 2005).

THIERY, J P et al., "Epithelial-mesenchymal transitions in development and disease," Cell, 139(5):871-890 (November 2009).

THOMSEN, L L et al., "Nitric oxide synthase activity in human breast cancer," Br. J. Cancer, 72(1):41-44 (July 1995).

TOWNSEND, D M et al., "Nitrosative stress-induced s-glutathionylation of protein disulfide isomerase leads to activation of the unfolded protein response," Cancer Res., 69(19):7626-7634 (October 2009).

TRIUMPH Investigators et al., "Effect of tilarginine acetate in patients with acute myocardial infarction and cardiogenic shock. The TRIUMPH randomized controlled trial," JAMA, 297(15):1657-1666 (April 2007).

UECHI, T et al., "A complete map of the human ribosomal protein genes. assignment of 80 genes to the cytogenetic map and implications for human disorders," Genomics, 72(3):223-230 (March 2001).

ULIANICH, L et al., "E R stress is associated with dedifferentiation and an epithelial-to-mesenchymal transition-like phenotype in PC C13 thyroid cells," J. Cell Sci., 121(Pt. 4):477-486 (February 2008).

VAKKALA, M et al., "Inducible nitric oxide synthase expression, apoptosis, and angiogenesis in in situ and invasive breast carcinomas," Clin. Cancer Res., 6(6): 2408-2416 (June 2000).

VAN D E VIJVER, M J et al., "A gene-expression signature as a predictor of survival in breast cancer," N. Engl. J Med., 347(25):1999-2009 (December 2002).

VERMEULEN, P B et al., "Quantification of angiogenesis in solid human tumours; an international consensus on the methodology and criteria of evaluation," Eur. J Cancer, 32A(14):2474-2484 (December 1996).

VOUTSADAKIS, I A, "The ubiquitin-proteasome system and signal transduction pathways regulating epithelial mesenchymal transition of cancer," J Biomed. Sci., 19:67 (July 2012).

WACKER, S A et al., "Using transcriptome sequencing to identify mechanisms of drug action and resistance," Nat. Chem. Biol., 8(3):235-237 (February 2012).

WINK, D A et al., "The effect of various nitric oxide-donor agents on hydrogen peroxide-mediated toxicity: a direct correlation between nitric oxide formation and protection," Arch. Biochem. Biophys., 331(2):241-248 (July 1996).

YANG, M H, and W U, K J, "TWIST activation by hypoxia inducible factor-1 (HIF-1): implications in metastasis and development," Cell Cycle, 7(14):2090-2096 (July 2008).

YASUOKA, H et al., "Cytoplasmic CXCR4 expression in breast cancer: induction by nitric oxide and correlation with lymph node metastasis and poor prognosis," BMC Cancer, 8:340 (November 2008).

YIN, X et al., "ATF3, an adaptive-response gene, enhances TGF{beta} signaling and
cancer-initiating cell features in breast cancer cells," J. Cell Sci., 123(Pt. 20):3558-3565 (October 2010).

ZHANG, X et al., "A renewable tissue resource of phenotypically stable, biologically and ethnically diverse, patient-derived human breast cancer xenograft models," Cancer Res., 73(15):4885-4897 (August 2013).

ZHONG, Q et al., "Role of endoplasmic reticulum stress in epithelial-mesenchymal transition of alveolar epithelial cells: effects of misfolded surfactant protein," Am. J. Respir. Cell Mol. Biol., 45(3):498-509 (September 2011).

ZHOU, L et al., "The prognostic role of cancer stem cells in breast cancer: a meta-analysis of published literatures," Breast Cancer Res. Treat., 122(3):795-801 (August 2010).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising," "having," "including," or "containing," with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A method of treating or ameliorating one or more symptoms of breast cancer in a mammal in need thereof, the method comprising administering to the mammal a composition comprising:
   1) a therapeutically-effective amount of $N^G$-monomethyl-L-arginine (L-NMMA); and
   2) a therapeutically-effective amount of amlodipine; and
   3) a therapeutically-effective amount of a first chemotherapeutic agent;

for a time sufficient to treat or ameliorate the one or more symptoms of breast cancer in the mammal.

2. The method of claim 1, wherein the breast cancer is identified as a refractory or a relapsed form of the disease.

3. The method of claim 1, wherein the breast cancer is characterized as treatment-resistant, radioresistant, metastatic, or any combination thereof.

4. The method of claim 1, wherein the composition further comprises: 4) one or more of an immunomodulating agent, a neuroactive agent, an anti-inflammatory agent, an anti-lipidemic agent, a hormone, a receptor agonist, a receptor antagonist, an anti-infective agent, a protein, a peptide, an antibody, an antigen-binding fragment of an antibody, an enzyme, an RNA, a DNA, an siRNA, an mRNA, a ribozyme, a hormone, a cofactor, a steroid, an antisense molecule, a second distinct antihypertensive agent, a second distinct chemotherapeutic agent, or any combination thereof.

5. The method of claim 4, wherein the antibody is selected from the group consisting of an anti-CDI antibody, an anti-PD1 antibody, an anti-PD-L1 antibody, and any combination thereof.

6. The method of claim 4, wherein the antigen-binding fragment is obtained from an anti-CDI antibody, an anti-PD1 antibody, an anti-PD-L1 antibody, or any combination thereof, or wherein the antigen-binding fragment comprises at least one antigenically-active fragment of one or more of said antibodies.

7. The method of claim 1, wherein the first chemotherapeutic agent comprises: one or more antineoplastic compounds, one or more cytotoxic compounds, one or more cytostatic compounds, one or more cytoreductive compounds, or any combination thereof.

8. The method of claim 1, wherein the first chemotherapeutic agent is selected from the group consisting of cyclophosphamide, doxorubicin, 5-fluorouracil, docetaxel, paclitaxel, trastuzumab, methotrexate, epirubicin, cis-platin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and any combination thereof.

9. The method of claim 1, wherein the first chemotherapeutic agent is docetaxel.

10. The method of claim 1, wherein the composition further comprises a pharmaceutically-acceptable carrier, buffer, diluent, vehicle, excipient, or any combination thereof.

11. The method of claim 1, wherein the composition is formulated for systemic administration to a human.

12. The method of claim 1, wherein the composition is administered to the mammal as a single systemic dose, or in a series of consecutive systemic doses administered over a period of several days to several weeks.

13. The method of claim 1, further comprising the additional step of administering to the mammal one or more chemotherapeutically-effective doses of radiation.

14. A method of treating or ameliorating one or more symptoms of breast cancer in a mammal, comprising: at least the steps of administering to the mammal one or more compositions that comprise: therapeutically-effective amounts of: a) $N^G$-monomethyl-L-arginine [L-NMMA]; b) amlodipine; c) docetaxel; and an anti-PD1 antibody, for a time sufficient to treat or ameliorate the one or more symptoms of breast cancer in the mammal.

15. The method of claim 14, wherein the breast cancer is diagnosed as triple-negative breast cancer (TNBC).

16. The method of claim 14, further comprising the additional step of administering to the body of the mammal one or more chemotherapeutically-effective doses of ionizing radiation.

17. A method of treating or ameliorating one or more symptoms of TNBC in a mammal, the method comprising: at least a step of administering to the mammal:
   1) a first composition that comprises: therapeutically-effective amounts of:
      a) $N^G$-monomethyl-L-arginine [L-NMMA]; and
      b) amlodipine; and
   2) a second composition that comprises a first chemotherapeutic agent selected from the group consisting of cyclophosphamide, doxorubicin, 5-fluorouracil, docetaxel, paclitaxel, trastuzumab, methotrexate, epirubicin, cis-platin, carboplatin, vinorelbine, capecitabine, gemcitabine, mitoxantrone, isabepilone, eribulin, lapatinib, carmustine, a nitrogen mustard, a sulfur mustard, a platin tetranitrate, vinblastine, etoposide, camptothecin, and any combination thereof;

for a time sufficient to treat or ameliorate the one or more symptoms of TNBC in the mammal.

18. The method of claim 17, further comprising: systemically administering to the mammal a third composition that comprises: a therapeutically-effective amount of pembrolizumab.

19. The method of claim 18, wherein the therapeutically-effective amount of pembrolizumab administered to the mammal is about 10 mg/kg/day.

20. The method of claim 17, further comprising the additional step of administering to the body of the mammal, one or more chemotherapeutically-effective doses of ionizing radiation.

21. The method of claim 17, wherein the therapeutically-effective amount of L-NMMA administered to the mammal is about 80 mg/kg to about 400 mg/kg/day.

22. The method of claim 17, wherein the therapeutically-effective amount of the first chemotherapeutic agent is about 20 mg/kg/day.

23. The method of claim 17, wherein the therapeutically-effective amount of amlodipine is about 10 mg/kg/day.

24. The method of claim 14, wherein the anti-PD1 antibody comprises pembrolizumab.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide XBP1 Forward Primer

<400> SEQUENCE: 1
gggtccaagt tgtccagaat gc                                              22

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide XBP1 Reverse Primer

<400> SEQUENCE: 2
ttacgagaga aaactcatgg c                                               21

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide Beta Actin Forward
      Primer

<400> SEQUENCE: 3
ctggaacggt gaaggtgaca                                                 20

<210> SEQ ID NO 4
<211> LENGTH: 23
<212> TYPE: DNA
<213> ORGANISM: Artificial Sequence
<220> FEATURE:
<223> OTHER INFORMATION: Synthetic Oligonucleotide Beta Actin Reverse
      Primer

<400> SEQUENCE: 4
aagggacttc ctgtaacaat gca                                             23
```